US011690919B2

(12) United States Patent
Ward Ober et al.

(10) Patent No.: US 11,690,919 B2
(45) Date of Patent: Jul. 4, 2023

(54) ENDOLYSOSOMAL TARGETING CONJUGATES FOR IMPROVED DELIVERY OF CARGO MOLECULES TO THE ENDOLYSOSOMAL COMPARTMENT OF TARGET CELLS

(71) Applicant: THE TEXAS A&M UNIVERSITY SYSTEM, College Station, TX (US)

(72) Inventors: Elizabeth Sally Ward Ober, College Station, TX (US); Raimund Johannes Ober, College Station, TX (US); Jeffrey Che-Wei Kang, College Station, TX (US); Wei Sun, College Station, TX (US); Ran Li, College Station, TX (US)

(73) Assignees: The Texas A&M University System, College Station, TX (US); Board of Regents of the University of Texas System, Austin, TX (US)

( * ) Notice: Subject to any disclaimer, the term of this patent is extended or adjusted under 35 U.S.C. 154(b) by 578 days.

(21) Appl. No.: 16/478,821

(22) PCT Filed: Jan. 17, 2018

(86) PCT No.: PCT/US2018/013952

§ 371 (c)(1),
(2) Date: Jul. 17, 2019

(87) PCT Pub. No.: WO2018/136455

PCT Pub. Date: Jul. 26, 2018

(65) Prior Publication Data

US 2019/0381183 A1 Dec. 19, 2019

Related U.S. Application Data

(60) Provisional application No. 62/447,411, filed on Jan. 17, 2017, provisional application No. 62/447,265, filed on Jan. 17, 2017.

(51) Int. Cl.

| | |
|---|---|
| ***A61K 47/68*** | (2017.01) |
| ***A61P 35/00*** | (2006.01) |
| ***C07K 16/32*** | (2006.01) |
| ***A61K 38/00*** | (2006.01) |

(52) U.S. Cl.

CPC ...... *A61K 47/6855* (2017.08); *A61K 47/6817* (2017.08); *A61P 35/00* (2018.01); *C07K 16/32* (2013.01); *A61K 38/00* (2013.01)

(58) Field of Classification Search

None

See application file for complete search history.

(56) References Cited

U.S. PATENT DOCUMENTS

| | | | | |
|---|---|---|---|---|
| 2008/0069823 | A1 | 3/2008 | Allison | |
| 2014/0219956 | A1 | 8/2014 | Govindan et al. | |
| 2014/0335089 | A1 | 11/2014 | Igawa et al. | |
| 2015/0098946 | A1* | 4/2015 | Bhakta .................. | C07K 16/30 424/139.1 |

FOREIGN PATENT DOCUMENTS

| | | | |
|---|---|---|---|
| WO | 2003105814 | A1 | 12/2003 |
| WO | 2009133362 | A2 | 11/2009 |
| WO | 2009149393 | A2 | 12/2009 |
| WO | WO 2011/111007 | | 9/2011 |
| WO | 2013102684 | A1 | 7/2013 |
| WO | 2013170272 | A2 | 11/2013 |
| WO | 2014012479 | A1 | 1/2014 |
| WO | 2014145159 | A2 | 9/2014 |
| WO | 2015048724 | A1 | 4/2015 |
| WO | WO 2016/000813 | | 1/2016 |
| WO | WO 2018/102668 | | 6/2018 |

OTHER PUBLICATIONS

WHO Drug Information vol. 19, No. 3, 2003, pp. 183-227.*

Vincent, K. J. et al. "Current strategies in antibody engineering: Fc engineering and pH-dependent antigen binding, bispecific antibodies and antibody drug conjugates" *Biotechnology Journal*, 2012, pp. 1444-1450, vol. 7.

International Search Report and Written Opinion dated May 24, 2018 for corresponding International Application No. PCT/US2018/013952.

Devanaboyina, S. et al. 2013 "The effect of pH dependence of antibody-antigen interactions on subcellular trafficking dynamics", mAbs, vol. 5, No. 6, pp. 851-859 See Abstract, Table 1 and Figure 1.

Kang, J. C. et al. "Engineering a HER2-specific antibody-drug conjugate to increase lysosomal delivery and therapeutic efficacy" *Nature Biotechnology*, May 2019, pp. 523-526, vol. 37, Brief Communication pp. 1-3, Reporting Summary pp. 1-7.

(Continued)

*Primary Examiner* — Patricia Duffy

(74) *Attorney, Agent, or Firm* — Edell, Shapiro & Finnan, LLC

(57) ABSTRACT

Endolysosomal targeting conjugates that are engineered to deliver cargo molecules such as cytotoxic drugs or imaging labels with improved efficiency to late endosomes and/or lysosomes in target cells such as tumor cells are described. The endolysosomal targeting conjugate includes a targeting component and a cargo component. The targeting component is configured to bind to a cell surface molecule of a target cell and the cargo component includes a cargo molecule. The targeting component and the cargo component may be fused by a covalent bond or associated by a non-covalent bond. The targeting component may bind to the cell surface molecule or the cargo component with higher affinity in the extracellular space than in an endolysosomal compartment of the target cell.

12 Claims, 37 Drawing Sheets

Specification includes a Sequence Listing.

(56) References Cited

OTHER PUBLICATIONS

Li, R. et al. "Targeting Phosphatidylserine with Calcium-dependent Protein-Drug Conjugates for the Treatment of Cancer" *Mol. Cancer Ther.*, Jan. 2018, pp. 1-29, vol. 17, No. 1.

* cited by examiner

| PERTUZUMAB (WT OR VARIANTS) | pH 7.4 | 7.0 | 6.5 | 5.8 |
|---|---|---|---|---|
| WT | 2.9 | 5.9 | 27.2 | 137.6 |
| SG | 8.2 | 46.4 | 150.1 | N.D.* |
| YS | 6.3 | 22.1 | 67.9 | 1627.2 |

*N.D. INDICATES AFFINITY TOO LOW TO DETERMINE AN ACCURATE DISSOCIATION CONSTANT.

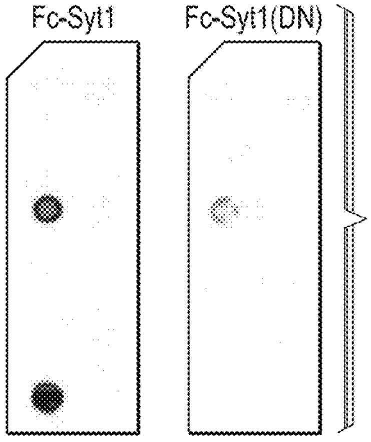
FIG. 16B
FIG. 16C
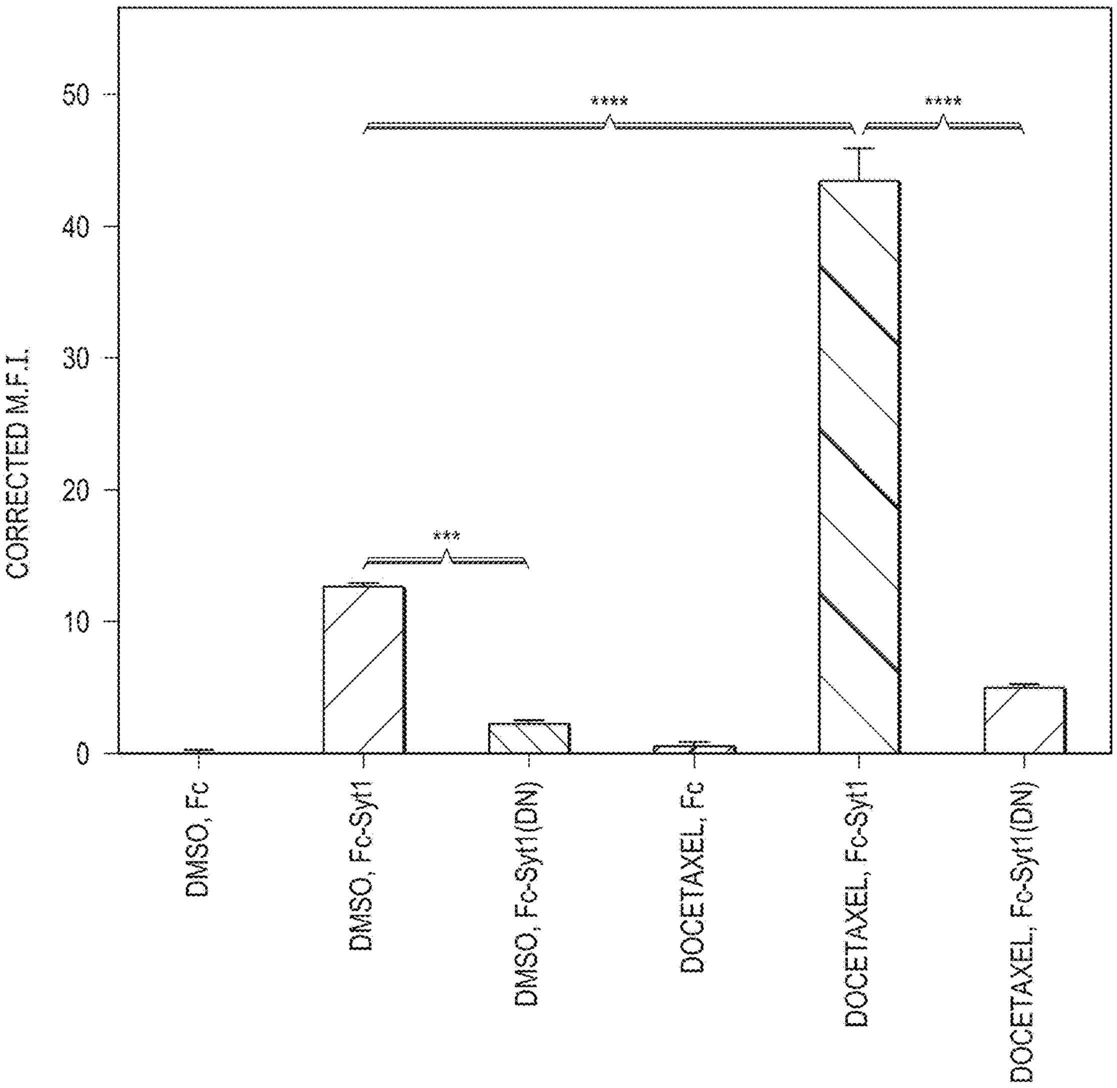

FIG. 16D
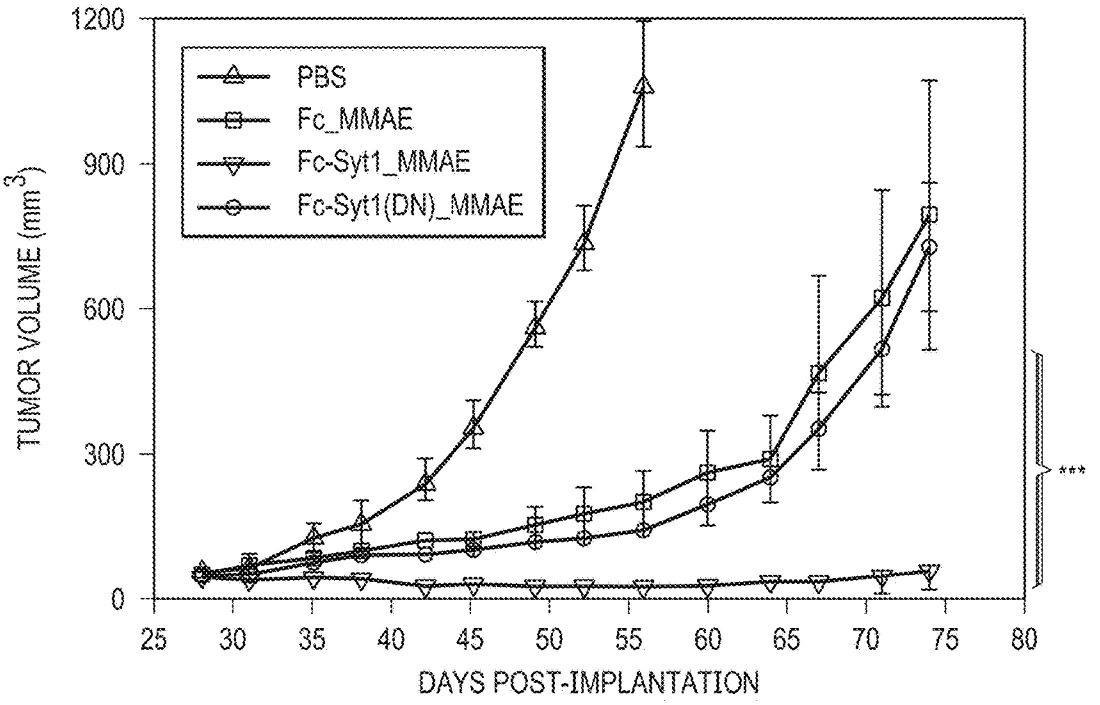
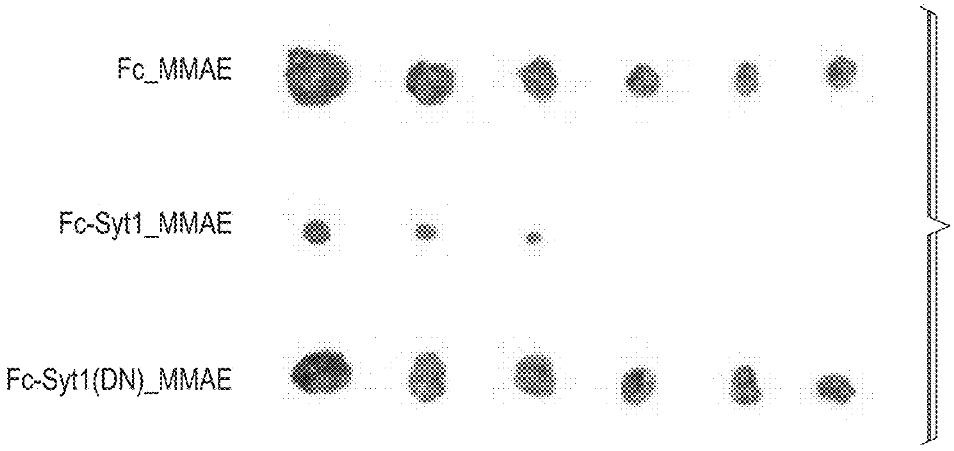
FIG. 16E

ENDOLYSOSOMAL TARGETING CONJUGATES FOR IMPROVED DELIVERY OF CARGO MOLECULES TO THE ENDOLYSOSOMAL COMPARTMENT OF TARGET CELLS

CROSS-REFERENCE TO RELATED APPLICATIONS

This application is the National Stage of International Application No. PCT/US2018/013952, filed Jan. 17, 2018; which claims the benefit of U.S. Provisional Application No. 62/447,411, filed Jan. 17, 2017 and U.S. Provisional Application No. 62/447,265, filed Jan. 17, 2017; all of which are incorporated by reference herein.

FIELD OF THE INVENTION

The invention disclosed herein generally relates to the generation of engineered proteins that can be used as platforms to deliver cytotoxic drugs, imaging labels or other cargo molecules to target cells such as tumor cells. These proteins are engineered to deliver the cargo molecules more efficiently to late endosomes and lysosomes in the targeted cells.

BACKGROUND

Antibody-drug conjugates (ADCs) or protein-drug conjugates (PDCs) represent a class of therapeutics that combine the high specificity of antibodies, antibody fragments or other proteins that bind to cancer cells or other unwanted cells such as inflammatory or virally infected cells with the delivery of highly toxic drugs. A problem with current ADCs or PDCs is that they have toxicities that can limit the dose. However, the development of ADCs and PDCs that allow more efficient delivery of cytotoxic drugs to tumor cells remains challenging.

In addition, antibodies, antibody fragments or other targeting proteins can be labeled with radiolabel, fluorescent label or near infrared label to be used as labeled conjugates (LCs) in diagnostic imaging. However, the development of LCs that allow more efficient labeling of tumors with higher contrast to background tissues also remains challenging.

SUMMARY

The present disclosure relates to engineered proteins, herein referred to as endolysosomal targeting conjugates, that are configured to allow improved delivery of cargo molecules such as cytotoxic drugs (e.g., in ADCs, or PDCs) or imaging labels (e.g., in LCs) to the endolysosomal pathway in target cells such as cancer cells or other cell types.

According to a first aspect, an endolysosomal targeting conjugate is described. The endolysosomal targeting conjugate has a targeting component that includes an antibody, an antibody fragment, an antibody domain, a nanobody, a protein, a protein fragment, or a protein domain, wherein the targeting component is configured to bind to a cell surface molecule of a target cell with a lower dissociation constant in an extracellular space than in an endolysosomal compartment of the target cell. The endolysosomal targeting conjugate also has a cargo component that includes a cargo molecule conjugated to an antibody, an antibody fragment, an antibody domain, a nanobody, a protein, a protein fragment, or a protein domain. The targeting component is fused directly or indirectly to the cargo component. Upon entry to the endolysosomal compartment, the targeting component is configured to dissociate from the cell surface molecule. The endolysosomal targeting conjugate is configured to deliver the cargo molecule to the endolysosomal compartment of the target cell.

According to a second aspect, an endolysosomal targeting conjugate is described. The endolysosomal targeting conjugate has a targeting component that includes an antibody, an antibody fragment, an antibody domain, a nanobody, a protein, a protein fragment, or a protein domain, wherein the targeting component is configured to bind to a cell surface molecule of a target cell. The endolysosomal targeting conjugate also has a cargo component that includes a cargo molecule conjugated to an antibody, an antibody fragment, an antibody domain, a nanobody, a protein, a protein fragment, or a protein domain. The targeting component is configured to bind to the cargo component with a lower dissociation constant in an extracellular space than in an endolysosomal compartment of the target cell. Upon entry to the endolysosomal compartment, the targeting component is configured to dissociate from the cargo component. The endolysosomal targeting conjugate is configured to deliver the cargo molecule to the endolysosomal compartment of the target cell.

According to a third aspect, a composition is described. The composition includes an endolysosomal targeting conjugate and a pharmaceutically acceptable vehicle.

According to a fourth aspect, a method of treating cancer is described. The method includes administering a subject with an effective dose of an endolysosomal targeting conjugate composition to a subject, wherein the cargo molecule is a cytotoxic drug and the administering of the composition suppresses growth of a tumor in the subject.

According to a fifth aspect, a method of imaging a tumor in a subject is described. The method includes the steps of: (1) administering a subject with an effective dose of an endolysosomal targeting conjugate composition to a subject, wherein the cargo molecule is an imaging label; and (2) performing an imaging method suitable for detecting the imaging label in the subject. The administering of the composition provides a sufficient concentration of the imaging label detectable by the imaging method.

According to a sixth aspect, a method of providing an endolysosomal targeting conjugate for the treatment of cancer is described. The method includes the steps of: (1) selecting a targeting component, wherein the targeting component includes an antibody, an antibody fragment, an antibody domain, a nanobody, a protein, a protein fragment, or a protein domain configured to selectively bind to a cell surface molecule on a selected type of tumor target cell, wherein the targeting component is configured to bind to a cell surface molecule with a lower dissociation constant in an extracellular space than in an endolysosomal compartment; (2) selecting a cargo component, wherein the cargo component includes an antibody, an antibody fragment, an antibody domain, a nanobody, a protein, a protein fragment, or a protein domain conjugated to a cargo molecule, wherein the cargo molecule is a cytotoxic drug having efficacy for suppressing growth of the selected type of tumor target cell; and (3) providing the endolysosomal targeting conjugate including the targeting component fused directly or indirectly to the cargo component.

According to a seventh aspect, a method of providing an endolysosomal targeting conjugate for the treatment of cancer is described. The method includes the steps of (1) selecting a targeting component, wherein the targeting component includes an antibody, an antibody fragment, a nanobody, a protein, a protein fragment, or a protein domain configured to selectively bind to a cell surface molecule on a selected type of tumor target cell; (2) selecting a cargo component, wherein the cargo component includes an antibody, an antibody fragment, an antibody domain, a nanobody, a protein, a protein fragment, or a protein domain conjugated to a cargo molecule, wherein the cargo molecule is a cytotoxic drug having efficacy for suppressing growth of the selected type of tumor target cell. In the method, the targeting component is engineered to further include a first protein domain; the cargo component is engineered to further include a second protein domain; and the first protein domain is configured to bind to the second domain with a lower dissociation constant in an extracellular space than in an endolysosomal compartment.

The above endolysosomal targeting conjugates and methods may further include the following details, which may be combined with one another unless clearly mutually exclusive: i) the targeting component may include an antibody, an antibody fragment or a nanobody that is configured to bind to the cell surface molecule in the extracellular space with a dissociation constant less than 500 nM; ii) the targeting component may include an antibody, an antibody fragment or a nanobody that is configured to bind to the cell surface molecule with a lower dissociation constant at a near neutral pH than at an acidic endolysosomal pH; iii) near-neutral pH may be greater than about pH 6.8 and less than about pH 7.5 and the acidic endolysosomal pH may be greater than about pH 5.0 and less than about pH 6.5; iv) the targeting component may include an antibody, an antibody fragment or a nanobody that is configured to bind to a cell surface molecule with a lower dissociation constant at an extracellular $Ca^{2+}$ concentration than at an endolysosomal $Ca^{2+}$ concentration; v) the extracellular $Ca^{2+}$ concentration may be about 2 mM and the endolysosomal $Ca^{2+}$ concentration may be about 2 μM; vi) the targeting component may include a protein, a protein fragment or a protein domain that is configured to bind to a cell surface molecule in the extracellular space with a dissociation constant less than 500 nM; vii) the targeting component may be a protein, a protein fragment or a protein domain that is configured to bind to a cell surface molecule with a lower dissociation constant at a near neutral pH than at an acidic endolysosomal pH; viii) the targeting component may include a protein, a protein fragment or a protein domain that is configured to bind to a cell surface molecule with a lower dissociation constant at an extracellular $Ca^{2+}$ concentration than at an endosomal $Ca^{2+}$ concentration; ix) the cargo component may include an antibody, an antibody fragment, which may be an antibody Fc region or a domain of the antibody Fc fragment; x) the antibody Fc region or the domain of the antibody Fc fragment may be derived from human IgG1; xi) the cargo component may include an albumin molecule or a domain of albumin; xii) the targeting component may include a Fab fragment or a scFv fragment of a HER2-specific antibody, wherein a heavy chain variable domain of the Fab fragment or the scFv fragment has mutations of Ser55 to histidine and Gly57 to glutamic acid; xiii) the targeting component may include a Fab fragment or a scFv fragment of a HER2-specific antibody, wherein in the Fab fragment or the scFv fragment a heavy chain variable domain has a mutation of Ser103 to histidine and a light chain variable domain has a mutation of Tyr55 to histidine; xiv) the endolysosomal targeting conjugate may include at least a first targeting component and a second targeting component, wherein the first targeting component is configured to bind to a different cell surface molecule than the second targeting component; xv) the at least first and second targeting components may be fused to a heterodimer of two immunoglobulin Fc fragments; xvi) the targeting component may include a phosphatidylserine-binding protein and the target cell may be a cell having a phosphatidylserine on the cell surface; xvii) the phosphatidylserine-binding protein may be selected from the group consisting of a core domain of AnxA1, a C2A domain of Syt1, and a C2 domain of PKCα; xviii) the phosphatidylserine-binding protein may be the C2A domain of Syt1; xix) the targeting component may include two of the C2A domains of Syt1; xx) the targeting component may include four of the C2A domains of Syt1; xxi) the targeting component may include more than four of the C2A domains of Syt1; xxii) the targeting component may include a phosphatidylserine-binding protein, the cargo component comprises an Fc portion of human IgG1, and the targeting component may be covalently fused to the cargo component by a linker protein; xxiii) the linker protein may be a Gly4Ser linker; xxiv) the cargo molecule may be a cytotoxic drug; xxv) the cytotoxic drug may be monomethylauristatin E (MMAE); xxvi) the cargo molecule may be an imaging label; xxvii) the targeting component may be configured to bind to the cargo compartment with a lower dissociation constant at near neutral pH than at acidic endosomal pH; xxviii) the targeting component may be configured to bind to the cargo component with a lower dissociation constant at an extracellular $Ca^{2+}$ concentration than at an endosomal $Ca^{2+}$ concentration; xxix) the targeting component may include a calbindin D9K domain 2 and the cargo component may include a calbindin D9K domain 1; xxx) the calbindin domain 1 D9K may be fused to the cargo component by a linker peptide and/or the calbindin D9K domain 2 may be fused to the targeting component by a linker peptide; xxxi) the composition may include at least one endolysosomal targeting conjugate configured to target tumors of one or more types of target cells; xxxii) the cargo molecule may be conjugated to the antibody fragment, the antibody domain, the nanobody, the protein, the protein fragment, or the protein domain by a polypeptide linker or through a chemical conjugation reaction; xxxiii) the imaging label may be a radiolabel, a fluorescent or a near infrared label; xxxiv) an N-terminus of the targeting component may be fused to a C-terminus of the cargo component; xxxv) a C-terminus of the targeting component may be fused to an N-terminus of the cargo component; xxxvi) the targeting component may be fused to the cargo component at a non-terminal location of the cargo component; xxxvii) the cargo component may include an immunoglobulin Fc fragment and the targeting component may be fused to the immunoglobulin Fc fragment of the cargo component at an N-terminus or a C-terminus of a hinge-CH2-CH3 domain of the immunoglobulin Fc fragment; xxxviii) the targeting component may include an antibody, an antibody fragment, an antibody domain, or a nanobody that is configured to bind to human epidermal growth factor receptor 2; xxxix) the targeting component may include an antibody, an antibody fragment, an antibody domain, or a nanobody that is configured to bind to prostate-specific membrane antigen; xl) the endolysosomal targeting conjugate may include one or more proteins having an amino acid sequence of at least one of SEQ ID NO: 2, SEQ ID NO: 4, SEQ ID NO: 6, SEQ ID NO:8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or a homolog thereof; xli) the endolysosomal targeting conjugate may include a heterodimer of proteins having amino acid sequences of SEQ ID NO: 2 plus SEQ ID No: 4, SEQ ID NO: 6 plus SEQ ID NO: 8, SEQ ID NO: 42 plus SEQ ID NO: 44, or SEQ ID NO: 46 plus SEQ ID NO: 48, or homologs thereof; xlii) the endolysosomal targeting conjugate may include a heterotrimer of proteins having amino acid sequence of SEQ ID NO: 18 plus SEQ ID NO: 20 plus SEQ ID NO: 22, SEQ ID NO: 22 plus SEQ ID NO: 24 plus SEQ ID NO: 26, or homologs thereof; xliii) the targeting component may include an antibody, an antibody fragment, an antibody domain, or a nanobody that is configured to bind to the cell surface molecule at an acidic pH with a dissociation constant greater than 1.5 μM; xliv) the targeting component may include a protein, a protein fragment or a protein domain that is configured to bind to the cell surface molecule at an acidic pH with a dissociation constant greater than 1.5 μM; xlv) the acidic pH may be about 5.8; xlvi) the targeting component may include an antibody, an antibody fragment, an antibody domain, or a nanobody that is configured to bind to the cell surface molecule with a lower dissociation constant at a pH from about 6.8 to about 7.5 than at a pH from about 5.0 to about 6.5; xlvii) the targeting component may include an antibody, an antibody fragment, an antibody domain, or a nanobody that is configured to bind to a cell surface molecule with a lower dissociation constant at a $Ca^{2+}$ concentration of about 2 mM than at a $Ca^{2+}$ concentration of about 2 μM; xlviii) the targeting component may include a protein, a protein fragment or a protein domain that is configured to bind to a cell surface molecule with a lower dissociation constant at a pH from about 6.8 to about 7.5 than at a pH from about 5.0 to about 6.5; xlix) the targeting component may include a protein, a protein fragment or a protein domain that is configured to bind to a cell surface molecule with a lower dissociation constant at a $Ca^{2+}$ concentration of about 2 mM than at a $Ca^{2+}$ concentration of about 2 μM; xlx) the targeting component may be configured to bind to the cargo compartment with a lower dissociation constant at a pH from about 6.8 to about 7.5 than at a pH from about 5.0 to about 6.5; xlxi) the targeting component may be configured to bind to the cargo component with a lower dissociation constant at a $Ca^{2+}$ concentration of about 2 mM than at a $Ca^{2+}$ concentration of about 2 μM; xlxii) the cargo molecule may be a cytotoxic radiolabel; xlxiii) the cargo molecule may be a drug or other agent that modifies a behavior of the target cell.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which:

FIG. 16B shows exemplary lipid binding profiles of exemplary PS-targeting endolysosomal targeting conjugates that bind to PS or a control endolysosomal targeting conjugate that is engineered to bind with low affinity (DN) to PS to lipid-coated nitrocellulose membranes;

FIG. 16C shows graphs reporting exemplary binding of exemplary PS-targeting endolysosomal targeting conjugates that bind to PS or are engineered to bind with low affinity (DN) to PS-positive 2H11 cells using flow cytometry analysis;

FIG. 16D shows graphs reporting exemplary data for the effects of exemplary PS-targeting endolysosomal targeting conjugates and control proteins on tumor growth (LNCaP cells) in mice;

FIG. 16E shows exemplary images of isolated tumors (LNCaP cells) from mice treated with exemplary PS-targeting endolysosomal targeting conjugates and control proteins;

DETAILED DESCRIPTION

Figure 1:
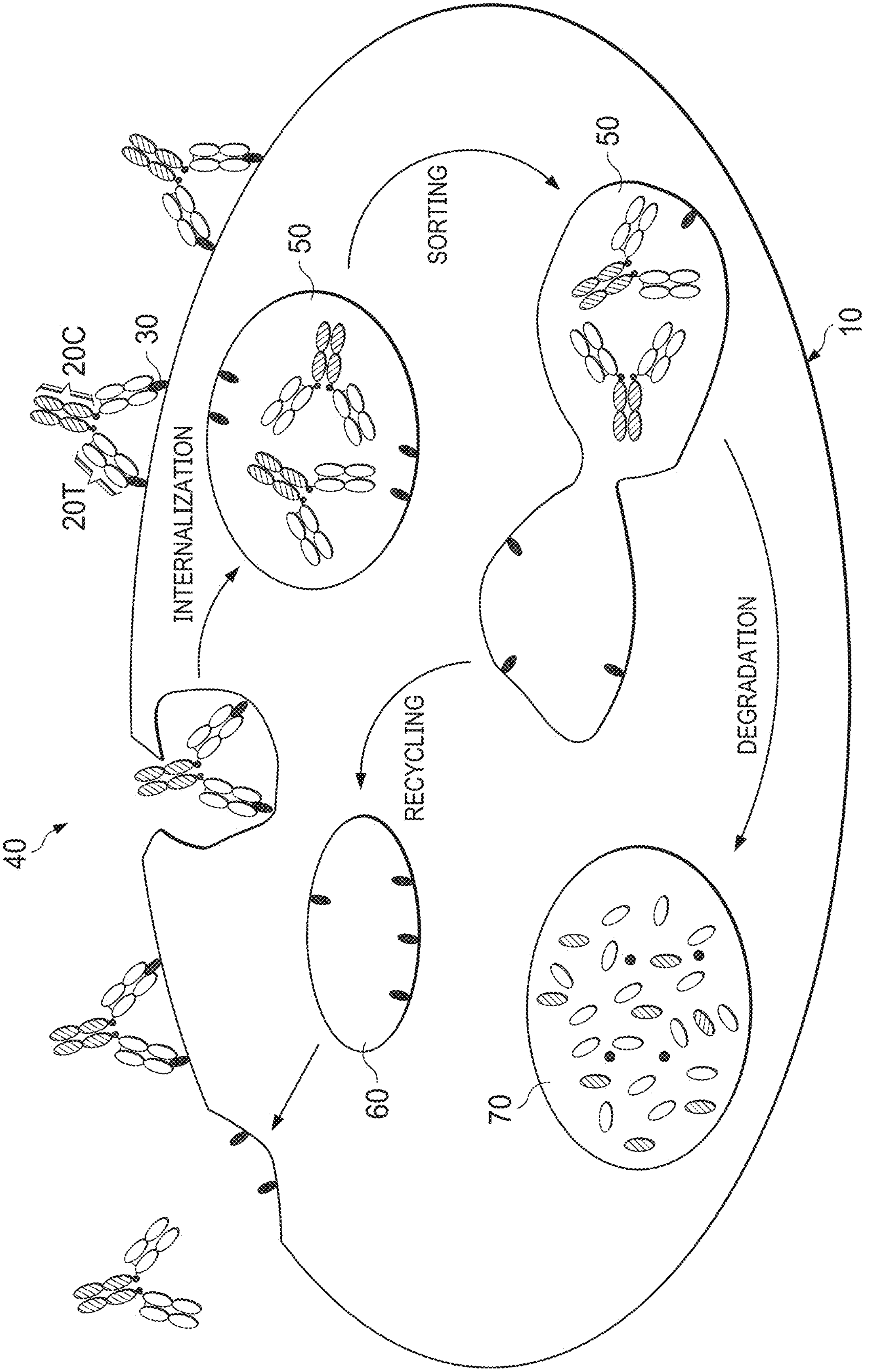
FIG. 1 is an exemplary schematic diagram of selected cellular events that lead to the delivery of cargo molecules into late endosomes and lysosomes by the endolysosomal targeted conjugates.

This disclosure relates to engineered antibodies or fusion proteins that are configured to allow improved delivery of a cargo molecule, such as a cytotoxic drug or an imaging label to late endosomes and lysosomes in a target cell. The terms "endolysosomal" and "endolysosomal compartment" as used herein refer to the early endosomes, late endosomes, lysosomes and associated tubulovesicular transport carriers of cells. Accordingly, the term "endolysosomal targeting conjugate" as used herein refers to an engineered antibody or fusion protein that is configured for improved delivery of a cargo molecule to the endolysosomal compartment of a target cell.

The antibodies or fusion proteins described herein include a targeting component and a cargo component. The targeting component may include an antibody, an antibody fragment, antibody domain, nanobody, protein, protein fragment, or protein domain that is configured to bind to a cell surface molecule, such as a cell surface receptor or other cell surface molecule that may be present on the extracellular surface of a cell's plasma membrane, wherein the molecule is at least partially exposed to an extracellular space. The cargo component may include an antibody, an antibody fragment, antibody domain, nanobody, protein, protein fragment, or protein domain that is conjugated to a cargo molecule, such as a cytotoxic drug or imaging label.

The terms "antibody-drug conjugate" or "ADC" as used herein refer to antibody-based conjugates that are configured to deliver a drug to a cell. In particular, the terms "antibody-drug conjugate" or "ADC" as used herein refers to an antibody that includes a targeting component and a cargo component. The targeting component may include an antibody Fab fragment, an antibody variable domain, or a nanobody. The targeting component is linked to a cargo component that may include an antibody constant region (Fc fragment) or a domain of a constant region. One or more cytotoxic drug molecules may be conjugated to the antibody constant region (Fc fragment) or a domain of a constant region of the cargo component of the ADC.

The terms "protein-drug conjugate", or "PDC" as used herein refer to protein-based conjugates that are configured to deliver a drug to a cell. In particular, the term "protein-drug conjugate" or "PDC" as used herein refers to a protein that includes a targeting component and a cargo component. The targeting component may include a protein that binds to a cell surface receptor or cell surface molecule, or a Fab fragment, an antibody variable domain, or a nanobody. The targeting component is linked to a cargo component that may include an antibody constant region (Fc fragment), a domain of a constant region, or a protein such as albumin. One or more cytotoxic drug molecules may be conjugated to the antibody constant region (Fc fragment), domain of a constant region, or a protein such as albumin of the cargo component of the PDC.

The term "labeled conjugate" or "LC" as used herein refers to an antibody or protein that includes a targeting component linked to a cargo component. Accordingly, the targeting component may include an antibody Fab fragment, an antibody variable domain, nanobody, or a protein that binds to a cell surface receptor or cell surface molecule. The cargo component may include an antibody constant region (Fc fragment) or domains of a constant region, or a protein such as albumin. The antibody constant region (Fc fragment), or domains of a constant region, or the protein of the cargo component may be conjugated to one or more imaging labels, such as radiolabels, fluorescent molecules or other labeled molecules.

In general, for ADCs or PDCs to effectively deliver a drug to a cell, they should selectively bind to target cells, be internalized into the cells, and enter degradative compartments called late endosomes and lysosomes. Prior to entering lysosomes, ADCs or PDCs enter early endosomes where sorting into the recycling or lysosomal pathway occurs. Improving delivery to late endosomes and lysosomes (the endolysosomal pathway) would result in more potent ADCs or PDCs and enable the use of lower dosages.

In addition, LCs that allow improved delivery of imaging labels to late endosomes and lysosomes in target cells would result in higher contrast for imaging target cells against a background of non-targeted cells or tissue.

Accordingly, the current invention generally relates to endolysosomal targeting conjugates that are engineered to more efficiently deliver cargo molecules to the endolysosomal compartment of target cells, whereby the engineered conjugates described herein are configured to respond to differences in chemical composition in endosomes or late endosomes and the extracellular environment, thereby achieving more efficient delivery of a cargo molecule such as a cytotoxic drug or an imaging label to target cells. Examples of the endolysosomal targeting conjugates described herein include improved ADCs, PDCs, and LCs that are configured for improved targeting of the conjugated cargo molecules such as drugs or imaging labels to the endolysosomal compartment of target cells, thereby resulting in more potent ADCs or PDCs, or higher contrast LCs.

Cargo molecules as described herein can include any molecule having a function useful to cause an effect in a target cell. For example, in addition to cytotoxic drugs or imaging labels, additional cargo molecules could be radiolabels that kill cells through radiation damage i.e. can be used therapeutically rather than for imaging. Examples of such radiolabels are Yttrium (Y)-90 and Iodine (I)-131. Additional types of cargo molecules are identifiable by skilled persons upon reading the present disclosure.

In addition to tumor cells, target cells in the sense of the disclosure may include other types of unwanted cells, such as inflammatory cells, or virally-infected cells, among others identifiable by skilled persons upon reading the present disclosure.

The term "cell surface molecule' as used herein refers to a protein or other biological molecule (e.g. phospholipid, carbohydrate) that is at least partially exposed on the extracellular surface of a plasma membrane of a cell.

Figure 2:
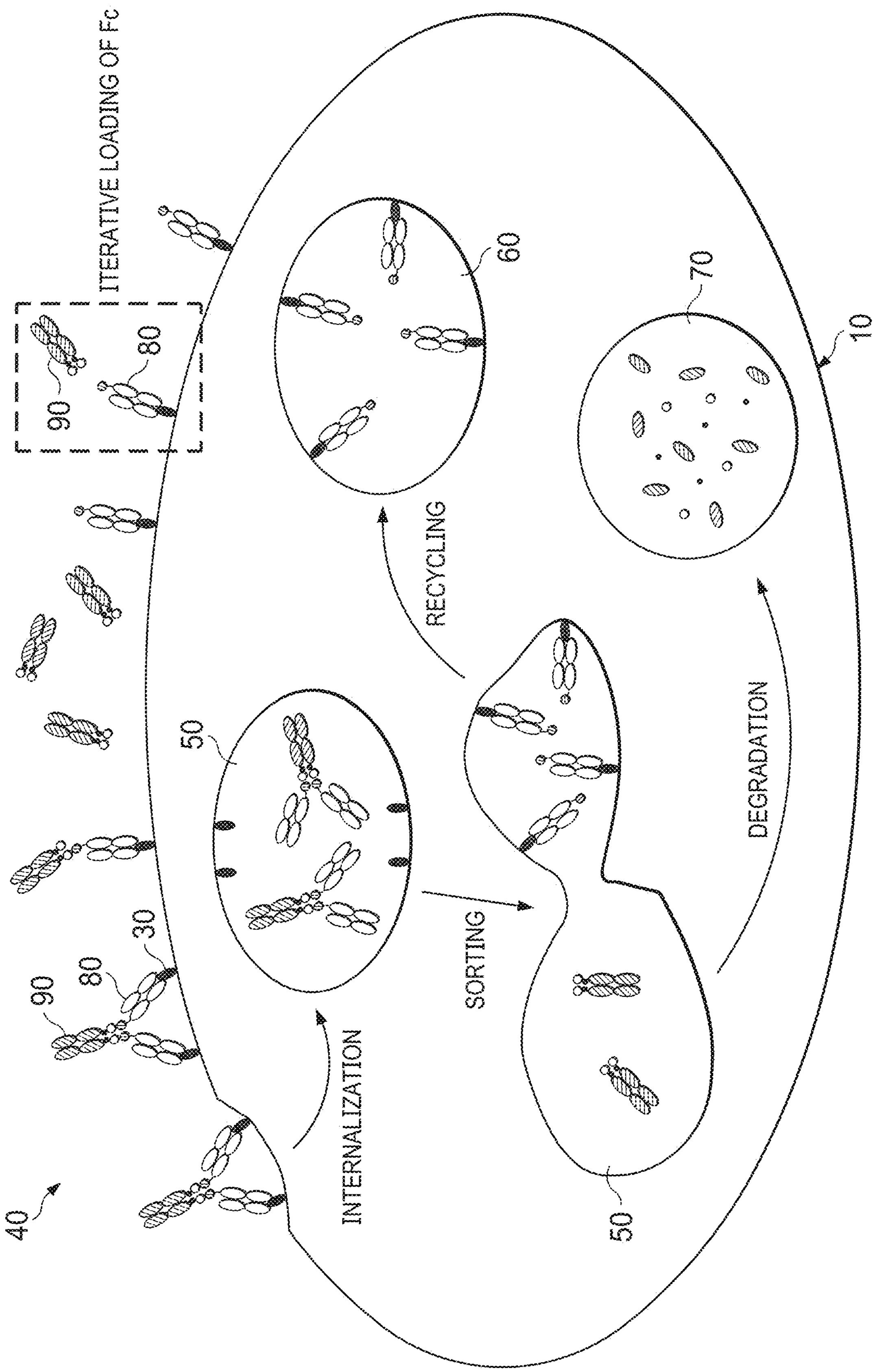
FIG. 2 is an exemplary schematic diagram of selected cellular events that lead to the dissociation of the cargo component and the targeting component of the endolysosomal targeting conjugates in endosomes followed by delivery of the cargo component into late endosomes and lysosomes.

FIGS. 1 and 2 show schematic diagrams of exemplary mechanisms of improved delivery of cargo molecules by the endolysosomal targeting conjugates of the disclosure. Upon binding of the targeting component to the cell surface molecule, the endolysosomal targeting conjugate is internalized into cells (FIGS. 1 and 2).

As shown in exemplary schematic form in FIG. 1, the endolysosomal targeting conjugate may dissociate in early or late endosomes from the receptor or cell surface molecule due to lower (acidic) pH, lower $Ca^{2+}$ concentrations, lower $Cl^-$ or $Na^+$ concentrations, higher $K^+$ concentrations or other environmental conditions that distinguish endosomes from the extracellular space (for example, as described in Scott, C. C., Gruenberg, J. (2010) Ion flux and the function of endosomes and lysosomes: pH is just the start. Bioessays 33, 103-110). Accordingly, in some examples of the endolysosomal targeting conjugates herein described, the affinity of the targeting component for the cell surface molecule is higher in the extracellular space than in the endolysosomal compartment. Thus, the targeting component and the cell surface molecule may bind with a lower dissociation constant in the extracellular space. The endolysosomal targeting conjugate is delivered to late endosomes or lysosomes, resulting in release of its drug or label.

In another example, as shown in exemplary schematic form in FIG. 2, the targeting and cargo components of the endolysosomal targeting conjugate may be associated with each other by non-covalent interactions that are stable at near neutral pH or extracellular $Ca^{2+}$ concentrations, but not at endosomal (acidic) pH or endosomal $Ca^{2+}$ concentrations or other environmental conditions that distinguish endosomes from the extracellular space. The cargo component is released in early or late endosomes and enters lysosomes, whereas the targeting component can be recycled and reloaded with cargo component. Accordingly, in some examples of the endolysosomal targeting conjugates herein described, the affinity of the targeting component for cargo component is higher in the extracellular space than in the endolysosomal compartment. Thus, the targeting component may bind the cargo component with a lower dissociation constant in the extracellular space.

The targeting component and the cargo component may be linked by a covalent bond or may be non-covalently associated with each other.

Examples of endolysosomal targeting conjugates described herein include targeting components that are configured to bind to cell surface molecules such as HER2 or prostate-specific membrane antigen (PSMA). In particular, the exemplary endolysosomal targeting conjugates may bind to cell surface molecules such as HER2 or PSMA with affinities of less than 500 nM at near-neutral pH.

Examples of endolysosomal targeting conjugates described herein include targeting components that are configured to bind to cell surface molecules such as PS. In particular, the exemplary PDCs may bind to cell surface molecules such as PS with affinities of less than 500 nM at near-neutral pH.

HER2 and PSMA are cell surface receptors that are overexpressed on tumors and are therefore well-characterized tumor targets. This endolysosomal targeting conjugates of the present disclosure are not limited to targeting these receptors or cell surface molecules such as prostate stem cell associated antigen, EpCAM, c-MET, carcinoembryonic antigen (CEA), CD19, CD20, CD20, CD33, CD38, epidermal growth factor receptor (EGFR), glypican-2, CD56, insulin-like growth factor receptor 1, tumor endothelial marker-8 (TEM-8), CD46 and many other targets are identifiable by persons with skill in the art upon reading the present disclosure.

PS resides in the inner leaflet of the plasma membrane of normal cells, but in response to oxidative stress and inflammatory factors in the tumor microenvironment, becomes exposed on the outer leaflet of the membrane of cancer endothelial cells. Based on studies in rodent models, exposure of PS is considered to be a 'universal' marker for tumor vasculature. Typically, less than half of tumor blood vessels are PS-positive and exposure can be increased by radiation and chemotherapy. In addition to tumor endothelium, PS has also been reported to be exposed on many non-apoptotic cancer cells, including melanoma, breast, prostate and renal carcinoma.

Accordingly, the targeting component can include any type of molecule that is configured to specifically bind to a cell surface receptor or other cell surface molecule. Such molecules can include proteins, protein fragments, polynucleotides such as ribonucleic acids or deoxyribonucleic acids, polypeptides, polysaccharides, lipids, amino acids, peptides, sugars and/or other small or large molecules and/or polymers identifiable by skilled persons upon reading the present disclosure.

As shown in FIG. 1, an endolysosomal targeting conjugate 20 including a targeting component 20T and a cargo component 20C. The cargo component has attached drug or label that is indicated by filled black circles. may reversibly bind to cell surface receptor or other molecule 30 on the surface of a cell 10. This binding typically occurs at near-neutral pH, such as at a pH greater than about 6.8 and less than about 7.5, because that is the typical pH of extracellular space 40. Binding to the cell surface receptor or cell surface molecule can also occur at typical extracellular $Ca^{2+}$ concentrations (approximately 2 mM). Cell surface receptor or molecule 30 with attached endolysosomal targeting conjugate 20 are internalized into the cell 10 through receptor-mediated uptake into endosome 50. The complex of endolysosomal targeting conjugate 20 and cell surface receptor or other molecule 30 dissociate from the receptor or other molecule 30 in the early or late endosome due to the acidic pH (from about pH 5.0 to about pH 6.5) or low $Ca^{2+}$ concentration (approximately 2 μM) in these compartments. Accordingly, receptor or cell surface molecule 30 may recycle back in a recycling endosome 60 to the cell surface and be reloaded with endolysosomal targeting conjugate 20, whereas the endosomally dissociated endolysosomal targeting conjugate 20 enters the lysosomes and is degraded into fragments (70). The endolysosomal targeting conjugate is configured to bind to the cell surface receptor or other molecule under the conditions in the extracellular space, with dissociation in the endosomes or late endosomes of at least 10% of the endolysosomal targeting conjugate that is internalized into the cell.

As shown in FIG. 2, an endolysosomal targeting conjugate including a targeting component 80 and cargo component 90 (with attached drug or other label) indicated by filled circles) may reversibly bind to cell surface receptor or other molecule 30 on the surface of a cell 10. The association of the targeting component 80 and cargo component 90 typically occurs at near-neutral pH, such as at a pH greater than 6.8 and less than 7.5, because that is the typical pH of extracellular space 40. Association of the targeting component 80 and cargo component 90 can occur at extracellular $Ca^{2+}$ concentrations (approximately 2 mM). Cell surface receptor or molecule 80 with attached endolysosomal targeting conjugate are internalized into the cell 10 through receptor-mediated uptake into endosome 50. The targeting component 80 and cargo component 90 dissociate in the early or late endosome due to the acidic pH (typically less than pH 6.8) or low $Ca^{2+}$ concentrations (approximately 2 μM) in these compartments. Accordingly, the targeting component 80 bound to the receptor or cell surface molecule may recycle back to the cell surface in a recycling endosome 60 and be reloaded with cargo component 90, whereas the endosomally dissociated cargo component 90 enters the lysosomes and is degraded into fragments (70). The endolysosomal targeting conjugate is configured to bind to the cell surface receptor or other molecule under the conditions in the extracellular space, with dissociation in the endosomes or late endosomes of at least 10% of the cargo component that is internalized into the cell.

Endolysosomal targeting conjugates according to this disclosure are configured to specifically bind a cell surface receptor/molecule at near-neutral pH or extracellular $Ca^{2+}$ concentrations via a targeting component. The term "specifically bind" as used herein refers to a detectable selective inter-molecular interaction between the targeting component and the cell surface receptor/molecule. For example, to specifically bind, the targeting component needs to show a detectable interaction with the cell surface receptor or cell surface molecule that is being targeted, whilst not showing a detectable interaction, or much lower affinity interaction, with other cell surface receptors or cell surface molecules. Techniques for detecting specific binding are known within the art, such as ELISA and other methods identifiable by skilled persons.

Accordingly, endolysosomal targeting conjugates allow the linked cargo component to be internalized into cells that express the targeted cell surface receptor or other targeted cell surface molecule and thereafter intracellularly degraded.

Endolysosomal targeting conjugates can include at least a first targeting component and a second targeting component, wherein the antibody Fab fragment, single chain Fv (scFv), nanobody, protein or protein fragment of the first targeting component is different to the antibody Fab fragment, single chain Fv (scFv), nanobody, protein or protein fragment of the second targeting component. Accordingly, endolysosomal targeting conjugates comprising at least a first targeting component and a second targeting component can bind to two different cell surface receptors or cell surface molecules.

In addition, endolysosomal targeting conjugates may contain human or humanized proteins or protein fragments to avoid or decrease the possibility of an immune reaction to the endolysosomal targeting conjugates when administered to a human. The targeting component and cargo component are preferably a human protein or protein fragment for administration of the endolysosomal targeting conjugate to a human. The targeting component and cargo component are preferably a human protein or protein fragment, such as a human antibody, antibody fragment or human albumin or albumin fragment, or a humanized antibody or humanized antibody fragment for administration of the endolysosomal targeting conjugate to a human. If an endolysosomal targeting conjugate is developed for use in a non-human animal, then proteins or protein fragments derived from or engineered to be immunologically compatible with that animal may be used instead.

Figure 3A:
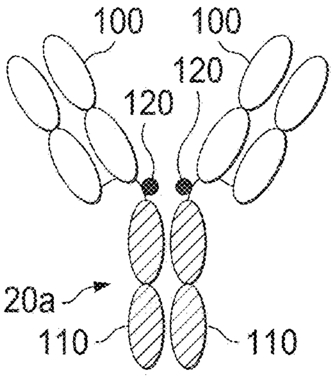
FIG. 3A is a schematic diagram of an exemplary endolysosomal targeting conjugate including an antibody that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3A is a schematic representation of an exemplary endolysosomal targeting conjugate (20*a*) including Fab fragments (100) of an antibody that is configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The Fc fragment (110) is homodimeric. As understood by persons skilled in the art, the Fc fragment of an IgG is all of the lower base of the antibody's Y-shape, which includes a sulfhydryl-bridged hinge region and CH2 and CH3 domains. In this example, the cargo molecule (120) is attached to the hinge region via chemical conjugation to cysteine residues.

Figure 3B:
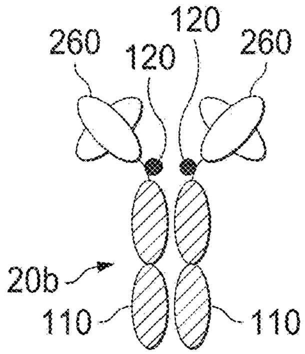
FIG. 3B is a schematic diagram of an exemplary endolysosomal targeting conjugate including an antibody scFv-Fc fusion protein that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3B is a schematic representation of an exemplary endolysosomal targeting conjugate (20*b*) including scFv fragments (260) of an antibody that is configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The Fc fragment (110) is homodimeric. In this example, the cargo molecule (120) is attached to the hinge region via chemical conjugation to cysteine residues.

Figure 3C:
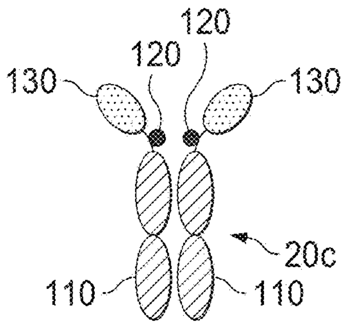
FIG. 3C is a schematic diagram of an exemplary endolysosomal targeting conjugate including an antibody variable domain/antibody variable domain fragment-Fc fusion protein that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3C is a schematic representation of an exemplary endolysosomal targeting conjugate (20*c*) including antibody variable domains or fragments (130) that are configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The Fc fragment (110) is homodimeric. In this example, the cargo molecule (120) is attached to the hinge region via chemical conjugation to cysteine residues.

Antibody variable region 130 may include portions of a non-variable region of an antibody that is configured to bind to a cell surface receptor or cell surface molecule. For example, antibody variable region 130 may be a single-domain antibody (sdAb) or camelid-derived VHH domain (also commonly referred to as a nanobody). Such variable regions have the overall fold of an immunoglobulin domain, comprising two anti-parallel β-sheets, and can also include domains from other members of the immunoglobulin superfamily such as T cell receptor variable domains, constant region domains of antibodies or domains of the coreceptor, CD4, among others identifiable by persons skilled-in-the-art. Antibody variable regions can also include heterodimers of heavy chain variable (VH) domains linked by peptide linkers to light chain variable (VL) domains to form scFv fragments (260). The linker sequences that are used to link VH and VL domains are well known to those with skill in the art and include the GGGGSGGGGSGGGGS [$(G_4S)_3$] sequence that connect the C-terminus of the VH domain to the N-terminus of the VL domain. The C-terminus of the VL domain can be connected to the N-terminus of the VH domain with similar linker sequences. ScFvs that bind to a cell surface receptor or other cell surface molecule with pH-dependence, $Ca^{2+}$-dependence etc. can be isolated from libraries of scFvs using phage display, yeast display or other antibody display approaches. The targeting component of an endolysosomal targeting conjugate may include Fab fragments of an antibody that can be isolated from libraries of Fab fragments using phage display or yeast display among other techniques known to skilled persons. For nanobodies, scFvs and Fab fragments, the desired binding properties (pH-dependence, $Ca^{2+}$-dependence) for the targeted cell surface receptor or cell surface molecule can be further improved by randomly mutating residues in the complementarity determining regions (CDRs), or by using error-prone polymerase chain reaction, to generate libraries of mutated nanobodies or variable domains, followed by selection. Exemplary CDR residues that would be targeted are those in CDR3 of the light chain variable domain (residues 89-97; Kabat numbering) and CDR3 of the heavy chain variable domain (residues 95-102; Kabat numbering). These libraries can be displayed on phage or yeast and variants with the required binding behavior selected using approaches known to those with skill in the art.

Figure 3D:
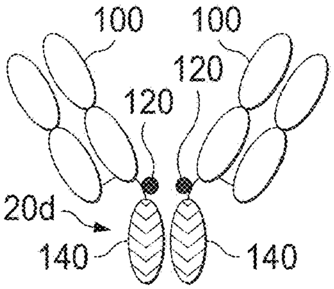
FIG. 3D is a schematic diagram of an exemplary endolysosomal targeting conjugate including Fab fragments fused to the N-terminal locations of immunoglobulin hinge and CH3 domains that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3D is a schematic representation of an exemplary endolysosomal targeting conjugate (20*d*) including Fab fragments (100) of an antibody that is configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The Fab fragments are linked to immunoglobulin CH3 domains (140) to form a homodimer. In this example, the cargo molecule (120) is attached to the hinge region via chemical conjugation to cysteine residues.

Figure 3E:
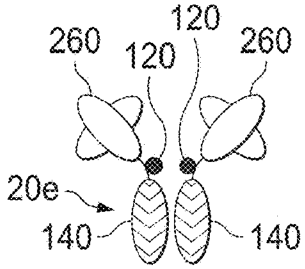
FIG. 3E is a schematic diagram of an exemplary endolysosomal targeting conjugate including scFv fragments fused to the N-terminal locations of immunoglobulin hinge and CH3 domains that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3E is a schematic representation of an exemplary endolysosomal targeting conjugate (20*e*) including scFv fragments (260) of an antibody that is configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The scFv fragments are linked to immunoglobulin CH3 domains (140) to form a homodimer. In this example, the cargo molecule (120) is attached to the hinge region via chemical conjugation to cysteine residues.

Figure 3F:
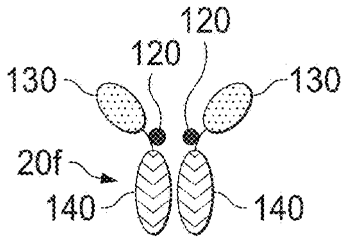
FIG. 3F is a schematic diagram of an exemplary endolysosomal targeting conjugate including antibody variable domain/antibody variable domain fragments fused to the N-terminal locations of immunoglobulin hinge and CH3 domains that bind to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3F is a schematic representation of an exemplary endolysosomal targeting conjugate (20*f*) including antibody variable domains or fragments (130) that are configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The protein fragments or domains are linked to immunoglobulin CH3 domains (140) to form a homodimer. In this example, the cargo molecule (120) is attached to the hinge region via chemical conjugation to cysteine residues.

Figure 3G:
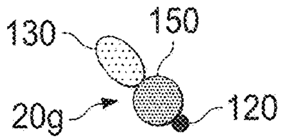
FIG. 3G is a schematic diagram of an exemplary endolysosomal targeting conjugate including an antibody variable domain/antibody variable domain fragments fused to albumin that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3G is a schematic representation of an exemplary endolysosomal targeting conjugate (20*g*) including an antibody variable domain or fragment (130) that is configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The antibody variable domain or fragment is linked to albumin or an albumin fragment (150), which may be mutated or modified so that it binds with increased affinity to a neonatal Fc receptor (FcRn). For example, mutations can be inserted into the FcRn binding domain (DIII) of (human serum) albumin using error prone PCR followed by display of libraries of mutated albumin variants on yeast or phage, and selection of higher affinity variants. Alternatively, higher affinity variants can be generated by mutating residues at or near the albumin:FcRn interface and either selecting or screening for albumin variants with increased binding affinity. Although FIG. 3G illustrates antibody variable domain or fragment (130) at a terminal location of albumin or albumin fragment 150, it may instead be located at a non-terminal location. The antibody variable domain or fragment may be fused to albumin or albumin fragment 150 in any suitable manner, including attachment via a chemical reaction or attachment through a peptide linker. In this example, the cargo molecule (120) is attached via chemical conjugation to an exposed amino acid such as cysteine or lysine.

Figure 3H:
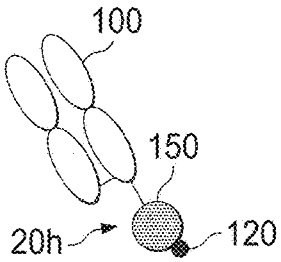
FIG. 3H is a schematic diagram of an exemplary endolysosomal targeting conjugate including an antibody Fab fragment fused to albumin that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3I:
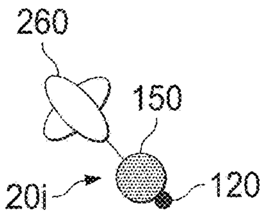
FIG. 3I is a schematic diagram of an exemplary endolysosomal targeting conjugate including an antibody scFv fragment fused to albumin that binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

In the exemplary schematic representations shown in FIG. 3H and FIG. 3I, the antibody variable domain or fragment 130 as shown in FIG. 3G is replaced by a Fab fragment 100 (FIG. 3H) or scFv fragment 260 (FIG. 3I) that are configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). In this example, the cargo molecule (120) is attached via chemical conjugation to an exposed amino acid such as cysteine or lysine.

Figure 3J:
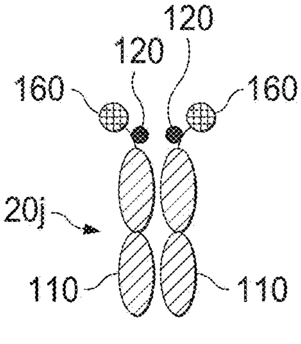
FIG. 3J is a schematic diagram of an exemplary endolysosomal targeting conjugate including a protein, protein domain or fragment fused to a N-terminal location of an Fc fragment. The protein, protein domain or protein fragment binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3J is a schematic representation of an exemplary endolysosomal targeting conjugate (20*j*) including protein fragments or domains (160) that are configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The protein fragments or domains are linked to the N-termini of an Fc fragment (110) to form homodimers. In this example, the cargo molecule (120) is attached to the hinge region via chemical conjugation to cysteine residues.

Figure 3K:
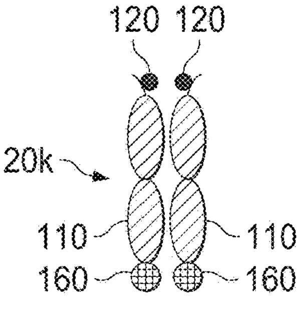
FIG. 3K is a schematic diagram of an exemplary endolysosomal targeting conjugate including a protein, protein domain or fragment fused to a C-terminal location of an Fc fragment. The protein, protein domain or protein fragment binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3L:
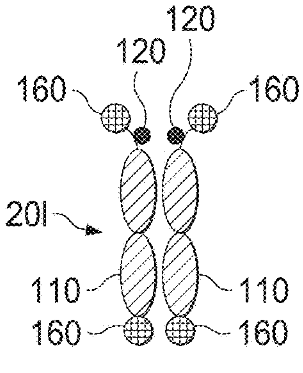
FIG. 3L is a schematic diagram of an exemplary endolysosomal targeting conjugate including a protein, protein domain or fragment fused to both the N-terminal and C-terminal locations of an Fc fragment. The protein, protein domain or protein fragment binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

In the exemplary schematic representations shown in FIG. 3K and FIG. 3L, the protein fragments or domains (160) are linked to the C-termini of an Fc fragment (110) to form homodimers (FIG. 3K) or to both the N- and C-termini of an Fc fragment (110) to form homodimers (FIG. 3L). In these examples, the cargo molecules (120) are attached to the hinge regions via chemical conjugation to cysteine residues.

Figure 3M:
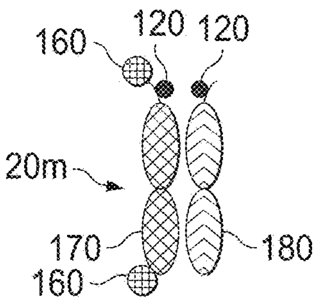
FIG. 3M is a schematic diagram of an exemplary endolysosomal targeting conjugate including a protein, protein domain or protein fragment fused to both the N-terminal and C-terminal locations of an Fc fragment to form a heterodimer with two protein domains or fragments molecule per Fc fragment. The protein, protein domain or protein fragment binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3N:
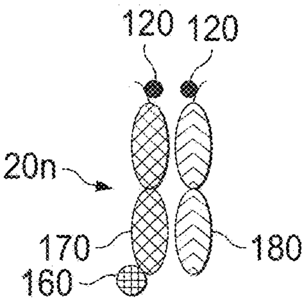
FIG. 3N is a schematic diagram of an exemplary endolysosomal targeting conjugate including a protein, protein domain or protein fragment fused to a C-terminal location of an Fc fragment to form a heterodimer with one protein, protein domain or fragment molecule per Fc fragment. The protein, protein domain or protein fragment binds to a cell surface protein or cell surface receptor with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3M is a schematic representation of an exemplary endolysosomal targeting conjugate (20*m*) including protein fragments or domains (160) that are configured to bind to a cell surface protein or cell surface molecule with higher affinity at near neutral pH (or at extracellular $Ca^{2+}$ concentrations) than at acidic, endosomal pH (or at endosomal $Ca^{2+}$ concentrations). The protein fragments or domains are linked to the N- and C-termini of an Fc fragment (170) that is configured to heterodimerize with another Fc fragment 180 lacking a protein fragment or domain, to produce a heterodimeric endolysosomal targeting conjugate 20*m* as shown in FIG. 3M. FIG. 3N shows a schematic representation of an exemplary PDC or LC 20*n* wherein the protein fragment or domain (160) is fused to the C-terminus of the Fc fragment (170). In the examples shown in FIGS. 3M and 3N, the cargo molecules (120) are attached to the hinge regions via chemical conjugation to cysteine residues. In order to avoid Fc fragment homodimers in which both Fc fragments have a fused protein fragment or domain (160), or no fused protein or protein domain, the endolysosomal targeting conjugate can be designed with knobs-into-holes mutations (for example, as described in Moore, G. L., Bautista, C., Pong, E., Nguyen, D. H., Jacinto, J., Eivazi, A., Muchhal, U. S., Karki, S., Chu, S. Y., Lazar, G. A. (2011) A novel bispecific antibody format enables simultaneous bivalent and monovalent co-engagement of distinct target antigens. MAbs 3, 546-557) and/or electrostatic steering mutations (for example, as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010) Enhancing antibody Fc heterodimer formation through electrostatic steering effects: applications to bispecific molecules and monovalent IgG. J. Biol. Chem. 285, 19637-19646) to promote heterodimer formation. Other approaches can also be used to generate heterodimers, such as the insertion of a $(G_4S)_{13}$ linker peptide between the C-terminus of the antigen-Fc fusion and N-terminus of a second Fc fragment (for example, as described in Zhou, L., Wang, H-Y., Tong, S., Okamoto, C. T., Shen, W-C., Zaro, J. L. (2016) Single chain Fc-dimer-human growth hormone fusion protein for improved drug delivery. Biomaterials, 117, 24-31). DNA and protein sequences of examples of endolysosomal targeting conjugate that include knobs-into-holes mutations, electrostatic steering mutations and/or other mutations are described in Example 14.

Examples of knobs-into-holes mutations include Y349T/T394F: S364H/F405A and Y349T/F405F: S364H/T394F (for example, as described in Moore, G. L., Bautista, C., Pong, E., Nguyen, D. H., Jacinto, J., Eivazi, A., Muchhal, U. S., Karki, S., Chu, S. Y., Lazar, G. A. (2011) A novel bispecific antibody format enables simultaneous bivalent and monovalent co-engagement of distinct target antigens. MAbs 3, 546-557) and T366W:T366S:L368A/Y407V (for example, as described in Atwell, S., Ridgway, J. B. B., Wells, J. A., Carter, P. (1997) Stable heterodimers from remodeling the domain interface of a homodimer using a phage display library. J. Mol. Biol., 270, 26-35) among others identifiable by persons skilled in the art. The residue numbering of these exemplary knobs-into-holes mutations refers to the EU antibody numbering system, as would be understood by persons skilled in the art.

Examples of electrostatic steering mutations include E356K/D399K:K392D/K409D and K409D/K370D: D357K/D399K (for example as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010) Enhancing antibody Fc heterodimer formation through electrostatic steering effects: applications to bispecific molecules and monovalent IgG. J. Biol. Chem. 285, 19637-19646) among others identifiable by persons skilled in the art. The residue numbering of these exemplary electrostatic steering mutations refers to the EU antibody numbering system, as would be understood by persons skilled in the art.

Figure 3O:
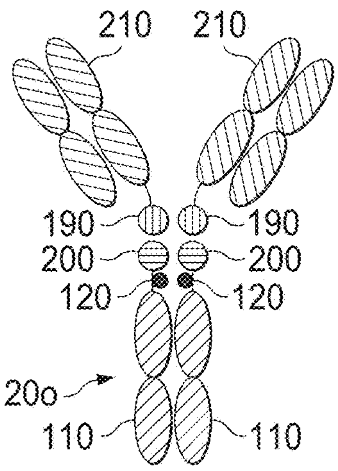
FIG. 3O is a schematic diagram of an exemplary endolysosomal targeting conjugate including a Fab-protein (domain) and protein (domain)-Fc fusion that are designed to associate with each other with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3P:
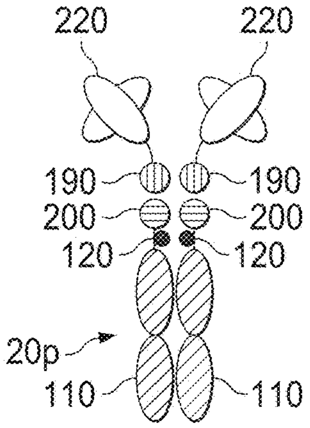
FIG. 3P is a schematic diagram of an exemplary endolysosomal targeting conjugate including an scFv fragment-protein (domain) and protein (domain)-Fc fusion that are designed to associate with each other with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3Q:
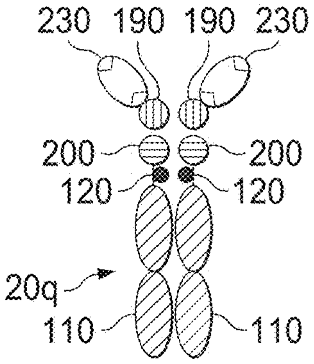
FIG. 3Q is a schematic diagram of an exemplary endolysosomal targeting conjugate including an antibody variable domain-protein (domain) and protein (domain)-Fc fusion that are designed to associate with each other with higher affinity (lower dissociation constant) at near neutral pH (or at extracellular $Ca^{2+}$ concentrations) than at acidic, endosomal pH (or at lower, endosomal $Ca^{2+}$ concentrations)
Figure 3R:
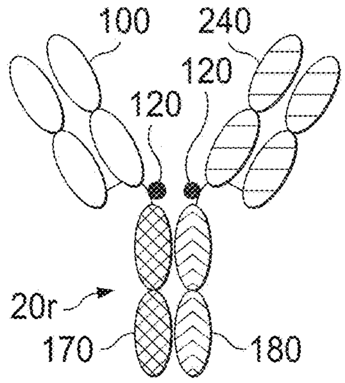
FIG. 3R is a schematic diagram of an exemplary endolysosomal targeting conjugate including an antibody that comprises two different Fab fragments that bind to two or more cell surface receptors or cell surface molecules with higher affinity (lower dissociation constant) at near neutral pH (or at extracellular $Ca^{2+}$ concentrations) than at acidic, endosomal pH (or at lower, endosomal $Ca^{2+}$ concentrations)

FIG. 3O is a schematic representation of an exemplary endolysosomal targeting conjugate (20*o*) including Fab fragments (210) of an antibody that are fused to domain 2 of calbindin (CalD2; 190). Fc fragments (110) are fused to domain 1 of calbindin (CalD1; 200). CalD1 (200) and CalD2 (190) associate with each other with higher affinity at extracellular $Ca^{2+}$ concentrations than at lower, endosomal $Ca^{2+}$ concentrations. Other examples may include protein or protein fragments (190, 200) that are fused to the Fab fragment (210) or Fc (110) and associate with each other in a $Ca^{2+}$- or pH-dependent way. Other examples of proteins that interact in a $Ca^{2+}$-dependent way are: calmodulin and the calmodulin binding peptide M13 (for example, as described in Miyawaki, A., Llopis, J., Heim, R., McCaffery, J. M., Adams, J. A., Ikura, M., Tsien, R. Y. (1997) Fluorescent indicators for $Ca^{2+}$ based on green fluorescent proteins and calmodulin. Nature, 388, 882-887.); S100C and the N-terminal 13 residues of annexin I (for example, as described in Seeman, J., Weber, K., Gerke, V. (1996) Structural requirements for annexin I-S100C complex-formation. Biochem. J., 319, 123-129; Malliard, W. S., Haigler, H. T., Schlaepfer, D. D. (1995) Calcium-dependent binding of S100C to the N-terminal domain of Annexin I. J. Biol. Chem., 2, 719-725); osteonectin and collagen IV (for example, as described in Maurer, P., Hohenadl, C., Hohenester, E., Gohring, W., Timpl, R., Engel, J. (1995) The C-terminal protein of BM-40 (SPARC/Osteonectin) is an autonomously folding and crystallizable domain that binds calcium and collagen IV. J. Mol. Biol., 253, 347-357). In other examples of endolysosomal targeting conjugates, the Fab fragment as shown in FIG. 3O is replaced by a scFv fragment (220) as shown in FIG. 3P, or an antibody variable domain, fragment or nanobody (230) as shown in FIG. 3Q. In the examples shown in FIGS. 3O, 3P and 3Q, the cargo molecules (120) are attached to the hinge regions via chemical conjugation to cysteine residues In the examples shown in FIG. 3A-FIG. 3S, the endolysosomal targeting conjugate has a targeting component that includes Fab fragments, scFvs or nanobodies, and the cargo component includes an Fc fragment, a sub-fragment of an Fc (e.g. $CH_2$ domains) or albumin linked to a cargo molecule such as a cytotoxic drug or imaging label such as radiolabel or fluorescent label. The cargo molecules shown in FIGS. 3A, 3B, 3C, 3D, 3E, 3F, 3J, 3K, 3L, 3M, 3N, 3O, 3P, 3Q, 3R and 3S are attached to the hinge regions via one or more cysteine residues. In other examples, one or more cargo molecules can be attached to the cargo component through different chemistries known to those with skill in the art, such as: amine-to-amine (NHS esters), sulfhydryl-to-sulfhydryl (maleimide), amine-to-sulfhydryl (NHS ester/maleimide), sulfhydryl-to-carbohydrate (maleimide/hydrazide), or attachment to via an unnatural amino acid with the desired chemical reactivity, among other approaches identifiable by skilled persons. The unnatural amino acid may be inserted during recombinant production of the targeting component. In other examples, such as those shown in FIG. 3R and FIG. 3S, the targeting components may bind to two or more different targets. Each of the targeting components may be fused to an Fc fragment with knobs-into-holes mutations and/or electrostatic steering mutations to drive heterodimer formation.

Figure 3S:
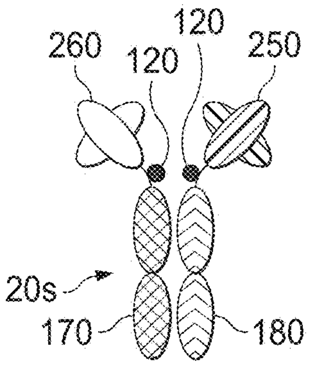
FIG. 3S is a schematic diagram of an exemplary endolysosomal targeting conjugate including an antibody that comprises two different scFv fragments that bind to two or more cell surface receptors or cell surface molecules with higher affinity (lower dissociation constant) at near neutral pH (or at extracellular $Ca^{2+}$ concentrations) than at acidic, endosomal pH (or at lower, endosomal $Ca^{2+}$ concentrations)

In the examples shown in FIG. 3A-FIG. 3S, the endolysosomal targeting conjugate has a targeting component that includes Fab fragments, scFvs or nanobodies, and the cargo component includes an Fc fragment, a sub-fragment of an Fc (e.g. CH2 domains) or albumin linked to a cargo molecule such as a cytotoxic drug or imaging label such as radiolabel or fluorescent label. The cargo molecules shown in FIGS. 3A, 3B, 3C, 3D, 3E, 3F, 3J, 3K, 3L, 3M, 3N, 3O, 3P, 3Q, 3R and 3S are attached to the hinge regions via one or more cysteine residues. In other examples, one or more cargo molecules can be attached to the cargo component through different chemistries known to those with skill in the art, such as: amine-to-amine (NHS esters), sulfhydryl-to-sulfhydryl (maleimide), amine-to-sulfhydryl (NHS ester/maleimide), sulfhydryl-to-carbohydrate (maleimide/hydrazide), or attachment to via an unnatural amino acid with the desired chemical reactivity, among other approaches identifiable by skilled persons. The unnatural amino acid may be inserted during recombinant production of the targeting component. In other examples, such as those shown in FIG. 3R and FIG. 3S, the targeting components may bind to two or more different targets. Each of the targeting components may be fused to an Fc fragment with knobs-into-holes mutations and/or electrostatic steering mutations to drive heterodimer formation.

In the examples shown in FIGS. 3J, 3K, 3L, 3M and 3N, the endolysosomal targeting conjugate may include, for example, PS-targeting agents produced by fusing PS-binding domains to the Fc fragment of human IgG1 or other Fc fragment. For example, the targeting component may be conjugated to a cargo component that includes a cytotoxic drug to produce endolysosomal targeting conjugate PDCs or the targeting component may be conjugated to a cargo component that includes an imaging label such as a radiolabel, fluorescent label or near infrared label, to produce endolysosomal targeting conjugate LCs. Accordingly, endolysosomal targeting conjugates described herein may include proteins or protein fragments or domains that are configured to dissociate from a target cell surface molecule upon exposure to the significant decrease in $Ca^{2+}$ levels in endosomes, for example by using PS-binding domains that interact with PS in a $Ca^{2+}$-dependent manner. For example, an endolysosomal targeting conjugate PDC or LC can include a targeting component such as Fc-Syt1. An endolysosomal targeting conjugate PDC that includes Fc-Syt1 may be bivalent, for example, as shown in FIGS. 3J, 3K, or tetravalent as shown in FIG. 3L.

The endolysosomal targeting conjugate may include one targeting domain fused to an Fc fragment that forms a heterodimer with an Fc fragment that does not have a fused protein. To promote heterodimer formation, the Fc fragments may be engineered with knobs-into-holes mutations and/or electrostatic steering mutations as shown in the examples in FIGS. 3M and 3N.

In some examples described herein, the targeting component and cargo component are not covalently linked, but instead are configured to associate with each other through a linkage to engineered domains that associate with each other non-covalently. In particular, the non-covalent association may have stronger affinity when in contact with the chemical environment in extracellular space that in the endolysosomal compartment. For example, the engineered domains may include those such as calbindin domain 1 (CalD1) and calbindin domain 2 (CalD2). CalD1 and CalD2, which bind to each other at extracellular $Ca^{2+}$ concentrations, but not at endosomal $Ca^{2+}$ concentrations (see Example 6). Other examples of proteins that interact in a $Ca^{2+}$-dependent way are: calmodulin and the calmodulin binding peptide M13 (for example, as described in Miyawaki, A., Llopis, J., Heim, R., McCaffery, J. M., Adams, J. A., Ikura, M., Tsien, R. Y. (1997) Fluorescent indicators for $Ca^{2+}$ based on green fluorescent proteins and calmodulin. Nature, 388, 882-887.); S100C and the N-terminal 13 residues of annexin I (for example, as described in Seeman, J., Weber, K., Gerke, V. (1996) Structural requirements for annexin I-S100C complex-formation. Biochem. J., 319, 123-129; Malliard, W. S., Haigler, H. T., Schlaepfer, D. D. (1995) Calcium-dependent binding of S100C to the N-terminal domain of Annexin I. J. Biol. Chem., 2, 719-725); osteonectin and collagen IV (for example, as described in Maurer, P., Hohenadl, C., Hohenester, E., Gohring, W., Timpl, R., Engel, J. (1995) The C-terminal protein of BM-40 (SPARC/Osteonectin) is an autonomously folding and crystallizable domain that binds calcium and collagen IV. J. Mol. Biol., 253, 347-357). Examples of several configurations containing such domains are shown in FIGS. 3O, 3P and 3Q, although other configurations are possible.

Endolysosomal targeting conjugates may include different numbers of targeting components and cargo components. The configurations shown in FIGS. 3A, 3B, 3C, 3D, 3E, 3F, 3G, 3H, 3I, 3J, 3K, 3L, 3M, 3N, 3O, 3P, 3Q, 3R and 3S are examples and are not limiting, since multiple other configurations are identifiable by those with skill in the art upon reading the present disclosure.

In some examples herein described, endolysosomal targeting conjugates may include a toxin, such as monomethyl auristatin E (MMAE), conjugated via a valine-citrulline-PAB linker. The endolysosomal targeting conjugate may include, for example, an antibody that binds a cell-surface molecule such as HER2 with higher affinity at near neutral pH than at acidic, endosomal pH (HER2-ADCs; see Examples 2-5). The engineered antibodies and proteins described herein can be expressed by mammalian cells at high yields and conjugated with the drug at high efficiency. Upon binding to HER2-positive cells, the exemplary HER2-ADCs are internalized into early endosomes, where the pH drops from near neutral to around pH 5.5-6.5. This decrease in pH causes HER2-ADCs to dissociate from the early/sorting endosomal membrane, leading to effective lysosomal delivery of the MMAE drug. In particular, for example (e.g., see FIG. 4B) the pertuzumab variants SG and YS have dissociation constants greater than 1.5 μM at pH 5.8, whereas the WT pertuzumab has a much lower dissociation constant at the same pH. Accordingly, the HER2-ADCs can effectively eradicate HER2-positive cells, and treatment with HER2-ADCs can suppress the tumor growth effectively without any sign of adverse effects in mouse models of HER2-expressing breast cancer.

In another example described herein, the endolysosomal targeting conjugate has a targeting component including a PS-binding domain such as the C2A domain of Synaptotagmin 1 (Syt1) fused to a cargo component such as the Fc region of an antibody, conjugated to MMAE via a maleimidocaproyl valine-citrulline-PAB linker (PS-PDCs; see Examples 7-13). The PS-targeting proteins can also be expressed by mammalian cells at high yields and conjugated with the drug at high efficiency. The exemplary PS-PDCs are configured to bind PS specifically in a calcium-dependent manner. Upon binding to PS-positive cells, PS-PDCs are internalized into early endosomes efficiently, where the calcium level drops from 2 mM to less than 2 μM. This drop of calcium concentration causes PS-PDCs to dissociate from the early/sorting endosomal membrane, leading to effective lysosomal delivery of the MMAE drug. The PS-PDCs can effectively eradicate PS-positive cells which include but are not limited to tumor endothelial cells, breast and prostate cancer cells. Treatment with PS-PDCs can suppress the tumor growth effectively without any sign of adverse effects in mouse models of human triple negative breast cancer as well as prostate cancer, while the unconjugated proteins have no efficacy. Since PS is a universal marker for cancer endothelial cells as well as stressed tumor cells, the PDCs can be applied to treatment of most solid tumors.

The targeting components of the endolysosomal targeting conjugates described herein that bind to a target cell surface molecule in a pH-dependent or $Ca^{2+}$-dependent way can be isolated from libraries of immunoglobulin variable domains, scFvs (VH:VL heterodimers in which VH and VL domains are connected to each other by linker peptides such as GGGGSGGGGSGGGGS) or Fab fragments using phage display, yeast display or other methods identifiable by those with skill in the art. These libraries can either be derived from naturally occurring antibody variable genes, can be generated using approaches that result in 'semi-synthetic' libraries wherein complementarity determining regions (CDRs) are produced using randomized oligonucleotide sequences, or can be derived from VH and VL domain genes of existing antibodies by insertion of random mutations into the CDRs. Random mutations in the CDRs can be inserted using error-prone PCR or with biases towards histidine residues (for pH-dependence) followed by selection using phage display or yeast display. Exemplary CDR residues that would be targeted are those in CDR3 of the light chain variable domain (residues 89-97; Kabat numbering) and CDR3 of the heavy chain variable domain (residues 95-102; Kabat numbering). Selection of scFvs or Fab fragments with desired pH-dependence or $Ca^{2+}$-dependence can be carried out using methods known to those with skill in the art. In addition, to isolate pH-dependent binders, CDR residues can be systematically mutated to histidine, the resulting Fab or scFv fragments expressed and analyzed for binding to target using, for example, surface plasmon resonance or ELISAs.

The endolysosomal targeting conjugates described herein may have variations in numbers of targeting components (e.g. Fab fragments or scFv fragments) that range from 1-4 targeting components (FIG. 3). These targeting components may be linked to immunoglobulin Fc fragments or other proteins such as albumin, and include linker sequences that vary in length and composition between the fusion proteins, domains or fragments e.g. GGGGS or 2-3 repeats of this linker, among other linker sequences identifiable by skilled persons. Domains such as CalD1 or CalD2 can also be linked to targeting components and cargo components using similar linkers. The Fc fragments of an endolysosomal targeting conjugate may also have mutations such as knobs-into-holes and/or electrostatic steering mutations so that heterodimers of Fc fragments with and without linked targeting components are formed.

The targeting component may be fused to an Fc region of an antibody, which retains the therapeutic functions and in vivo persistence elicited by the Fc region while reducing the size of the protein. In other examples, the Fc region may be replaced by albumin, or domain III of albumin, which have prolonged in vivo persistence due to the interaction of albumin (or DIII) with the recycling receptor, FcRn.

The exemplary endolysosomal targeting conjugate ADCs and PDCs described herein show improved efficacy in killing cancer cells through improved intracellular release of the toxin (see Examples 3-5, 9-13). In addition to the exemplary cytotoxic drug, MMAE, other cytotoxic drugs may be used such as a maytansinoid, tubulysin, benzodiazepine, duocarmycin, among drugs identifiable by those with skill in the art. The drug may be conjugated to the antibody fragment, antibody domain, nanobody, protein, protein fragment or protein domain of the cargo component through chemical conjugation. Examples of chemical coupling that may be used are: amine-to-amine (NHS esters), sulfhydryl-to-sulfhydryl (maleimide), amine-to-sulfhydryl (NHS ester/maleimide), sulfhydryl-to-carbohydrate (maleimide/hydrazide), or attachment via an unnatural amino acid with the desired chemical reactivity, among other approaches identifiable by skilled persons. The unnatural amino acid may be inserted during recombinant production of the targeting component. Polyethyleneglycol (PEG) spacers may be inserted between the chemically conjugated proteins, protein fragments or other molecules. Linkers may be cleavable, such as valine-citrulline to enable release of the cytotoxic drug in the late endosomes or lysosomes by resident proteases such as cathepsins. In cases where the linkage is not cleavable, such as for trastuzumab-DM1, the antibody may be proteolysed to release the drug. Linkage chemistry, sites of linkage and choice of peptide can be guided by molecular modeling, and can be designed to minimize loss of binding activity of the ADC or PDC for cell surface receptor or other cell surface molecule, as would be understood by skilled persons.

The cargo component of endolysosomal targeting conjugate LCs can be generated by conjugation of an imaging label identifiable by persons skilled in the art to the antibody fragment, antibody domain, protein, protein fragment or protein domain of the cargo component. Non-limiting examples of imaging labels include near infrared dyes such as IRDye800CW, or radiolabels such as I-124, Cu-64 or Zr-89. Conjugation to Cu-64 or Zr-89 can be achieved through chelation to 1,4,7,10-tetraazacyclododecane-1,4,7,10-tetraacetic acid (IOTA) which chelates these radiolabels, among other methods identifiable by persons skilled in the art.

In further examples, the cargo component of the endolysosomal targeting conjugate can be a cytotoxic radiolabel (e.g. Yttrium-90, Y-90, or iodine-131, I-131) or drug or other agent that modifies the behavior of the targeted cell. For example, the drug could be an antagonistic ligand for the androgen receptor (AR) and could be used to downregulate AR activity.

The term "behavior" in relation to a target cell or other cell may refer to an activity, a function, an output, or any other attribute or action regarding the phenotype or genotype of the target cell or other cell. In general, a drug or other agent can be used to produce an effect, such as a particular therapeutic effect, a cytotoxic effect, and so on, with regard to a target cell, as would be understood by skilled persons upon reading the present disclosure.

In several examples described herein, the endolysosomal targeting conjugate may include the amino acid sequences of SEQ ID NO: 2 plus SEQ ID NO: 4, SEQ ID NO: 6 plus SEQ ID NO: 8, SEQ ID NO: 10; SEQ ID NO:12; SEQ ID NO:14; SEQ ID NO:16; SEQ ID NO: 18 plus SEQ ID NO:20 plus SEQ ID NO: 22, SEQ ID NO: 22 plus SEQ ID NO: 24 plus SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 plus SEQ ID NO: 44, SEQ ID NO: 46 plus SEQ ID NO: 48, or homologs thereof.

The endolysosomal targeting conjugate may include an amino acid sequence having at least 50% identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, SEQ ID NO:36, SEQ ID NO: 38, SEQ ID NO: 40, SEQ ID NO: 42, SEQ ID NO: 44, SEQ ID NO: 46, SEQ ID NO: 48.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine is considered to be a functionally equivalent residue to lysine.

A person skilled in the art would understand that similarity between sequences is typically measured by a process that includes the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may include additions or deletions (gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can be, for example, a sequence identifiable in a database such as GenBank and UniProt and others identifiable to those skilled in the art.

As understood by those skilled in the art, determination of percent identity between any two sequences can be accomplished using a mathematical algorithm. Computer implementations of suitable mathematical algorithms can be utilized for comparison of sequences to determine sequence identity. Such implementations include, but are not limited to: CLUSTAL, ALIGN, GAP, BESTFIT, BLAST, FASTA, among others identifiable by skilled persons.

For example, endolysosomal targeting conjugates according to the present disclosure may include an amino acid sequence having at least 50% sequence identity, preferably at least 80%, more preferably at least 90%, most preferably at least 95% sequence identity compared to SEQ ID NO: 2, SEQ ID NO: 4, SEQ ID NO: 6, or SEQ ID NO: 8, or SEQ ID NO: 10, or SEQ ID NO: 12, or SEQ ID NO: 14, or SEQ ID NO: 16, or SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, or SEQ ID NO: 36, or SEQ ID NO: 38, or SEQ ID NO: 40, or SEQ ID NO: 42, or SEQ ID NO: 44, or SEQ ID NO: 46, or SEQ ID NO: 48.

The endolysosomal targeting conjugates herein described may be provided in a composition that includes an endolysosomal targeting conjugate and a pharmaceutically acceptable vehicle.

The endolysosomal targeting conjugates or compositions thereof described herein may be administered using any suitable method to deliver them to a subject, such as a cell, a plurality of cells, or a multicellular organism, in particular an animal or a human, and in particular an animal or a human that may have one or more tumors, such as via injection, particularly intravenous, subcutaneous or intramuscular injection, among other methods identifiable by skilled persons.

The endolysosomal targeting conjugates or compositions thereof herein described may be used in a method of treating cancer. The method includes administering a subject with an effective dose of an endolysosomal targeting conjugate or a composition thereof to a subject, wherein the cargo molecule is a cytotoxic drug and the administering of the composition suppresses growth of a tumor in the subject.

The endolysosomal targeting conjugates or compositions thereof herein described may be used in a method of imaging a tumor in a subject. The method includes the steps of: administering a subject with an effective dose of an endolysosomal targeting conjugate composition to a subject, wherein the cargo molecule is an imaging label; and performing an imaging method suitable for detecting the imaging label in the subject. In the method, the administering of the composition is performed at an effective dose to provide a sufficient concentration of the imaging label that is detectable by the imaging method, as would be identifiable by skilled persons.

The endolysosomal targeting conjugates or compositions thereof herein described may be administered at suitable time intervals, for example weekly, monthly or, for example, whenever 50% of subjects are expected to have shown tumor regression.

In diagnostic/theranostic imaging, it is expected that the administration to a subject of an endolysosomal targeting conjugate LC that includes an imaging label such as a radiolabel, near infrared label, or fluorescent label may be followed by a period of 1-7 days to allow localization of the target cell in the subject, for example, tumor localization in the subject. Following this period, the subject may be imaged using positron emission tomography or other suitable imaging modality, such as localized or whole-body imaging, to allow detection of the location of the target cell such as the tumor.

The endolysosomal targeting conjugates described herein may be designed to selectively target a particular cell type, and thereby deliver a cargo molecule to a selected target cell. In particular, the endolysosomal targeting conjugates described herein may be designed to target a particular type of tumor cell in a subject. Accordingly, a method of providing the endolysosomal targeting conjugates described herein may include the steps of: (1) selecting a targeting component, wherein the targeting component includes an antibody, an antibody fragment, an antibody domain, a nanobody, a protein, a protein fragment, or a protein domain configured to selectively bind to a cell surface molecule on a selected type of cell, such as a tumor target cell, wherein the targeting component is configured to bind to a cell surface molecule that is expressed on the target cell with higher affinity in an extracellular space than in an endolysosomal compartment; (2) selecting a cargo component, wherein the cargo component includes an antibody, an antibody fragment, an antibody domain, a nanobody, a protein, a protein fragment, or a protein domain conjugated to a cargo molecule, wherein the cargo molecule may be, for example, a cytotoxic drug having efficacy for suppressing growth of the selected type of tumor target cell or an imaging label suitable for imaging of the selected tumor cell; and (3) providing the endolysosomal targeting conjugate including the targeting component fused directly or indirectly to the cargo component.

Alternatively, the method of providing an endolysosomal targeting conjugate for the treatment of cancer and/or imaging of tumors in a subject may include the steps of: (1) selecting a targeting component, wherein the targeting component includes an antibody, an antibody fragment, a nanobody, a protein, a protein fragment, or a protein domain configured to selectively bind to a cell surface molecule on a selected type of tumor target cell; (2) selecting a cargo component, wherein the cargo component includes an antibody, an antibody fragment, an antibody domain, a nanobody, a protein, a protein fragment, or a protein domain conjugated to a cargo molecule, wherein the cargo molecule is a cytotoxic drug having efficacy for suppressing growth of the selected type of tumor target cell or an imaging label suitable for imaging of the selected tumor cell. In particular, in the method, the targeting component is engineered to further include a first protein domain, the cargo component is engineered to further include a second protein domain, and the first protein domain is configured to bind to the second domain with higher affinity in an extracellular space than in an endolysosomal compartment, as described herein.

EXAMPLES

The following non-limiting examples are provided to further illustrate the endolysosomal targeting conjugates and methods disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific examples that are disclosed and still obtain a like or similar result without departing from the spirit and scope of the invention.

Example 1. Materials and Methods

Cell lines and culture conditions. The mouse endothelial cell line 2H11 (ATCC, CRL-2163) was cultured in Dulbecco's modified Eagle's medium (DMEM) supplemented with 5% heat-inactivated fetal bovine serum (FBS). The human breast cancer cell line MDA-MB-231 (ATCC, HTB-26) was cultured in DMEM with supplemented 10% FBS. The human breast cancer cell lines T-47D (ATCC, HTB-133), MDA-MB-453 (ATCC, HTB-131), and MDA-MB-468 (ATCC, HTB-132) were cultured in RPMI 1640 medium supplemented with 10% FBS. The human breast cancer cell line SK-BR-3 (ATCC, HTB-30) and human ovarian cancer cell line SK-OV-3 (ATCC, HTB-77) were cultured in McCoy's 5A medium supplemented with 10% FBS. The human prostate cancer cell lines LNCaP and 22Rv1 (ATCC, CRL-1740 and CRL-2505, respectively) were cultured in RPMI 1640 medium supplemented with 10% FBS. The human breast cancer cell line HCC1954 (Gazdar, A. F., Kurvari, V., Virmani, A., Gollahon, L., Sakaguchi, M., Westerfield, M., Kodagoda, D., Stasny, V., Cunningham, H. T., Wistuba, I. I., Tomlinson, G., Tonk., V, Ashfaq., R., Leitch, A. M., Minna, J. D., Shay, J. W. (1998) Characterization of paired tumor and non-tumor cell lines established from patients with breast cancer. Int. J. Cancer. 78, 766-774) was cultured in RPMI 1640 medium supplemented with 10% FBS. All cancer cell lines were authenticated with DNA fingerprinting by the University of Arizona Genetics Core (UAGC). Cells were cultured at 37° C. with 5% $CO_2$. Expi293F cells (Life Technologies, catalog number A14635) used for protein expression were cultured in Expi293 expression medium at 37° C. with 8% $CO_2$ and 80% humidity.

Antibodies, antibody-drug conjugates and dextrans. The following antibodies were used in this study: rat anti-mouse LAMP1, mouse anti-human LAMP1 and mouse anti-beta tubulin antibodies (Developmental Studies Hybridoma Bank, clone #1D4B, H4A3 and E7); mouse anti-human EEA1 and rat anti-mouse CD31 antibodies (BD Biosciences, catalog #610456 and 557355); goat anti-human IgG (H+L) antibody conjugated with HRP, donkey anti-rat (H+L) antibody conjugated with Alexa Fluor 488 and donkey anti-human IgG (H+L) antibody conjugated with Cy3 (Jackson ImmunoResearch, catalog #109-035-003, 712-545-153 and 709-165-149); goat anti-human IgG (H+L) antibody conjugated with Alexa Fluor 555, goat anti-mouse IgG (H+L) antibody conjugated with Alexa Fluor 488 and goat anti-human IgG (H+L) antibody conjugated with Alexa Fluor 647 (Life Technologies, catalog #A21433, A11029 and A21445); rabbit anti-human Ki-67 antibody (Abcam, catalog #92742). Trastuzumab-DM1 (T-DM1, Kadcyla®) was obtained from the UT Southwestern Medical Center Pharmacy (Dallas). Alexa Fluor 647-labeled dextran, 10 kDa molecular weight, was purchased from Life Technologies (catalog #D22914).

Generation of expression constructs for production of protein-drug conjugates. For use as controls, the Fc region including the hinge region (residues 215-447 of the heavy chain; EU numbering) of the hen egg lysozyme-specific human IgG1, HuLys10 (Foote, J., Winter, G. (1992) Antibody framework residues affecting the conformation of the hypervariable loops. J. Mol. Biol. 224, 487-499), was cloned into the pcDNA3.4 vector with the N-terminal leader peptide derived from a mouse IgG heavy chain (Foote, J., Winter, G. (1992) Antibody framework residues affecting the conformation of the hypervariable loops. J. Mol. Biol. 224, 487-499; Neuberger, M. S. (1983) Expression and regulation of immunoglobulin heavy chain gene transfected into lymphoid cells. EMBO J. 2:1373-1378). Similarly, the genes encoding the heavy and light chain genes (cDNA) of the HuLys10 antibody were cloned into pcDNA3.4. For the control IgG heavy and light chain constructs, Cys214 (EU numbering) in the light chain, which forms a sulfhydryl bridge with Cys220 (EU number) in the heavy chain of HuLys10 were both mutated to serine residues using the QuikChange II Site-Directed Mutagenesis Kit (Agilent Technologies, catalog #200523).

cDNA clones for human Annexin A1 (AnxA1), human synaptotagmin 1 (Syt1) and human PKCα were purchased from Open Biosystems (clone ID: 3459615, clone ID: 6187902 and clone ID: 40028305, respectively). Genes encoding the AnxA1 PS-binding core domain (amino acids 41-346), the Syt1 PS-binding C2A domain (amino acids 141-266) and PKCα PS-binding C2 domain (amino acids 157-288) were fused via a Gly4Ser linker sequence to the CH3 domain of the human IgG1 Fc region (residues 215-447; EU numbering) with a leader peptide derived from the mouse IgG heavy chain (Foote, J., Winter, G. (1992) Antibody framework residues affecting the conformation of the hypervariable loops. J. Mol. Biol. 224, 487-499; Neuberger, M. S. (1983) Expression and regulation of immunoglobulin heavy chain gene transfected into lymphoid cells. EMBO J. 2:1373-1378). Cys220 (EU numbering) in the hinge region was mutated in all Fc fusion constructs so that there are two cysteine residues per hinge. The genes encoding the Fc fusions were cloned into the pcDNA3.4 vector (Invitrogen, catalog #14308).

To generate Syt1-Fc-Syt1, the Syt1 PS-binding C2A domain (amino acids 141-266) was linked to the N-terminus of the hinge region of the Fc-Syt1 construct via a Gly4Ser linker sequence. The leader peptide derived from a mouse IgG heavy chain (Foote, J., Winter, G. (1992) Antibody framework residues affecting the conformation of the hypervariable loops. J. Mol. Biol. 224, 487-499; Neuberger, M. S. (1983) Expression and regulation of immunoglobulin heavy chain gene transfected into lymphoid cells. EMBO J. 2:1373-1378) was appended to the N-terminus of the hinge-linked Syt1 PS-binding C2A domain, and the resulting Fc fusion was cloned into the pcDNA3.4 vector. Mutations to reduce PS-binding of the Syt1 C2A domain (D173N, D179N, D231N, D233N and D239N) (Striegel, A. R., Biela, L. M., Evans, C. S., Wang, Z., Delehoy, J. B., Sutton, R. B., Chapman, E. R. and Reist, N. E. 2012. Calcium binding by synaptotagmin's C2A domain is an essential element of the electrostatic switch that triggers synchronous synaptic transmission. J. Neurosci. 32, 1253-1260) were inserted in the Syt1-Fc construct to generate Fc-Syt1(DN) and cloned into the pcDNA3.4 vector. All constructs were generated using standard methods of molecular biology and designed oligonucleotides.

Generation of expression constructs for antibody-drug conjugates. Synthetic genes encoding the heavy chain variable domain and pertuzumab light chain variable domain of the HER2-specific antibody, pertuzumab (Franklin, M. C., Carey, K. D., Vajdos, F. F., Leahy, D. J., de Vos, A. M., Sliwkowski, M. X. (2004) Insights into ErbB signaling from the structure of the ErbB2-pertuzumab complex. Cancer Cell, 4, 317-328), were purchased from Genescript and cloned into an expression vector for Fab fragment production, containing the human heavy chain constant region domain 1 (CH1) and human light chain constant domain (kappa chain, $C_\kappa$. To identify residues in the pertuzumab heavy and light chain variable domains to target for histidine scanning, the crystal structure of pertuzumab in complex with antigen, HER2, (Protein Data Bank accession code 1N8Z) was analyzed in PyMOL. Residues located in the CDRs of pertuzumab (VH domain: Asp31, Tyr32, Asn54, Tyr60, Leu100, Gly101, Pro102, Ser103, Tyr105, Asp107; VL domain: Tyr55; amino acid numbers referred to are those in the protein sequence of the pertuzumab heavy and light chain variable domains, and do not refer to other numbering conventions) that interact with residues in domain II of HER2 (His245, Val286, Ser288, Leu295, His296, and Lys311 as described in Franklin, M. C., Carey, K. D., Vajdos, F. F., Leahy, D. J., de Vos, A. M., Sliwkowski, M. X. (2004) Insights into ErbB signaling from the structure of the ErbB2-pertuzumab complex. Cancer Cell, 4, 317-328) were systematically replaced by histidine using splicing by overlap extension (Horton, R. M., Hunt, H. D., Ho, S. N., Pullen, J. K., Pease, L. R. (1989) Engineering hybrid genes without the use of restriction enzymes: gene splicing by overlap extension. Gene 77, 61-68). The resulting genes were cloned and expressed as periplasmically secreted Fab fragments in *E. coli.*

To generate the pertuzumab scFv gene in the phage display vector, pHEN1 (Hoogenboom, H. R., Griffiths, A. D., Johnson, K. S., Chiswell, D. J., Hudson, P., Winter, G. (1991) Multi-subunit proteins on the surface of filamentous phage: methodologies for displaying antibody (Fab) heavy and light chains. Nucl. Acids Res. 19, 4133-4137), the Fab fragment expression vector for pertuzumab was modified using standard methods of molecular biology to insert a linker peptide [$(Gly_4Ser)_3Gly_2Ser$ linker] between the heavy and light chain variable domain gene, followed by recloning of the scFv gene into pHEN1. To generate libraries of mutated pertuzumab scFvs with randomly mutated residues in the CDRs, the following oligonucleotides were used. For each oligonucleotide, DNA sequence is shown in 5' to 3' direction: CDRH1Back, GCTTCTGGATTCACATTCACANNBNNBNNBATGGATTGGGTGAGACAGGCT (SEQ ID NO:49); CDRH1For, TGTGAATGTGAATCCAGAAGC (SEQ ID NO:50); CDRH2Back, TGGGTGGCTGATGTGAATCCTNNBNNBNNBNNBTCTATCTACAATCAGAGATTC (SEQ ID NO:51); CDRH2For, AGGATTCACATCAGCCACCCA (SEQ ID NO: 52); CDRH3Back, TACTACTGTGCTAGAAATCTGNNBCCTNNBTTCNNBTTCGATNNBTGGGGACAGGGAACACTG (SEQ ID NO:53); CDRH3For, CAGATTTCTAGCACAGTAGTA (SEQ ID NO:54); CDRL2-1Back, CCTAAGCTGCTGATCTACTCTNNBTCTNNBAGANNBACAGGAGTGCCTTCTAGA (SEQ ID NO: 55); CDRL2-1For, AGAGTAGATCAGCAGCTTAGG (SEQ ID NO: 56); CDRL2-2Back, GGAAAGGCTCCTAAGCTGCTGNNBNNBNNBGCTTCTTACAGATACACAGGA (SEQ ID NO: 57); and CDRL2-2For5, CAGCAGCTTAGGAGCCTTTCC (SEQ ID NO: 58). Molecular biology methods known to those with skill in the art were used to generate the libraries of scFvs genes, and electroporation of *E. coli* TG1 (Lucigen, catalog #60502) was used to generate libraries of around $5\times10^7$ mutants for each targeted CDR.

Colonies from libraries were pooled and used to inoculate cultures supplemented with M13KO7 helper phage (NEB, catalog #N0315S), 100 μg/mL ampicillin, and 50 μg/mL kanamycin overnight at 30° C. Extruded phage were harvested from the supernatant by precipitation with 4% polyethylene glycol 8000, 3% NaCl. Phage (100 μL of $2\times10^{12}$ pfu/mL) were pre-panned using 4% skimmed milk/phosphate-buffered saline (PBS) coated Maxisorp 96 well microtiter plates (Thermofisher, catalog #44-2404-21) prior to panning using Maxisorp 96 cell plates coated with 2 μg/mL recombinant human HER2 (extracellular domain)-Fc fusion protein (HER2-ECD-Fc; R&D Research, catalog #1129-ER-050). Phage were incubated with 4% skimmed milk pH 7.4 for 2 hours in the 96 well plate. Plates were extensively washed with PBS pH 7.4 supplemented with 0.1% Tween-20 (PBST) followed by PBS pH 7.4. Phage with pH-dependent binding were selectively eluted using 20 mM 2-(N-morpholino) ethanesulfonic acid (MES) pH 5.8 for 10 minutes at room temperature. Eluted phage were used to infect exponentially growing *E. coli* TG1. Four rounds of panning were carried out, and isolated phage screened for higher affinity binding to HER2 at pH 7.0 relative to pH 5.8. Recombinant scFvs encoded by the selected phage were analyzed for binding to HER2 by ELISA and/or surface plasmon resonance.

The heavy and light chain variable domain genes for pertuzumab scFv or Fab fragments with higher affinity at pH 7.0 relative to pH 5.8 were cloned into cassette vectors for the expression of human IgG1 heavy chains and light chain ($C_\kappa$) sequences, respectively, using pcDNA3.4 as backbone vector. The hinge disulfide bonds that link the $C_\kappa$ domain to hinge region, and one hinge disulfide that links the two heavy chains to each other, were removed from the heavy and light chains by mutating the light chain cysteine (Cys214; EU numbering) and two heavy chain cysteines (Cys220, Cys229; EU numbering) to serine.

To generate an expression construct encoding the HER2-specific Fab fragment of trastuzumab fused to the Calbindin D9K domain 2 (CalD2), the genes encoding trastuzumab heavy and light chain variable domains (Carter, P., Presta, L., Gorman, C. M., Ridgway, J. B., Henner, D., Wong, W. L., Rowland, A. M., Kotts, C., Carver, M. E., Shepard, H. M. (1992) Humanization of an anti-p185HER2 antibody for human cancer therapy. Proc Natl Acad Sci USA, 89, 4285-4289) were synthesized by Genescript. The Calbindin D9K gene (Berggard, T., Julenius, K., Ogard, A., Drakenberg, T., Linse, S. (2001) Fragment complementation studies of protein stabilization by hydrophobic core residues. Biochemistry, 5, 1257-1264) was synthesized by Genescript and the trastuzumab Fab heavy chain (VH-CH1-linker including part of hinge), and the CalD2 domain genes were fused together with a Ser-Gly-Gly linker using splicing by overlap extension (Horton, R. M., Hunt, H. D., Ho, S. N., Pullen, J. K., Pease, L. R. (1989) Engineering hybrid genes without the use of restriction enzymes: gene splicing by overlap extension. Gene 77, 61-68). The VH-CH1-CalD2 fusion protein gene and gene encoding the trastuzumab light chain (with a C-terminal polyhistidine tag) were cloned separately into the pcDNA3.4 vector.

Similar methods were used to generate expression constructs encoding the PSMA-specific (026) VH-CH1-linker peptide fused to the CalD2 domain. Genes encoding the 026 heavy and light chain variable domains (U.S. Pat. No. 7,850,971B2) were synthesized by Genescript. The CalD2 domain gene and 026 VH-CH1-linker were fused together by splicing by overlap extension and the resulting fusion protein gene cloned into pcDNA3.4. The gene encoding the 026 light chain with a C-terminal polyhistidine tag was cloned into a separate pcDNA3.4 vector.

To generate an expression construct encoding Calbindin D9K domain 1 (CalD1) fused to the human IgG1-derived Fc fragment, the Fc domain (hinge-CH2-CH3, human IgG1-derived) gene was fused via a Gly-Ser-Ser linker to the Calbindin D9K domain 1 gene through splicing by overlap extension (Horton, R. M., Hunt, H. D., Ho, S. N., Pullen, J. K., Pease, L. R. (1989) Engineering hybrid genes without the use of restriction enzymes: gene splicing by overlap extension. Gene 77, 61-68) and cloned into the pcDNA3.4 vector.

Protein expression and purification. Recombinant antibodies and Fc fusion proteins were produced using the Expi293 expression system from Life Technologies following the manufacturer's instructions. Briefly, cells were transfected with expression constructs (above) for 6-7 days and recombinant PDCs or ADCs purified from culture supernatants using protein G-Sepharose. Bound proteins were eluted using 50 mM diethylamine with 150 mM NaCl. The eluted protein was neutralized by 2 M Tris pH 7.0, dialyzed against PBS, concentrated and loaded onto a Hiload 16/600 Superdex 200 gel filtration column (GE Healthcare). The monomeric form of the protein was separated, concentrated and analyzed using a Superdex 200 5/150 gel filtration column (GE Healthcare) or Yarra 3 μm SEC-3000 column (Phenomenex).

Trastuzumab Fab-CalD2, 026 Fab-CalD2 and CalD1-Fc fusion proteins were produced using the Expi293 expression system described above and recombinant proteins purified from culture supernatants using $Ni^{2+}$-NTA-agarose.

Pertuzumab scFv and Fab fragments were expressed as recombinant proteins using *E. coli* as a host. scFv and Fab fragments were secreted into the periplasm and purified from osmotically shocked *E. coli* cells using $Ni^{2+}$-NTA-agarose.

Protein conjugation with maleimidocaproyl-val-cit-PAB-MMAE. Fc fusion or control antibody in PBS were reduced by addition of 16 molar equivalents (8 molar equivalents multiplied by the number of hinge disulfides) of TCEP at room temperature for 3 hours to reduce the hinge disulfide bonds. Maleimidocaproyl-val-cit-PAB-MMAE (MC-VC-PAB-MMAE; Levena Biopharma, catalog #SET0201) was then added to the reduced Fc fusion at 8 molar equivalents (4 molar equivalents multiplied by the number of free cysteines) and incubated at room temperature for 3 hours. Following the conjugation reaction, free MMAE was removed by extensively dialyzing the protein against PBS. The conjugated Fc fusion or control antibody was stored at 4° C.

To generate ADCs, analogous methods were used except 8 molar equivalents of TCEP and 4 molar equivalents of MC-VC-PAB-MMAE were used due to the presence of only one hinge disulfide. Additionally, the antibody was reduced at 37° C. for 2 hours.

Surface plasmon resonance analyses. Binding analyses were carried out using a BIAcore T200 (GE Healthcare). Flow cells of CM5 sensor chips were coupled using amine coupling chemistry with recombinant HER2-ECD-Fc (fusion of HER2 extracellular domain to immunoglobulin Fc fragment), wild type (WT) pertuzumab, mutated pertuzumab variants or coupling buffer (10 mM sodium acetate pH 4.8) as a reference. Antibodies were injected over immobilized HER2-ECD-Fc, or HER2-ECD-Fc over the immobilized antibodies, at a flow rate of 5 or 10 μL/minute at 25° C. in phosphate buffered saline (PBS) plus 0.01% (v/v) Tween-20 and 0.05% (v/v) NaN3 (pH 7.4, 7.0, 6.5, and 5.8). Flow cells were regenerated following each injection using 0.15M NaCl/0.1M glycine (pH 2.8) buffer. To determine equilibrium dissociation constants, antibodies were injected over immobilized HER2-ECD-Fc and the interactions were modeled as a 1:1 interaction using custom written software (Ober, R. J., Ward, E. S. (2002) Compensation for loss of ligand activity in surface plasmon resonance experiments. Anal. Biochem., 306, 228-236) to yield apparent dissociation constants (due to bivalent binding of the antibodies to immobilized HER2-ECD-Fc).

To investigate the calcium-dependence of the interaction of the Fab-CalD2 fusion protein and CalD1-Fc fusion protein, Fab-CalD2 was injected followed by co-injection of CalD1-Fc in buffer containing different calcium concentrations. Specifically, 100 nM trastuzumab Fab-CalD2 fusion was injected over immobilized HER2-ECD-Fc at a flow rate of 10 μL/min at 25° C. in PBS, 0.01% (v/v) Tween-20, 0.05% (v/v) $NaN_3$ pH 7.4 ($PBS^+$) plus 2 mM $CaCl_2$, followed by 100 nM CalD1-Fc fusion at a flow rate of 10 μL/min at 25 C in $PBS^+$ plus 2 mM $CaCl_2$. $PBS^+$ with different concentrations of $CaCl_2$ or $EDTA_2Na$ were injected during the dissociation phase. Data were processed using BIAevaluation and custom-written software.

Membrane lipid strip binding assay for PS-targeting proteins. Lipid-coated membrane strips (Echelon, catalog #P-6002) were first hydrated with TBST (20 mM Tris, 150 mM NaCl, 0.1% Tween 20, pH 7.5) and then incubated with blocking solution (4% fatty acid free BSA dissolved in TBST) at room temperature for 1 hour. Proteins were diluted at 2 μg/ml in blocking buffer and incubated with membranes at room temperature for 2 hours. The lipid strip was then washed with TBST and bound proteins detected using horse-radish peroxidase (HRP)-conjugated goat anti-human IgG (H+L) antibody.

Flow cytometry analyses of internalization of antibody-drug conjugates. Cancer cells were plated in 48 well plates and incubated at 37° C. overnight. Cells were treated with 10 nM Alexa 488-labeled ADCs for 0.5, 4, and 20 hours. Treated cells were cooled on ice and surface signal of Alexa 488 was quenched with 5 μg/mL rabbit anti-Alexa 488 antibody for 30 minutes at 4° C. Samples were washed, harvested by trypsinization, resuspended in PBS, analyzed using FACS-Accuri and data processed with FlowJo (FLOWJO, LLC).

To analyze the accumulation of CalD1-Fc within cells, LNCaP cells were plated in a 48 well plate and allowed to adhere. LNCaP cells were then pulsed with 100 nM Alexa 647-labeled CalD1-Fc or with a mixture of 100 nM Alexa 647-labeled CalD1-Fc plus 100 nM 026 Fab-CalD2 for 1 or 2 hours. Cells were washed, trypsinized using trypsin-EDTA (Gibco catalog #25200056) to detach the cells and dissociate Alexa 647-labeled CalD1-Fc from cell surface bound 026 Fab-CalD2. Cells were harvested, washed and analyzed using a BD Accuri C6 flow cytometer.

Fluorescence microscopy analyses of PS- and HER2-targeting agents. To study the subcellular localization of PS-targeting agents, 2H11 or MDA-MB-231 cells were grown on coverslips (Zeiss, ref #0109030091) and incubated with either 50 nM control IgG (HuLys10) or 50 nM PS-targeting agents diluted in growth medium for 3 hours. Cells were then washed with PBS and fixed with ice-cold 4% paraformaldehyde (PFA) at room temperature for 20 minutes. Following fixation, cells were permeabilized with 0.1% Triton X-100 and incubated with blocking buffer (PBS, 5% serum and 0.1% Tween 20) at room temperature for 30 minutes. Primary antibodies specific for mouse LAMP-1 (clone 1D4B), human LAMP-1 (clone H4A3) or mouse EEA1 were diluted in blocking buffer and incubated with cells at room temperature for 2 hours. Cells were then washed with PBST (PBS with 0.1% Tween 20) and incubated with fluorescently-labeled secondary antibodies diluted in the blocking buffer for 1 hour at room temperature. To detect internalized PS-targeting agents, fluorescently-labeled goat or donkey anti-human IgG (H+L) antibody was used. Following the incubation, cells were washed with PBST and mounted with ProLong Gold antifade mountant (Life Technologies, catalog #P36930). Fluorescent images were acquired using a Zeiss Axiovert 200M inverted fluorescence microscope with a 63×, 1.4 NA plan apochromat objective (Carl Zeiss) and a 1.6× internal optovar. The acquired data were processed using the microscopy image analysis tool (MIATool) software (www4.utsouthwestern.edu/wardlab/miatool.asp).

To study the subcellular fate of internalized HER2-targeting ADCs, MDA-MB-453 cells were plated on Mattek dishes. Cells were pre-treated with 5 μM Alexa 647-labeled dextran (pulsed for 2 hours, chased for 3 hours), and subsequently treated with 10 nM Alexa 488-labeled mutated variants of pertuzumab conjugated to MMAE (SG-MMAE, YS-MMAE) or T-DM1 for 20 hours. Wild type (WT) pertuzumab conjugated to MMAE was used as a control. Samples were treated with 33.3 nM rabbit anti-Alexa 488 antibody (Thermofisher, catalog #A11094) for 30 minutes on ice to quench surface fluorescence. Cells were fixed with 1.7% (w/v) paraformaldehyde supplemented with 0.025% glutaraldehyde for 10 minutes at room temperature. Samples were imaged and data processed as above.

PS pull-down assay for PS-targeting agents. To study the $Ca^{2+}$-dependence of binding of the PS-targeting Fc fusions to PS, proteins were diluted at 100 nM in binding buffer (10 mM HEPES pH 7.4 and 150 mM NaCl with 2 mM or 2 μM $Ca^{2-}$). 50 μl PS-coated beads (Echelon, catalog #P-BOPS) were added and incubated at room temperature for 2 hours. The beads were then washed with the binding buffer and bound proteins detected by immunoblotting with HRP-conjugated goat anti-human IgG (H+L) antibody. To examine the pH-dependent binding to PS, proteins were diluted at 100 nM in PBS pH 7.4 or 6.0. 50 μl (bed volume) PS-coated beads were added and incubated at room temperature for 2 hours. The beads were then washed with PBS and bound proteins detected by immunoblotting with HRP-conjugated goat anti-human IgG (H+L) antibody.

Annexin V binding assay to analyze levels of exposed PS on cells. One million cells were suspended in Annexin V binding solution (10 mM HEPES pH 7.4 with 150 mM NaCl and 2.5 mM $CaCl_2$). Annexin V conjugated with Alexa 488 Fluor (Life Technologies, catalog #A13201) was added to the cell suspension at a 1:100 dilution and incubated with the cells for 10 minutes at room temperature. Cells were then washed once with the Annexin V binding solution and analyzed by flow cytometry (BD FACSCalibur). Flow cytometry data were processed using FlowJo (FLOWJO, LLC).

Flow cytometry analyses of PS-targeting agents. Cells were trypsinized and resuspended with flow cytometry buffer (PBS w/$Ca^{2+}$/$Mg^{2+}$ and 1% BSA). 50 nM PS-targeting Fc fusions were incubated with the cells for 30 minutes at either room temperature or on ice depending on the assay. Cells were washed with flow cytometry buffer and incubated with fluorophore-conjugated secondary antibodies on ice for 30 minutes. Cells were then washed and analyzed by flow cytometry (BD FACSCalibur). Flow cytometry data were processed using FlowJo (FLOWJO, LLC).

Cell growth and survival assays. Cancer cell lines (2H11, MCF-7, SK-BR-3, SK-OV-3, LNCaP, 22Rv1, MDA-MB-231, MDA-MB-453, MDA-MB-468, and HCC1954) were plated in 96 well plates. Cells were grown overnight followed by the addition of PS-targeting PDCs or HER2-targeting ADCs. Cell growth and survival were measured after 3-5 days incubation with the Cell Proliferation AQ One Solution Cell Proliferation Assay kit (Promega, catalog #G3581). Dose-response curves were plotted using GraphPad Prism software.

Whole body imaging, pharmacokinetic and therapy studies in mice. Animal procedures used in all mouse studies were approved by the Institutional Animal Care and Use Committee of the University of Texas Southwestern Medical Center and Texas A&M University. BALB/c SCID mice were purchased from the Jackson Laboratory (stock #001803) and bred in-house. Pharmacokinetic studies were performed as described previously (19). Briefly, Lugol solution was added to drinking water 96 hours before the experiments. SCID BALB/c female mice (8 weeks old; 18-22 g weight) were anesthetized using 2% isoflurane in oxygen and injected (i.v.) with $^{125}I$-labeled proteins (100-120 μCi, 10-12 μg/mouse). Whole body counting was performed using a dose calibrator (Capintec Inc.) at different time points.

For whole body, near infrared imaging (NIR) with PS-targeting agents, female nude mice (6-7 weeks old; purchased from Envigo, catalog #6903F) or BALB/c SCID mice (6-8 weeks old) were used. For implantation of MDA-MB-231 tumors, mice were anesthetized with 2% isoflurane in oxygen and a small surgical cut was performed to expose the mammary fat pad. MDA-MB-231 cells were trypsinized and dispersed into single cell suspensions in PBS. $5\times10^6$ cells/mouse were injected in 100 μl into the mammary fat pad, using a 25 G needle, and the wound was then sealed with a wound clip. Buprenorphine was administered (s.c.) at 50 μg/kg immediately following the surgery and 12 hours later. Mice were monitored daily and the wound clip was removed one week post-surgery. For imaging of nude mice, mice were divided into 3 groups (n=3 mice per group) when tumors reached sizes of approximately 150 $mm^3$ and anesthetized with 2% isoflurane in oxygen. Anesthetized mice were injected (i.v.) with 1 nmol IRDye800CW-labeled PS-specific agents in PBS. Fluorescence imaging (FLI) was performed using a Caliper Xenogen IVIS Spectrum (Perkin Elmer) in vivo imaging system at 0 (before injection) and 3, 24 and 48 hours post-injection. FLI was performed using 745 nm excitation, 800 nm emission, binning 8, FOV 12.9 cm, f-stop 2 and auto-exposure. Data were quantitated with the Living Imaging software using absolute Radiant Efficiency (photons/s) in an ROI, manually drawn to outline the FLI signal of the tumor and normalized to the tumor volumes. For imaging in BALB/c SCID mice, mice were divided into 3 groups (n=3 mice per group) when tumors reached sizes of approximately 300 $mm^3$ and injected (i.v.) with 1 nmol of IRDye800CW-labeled PS-specific agents in PBS. 48 hours following injection, tumors were dissected out and imaged as above. Fluorescence in an ROI, manually drawn to outline the FLI signal of the tumor was quantitated and normalized to the tumor weight.

For tumor treatment studies with PS-targeting PDCs, implantation of MDA-MBA-231 tumor xenografts in BALB/c SCID mice was carried out as described for the whole body imaging experiments. For implantation of LNCaP tumors, 7-8 week old male BALB/c SCID mice (18-22 g weight) were anesthetized with 2% isoflurane in oxygen and $5\times10^6$ LNCaP cells suspended in 50% RPMI and 50% Matrigel (BD Biosciences) were injected (s.c.). When MDA-MBA-231 or LNCaP tumors reached a size of ~100 $mm^3$, mice were injected (i.p.) with 5 mg/kg docetaxel 72 and 48 hours before the treatment. Mice were then injected (i.v.) with 1 nmole unconjugated proteins, PDCs or PBS vehicle twice per week. Tumors and body weights were measured twice a week. For the treatment experiment using Fc-Syt1(DN)_MMAE (FIG. 16D), mice were treated for 4 weeks and monitored for another 2.5 weeks. Experiments were terminated when the tumor size reached 2 cm in any dimension.

For therapy with HER2-specific ADCs, 6-8 week old female BALB/c SCID mice were implanted with $4\text{-}5\times10^6$ MDA-MB-453 cells using methods described for the whole body imaging experiments. When the tumors reached a size of ~60-100 $mm^3$, mice were injected (i.v.) with 2 mg/kg ADC, T-DM1, unconjugated protein, or with PBS vehicle once every 3 weeks (two doses total).

Immunohistochemical analyses. Female BALB/c SCID mice bearing MDA-MB-231 tumors were treated (i.p.) with 5 mg/kg docetaxel 72 and 48 hours before delivery (i.v.) of either PBS or 1 nmole Fc-Syt1 conjugated with MMAE. At different time points, mice were perfused with PBS followed by 4% PFA. Tumors were then dissected out, embedded in OCT (Fisher Scientific, catalog #23-730-571) and stored at −80° C. 10 μm tissue sections were cut and hydrated with PBS at room temperature before fixation with 4% PFA for 30 minutes. Tumor sections were then washed with PBS and incubated with the permeabilization/blocking solution (PBS+0.5% Triton X-100 and 3% BSA) at room temperature for 1 hour. Primary antibodies for human Ki-67 and mouse CD31 were diluted in the blocking buffer (PBS+0.1% Tween 20+5% serum) and incubated with the tissue sections at 4° C. overnight. The next day, tissue sections were washed with PBST (PBS+0.1% Tween 20) and incubated with the fluorophore-conjugated secondary antibodies diluted in the blocking buffer at room temperature for 2 hours. After washing with PBST, tissue sections were mounted with ProLong Gold antifade mounting medium. Confocal images were acquired using a Nikon MR confocal microscope with a 40×, 1.3 NA plan fluor objective and processed with the NIS-Elements software (Nikon).

Example 2. Generation of HER2-Targeting Agents with pH-Dependent Binding to HER2

Figures 4A, 4B:
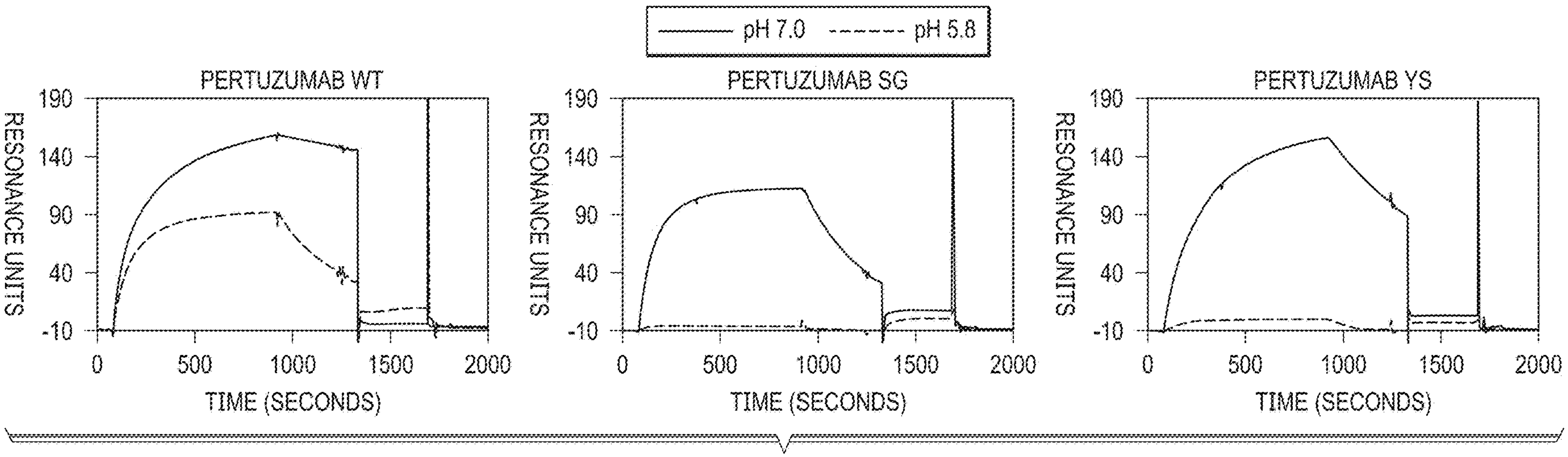
FIG. 4A shows exemplary data for binding analyses of exemplary HER2-targeting endolysosomal targeting agents (without conjugated drug) to HER2 at different pH values.
FIG. 4B shows exemplary data for dissociation constants of exemplary HER2-targeting endolysosomal targeting agents (without conjugated drug) to HER2 at different pH values.

FIGS. 4A and 4B show analyses of the binding of two mutated variants of pertuzumab: SG mutant; Ser55 mutated to histidine and Gly57 mutated to glutamic acid in the heavy chain variable domain (SEQ ID NO: 4); YS mutant, Tyr55 mutated to histidine in the light chain variable domain and Ser103 mutated to histidine in the heavy chain variable domain (SEQ ID NOS: 6, 8) that target HER2. The data were obtained using surface plasmon resonance. FIG. 4A shows representative sensorgrams at pH 7.0 and 5.8 for the interactions of 1 μM HER-extracellular domain (ECD)-Fc fusion with mutated variants and wild type (WT) pertuzumab. For the analyses shown in FIG. 4A, the antibodies were immobilized on the flow cells. FIG. 4B shows the equilibrium dissociation constants (nM) for WT pertuzumab, SG and YS obtained by injecting the antibodies over immobilized HER2-ECD-Fc. The data demonstrate that both the SG and YS variants of pertuzumab have greater pH dependence than WT pertuzumab for binding to HER2.

Figure 5A:
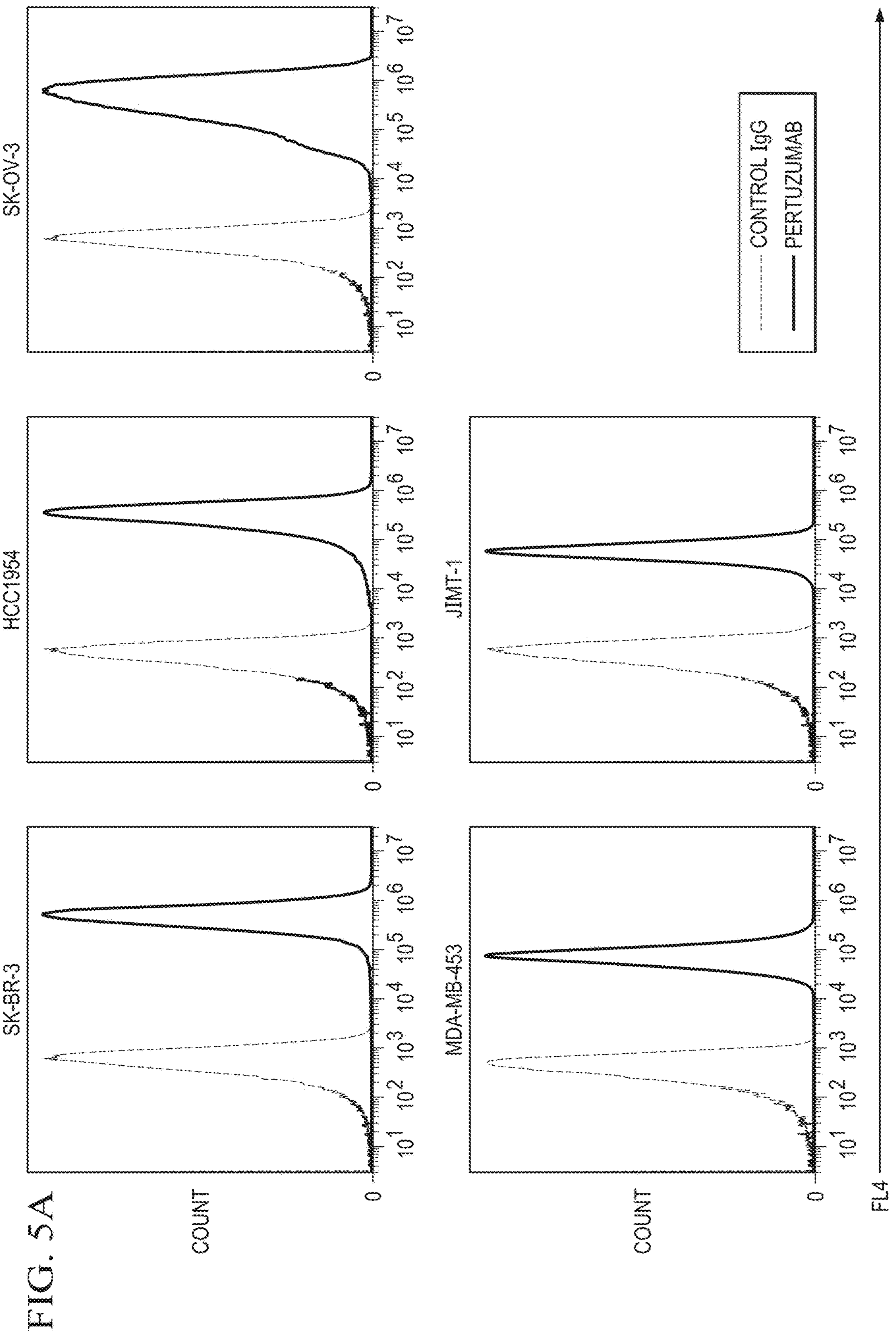
FIG. 5A shows graphs of exemplary data for flow cytometry analyses of expression levels of HER2 on different tumor cell lines.
Figure 5B:
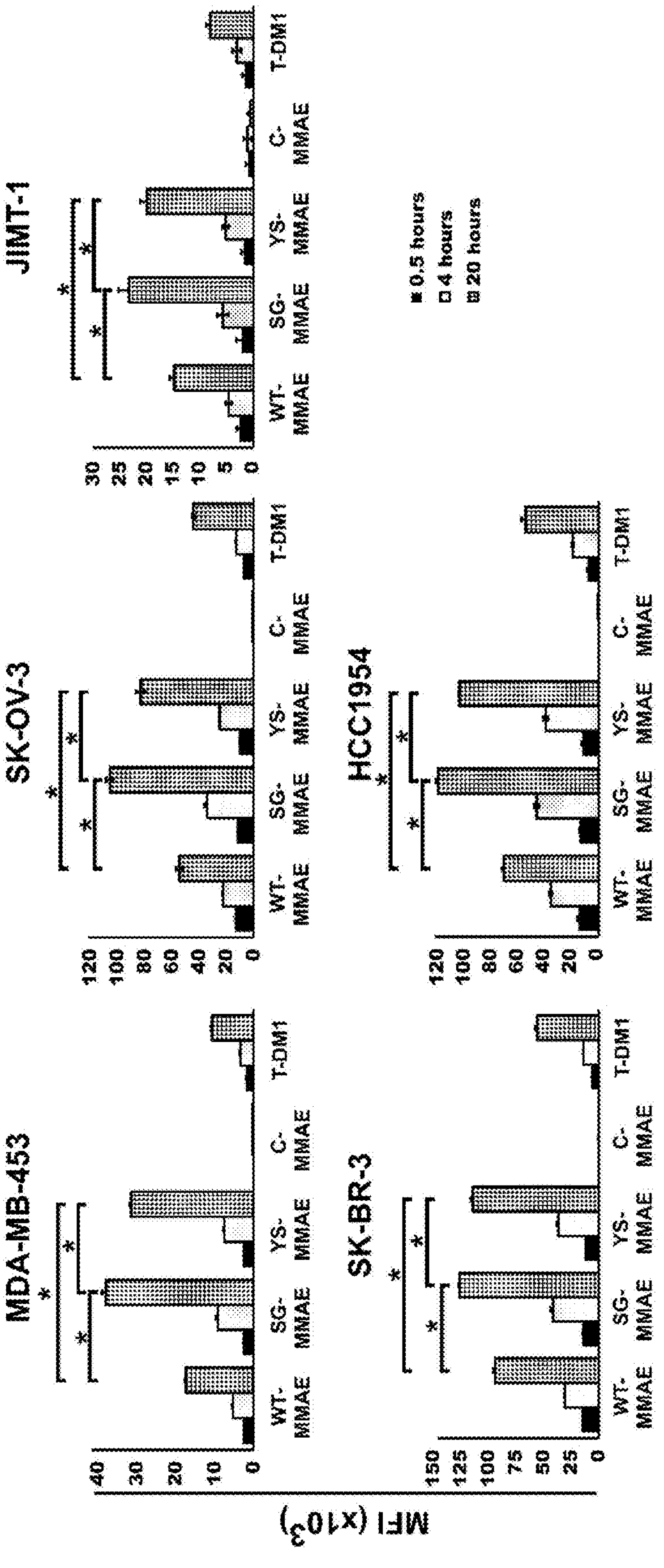
FIG. 5B shows graphs of exemplary data for flow cytometry analyses of internalization and accumulation of exemplary HER2-targeting endolysosomal targeting conjugates in different tumor cell lines.
Figure 5C:
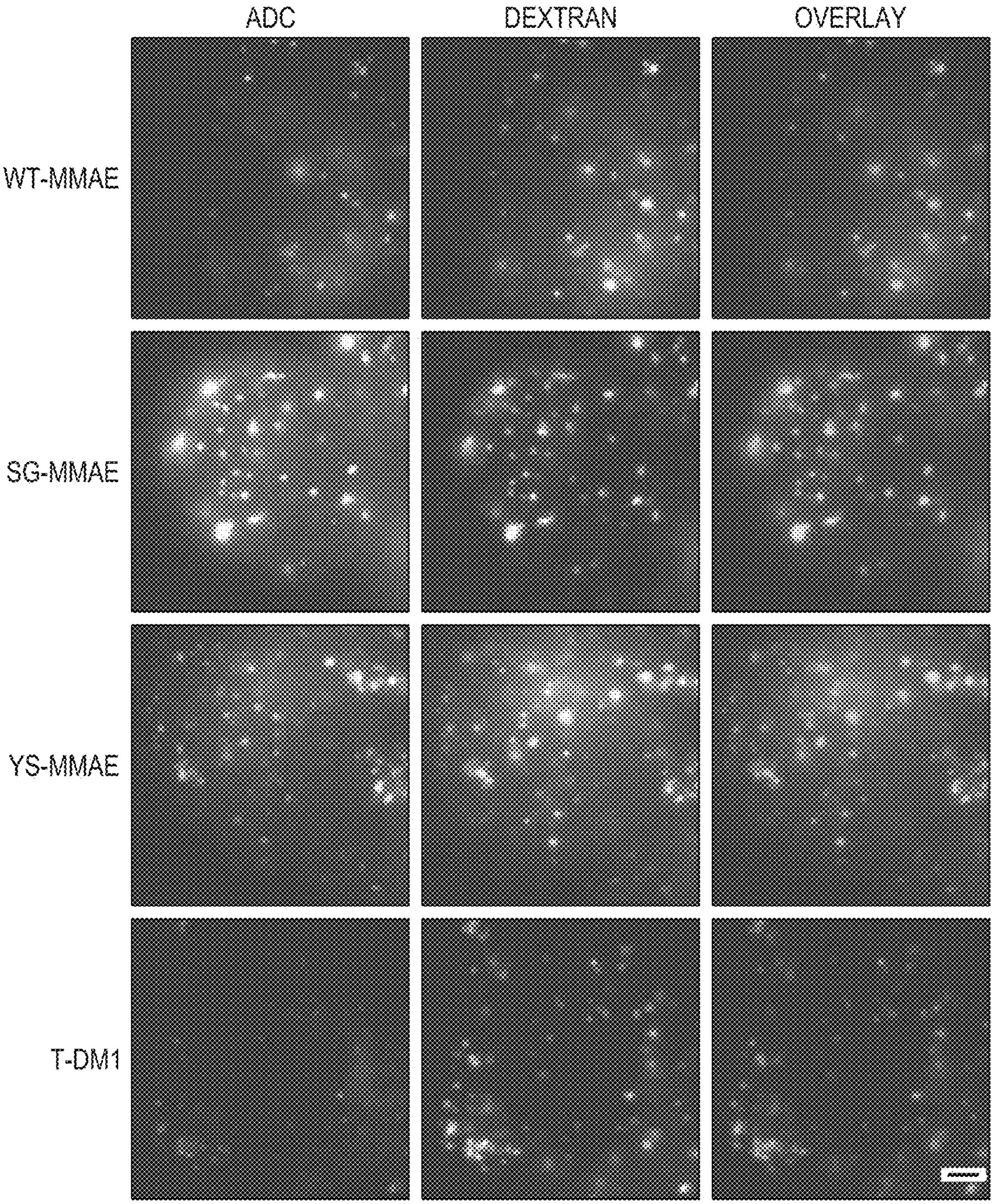
FIG. 5C shows a series of exemplary microscopic images comparing the localization of exemplary HER2-targeting endolysosomal targeting conjugates in dextran-positive lysosomes.

Example 3. Internalization and Accumulation of HER2-Targeting Agents in HER2-Expressing Cells Pertuzumab (WT) and mutated variants SG and YS were conjugated through two hinge cysteine residues to maleimidocaproyl-val-cit-PAB-MMAE (MC-VC-PAB-MMAE) at a drug to antibody ratio (DAR) of 2 drugs per antibody, followed by analyses of binding and accumulation of the HER2-targeting ADCs (HER2-ADCs) within a panel of different HER2-expressing cell lines. FIG. 5A shows the expression levels of HER2 on the different cancer cell lines, detected using Alexa 647-labeled pertuzumab (solid lines) or Alexa 647-labeled control antibody (dotted lines) and flow cytometry. FIG. 5B shows the levels of internalized Alexa 488-labeled WT pertuzumab-MMAE (WT-MMAE), SG-MMAE, YS-MMAE, control antibody-MMAE (C-MMAE) or trastuzumab-DM1 (T-DM1) following 0.5, 4 and 20 hours incubation. Cell surface bound ADC was quenched using an Alexa 488-specific antibody. Error bars indicate standard deviation, with * indicating statistically significant differences (Student's t-test, $p<0.05$). The data show that for all cancer cell lines tested, SG-MMAE and YS-MMAE accumulate to higher levels relative to WT-MMAE and T-DM1. The delivery of the ADCs to lysosomes in MDA-MB-453 cancer cells, that express intermediate levels of HER2 (FIG. 5A) was also investigated using fluorescence microscopy (FIG. 5C). Lysosomes in MDA-MB-453 cells were labeled by pulse chasing with Alexa 647-labeled dextran. Cells were subsequently incubated with 10 nM Alexa 488-labeled ADCs for 20 hours, washed and surface signal quenched using an Alexa-488 specific antibody. The microscopy images (size bar=3 μm) show substantially higher levels of accumulation of SG-MMAE and YS-MMAE in lysosomes compared with WT-MMAE or T-DM1.

Figure 6:
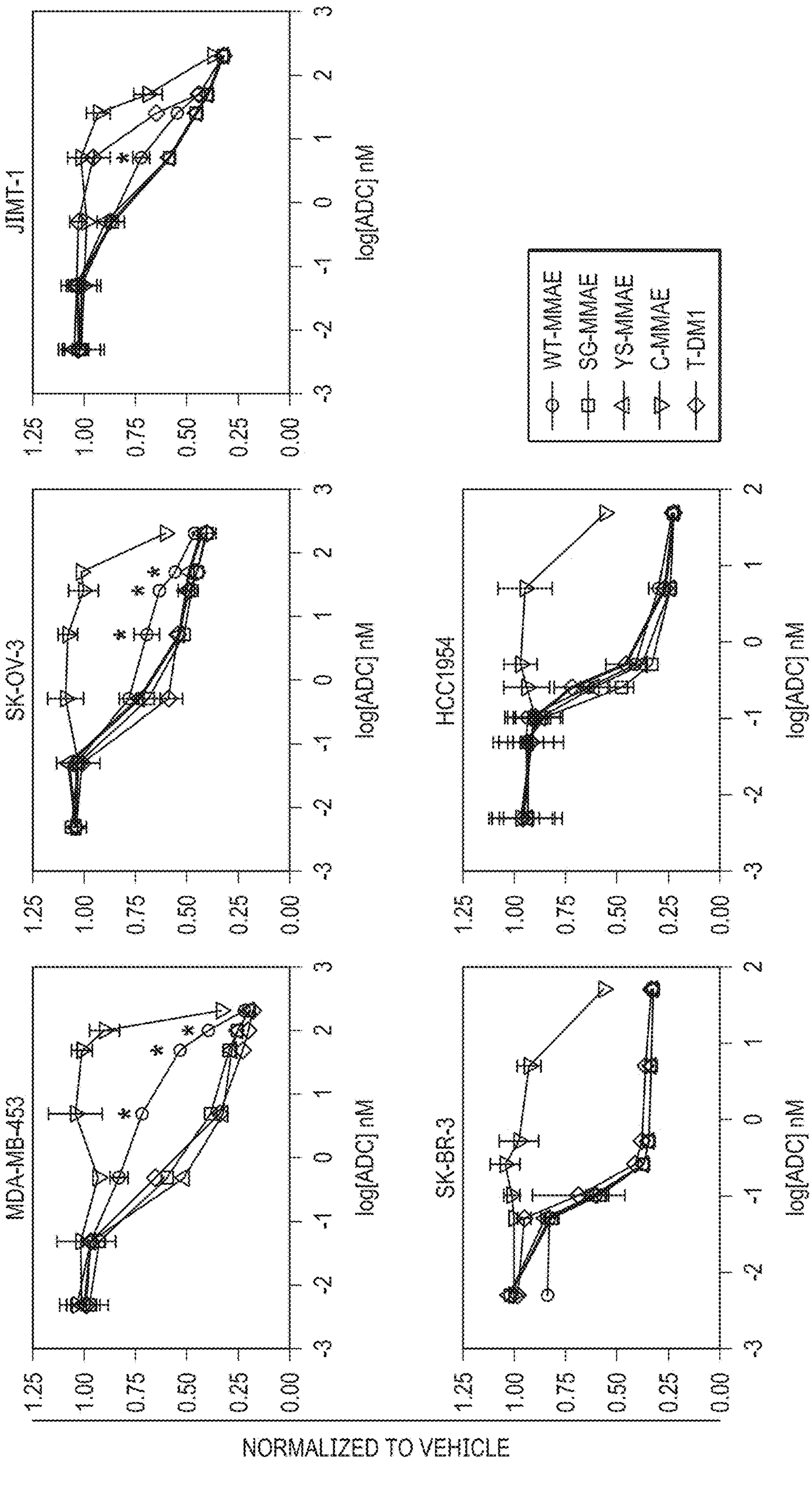
FIG. 6 shows graphs reporting exemplary data for the effects of the HER2-targeting endolysosomal targeting conjugates and control MMAE-conjugate on the viability of tumor cells.

Example 4. Inhibition of Growth and Survival of HER2-Positive Cells by HER2-ADCs Analyses of the effects of the HER2-ADCs on the viability of HER2+ breast cancer cells show that SG-MMAE and YS-MMAE are more effective in reducing the viability of MDA-MB-453, SK-OV-3 and JIMT-1 cells than WT pertuzumab conjugated to MMAE (WT-MMAE) or T-DM1 (FIG. 6). Error bars indicate standard deviation, with * indicating statistically significant differences (Student's t-test, $p<0.05$).

Example 5. Inhibition of Tumor Growth by HER2-ADCs in Mouse Xenograft Models

Figure 7A:
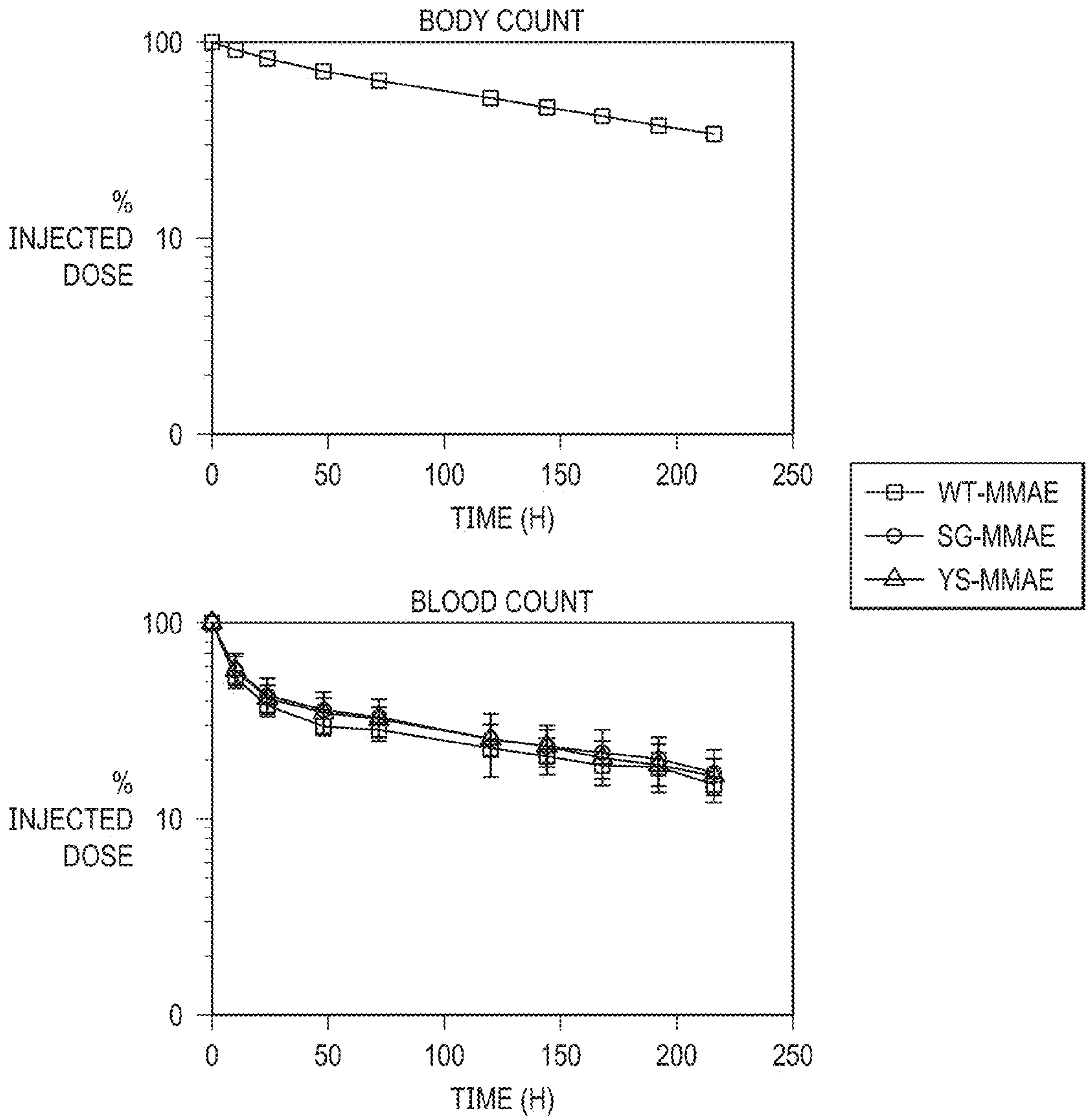
FIG. 7A shows graphs reporting exemplary whole body counts and blood counts against time for exemplary HER2-targeting endolysosomal targeting conjugates in mice.
Figure 7B:
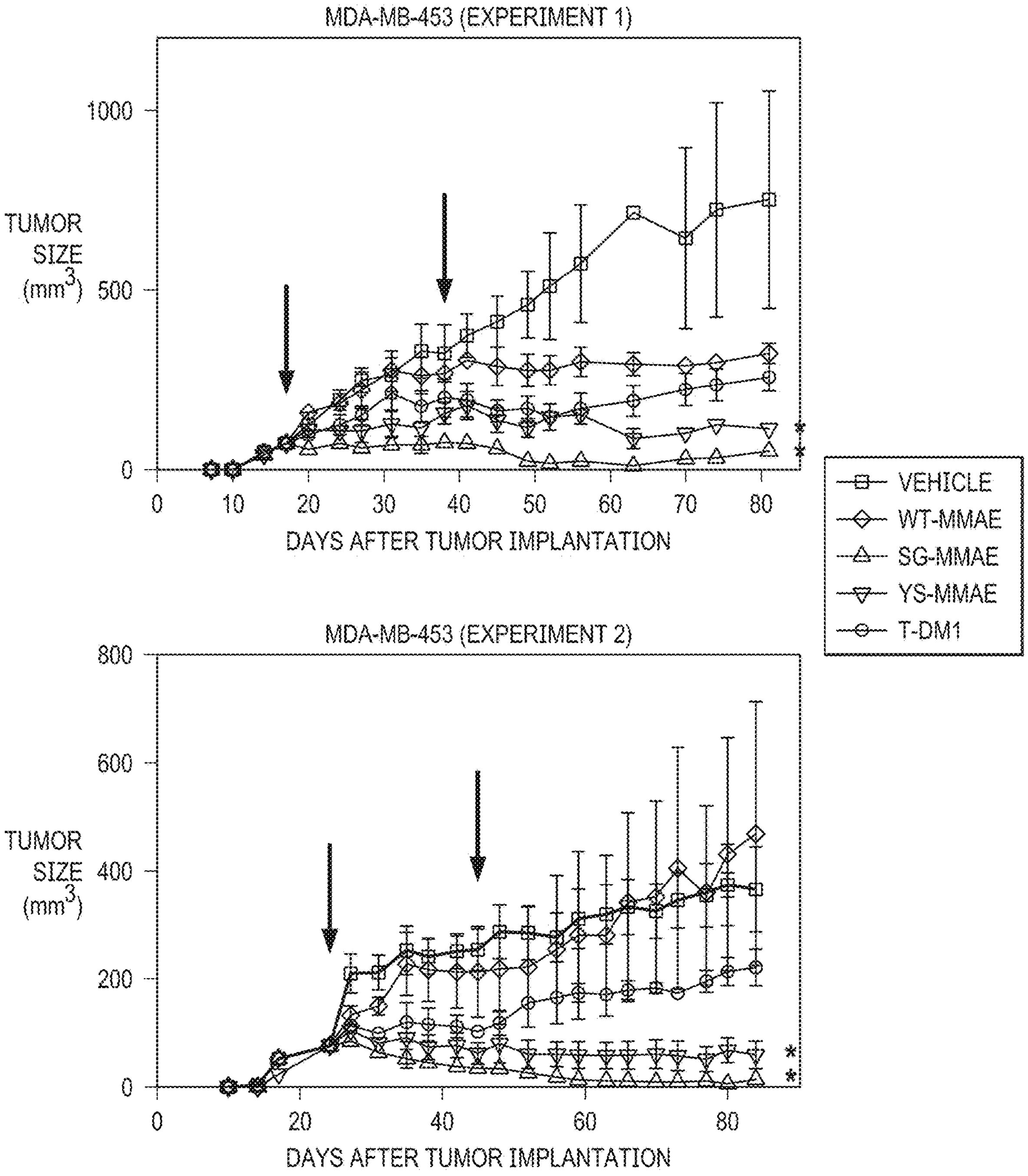
FIG. 7B shows graphs reporting exemplary data for the effects of exemplary HER2-targeting endolysosomal targeting conjugates and control proteins on tumor growth (MDA-MB-453 cells) in mice.

Analyses of the pharmacokinetics of HER2-ADCs (WT-MMAE, SG-MMAE and YS-MMAE) demonstrates that the in vivo persistence of SG-MMAE and YS-MMAE in BALB/c SCID mice is similar to that of WT-MMAE (FIG. 7A; n=5 mice/group). ADCs were radiolabeled with 125-I, injected into mice (5 mice/group) and remaining radioactivity in blood and at the whole body level determined at the indicated time points. Therapy studies with the ADCs in BALB/c SCID mice bearing MDA-MB-453 xenografts (intermediate HER2 expression levels) show that SG-MMAE and YS-MMAE are more effective in treatment than WT-MMAE or T-DM1 (FIG. 7B). Mice were treated with two doses of 2 mg/kg ADC at days 17 and 38 (experiment 1; indicated by arrows) or days 24 and 45 (experiment 2; indicated by arrows). Error bars indicate standard errors, with statistically significant difference SG-MMAE vs. WT-MMAE or T-DM1; YS-MMAE vs. WT-MMAE or T-DM1) at treatment endpoints are indicated by * (Student's t-test; $p<0.05$; n=5-8 mice/group). Collectively, the data indicate that SG-MMAE and YS-MMAE have favorable pharmacokinetics and are also more effective than their parent, WT pertuzumab and clinically approved HER2-specific ADC, T-DM1, in reducing tumor growth.

Figure 8A:
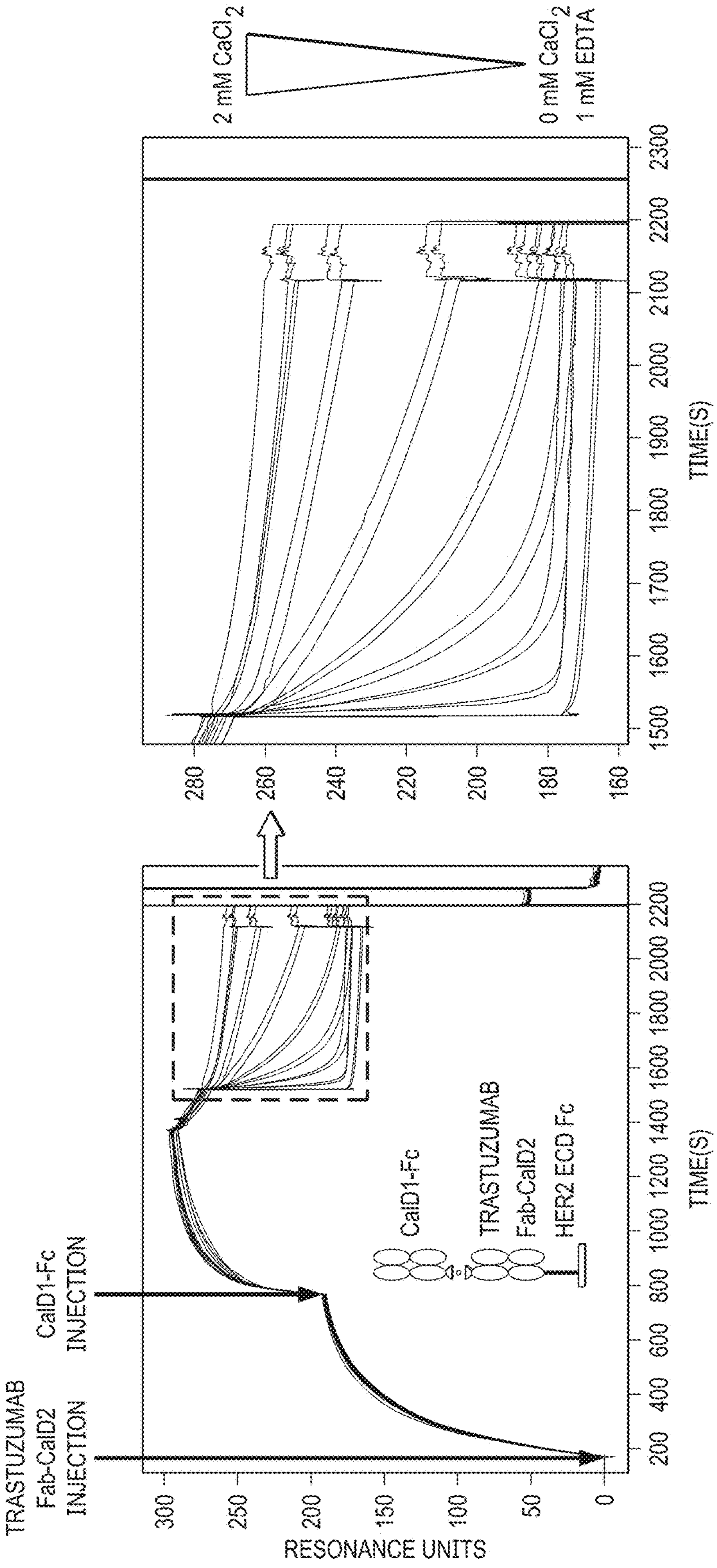
FIG. 8A shows exemplary binding data for the interaction of exemplary HER2-targeting fusion proteins comprising calbindin domains 2 and 1 fused to antibody Fab (HER2-specific) and Fc fragments, respectively.
Figure 8B:
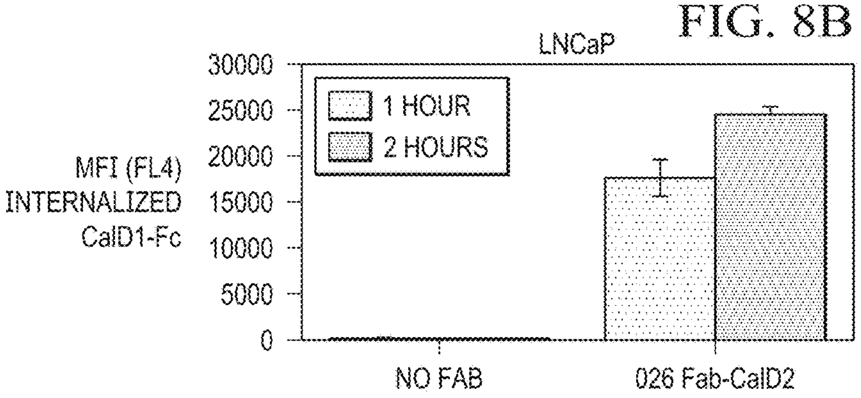
FIG. 8B shows graphs of exemplary data for flow cytometry analyses of internalization and accumulation of exemplary prostate-specific membrane antigen (PSMA)-targeting antibodies comprising calbindin domains 2 and 1 fused to antibody Fab (026, PSMA-specific) and Fc fragments, respectively, in prostate cancer cells.

Example 6. Generation and Characterization of ADCs with Calcium Dependent Association The interaction of a HER2-specific Fab fragment (derived from trastuzumab) fused at the C-terminus of the CH1 domain via a hinge-SGG linker to domain 2 of calbindin D9K (CalD2) (trastuzumab Fab-CalD2; SEQ ID NO: 18, associated with trastuzumab light chain, SEQ ID NO: 20) and a human-IgG1-derived Fc fragment fused with domain 1 of calbindin D9K (CalD1-Fc; SEQ ID NO: 22) using surface plasmon resonance demonstrates $Ca^{2+}$-dependent association (FIG. 8A). The sensorgrams show binding of 100 nM trastuzumab Fab-CalD2 to immobilized HER2-ECD, followed by injection of 100 nM CalD1-Fc and then buffer with different concentrations of $Ca^{2+}$ ranging from 0-2 mM (boxed region, shown enlarged in right panel). The data show representative sensorgrams, demonstrating that as the $Ca^{2+}$-concentration decreases, the dissociation of the Fab-CalD2 and CalD1-Fc increases. In additional experiments, a fusion protein including the PSMA-specific VH-CH1 domains (PRGX1-XG1-029; abbreviated to 026; Schülke, N., Varlamova, O. A., Donovan, G. P., Ma., D., Gardner, J. P., Morrissey, D. M., Arrigale, R. R., Zhan, C., Chodera, A. J., Surowitz, K. G., Maddon, P. J., Heston, W. D. W., Olson, W. C. (2003) The homodimer of prostate-specific membrane antigen is a functional target for cancer therapy. Proc. Natl. Acad. Sci., USA, 100, 1259-12595) fused at the C-terminus via a hinge-SGG linker to CalD2 (026-CalD2; SEQ ID NO: 24) was also generated. In association with the 026 light chain (SEQ ID NO: 26), this CalD2 fusion forms Fab-CalD2. Flow cytometry analyses demonstrated that the accumulation of fluorescently labeled CalD1-Fc (SEQ ID NO: 22) within PSMA-expressing LNCaP cells was enhanced when cells were treated with a mixture (100 nM each) of 026-CalD2 and Alexa 647-labeled CalD1-Fc compared with treatment with 100 nM Alexa 647-labeled CalD1-Fc without added 026-CalD2 (no Fab') (FIG. 8B).

Example 7. Generation and Characterization of PS-Targeting Agents

Figure 9:
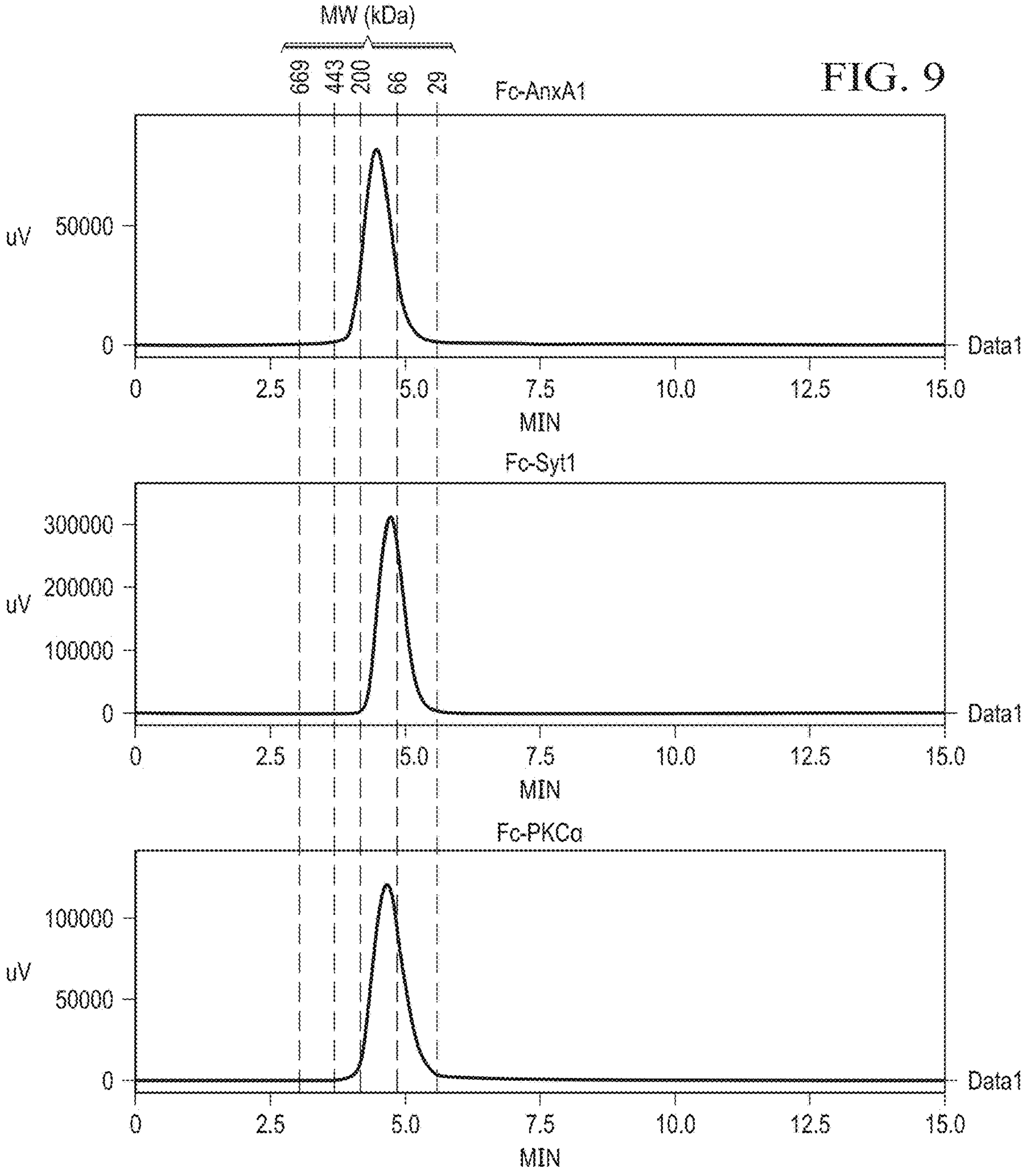
FIG. 9 shows graphs reporting exemplary gel filtration chromatography analyses of exemplary PS-targeting Fc fusion proteins.
Figure 10A:
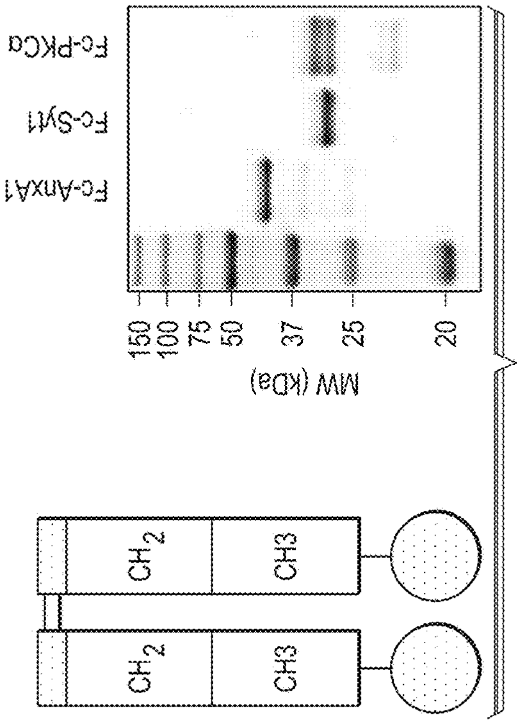
FIG. 10A is a schematic representation and analysis of exemplary PS-targeting agents (Fc fusions comprising human IgG1-derived Fc linked to PS-targeting proteins, AnxA1, C2A domain of synaptotagmin 1 (Syt1) and PKCα). Filled circles and rectangles represent the PS-targeting domains and IgG1 hinge region, respectively. Right panel shows SDS-PAGE analyses of the endolysosomal targeting agents, with molecular weights (MW) shown in kDa on the left.
Figure 10B:
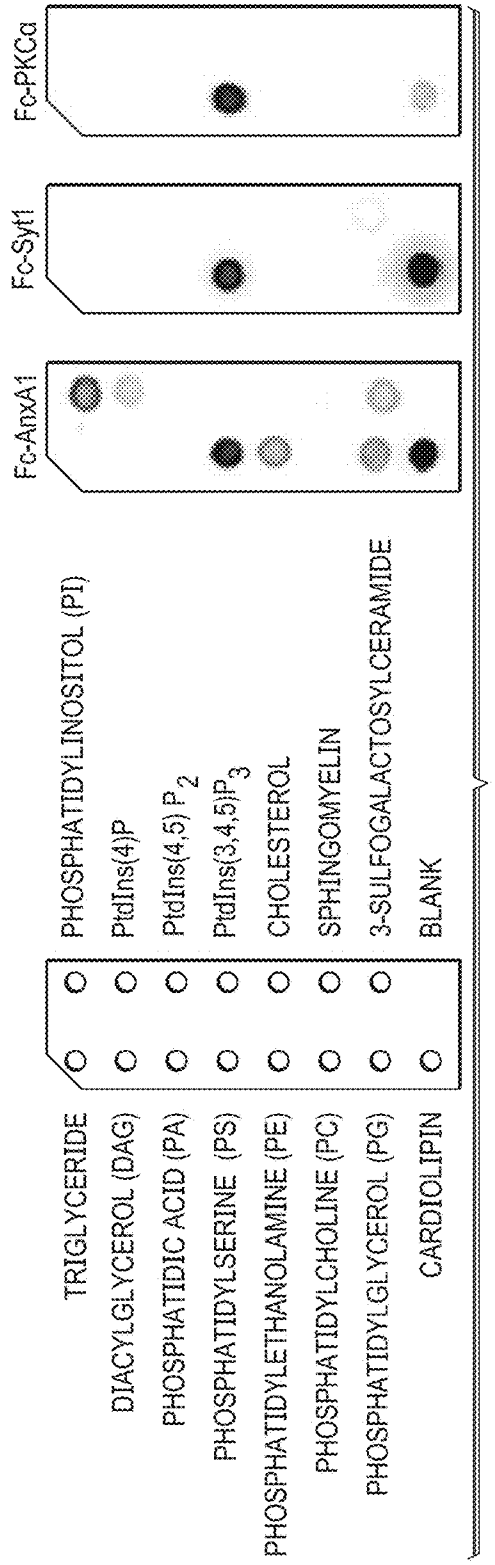
FIG. 10B shows exemplary lipid binding profiles of exemplary PS-targeting agents using lipid-coated nitrocellulose membranes.

A panel of PS-targeting agents was generated by fusing the Fc region of human IgG1 to the following PS-binding domains: core domain of Annexin A1 (AnxA1), C2A domain of Synaptotagmin 1 (Syt1) and C2 domain of PKCα. The resulting fusion proteins were designated Fc-AnxA1, Fc-Syt1 and Fc-PKCα, respectively. The PS-targeting agents were purified as homodimers (FIG. 9, FIG. 10A; assessed using SDS-PAGE and HPLC), and bound to PS in a lipid binding assay using lipid strips (FIG. 10B). They also bound to cardiolipin, which is located on the inner mitochondrial membrane of eukaryotic cells and therefore not relevant to targeting. Fc-AnxA1 exhibited a broad lipid binding profile and bound both neutral and negatively-charged lipids (FIG. 10B). Importantly, none of the PS-binding agents bound phosphatidylcholine (PC) and sphingomyelin, lipids that are present in the plasma membrane outer leaflet.

Figure 10C:
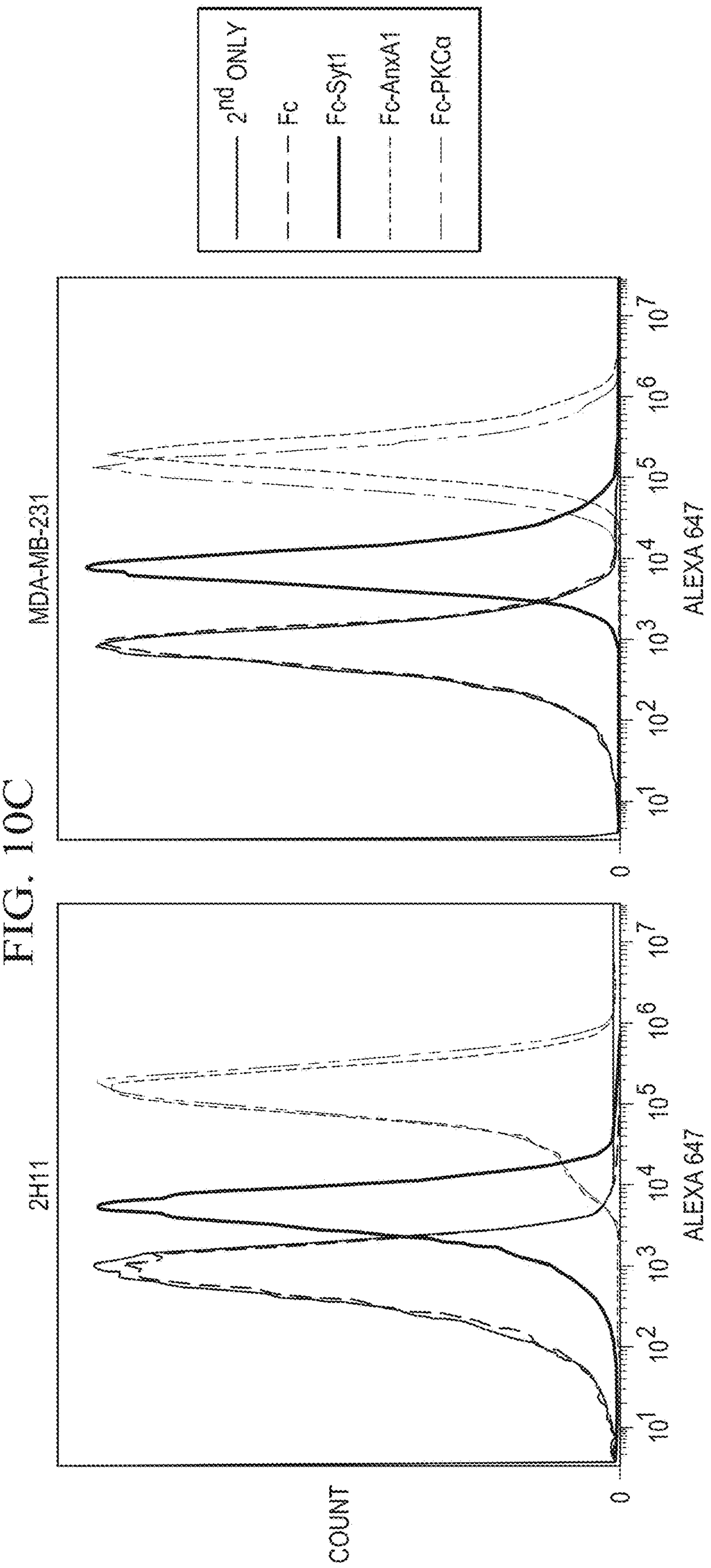
FIG. 10C shows graphs reporting exemplary binding of exemplary PS-targeting agents to PS-positive 2H11 and MDA-MB-231 cells using flow cytometry analysis.

The tumor endothelial cell line 2H11 was used to investigate the ability of the PS-binding agents to interact with lipids on the cell surface. Binding of fluorescent Annexin V showed that these cells exposed PS and that PS exposure increased following docetaxel treatment. Flow cytometry analyses showed that all PS-binding agents interacted with PS-positive cells, with Fc-Syt1 showing lower levels of binding (FIG. 10C; 2nd only indicates secondary antibody control, and Fc indicates Fc fragment without PS-targeting protein or domain).

Figure 10D:
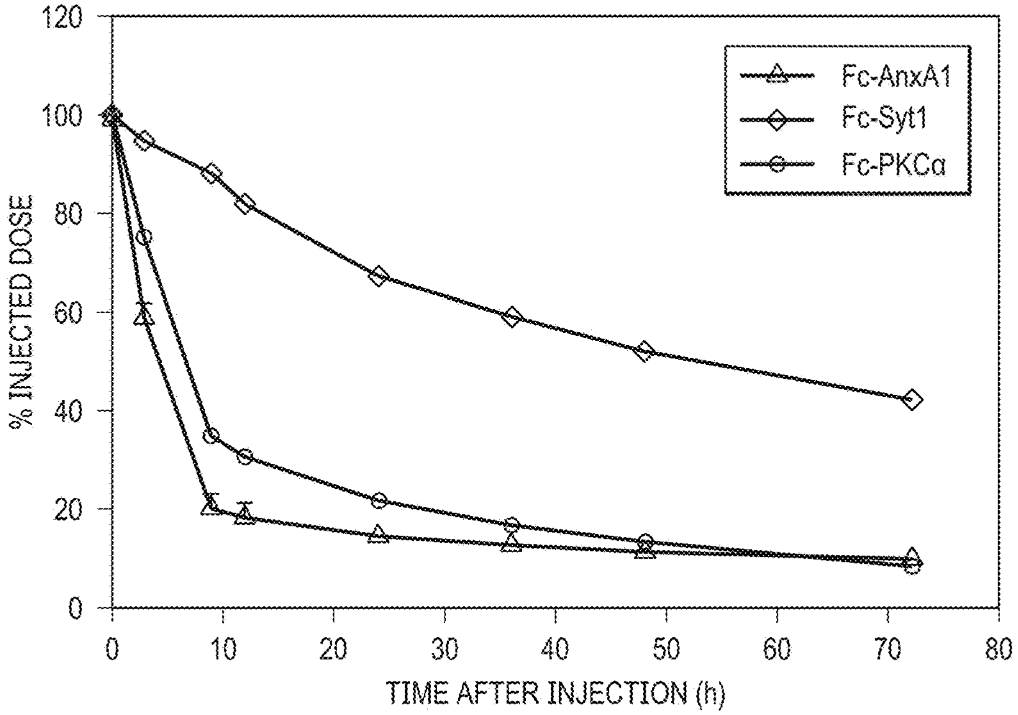
FIG. 10D shows graphs reporting exemplary whole body counts vs. time of exemplary PS-targeting agents.
Figure 10E:
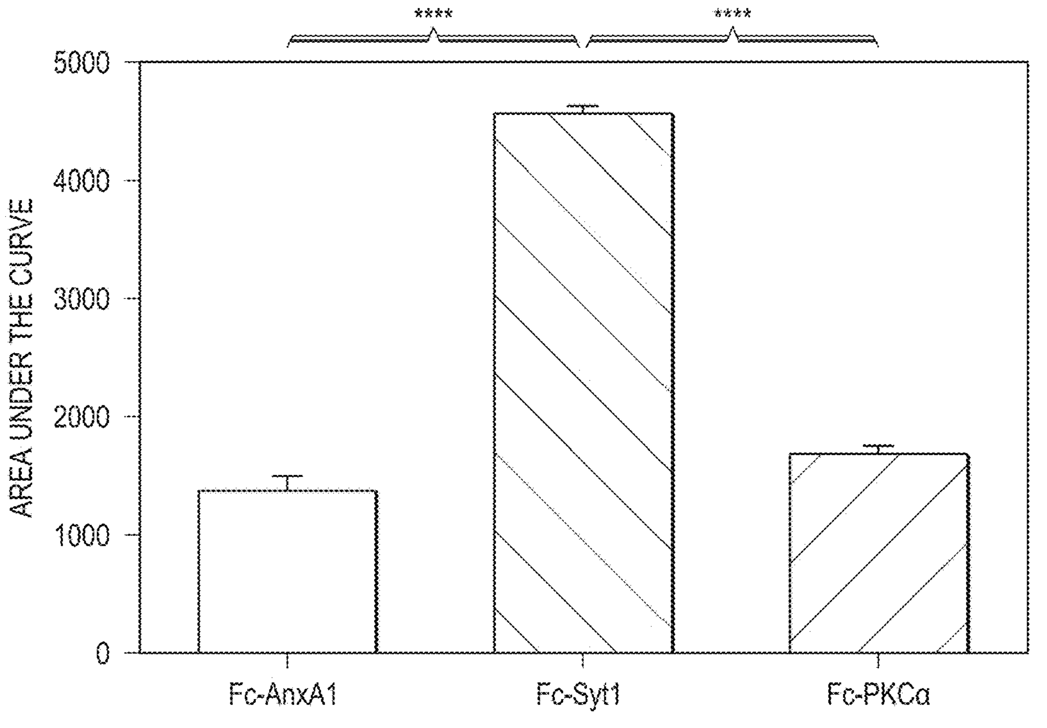
FIG. 10E shows graphs reporting exemplary areas under curves for the data shown in FIG. 10D for exemplary PS-targeting agents.
Figure 10F:
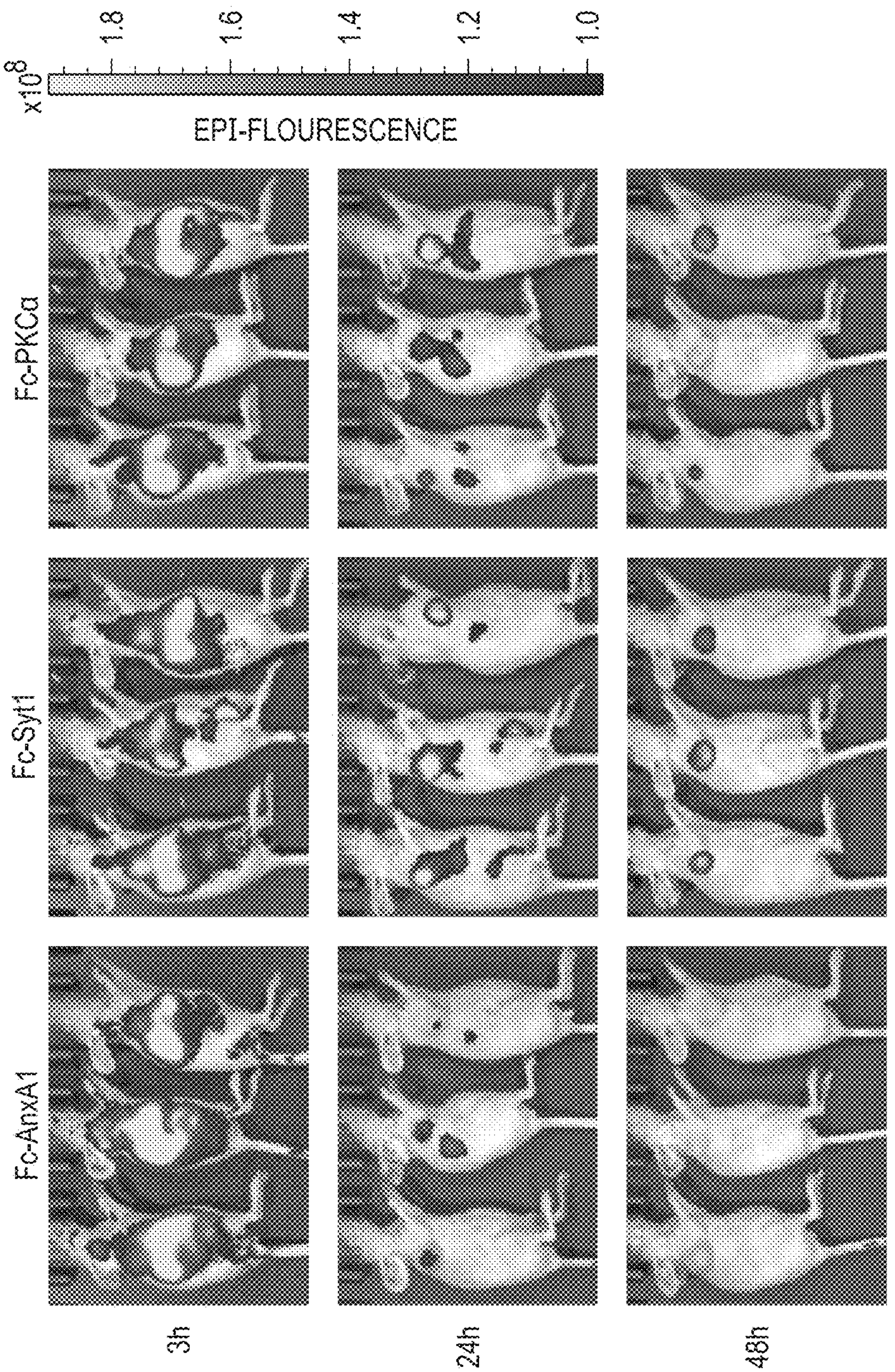
FIG. 10F shows exemplary whole body images of tumor-bearing mice injected with exemplary PS-targeting agents labeled with a near infrared dye (IRDye800CW)
Figure 10G:
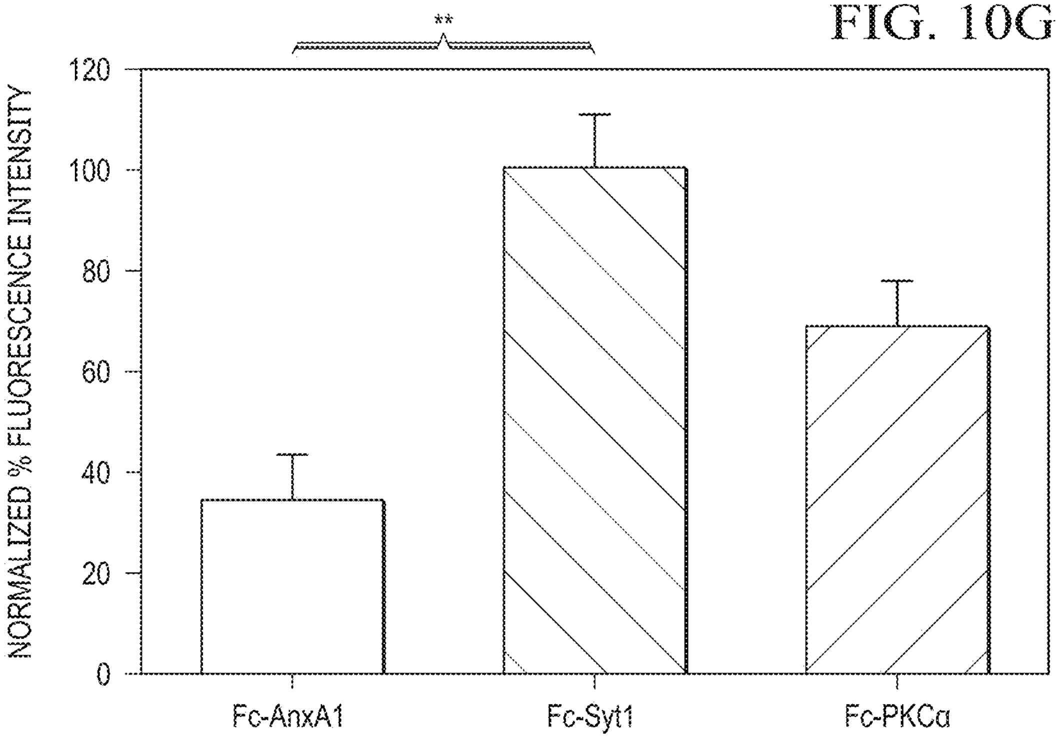
FIG. 10G shows graphs reporting exemplary tumor-associated fluorescence for exemplary PS-targeting agents labeled with a near infrared dye (IRDye800CW) for the images shown in FIG. 10F.
Figure 10H:
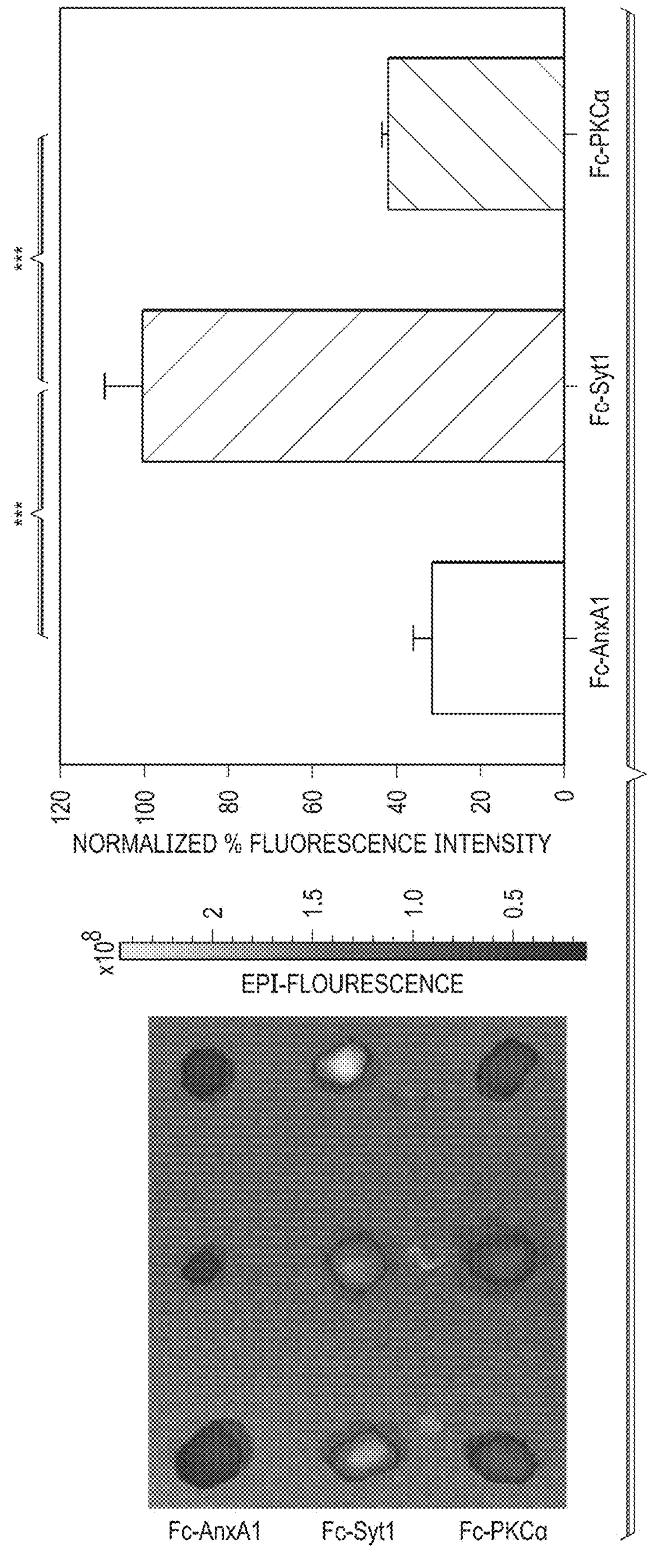
FIG. 10H shows exemplary images of tumors and a graph reporting mean dye intensities for exemplary PS-targeting agents labeled with a near infrared dye (IRDye800CW) following 48 hours of injection into tumor-bearing mice.

The pharmacokinetic behavior and tumor localization of the three PS-binding agents in mice were evaluated to determine which recombinant proteins were suitable for further development as protein-drug conjugates (PDCs). Pharmacokinetic studies of the PS-binding agents revealed that Fc-Syt1 had a significantly longer half-life in mice (FIG. 10D, E). Whole body counts following injection of radioiodinated PS-targeting fusion proteins into mice (n=5 mice/group) are shown in the graph in FIGS. 10D, and 10E shows the corresponding areas under the curve for each radiolabeled protein. In addition, proteins were labeled with the residualizing dye, IRDye800CW, and injected (i.v.) into female nude mice bearing MDA-MB-231 xenografts (n=3 mice/group) and imaged at the indicated time points (FIG. 10F), with tumor fluorescence quantitated in extracted tumors at 48 hours post-injection (FIG. 10G). Similar experiments were carried out in tumor-bearing BALB/c SCID mice (n=3 mice/group) and 48 hours later, tumors were excised and dye levels determined (FIG. 10H). Amongst the three PS-specific agents, Fc-Syt1 exhibited the highest level of tumor localization. Statistically significant differences for FIGS. 10E, 10G and 10H were analyzed using one-way ANOVA followed by Tukey post-hoc test (, $p<0.01$; *, $p<0.001$; ****, $p<0.0001$), and error bars represent SEM.

Figure 11A:
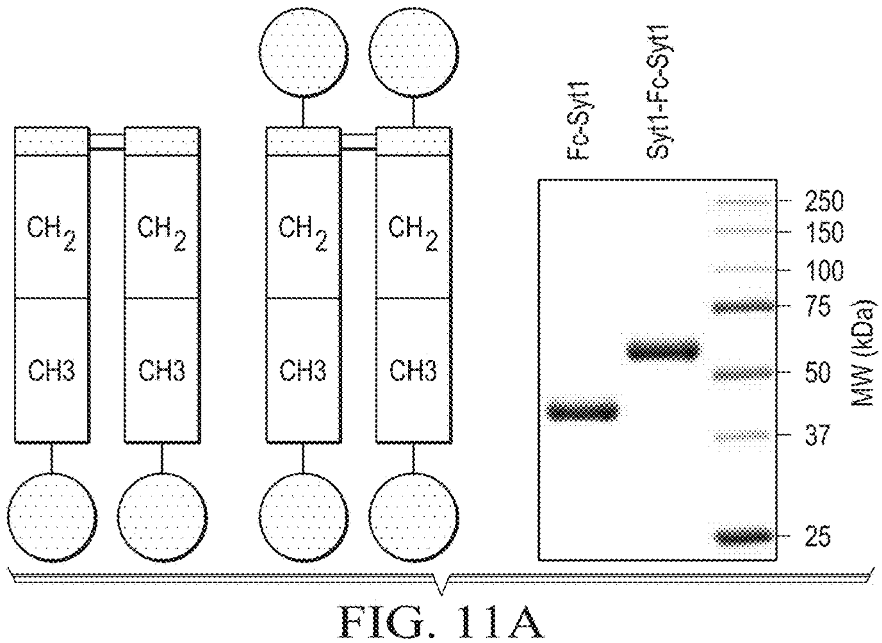
FIG. 11A is a schematic representation and analysis of exemplary bivalent and tetravalent PS-targeting agents with filled circles representing the Syt1 C2A domain (left panel). Right panel shows SDS-PAGE analyses of the Syt1-Fc fusions, with molecular weights (MW) shown in kDa on the right.
Figure 11B:
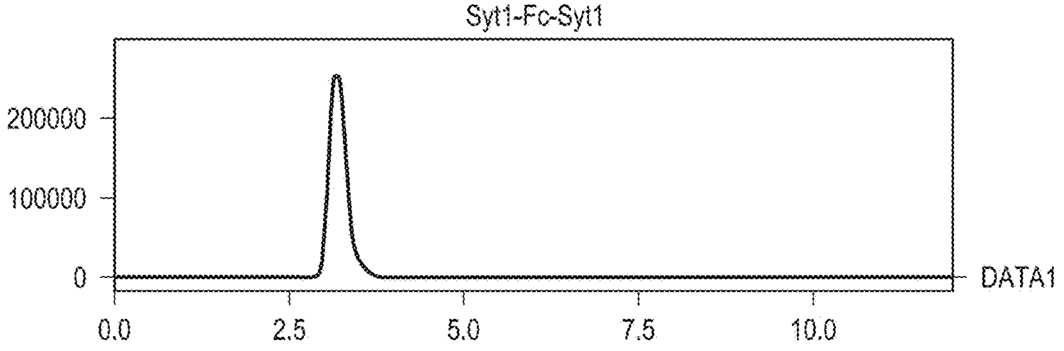
FIG. 11B shows exemplary gel filtration chromatography analyses of an exemplary PS-targeting Fc-fusion proteins containing four Syt1 molecules per Fc fragment.
Figure 11C:
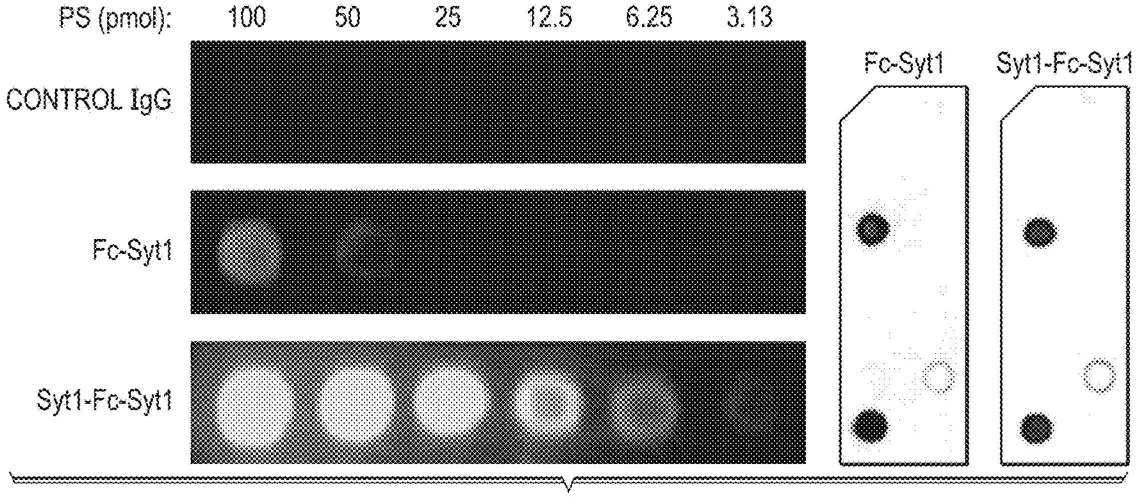
FIG. 11C shows exemplary binding of exemplary PS-targeting agents to PS on PS-coated nitrocellulose membranes and to lipid-coated nitrocellulose membranes.
Figure 11D:
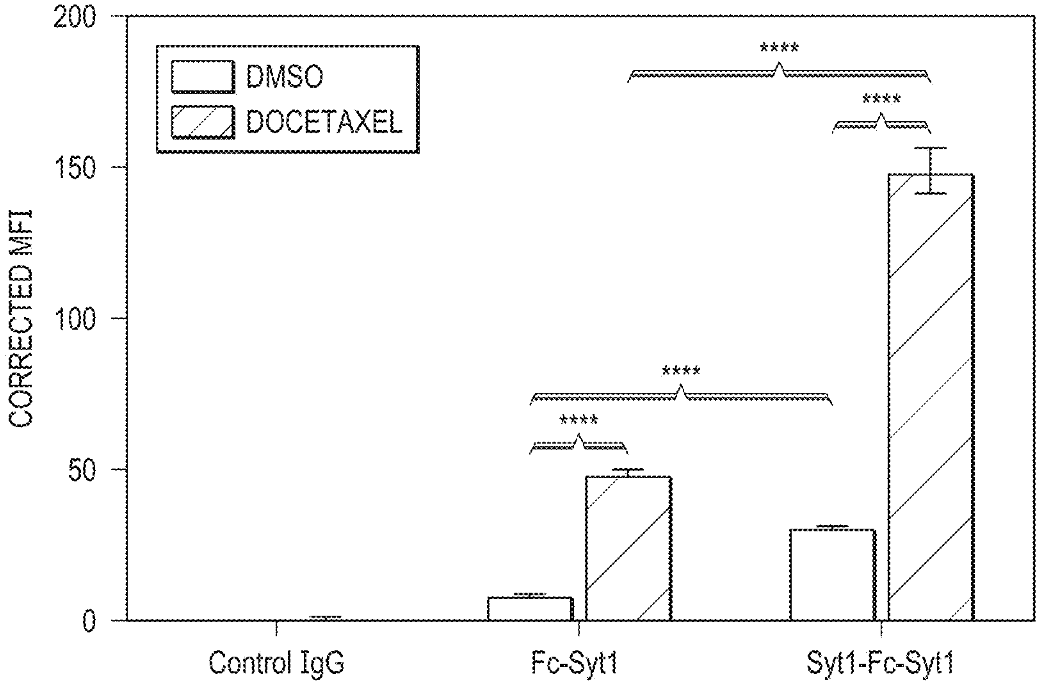
FIG. 11D shows graphs reporting exemplary binding of exemplary PS-targeting agents and control protein to cells with exposed PS.

Example 8. Tetravalency of the PS-Targeting Agent Increases Binding and Internalization into Target Cells In several receptor systems it has been shown that multivalent ligands, or mixtures of cross-linking ligands such as antibodies, promote receptor internalization and degradation. To study the role of avidity in the behavior of PS-targeting PDCs, the tetravalent Syt1-Fc-Syt1 that contains four Syt1 C2A domains was generated (shown schematically in FIG. 11A). The tetravalent protein was purified as homodimers (FIG. 11A, B; assessed using SDS-PAGE and HPLC). Binding analyses using lipids immobilized on nitrocellulose demonstrated that Syt1-Fc-Syt1 had higher affinity/avidity for PS and the same lipid selectivity as its bivalent parent, Fc-Syt1 (FIG. 11C). Consistent with the binding data shown in FIG. 11C, the tetravalent Syt1-Fc-Syt1 bound to 2H11 cells at significantly higher levels when analyzed using flow cytometry (FIG. 11D).

Figure 11E:
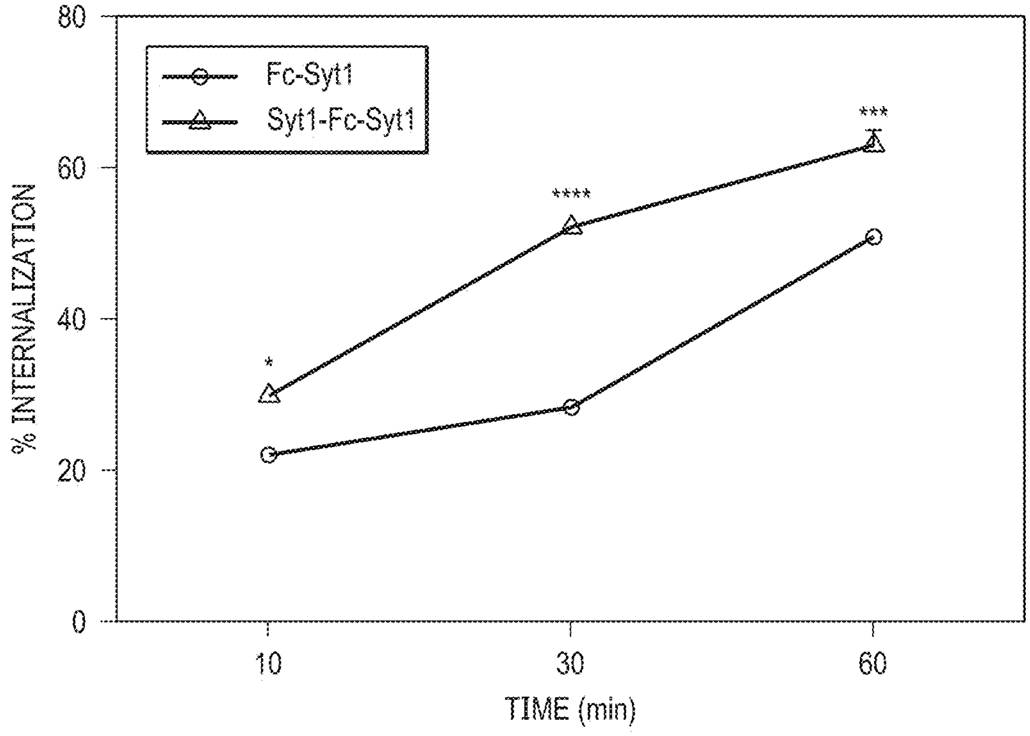
FIG. 11E shows graphs reporting exemplary internalization of exemplary PS-targeting agents into cells with exposed PS.
Figure 11G:
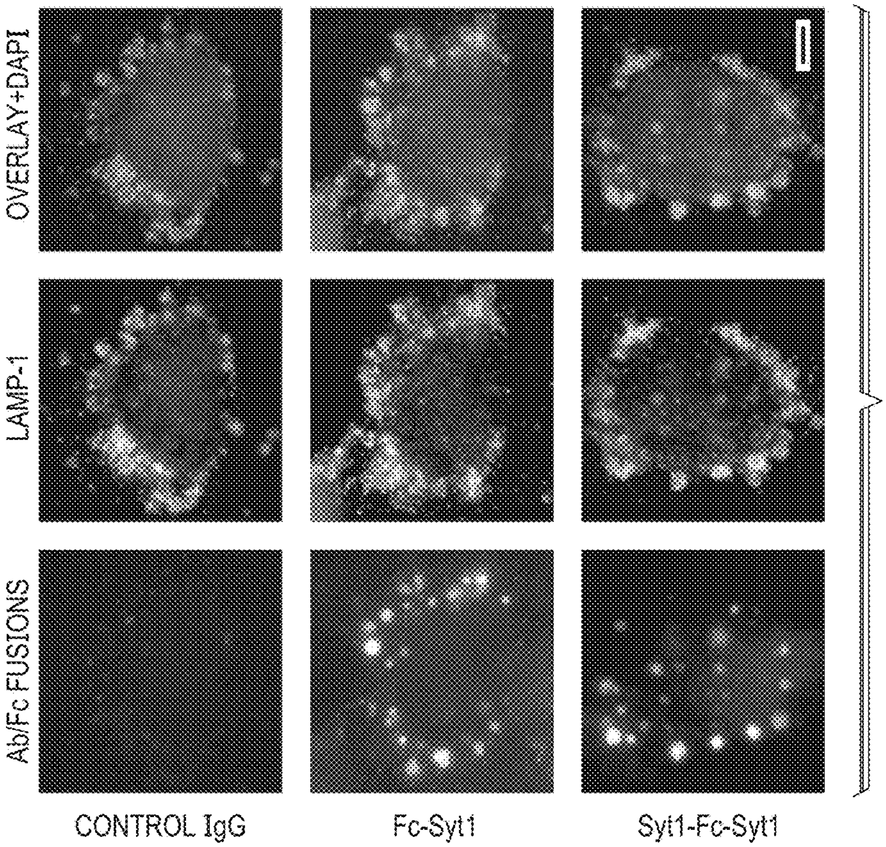
FIG. 11G shows another series of exemplary microscopic images of exemplary PS-targeting agents and control protein in tumor cells (MDA-MB-231) with the lysosomes in the cells labeled with LAMP-1-specific antibody.
Figure 11F:
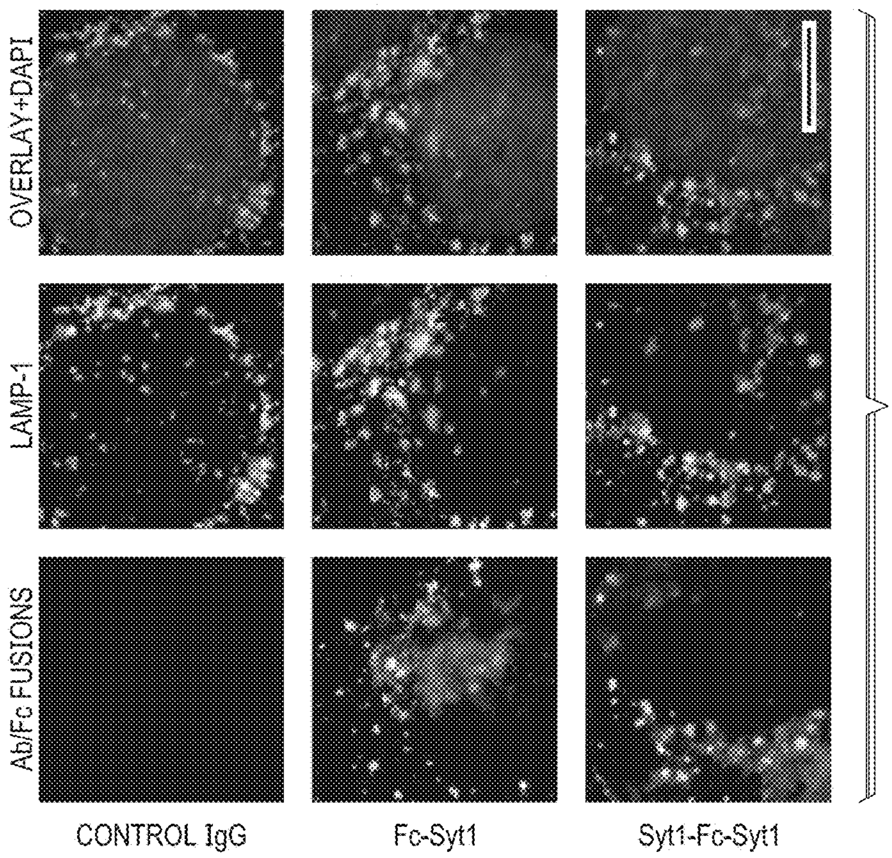
FIG. 11F shows a series of exemplary microscopic images of exemplary PS-targeting agents and control protein in endothelial cells (2H11) with the lysosomes in the cells labeled with LAMP-1-specific antibody.

The internalization of Fc-Syt1 and Syt1-Fc-Syt1 using Alexa 647-labeled proteins was also studied. 2H11 cells were incubated with labeled Fc-Syt1 and Syt1-Fc-Syt1 on ice at different concentrations to achieve similar surface binding followed by incubation at 37° C. to allow internalization for different times. Surface-bound proteins were stripped off with EDTA (due to the $Ca^{2+}$-dependence of binding) and internalized levels (resistant to stripping) were determined by flow cytometry. These studies indicated that although both proteins efficiently accumulated within cells, the tetravalent Syt1-Fc-Syt1 was internalized more quickly (FIG. 11E). For FIGS. 11D and 11E, statistically significant differences were analyzed using two-way ANOVA followed by Tukey post hoc test (*, $p<0.05$; , $p<0.01$; *, $p<0.001$; **, $p<0.0001$). Error bars in FIGS. 11D and 11**E represent SEM.

Fluorescent microscopy was also used to study the subcellular trafficking behavior of the Syt1-Fc fusion proteins. 2H11 and MDA-MB-231 cells were incubated with 50 nM PS-targeting agent or control IgG for 4 hours, followed by washing, fixation and staining with Cy3/Alexa 555-labeled anti-human IgG (H+L). The lysosomal marker, LAMP-1, was detected using a LAMP-1 specific antibody followed by Alexa 488-labeled secondary conjugate. Fc-Syt1 and Syt1-Fc-Syt1 were internalized and delivered into LAMP-1 positive lysosomes in 2H11 (FIG. 11F) and MDA-MB-231 (FIG. 11G) cells. Scale bars: 10 μm (F) and 5 μm (G).

Example 9. Calcium Sensing and Endosomal Release of PS-PDCs

Figure 12A:
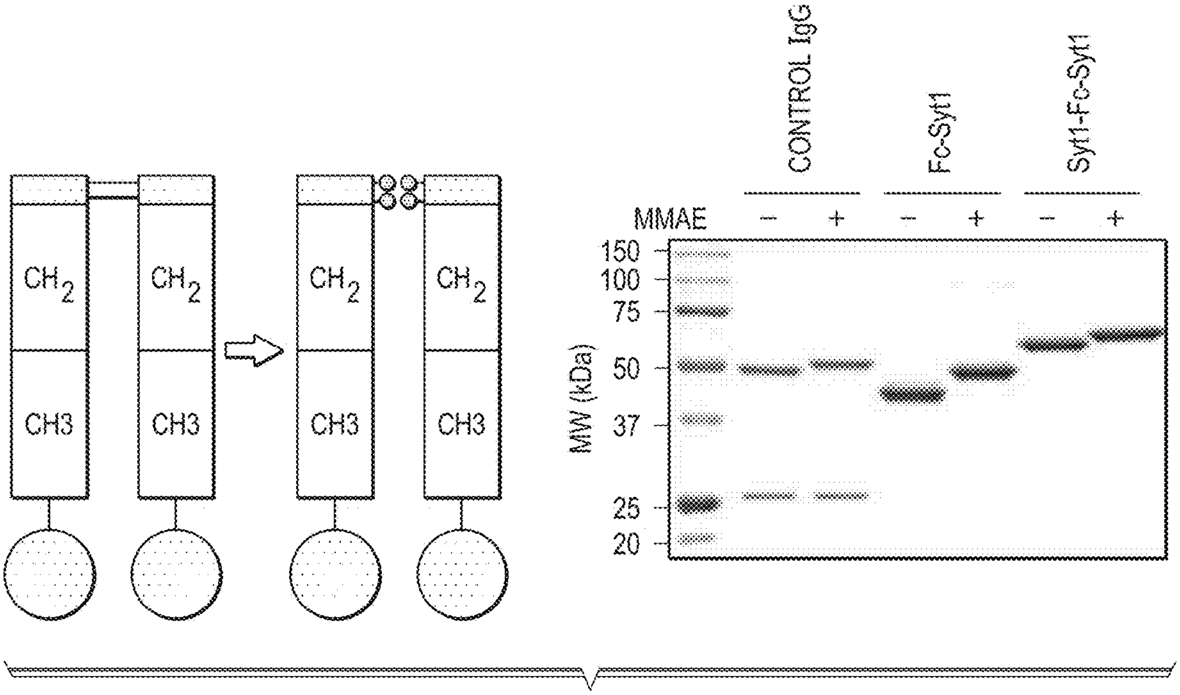
FIG. 12A shows a schematic representation and analysis of exemplary PS-targeting endolysosomal targeting conjugates (left panel), with the cargo component conjugated with MMAE (small filled circles). Right panel shows SDS-PAGE analyses of the unconjugated or MMAE-conjugated PS-targeting agents, with molecular weights (MW) shown in kDa on the left.
Figure 12D:
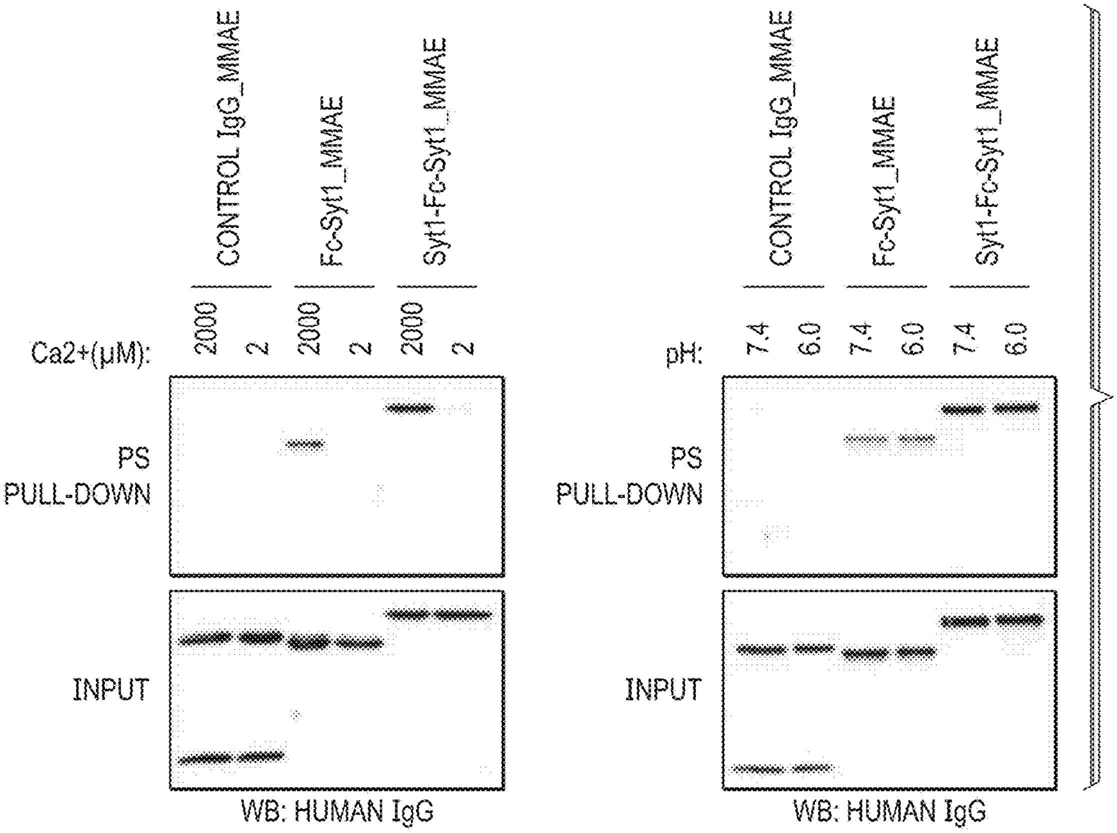
FIG. 12D shows an exemplary analysis of the binding of exemplary PS-targeting endolysosomal targeting conjugates to PS in the presence of the indicated $Ca^{2+}$ concentrations (left panel) or pH levels (right panel). Bead-associated proteins were analyzed using immunoblotting.
Figure 12B:
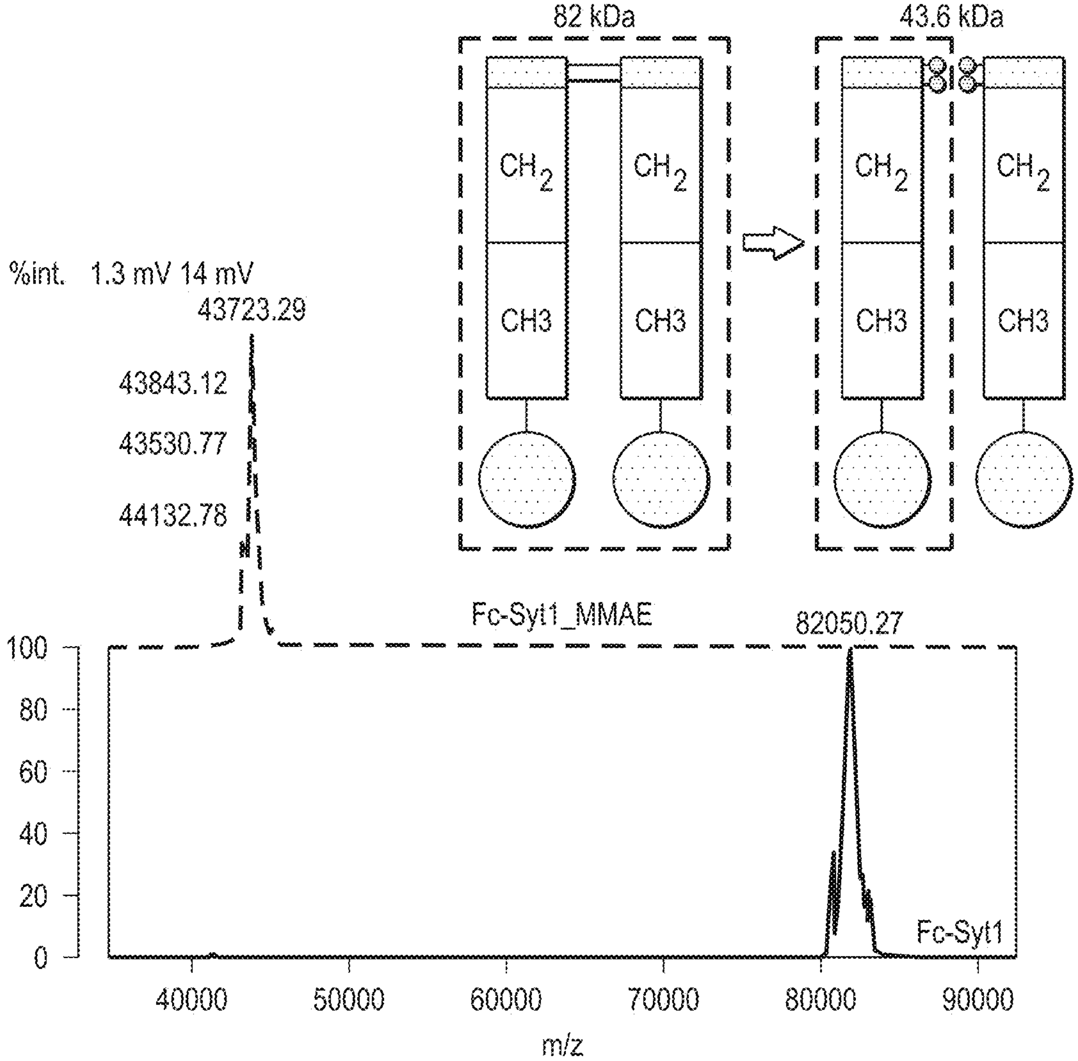
FIG. 12B shows exemplary mass spectrometry analyses of exemplary MMAE-conjugated PS-targeting endolysosomal targeting conjugates.
Figure 12C:
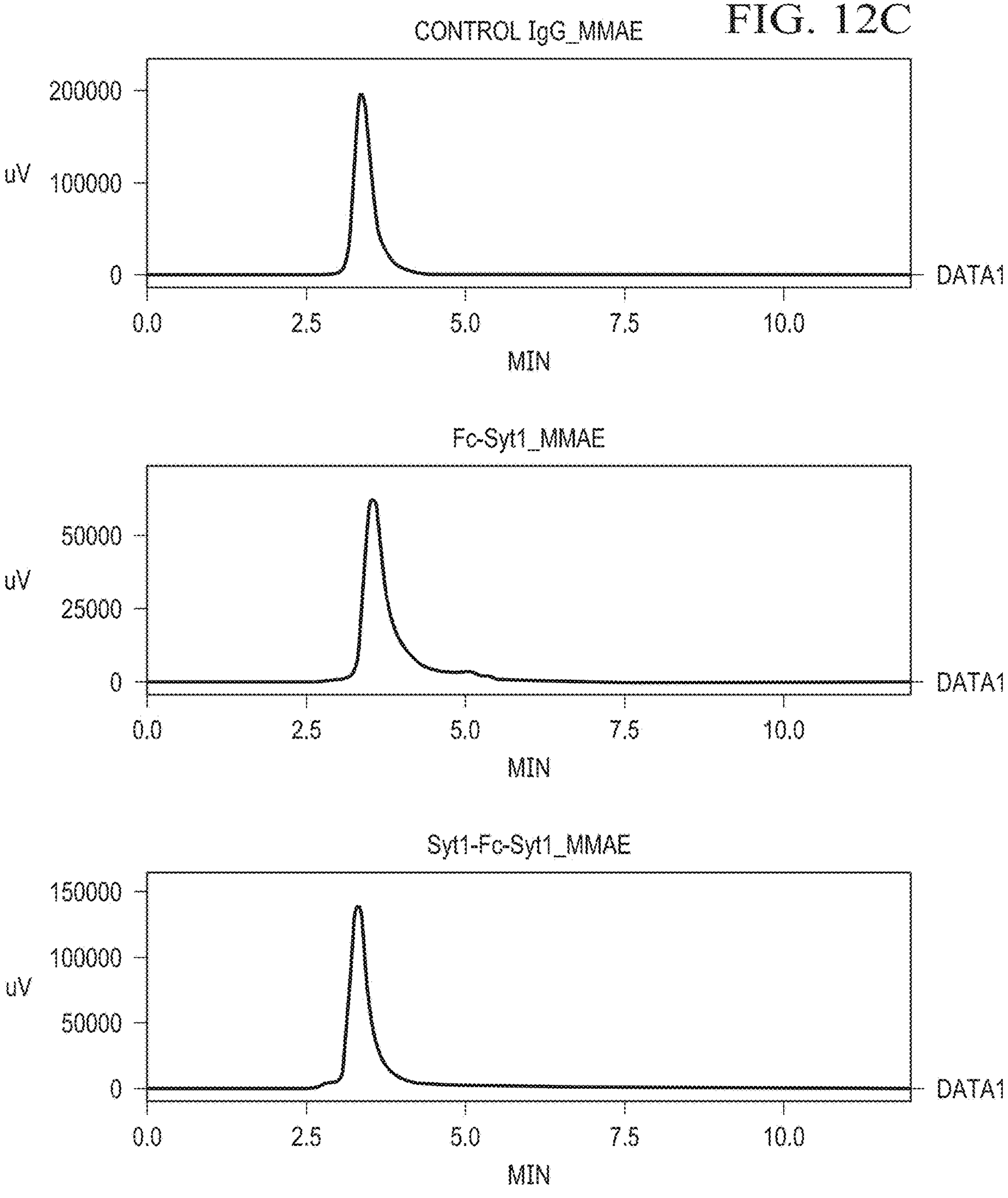
FIG. 12C shows exemplary gel filtration chromatography analyses of exemplary PS-targeting endolysosomal targeting conjugates.

The lysosomal trafficking and internalization behavior of Fc-Syt1 and Syt1-Fc-Syt1 indicated that they could be effective as delivery vehicles for conjugated drugs. Maleimidocaproyl-val-cit-PAB-MMAE was conjugated to hinge cysteines (FIG. 12A, left panel). For use as a negative control, maleimidocaproyl-val-cit-PAB-MMAE was conjugated to a hen egg lysozyme-specific human IgG1 in which the light/heavy chain-interacting cysteine residues were mutated to serine. SDS-PAGE analyses indicated that the conjugations had gone to completion and resulted in a drug to antibody ratio (DAR) of four (FIG. 12A, right panel). This was confirmed by MALDI-TOF mass spectrometry for Fc-Syt1_MMAE. Since complete conjugation disrupted the two disulfide bonds in the hinge region, a molecular weight of 43.6 kDa was obtained using mass spectrometry (FIG. 12B). This contrasted with the unconjugated or partially conjugated protein that retained two or one disulfide bonds respectively, resulting in an apparent molecular weight of approximately 82 kDa (FIG. 12B). Importantly, HPLC analyses demonstrated that the conjugation process did not lead to protein aggregation (FIG. 12C).

The Syt1 C2A domain requires $Ca^{2+}$ for PS binding. The lower $Ca^{2+}$ concentration in early/sorting endosomes (~2 μM) compared with the extracellular $Ca^{2+}$ levels (1-2 mM) suggests that following internalization, PS-targeting PDCs (PS-PDCs) will dissociate from the limiting membrane of these endosomes. This dissociation is expected to lead to improved lysosomal delivery. Both PS-PDCs containing Syt1 domains bound to PS-beads in buffer containing 2 mM $Ca^{2+}$, but no detectable interaction was observed when the $Ca^{2+}$ concentration was decreased to 2 μM (FIG. 12D). In addition, because the pH within sorting endosomes is acidic (pH 6.0-6.5), the effect of pH on PDC:PS interactions was analyzed. Both PDCs bound to PS at similar levels in the pH range 6.0-7.4 (FIG. 12D). For FIG. 12D, bead-associated proteins were analyzed using immunoblotting and detection with goat anti-human IgG (H+L) conjugated with horseradish peroxidase.

Figure 13A:
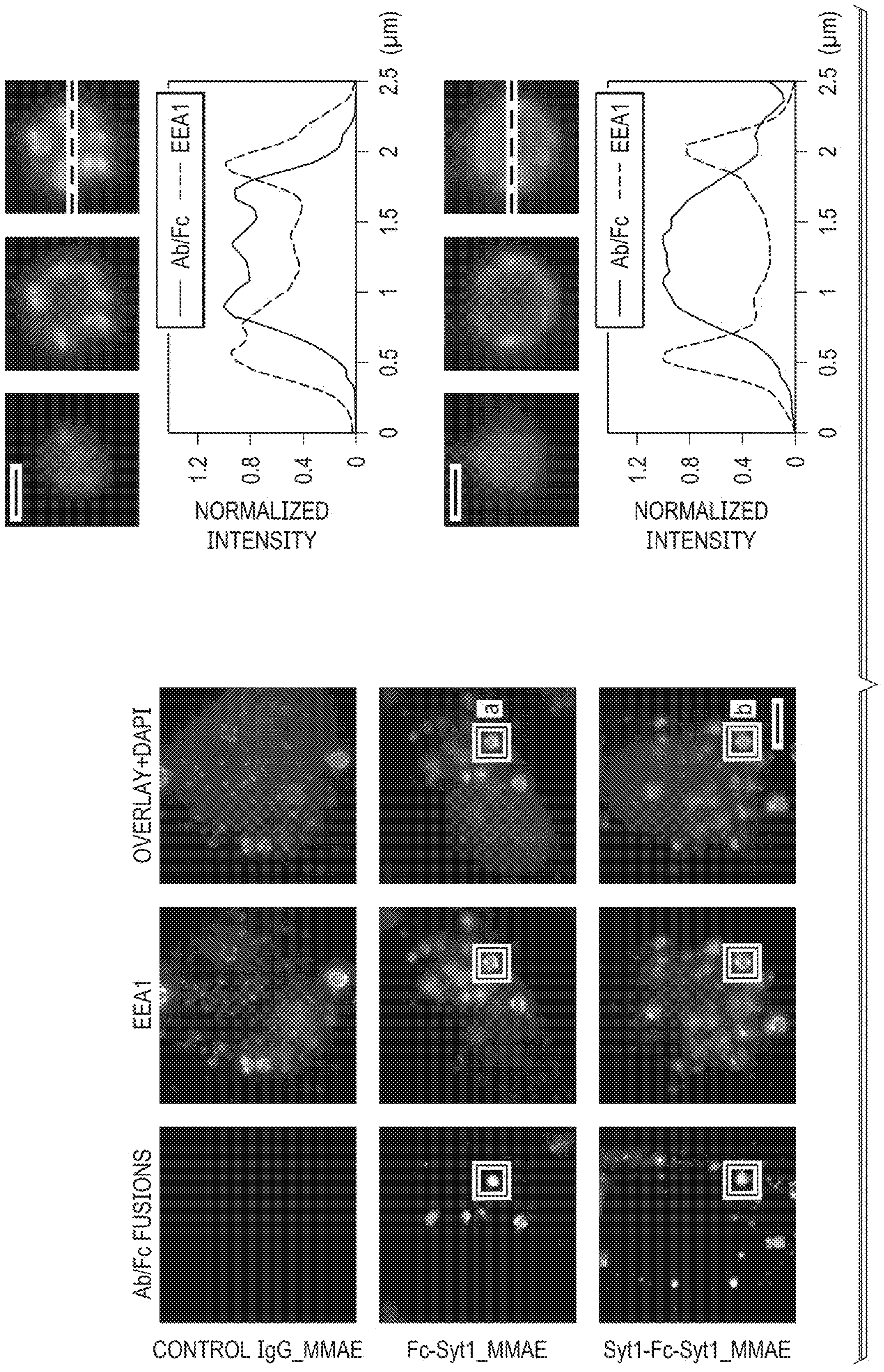
FIG. 13A shows an exemplary series of microscopic images of exemplary PS-targeting endolysosomal targeting conjugates and control MMAE-conjugate in tumor cells (MDA-MB-231) with the early endosomes in the cells labeled with EEA-1-specific antibody. Specific endosomes are cropped and enlarged (labeled a and b)
Figure 13B:
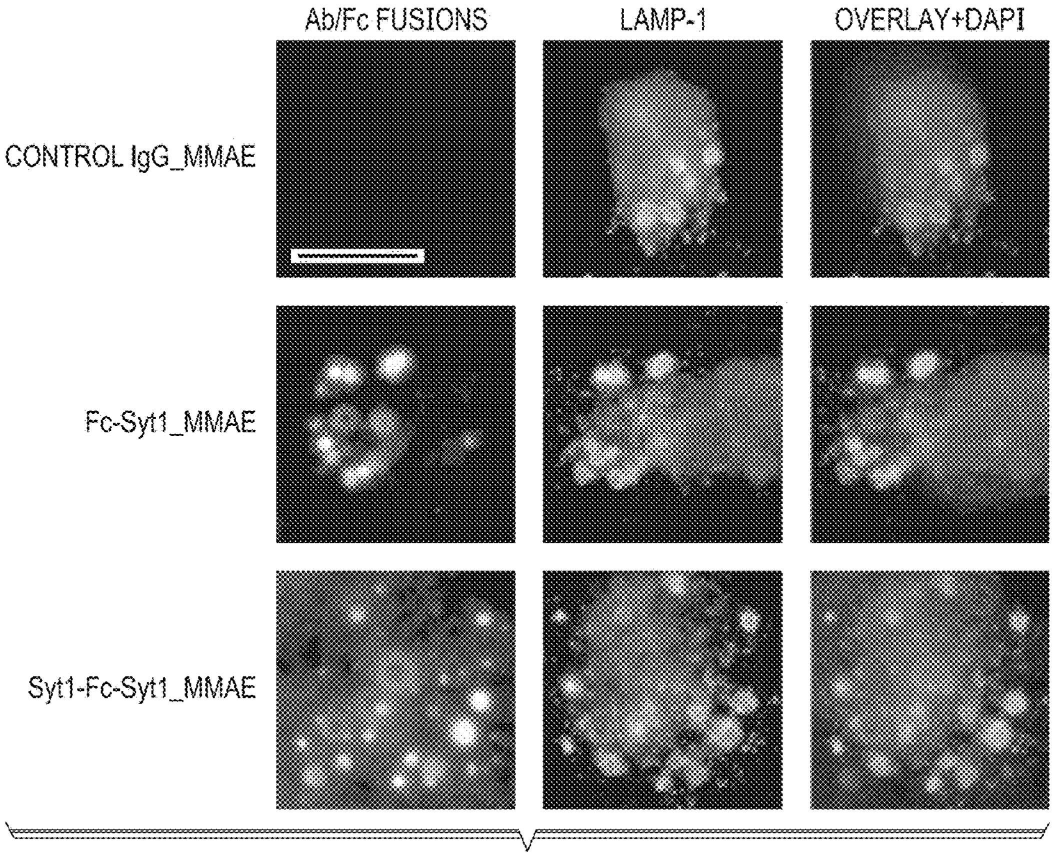
FIG. 13B shows an exemplary series of microscopic images of exemplary PS-targeting endolysosomal targeting conjugates and control MMAE-conjugate in tumor cells (MDA-MB-231) with the lysosomes in the cells labeled with LAMP-1-specific antibody.
Figure 13C:
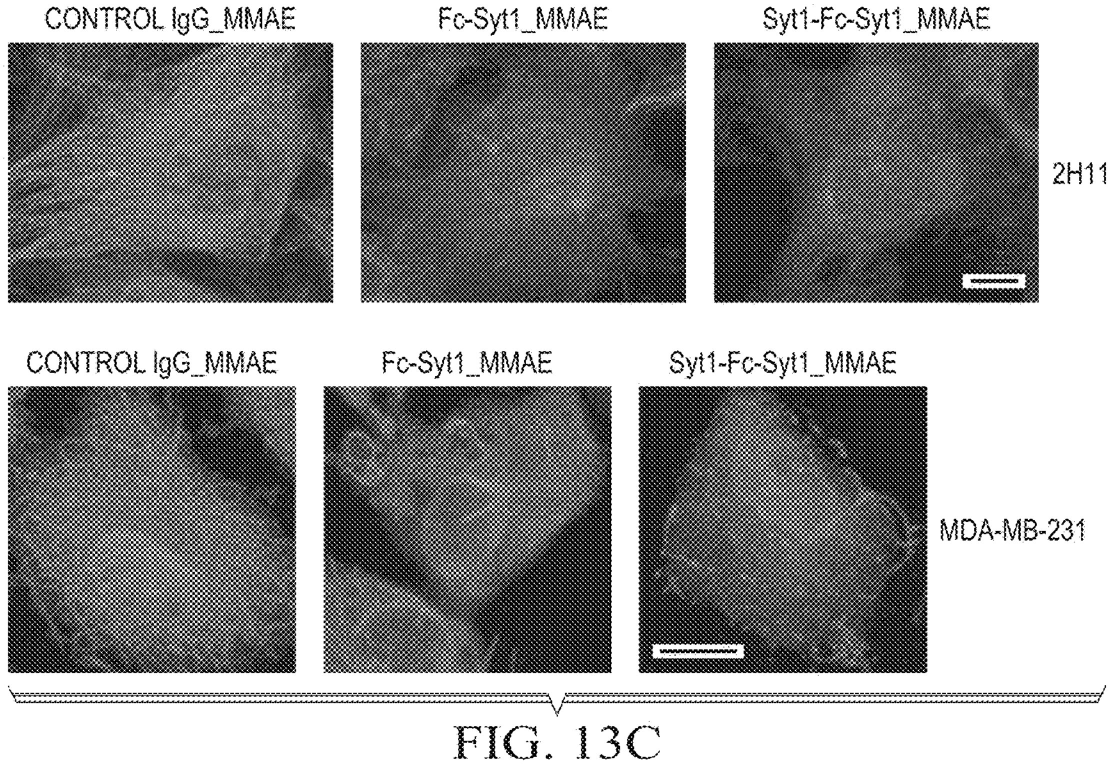
FIG. 13C shows a series of exemplary microscopic images of the effects of exemplary PS-targeting endolysosomal targeting conjugates and control MMAE conjugate on tubulin in endothelial cells (2H11) and in tumor cells (MDA-MB-231)

Consistent with the in vitro binding analyses demonstrating $Ca^{2+}$-dependent binding, fluorescence microscopy analyses following incubation of MDA-MB-453 cells with 100 nM PS-PDC or MMAE-conjugated control for 30 minutes, followed by washing and staining early endosomes with early endosomal antigen 1 (EEA1)-specific antibody, showed the presence of the PS-PDCs in the lumen, rather than limiting membrane of sorting endosomes following internalization into the cells (FIG. 13A). The PS-PDCs were detected using an Alexa 555-labeled anti-human IgG (H+L) antibody in these experiments, and intensity analyses of early endosomes (labeled a and b) that have been cropped and expanded are shown on the right side of the figure panel. In addition, Fc-Syt1_MMAE and Syt1-Fc-Syt1_MMAE could be detected in lysosomes (detected using a LAMP-1-specific antibody) within four hours of delivery (FIG. 13B). Both PS-PDCs disrupted the microtubular network in 2H11 and MDA-MB-231 cells following incubation of 2H11 or MDA-MB-453 cells with 100 nM or 50 nM PS-PDCs for 10 or 20 hours, respectively (FIG. 13C). Scale bars=5 (FIG. 13A), 10 μm (FIG. 13B), 15 μm (FIG. 13C, upper panels) and 10 μm (FIG. 13C, lower panels).

Figure 14A:
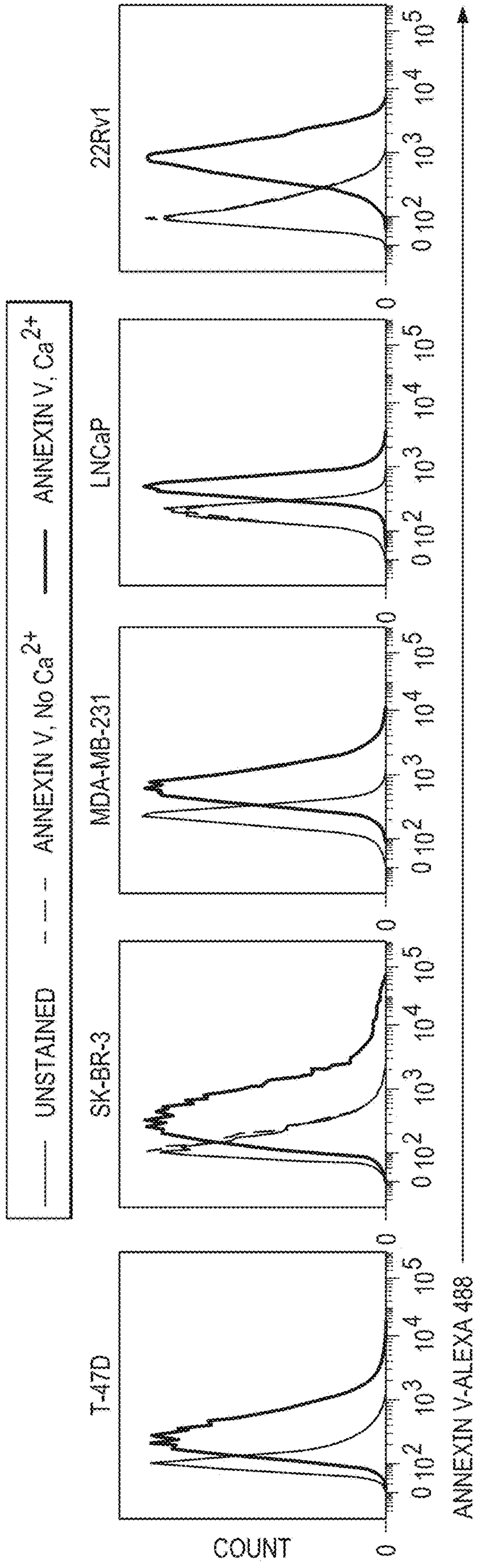
FIG. 14A shows graphs of exemplary flow cytometry data to indicate the levels of exposed PS on tumor cells.
Figure 14B:
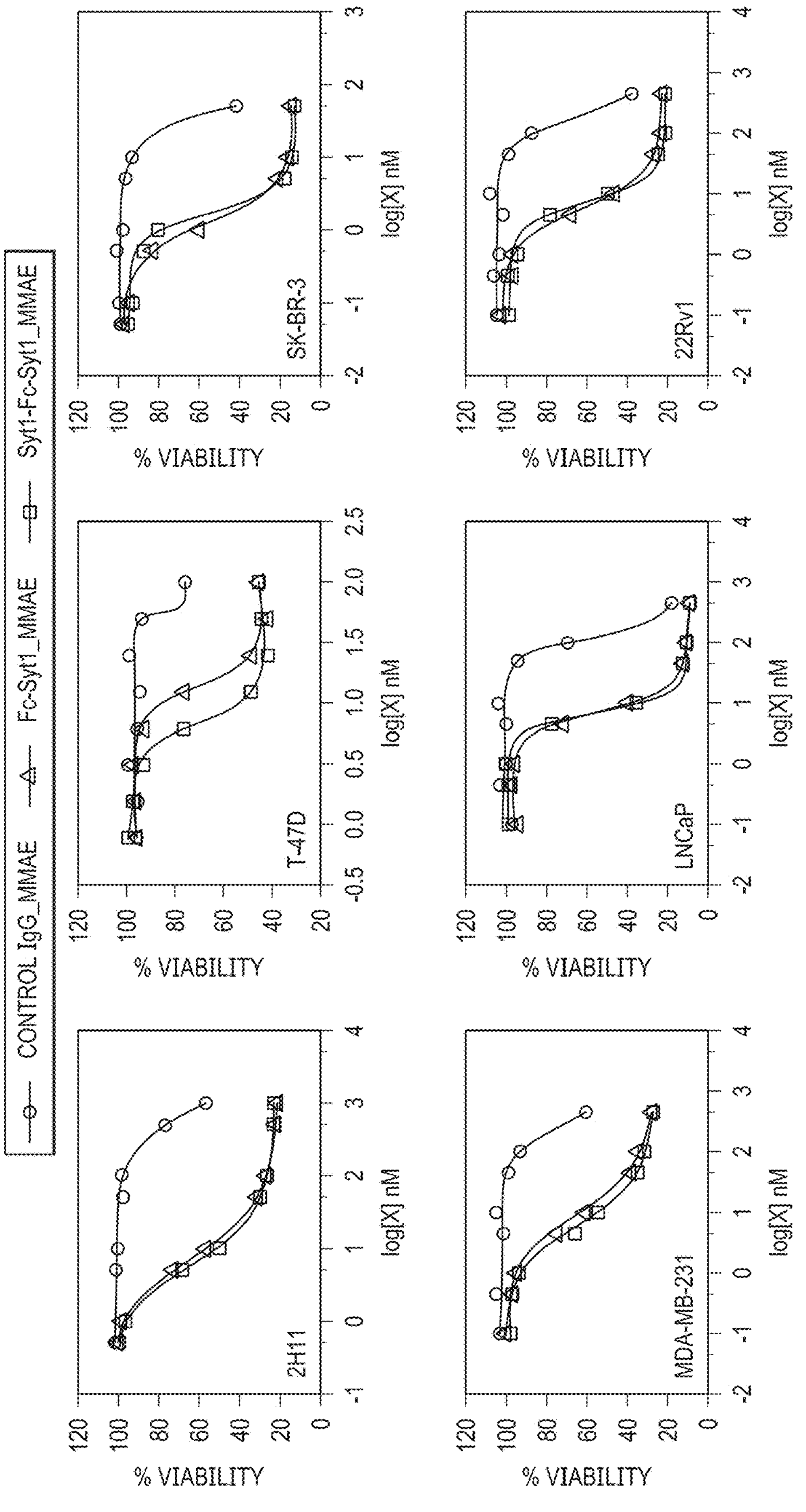
FIG. 14B shows graphs reporting exemplary data for the effects of the exemplary PS-targeting endolysosomal targeting conjugates and control MMAE-conjugate on the viability of tumor cells.
Figure 14C:
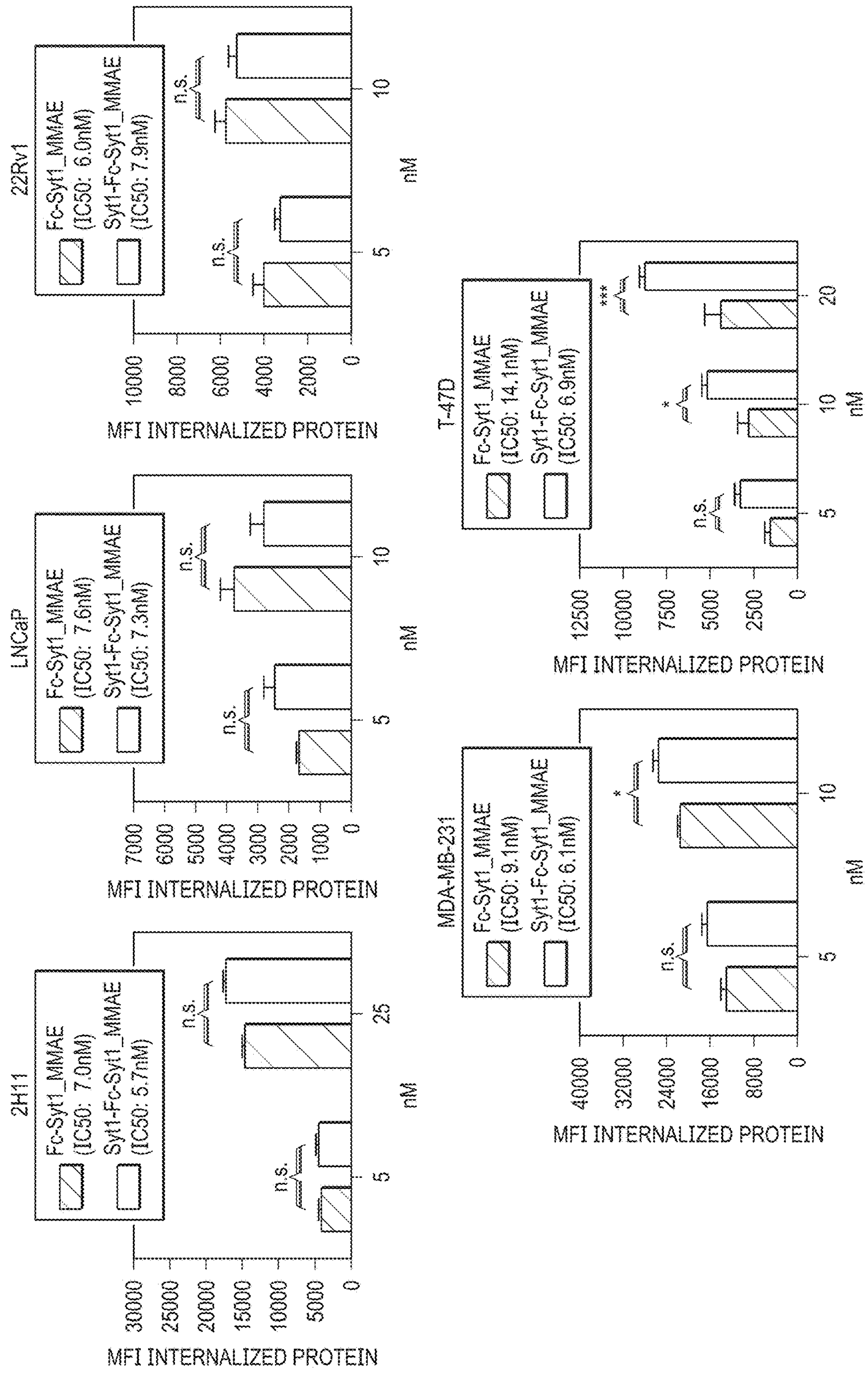
FIG. 14C shows graphs of exemplary flow cytometry data to indicate the levels of internalized exemplary PS-targeting endolysosomal targeting conjugates into tumor cells following two hours of incubation.
Figure 14D:
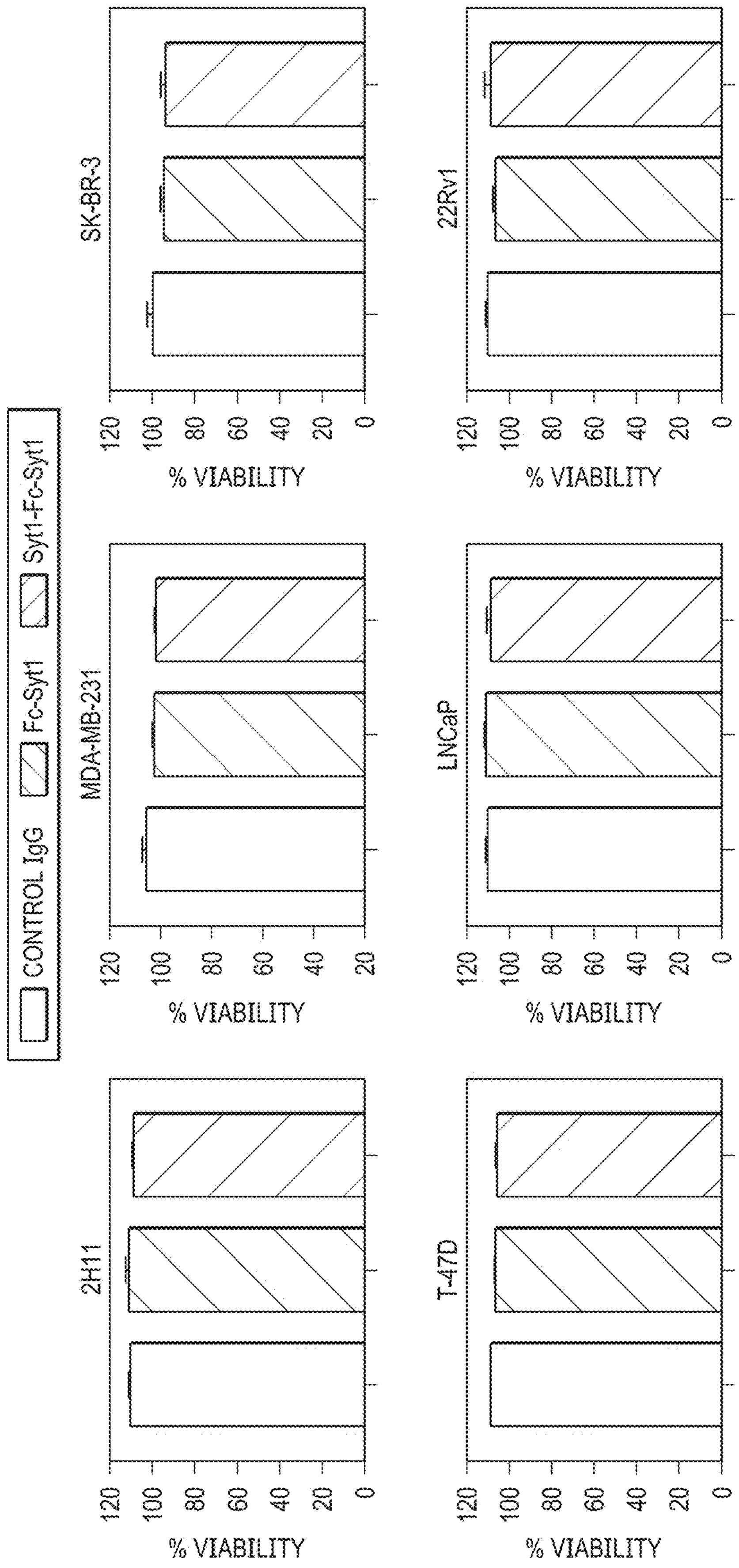
FIG. 14D shows graphs of exemplary data indicating that exemplary PS-targeting Fc fusions (without conjugated drug) do not affect cell viability.

Example 10. Inhibition of Growth and Survival of PS-Positive Cells by PS-PDCs The effects of PS-specific PDCs on the growth of multiple cell lines were examined, including tumor endothelium (2H11), ER positive breast cancer (T-47D), HER2-positive breast cancer (SK-BR-3), triple negative breast cancer (MDA-MB-231), androgen sensitive prostate cancer (LNCaP) and androgen insensitive prostate cancer (22Rv1). Staining of the cells with fluorescently labeled Annexin V followed by flow cytometry analyses showed that all of these cell lines were PS-positive (FIG. 14A). Incubation of the cells with PS-PDCs effectively inhibited the growth and survival of the cells in a dose-dependent manner (FIG. 14B). Cell viability following 72 hours (2H11), 96 hours (SK-BR-3, MDA-MB-231 and 22Rv1) or 120 hours (T-47D) incubation is shown. Although the tetravalent Syt1-Fc-Syt1_MMAE was more potent in inhibiting T-47D cell growth than the divalent Fc-Syt1_MMAE, the two PDCs exhibited similar effects on the other cell lines. By contrast, relatively high concentrations of the control IgG (hen egg lysozyme-specific human IgG1) conjugated with MMAE resulted in inhibition of cell growth (FIG. 14B), possibly due to nonspecific fluid phase uptake of the drug. Consistent with the growth inhibitory effects of the PS-PDCs, flow cytometry analyses of the internalization of the two PDCs at concentrations close to their corresponding IC50s showed similar behavior for all other cell lines following 2 hours incubation, except that Syt1-Fc-Syt1_MMAE was internalized at a higher level in T-47D cells (FIG. 14C). For FIG. 14C, statistically significant differences were analyzed using two-way ANOVA followed by Bonferroni post hoc test (n.s., no significant difference; *, $p<0.05$; *, $p<0.001$, and error bars represent SEM). In addition, unconjugated PS-targeting proteins showed no effect on cell growth in cell viability assays when added to cells at a concentration of 1 μM for 96 hours (FIG. 14**D). Thus, the data indicate that Syt1-based PDCs are potent inhibitors of tumor endothelial and cancer cell growth in vitro.

Example 11. Inhibition of Tumor Growth by PS-PDCs in Mouse Xenograft Models

Figure 15A:
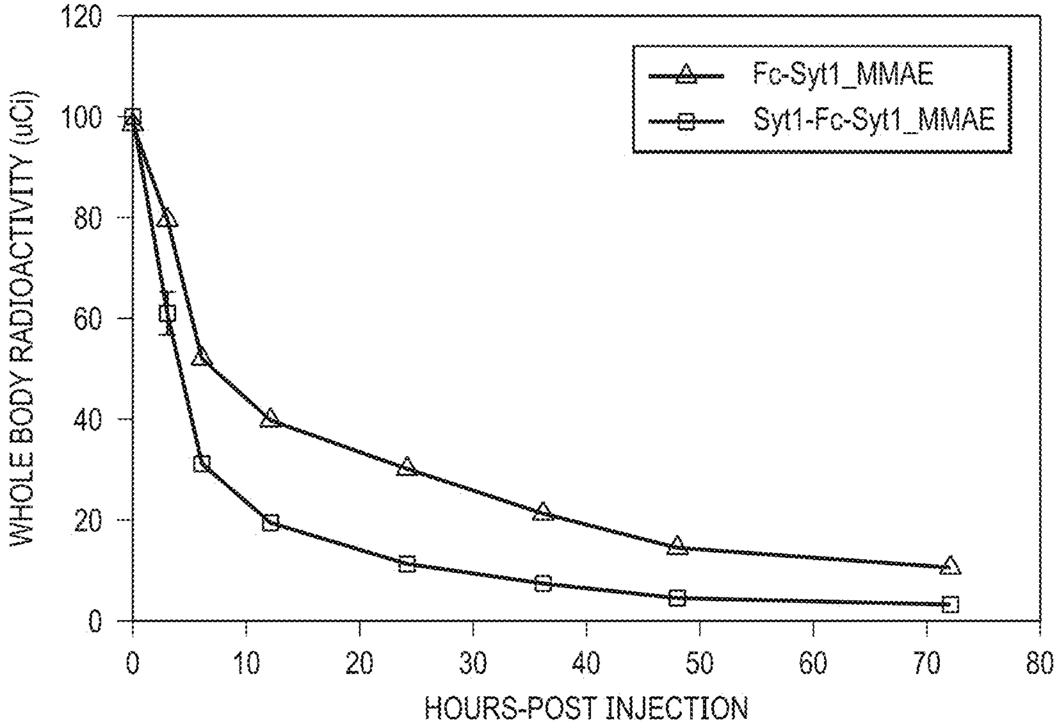
FIG. 15A shows graphs reporting exemplary whole body counts vs. time of exemplary PS-targeting endolysosomal targeting conjugates.
Figure 15B:
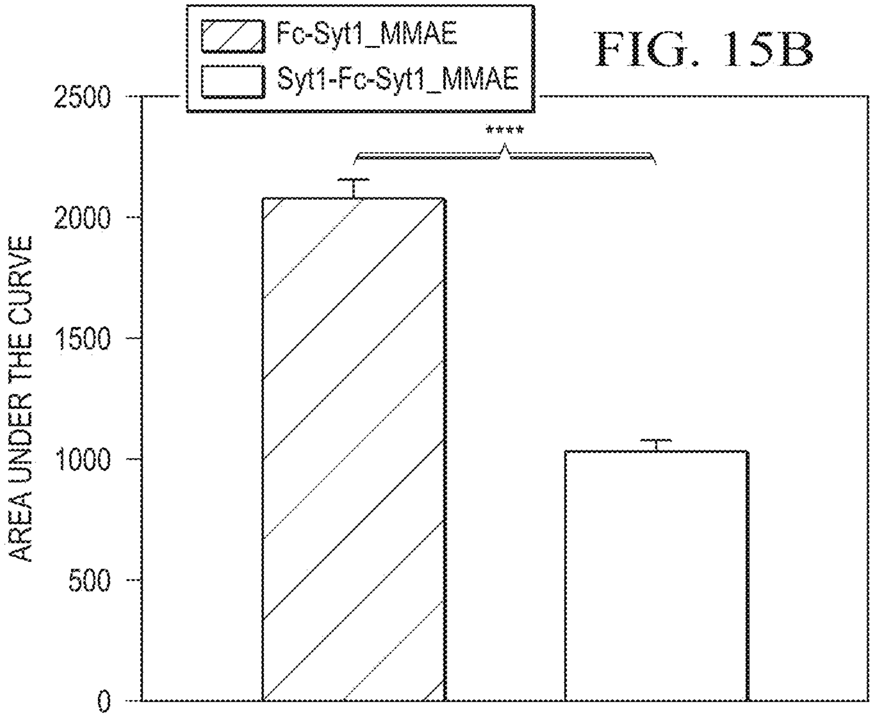
FIG. 15B shows exemplary graphs reporting the areas under curves for the data shown in FIG. 15A for exemplary PS-targeting endolysosomal targeting conjugates.
Figure 15C:
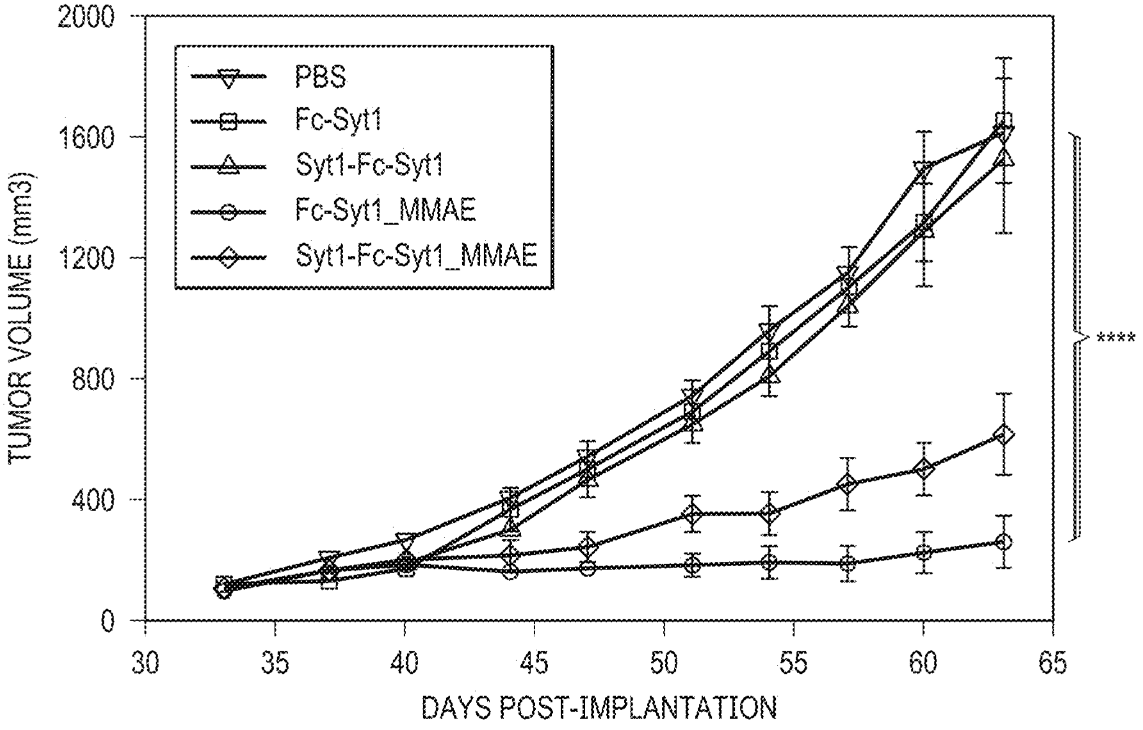
FIG. 15C show graphs reporting exemplary data for the effects of exemplary PS-targeting endolysosomal targeting conjugates and control proteins on tumor growth (MDA-MB-231 cells) in mice.
Figure 15D:
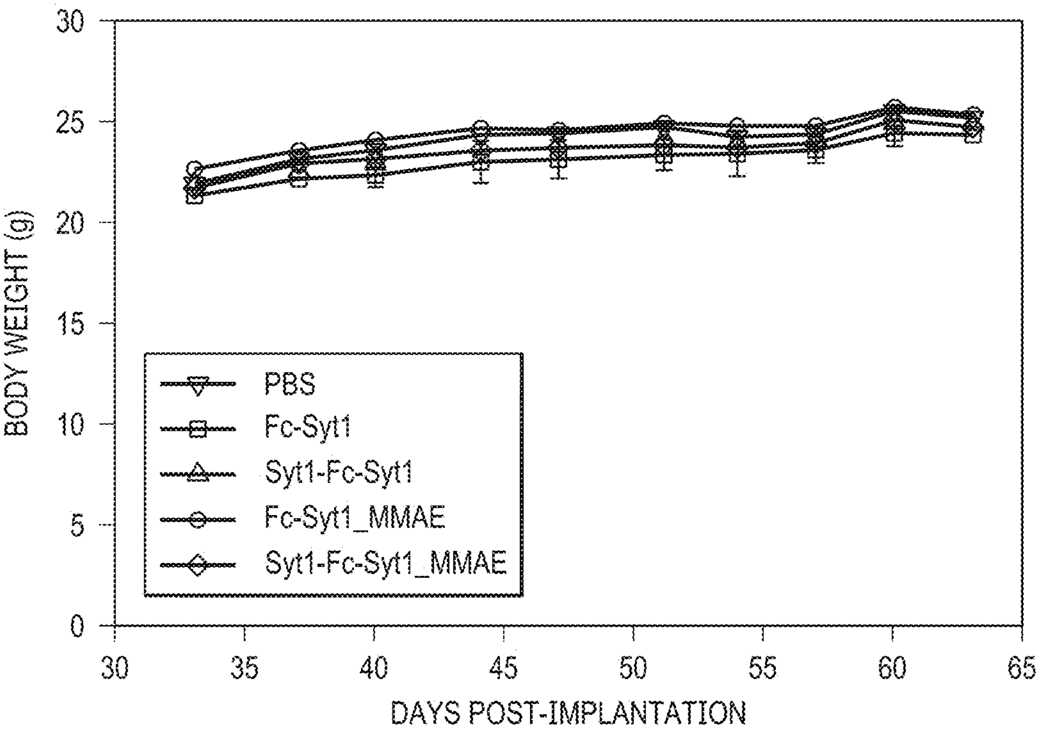
FIG. 15D show graphs reporting exemplary data for the effects of exemplary PS-targeting endolysosomal targeting conjugates and control proteins on the body weight of tumor-bearing mice.

The therapeutic effects of the PS-PDCs against tumor xenografts in BALB/c SCID mice were investigated. Prior to therapy, pharmacokinetic studies of the PS-PDCs demonstrated that tetravalent Syt1-Fc-Syt1_MMAE had a shorter half-life than bivalent Fc-Syt1_MMAE (FIG. 15A, B), possibly due to increased target-mediated uptake. FIG. 15A shows whole body counts in BALB/c SCID mice (n=5 mice/group) following injection of radioiodinated PS-PDC. FIG. 15B shows the areas under the curve for the clearance curves shown in FIG. 15A, with statistically significant differences analyzed using unpaired Student's t-test (**, p<0.0001). To investigate their therapeutic effects, the PDCs were delivered into female BALB/c SCID mice (n=5-6 mice/group) bearing orthotopic MDA-MB-231 breast tumors. Tumor-bearing mice were pretreated with docetaxol, and the following doses (equivalent to 1 nmole protein) of PDCs or control unconjugated proteins were delivered twice per week: 4.1 mg/kg for Fc-Syt1 or Fc-Syt1_MMAE, 5.6 mg/kg for Syt1-Fc-Syt1 or Syt1-Fc-Syt1_MMAE. In these experiments, bivalent Fc-Syt1_MMAE potently blocked breast tumor growth (FIG. 15C). Tetravalent Syt1-Fc-Syt1_MMAE also inhibited tumor growth, but less effectively than bivalent Fc-Syt1_MMAE. Treatment of unconjugated Fc-Syt1 and Syt1-Fc-Syt1 had no effect on tumor growth (FIG. 15C). Importantly, no weakness or loss of body weight in any of the treatment groups was observed (FIG. 15**D), indicating that PS-specific PDCs are well-tolerated in vivo.

Figure 15E:
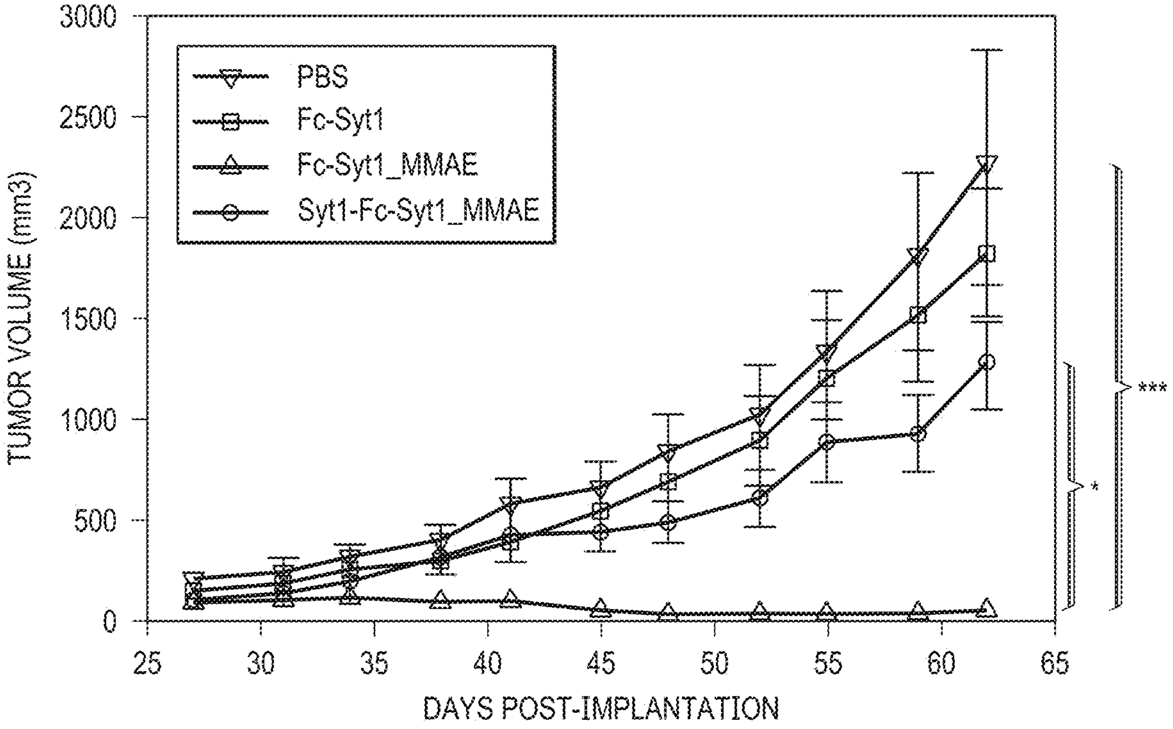
FIG. 15E shows graphs reporting exemplary data for the effects of exemplary PS-targeting endolysosomal targeting conjugates and control proteins on tumor growth (LNCaP cells) in mice.

Similar to the efficacy in the breast tumor model, bivalent Fc-Syt1_MMAE completely blocked tumor growth in male BALB/c SCID mice bearing prostate cancer LNCaP xenografts that had been pretreated with docetaxel (FIG. 15E). Tumor-bearing mice were dosed as for the MDA-MB-231 xenograft experiments (above). Consistent with the in vitro data (FIG. 14D), the unconjugated PS-targeting fusion proteins had no effect. However, tetravalent Syt1-Fc-Syt1_MMAE did not significantly inhibit tumor growth in the LNCaP model. The most likely explanation for this difference is the shorter in vivo persistence of the tetravalent PDC. For both FIGS. 15C and 15E, statistical analyses at treatment end points were analyzed using one-way ANOVA followed by Bonferroni post hoc test (*, p<0.05; *, p<0.001; , p<0.0001). Error bars in FIGS. 15A, 15C and 15**E represent SEM.

Figure 16A:
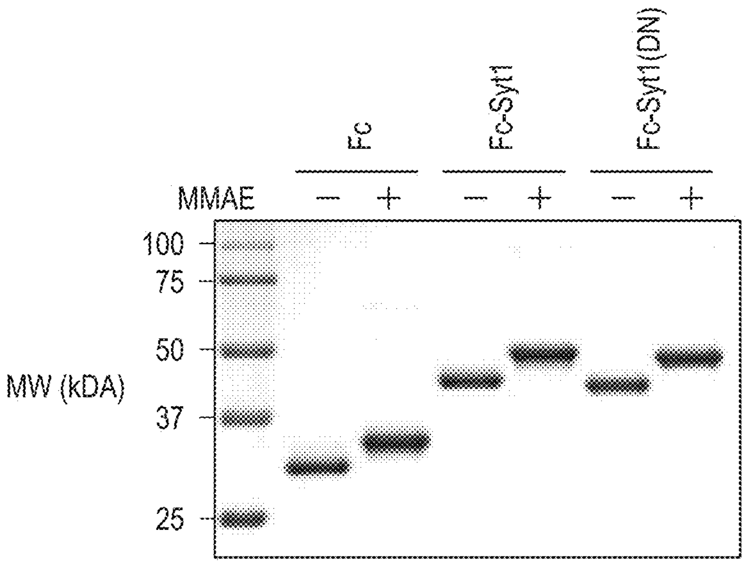
FIG. 16A shows SDS-PAGE analyses of a control endolysosomal targeting conjugate that has been engineered to reduce PS-binding activity (using DN mutations) and control proteins with and without conjugation to MMAE.

Example 12. Inhibition of Tumor Growth by Fc-Syt1_MMAE is Dependent on PS-Binding To exclude the possibility that the drug accumulated in the tumor through non-specific mechanisms such as the enhanced permeability and retention (EPR) effect and to show that the in vivo efficacy was dependent on PS binding, a mutated variant of the synaptotagmin 1 C2A domain was generated with decreased affinity for PS. The C2A domain of synaptotagmin 1 interacts with PS through three $Ca^{2+}$ ions chelated by five aspartic acids (D) in domain loops I and III (Striegel, A. R., Biela, L. M., Evans, C. S., Wang, Z., Delehoy, J. B., Sutton, R. B., Chapman, E. R. and Reist, N. E. 2012. Calcium binding by synaptotagmin's C2A domain is an essential element of the electrostatic switch that triggers synchronous synaptic transmission. J. Neurosci. 32, 1253-1260). To ablate the $Ca^{2+}$ binding, all five aspartic acid residues (D173N, D179N, D231N, D233N and D239N) were mutated to asparagines (N) to produce Fc-Syt1(DN). Fc-Syt1(DN) was purified and conjugated to MMAE with a DAR of four (FIG. 16A), and interacted with PS at essentially background levels in the protein-lipid overlay assay using lipid-coated nitrocellulose strips (FIG. 16B). Moreover, flow cytometry analyses demonstrated that Fc-Syt1 (DN) had significantly reduced binding to PS-positive cells compared with its wild-type counterpart (FIG. 16C). In FIG. 16C, statistically significant differences were analyzed using two-way ANOVA followed by Tukey post hoc test (*, p<0.001; **, p<0.0001), and error bars indicate SEM.

BALB/c SCID mice bearing orthotopic MDA-MB-231 tumors (n=6 mice/group) were pretreated with docetaxel prior to treatment with PS-PDCs or controls for four weeks, until mice in the control (PBS) group were euthanized due to their large tumor sizes. Mice were treated twice per week for four weeks (days 28-56) with the following doses (equivalent to 1 nmole protein): 4.1 mg/kg for Fc-Syt1_MMAE or Fc-Syt1(DN) MMAE, 2.6 mg/kg for Fc_MMAE. Treatment of MDA-MB-231 tumors with Fc-Syt1_MMAE led to potent growth inhibition (FIG. 16D). More importantly, tumor growth remained inhibited after the delivery of Fc-Syt1_MMAE was stopped at four weeks. Statistically significant differences between Fc-Syt1_MMAE and Fc-Syt1(DN)_MMAE treatment groups at the treatment end point were analyzed using one-way ANOVA followed by Bonferroni post hoc test (*, p<0.001), and error bars indicate SEM. Tumors from mice within each group were isolated at the end of the experiment, and no tumors could be isolated from three of six mice in the Fc-Syt1_MMAE treatment group (FIG. 16E). Although the delivery of Fc_MMAE or Fc-Syt1(DN) MMAE slowed tumor growth initially, rapid proliferation was observed following the end of treatment (FIG. 16**D). Collectively, the data indicate that PS-binding is essential for the activity of Fc-Syt1_MMAE.

Figure 17A:
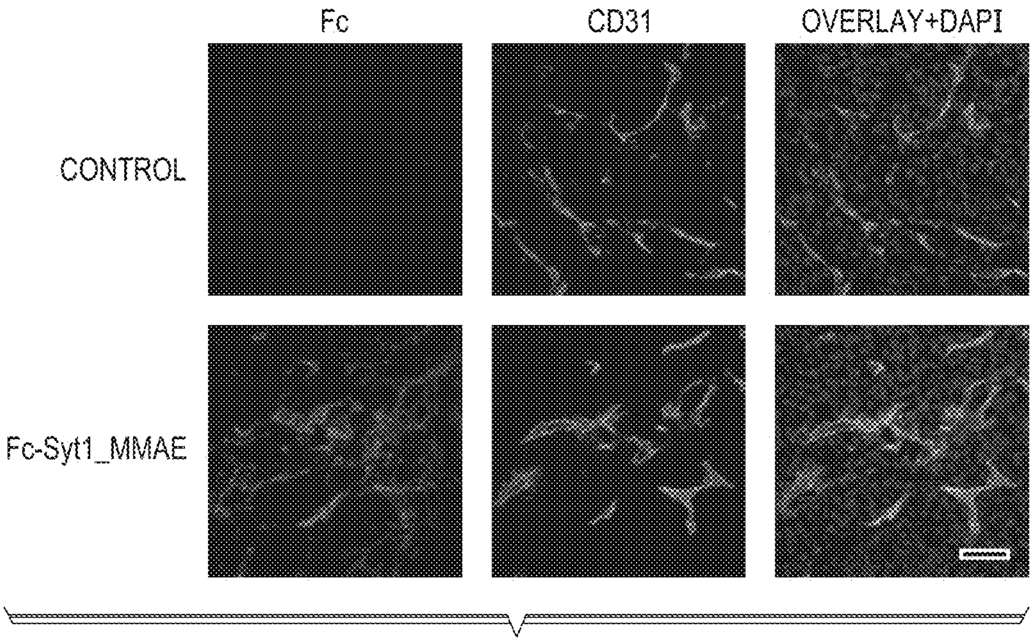
FIG. 17A shows a series of exemplary microscopic images showing the location of exemplary PS-targeting endolysosomal targeting conjugates and control (PBS vehicle) with respect to CD31-positive endothelial cells in tumor tissue.
Figure 17B:
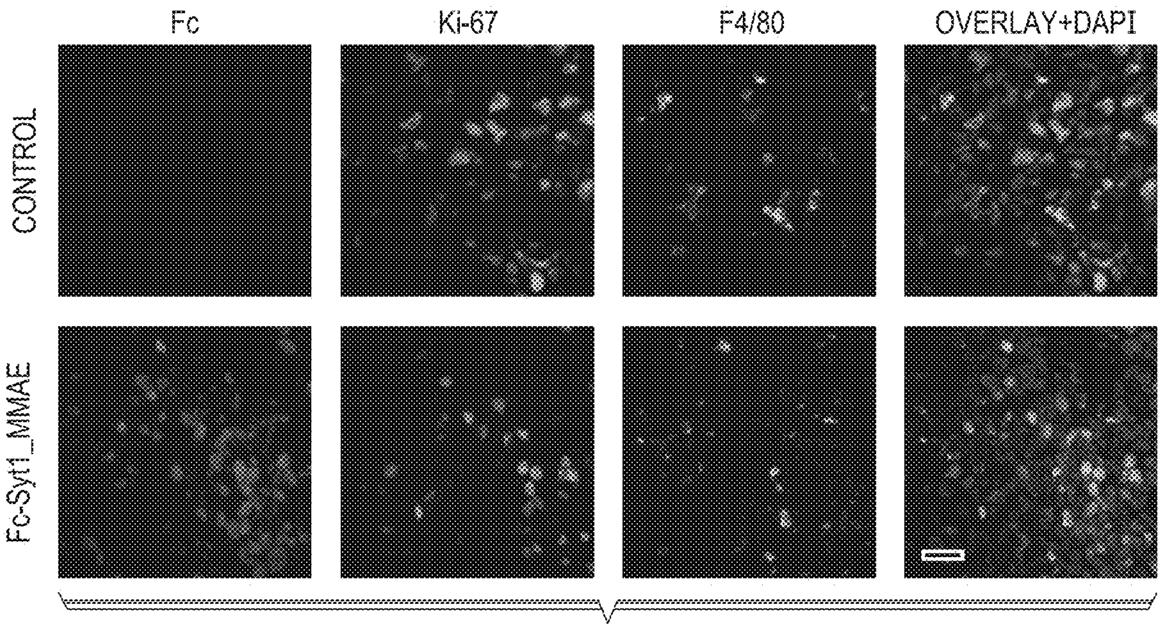
FIG. 17B shows a series of exemplary microscopic images showing the location of exemplary PS-targeting endolysosomal targeting conjugates and control (PBS vehicle) with respect to F4/80-positive macrophages in tumor tissue.

Example 13. Fc-Syt1_MMAE Targets Multiple Cell Types Including Both Tumor Endothelium and Cancer Cells in Tumor Tissues To further validate that Fc-Syt1_MMAE binds PS-positive cells in tumor tissue following docetaxel treatment, immunohistochemistry was performed at 1 hour (FIG. 17A) or 24 hours (FIG. 17B) following delivery of this PDC into tumor-bearing mice. PBS was injected as a vehicle control, and Fc-Syt1_MMAE was detected using Alexa 555-labeled anti-human IgG (H+L). Fc-Syt1_MMAE was localized to CD31-positive blood vessels (FIG. 17A), tumor cells and tumor-infiltrating F4/80-positive macrophages (FIG. 17B) which can expose PS. The data indicate that cancer cells not only expose PS in vitro (FIG. 14A), but retain this loss of PS asymmetry in vivo.

Example 14. DNA and Protein Sequences of Exemplary Antibody-Drug Conjugates, Protein-Drug Conjugates Table 1 shows DNA sequences of polynucleotides encoding exemplary proteins described herein, and Table 2 shows amino acid sequences of exemplary proteins encoded by the polynucleotides shown in Table 1, wherein the DNA sequence of SEQ ID NO: 1 encodes the protein of SEQ ID NO: 2, the DNA sequence of SEQ ID NO: 3 encodes the protein of SEQ ID NO: 4, the DNA sequence of SEQ ID NO: 5 encodes the protein of SEQ ID NO: 6, the DNA sequence of SEQ ID NO: 7 encodes the protein of SEQ ID NO: 8, the DNA sequence of SEQ ID NO: 9 encodes the protein of SEQ ID NO: 10, the DNA sequence of SEQ ID NO: 11 encodes the protein of SEQ ID NO: 12, the DNA sequence of SEQ ID NO: 13 encodes the protein of SEQ ID NO: 14, the DNA sequence of SEQ ID NO: 15 encodes the protein of SEQ ID NO: 16, the DNA sequence of SEQ ID NO: 17 encodes the protein of SEQ ID NO: 18, the DNA sequence of SEQ ID NO: 19 encodes the protein of SEQ ID NO: 20, the DNA sequence of SEQ ID NO: 21 encodes the protein of SEQ ID NO: 22, the DNA sequence of SEQ ID NO: 23 encodes the protein of SEQ ID NO: 24, the DNA sequence of SEQ ID NO: 25 encodes the protein of SEQ ID NO: 26, the DNA sequence of SEQ ID NO: 27 encodes the protein of SEQ ID NO: 28, the DNA sequence of SEQ ID NO: 29 encodes the protein of SEQ ID NO: 30, the DNA sequence of SEQ ID NO: 31 encodes the protein of SEQ ID NO: 32, the DNA sequence of SEQ ID NO: 33 encodes the protein of SEQ ID NO: 34, the DNA sequence of SEQ ID NO: 35 encodes the protein of SEQ ID NO: 36, the DNA sequence of SEQ ID NO: 37 encodes the protein of SEQ ID NO: 38, the DNA sequence of SEQ ID NO: 39 encodes the protein of SEQ ID NO: 40, the DNA sequence of SEQ ID NO: 41 encodes the protein of SEQ ID NO: 42, the DNA sequence of SEQ ID NO: 43 encodes the protein of SEQ ID NO: 44, the DNA sequence of SEQ ID NO: 45 encodes the protein of SEQ ID NO: 46 and the DNA sequence of SEQ ID NO: 47 encodes the protein of SEQ ID NO: 48.

TABLE 1

DNA sequences of polynucleotides encoding exemplary proteins.

| Polynucleotide encoding protein | DNA sequence | SEQ ID NO: |
|---|---|---|
| Pertuzumab light chain with Cys mutation | GACATCGAGCTCACACAGTCTCCTTCTTCTCTGTCTGCTTC<br>TGTGGGAGATAGAGTGACAATCACATGTAAGGCTTCTCA<br>GGATGTGTCTATCGGAGTGGCTTGGTACCAGCAGAAGCC<br>TGGAAAGGCTCCTAAGCTGCTGATCTACTCTGCTTCTTAC<br>AGATACACAGGAGTGCCTTCTAGATTCTCTGGATCTGGAT<br>CTGGAACAGATTTCACACTGACAATCTCTTCTCTACAGCC<br>TGAGGATTTCGCTACATACTACTGTCAGCAGTACTACATC<br>TACCCTTACACATTCGGACAGGGAACAAAGCTCGAGATC<br>AAACGAACTGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGT<br>ACAGTGGAAGGTGGATAACGCCCTCCAATCGGGTAACTC<br>CCAGGAGAGTGTCACAGAGCAGGACAGCAAGGACAGCA<br>CCTACAGCCTCAGCAGCACCCTGACGCTGAGCAAAGCAG<br>ACTACGAGAAACACAAAGTCTACGCCTGCGAAGTCACCC<br>ATCAGGGCCTGAGTTCGCCCGTCACAAAGAGCTTCAACA<br>GGGGAGAGTCT | 1 |
| SG heavy chain with Cys mutations | CAGGTCCAACTGCAGGAGTCTGGAGGAGGACTGGTGCAG<br>CCTGGAGGATCTCTGAGACTGTCTTGTGCTGCTTCTGGAT<br>TCACATTCACAGATTACACAATGGATTGGGTGAGACAGG<br>CTCCTGGAAAGGGACTGGAGTGGGTGGCTGATGTGAATC<br>CTAATCACGGAGAATCTATCTACAATCAGAGATTCAAGG<br>GAAGATTCACACTGTCTGTGGATAGATCTAAGAATACAC<br>TGTACCTACAGATGAACTCTCTGAGAGCTGAGGATACAG<br>CTGTGTACTACTGTGCTAGAAATCTGGGACCTTCTTTCTA<br>CTTCGATTACTGGGGACAGGGAACACTGGTCACCGTCTCC<br>TCAGCCTCCACCAAGGGCCCATCGGTCTTCCCCCTGGCAC<br>CCTCCTCCAAGAGCACCTCTGGGGGCACAGCGGCCCTGG<br>GCTGCCTGGTCAAGGACTACTTCCCCGAACCGGTGACGG<br>TGTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACTGTGCCCTCCAGCAGCTTGGGCAC<br>CCAGACCTACATCTGCAACGTGAATCACAAGCCCAGCAA<br>CACCAAGGTGGACAAGAAAGTTGAGCCCAAATCTTCTGA<br>CAAAACTCACACATGCCCACCGTCCCCAGCACCTGAACT<br>CCTGGGGGGACCGTCAGTCTTCCTCTTCCCCCCAAAACCC<br>AAGGACACCCTCATGATCTCCCGGACCCCTGAGGTCACA<br>TGCGTGGTGGTGGACGTGAGCCACGAAGACCCTGAGGTC<br>AAGTTCAACTGGTACGTGGACGGCGTGGAGGTGCATAAT<br>GCCAAGACAAAGCCGCGGGAGGAGCAGTACAACAGCAC<br>GTACCGTGTGGTCAGCGTCCTCACCGTCCTGCACCAGGAC<br>TGGCTGAATGGCAAGGAGTACAAGTGCAAGGTCTCCAAC<br>AAAGCCCTCCCAGCCCCCATCGAGAAAACCATCTCCAAA<br>GCCAAAGGGCAGCCCCGAGAACCACAGGTGTACACCCTG<br>CCCCCATCCCGGGATGAGCTGACCAAGAACCAGGTCAGC<br>CTGACCTGCCTGGTCAAAGGCTTCTATCCCAGCGACATCG<br>CCGTGGAGTGGGAGAGCAATGGGCAGCCGGAGAACAAC<br>TACAAGACCACGCCTCCCGTGCTGGACTCCGACGGCTCCT<br>TCTTCCTCTACAGCAAGCTCACCGTGGACAAGAGCAGGT<br>GGCAGCAGGGGAACGTCTTCTCATGCTCCGTGATGCATG<br>AGGCTCTGCACAACCACTACACGCAGAAGAGCCTCTCCC<br>TGTCTCCGGGTAAA | 3 |
| YS light chain with Cys mutation | GACATCGAGCTCACACAGTCTCCTTCTTCTCTGTCTGCTTC<br>TGTGGGAGATAGAGTGACAATCACATGTAAGGCTTCTCA<br>GGATGTGTCTATCGGAGTGGCTTGGTACCAGCAGAAGCC<br>TGGAAAGGCTCCTAAGCTGCTGATCTACTCTGCTTCTTAC<br>AGACACACAGGAGTGCCTTCTAGATTCTCTGGATCTGGAT<br>CTGGAACAGATTTCACACTGACAATCTCTTCTCTACAGCC | 5 |

TABLE 1-continued

DNA sequences of polynucleotides encoding exemplary proteins.

| Polynucleotide encoding protein | DNA sequence | SEQ ID NO: |
|---|---|---|
| | TGAGGATTTCGCTACATACTACTGTCAGCAGTACTACATC<br>TACCCTTACACATTCGGACAGGGAACAAAGCTCGAGATC<br>AAACGAACTGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGT<br>ACAGTGGAAGGTGGATAACGCCCTCCAATCGGGTAACTC<br>CCAGGAGAGTGTCACAGAGCAGGACAGCAAGGACAGCA<br>CCTACAGCCTCAGCAGCACCCTGACGCTGAGCAAAGCAG<br>ACTACGAGAAACACAAAGTCTACGCCTGCGAAGTCACCC<br>ATCAGGGCCTGAGTTCGCCCGTCACAAAGAGCTTCAACA<br>GGGGAGAGTCT | |
| YS heavy chain with Cys mutations | CAGGTCCAACTGCAGGAGTCTGGAGGAGGACTGGTGCAG<br>CCTGGAGGATCTCTGAGACTGTCTTGTGCTGCTTCTGGAT<br>TCACATTCACAGATTACACAATGGATTGGGTGAGACAGG<br>CTCCTGGAAAGGGACTGGAGTGGGTGGCTGATGTGAATC<br>CTAATTCTGGAGGATCTATCTACAATCAGAGATTCAAGG<br>GAAGATTCACACTGTCTGTGGATAGATCTAAGAATACAC<br>TGTACCTACAGATGAACTCTCTGAGAGCTGAGGATACAG<br>CTGTGTACTACTGTGCTAGAAATCTGGGACCTCACTTCTA<br>CTTCGATTACTGGGGACAGGGAACACTGGTCACCGTCTCC<br>TCAGCCTCCACCAAGGGCCCATCGGTCTTCCCCCTGGCAC<br>CCTCCTCCAAGAGCACCTCTGGGGGCACAGCGGCCCTGG<br>GCTGCCTGGTCAAGGACTACTTCCCCGAACCGGTGACGG<br>TGTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACTGTGCCCTCCAGCAGCTTGGGCAC<br>CCAGACCTACATCTGCAACGTGAATCACAAGCCCAGCAA<br>CACCAAGGTGGACAAGAAAGTTGAGCCCAAATCTTCTGA<br>CAAAACTCACACATGCCCACCGTCCCCAGCACCTGAACT<br>CCTGGGGGGACCGTCAGTCTTCCTCTTCCCCCCAAAACCC<br>AAGGACACCCTCATGATCTCCCGGACCCCTGAGGTCACA<br>TGCGTGGTGGTGGACGTGAGCCACGAAGACCCTGAGGTC<br>AAGTTCAACTGGTACGTGGACGGCGTGGAGGTGCATAAT<br>GCCAAGACAAAGCCGCGGGAGGAGCAGTACAACAGCAC<br>GTACCGTGTGGTCAGCGTCCTCACCGTCCTGCACCAGGAC<br>TGGCTGAATGGCAAGGAGTACAAGTGCAAGGTCTCCAAC<br>AAAGCCCTCCCAGCCCCCATCGAGAAAACCATCTCCAAA<br>GCCAAAGGGCAGCCCCGAGAACCACAGGTGTACACCCTG<br>CCCCCATCCCGGGATGAGCTGACCAAGAACCAGGTCAGC<br>CTGACCTGCCTGGTCAAAGGCTTCTATCCCAGCGACATCG<br>CCGTGGAGTGGGAGAGCAATGGGCAGCCGGAGAACAAC<br>TACAAGACCACGCCTCCCGTGCTGGACTCCGACGGCTCCT<br>TCTTCCTCTACAGCAAGCTCACCGTGGACAAGAGCAGGT<br>GGCAGCAGGGGAACGTCTTCTCATGCTCCGTGATGCATG<br>AGGCTCTGCACAACCACTACACGCAGAAGAGCCTCTCCC<br>TGTCTCCGGGTAAA | 7 |
| SG scFv linked to N-terminus of heavy chain with Cys mutations | CAGGTGCAGCTGCAGGAGTCTGGAGGAGGACTGGTGCAG<br>CCTGGAGGATCTCTGAGACTGTCTTGTGCTGCTTCTGGAT<br>TCACATTCACAGATTACACAATGGATTGGGTGAGACAGG<br>CTCCTGGAAAGGGACTGGAGTGGGTGGCTGATGTGAATC<br>CTAATCACGGAGAATCTATCTACAATCAGAGATTCAAGG<br>GAAGATTCACACTGTCTGTGGATAGATCTAAGAATACAC<br>TGTACCTACAGATGAACTCTCTGAGAGCTGAGGATACAG<br>CTGTGTACTACTGTGCTAGAAATCTGGGACCTTCTTTCTA<br>CTTCGATTACTGGGGACAGGGAACACTGGTCACGGTCTC<br>CTCGGGAGGTGGCGGATCTGGTGGAGGTGGCAGTGGTGG<br>AGGTGGCTCAGACATCGAGCTCACACAGTCTCCTTCTTCT<br>CTGTCTGCTTCTGTGGGAGATAGAGTGACAATCACATGTA<br>AGGCTTCTCAGGATGTGTCTATCGGAGTGGCTTGGTACCA<br>GCAGAAGCCTGGAAAGGCTCCTAAGCTGCTGATCTACTC<br>TGCTTCTTACAGATACACAGGAGTGCCTTCTAGATTCTCT<br>GGATCTGGATCTGGAACAGATTTCACACTGACAATCTCTT<br>CTCTACAGCCTGAGGATTTCGCTACATACTACTGTCAGCA<br>GTACTACATCTACCCTTACACATTCGGACAGGGAACAAA<br>GCTCGAGATCAAACGGGGTGGCAGCGTTGAGCCCAAATC<br>TTCTGACAAAACTCACACATGCCCACCGTCCCCAGCACCT<br>GAACTCCTGGGGGGACCGTCAGTCTTCCTCTTCCCCCCAA<br>AACCCAAGGACACCCTCATGATCTCCCGGACCCCTGAGG<br>TCACATGCGTGGTGGTGGACGTGAGCCACGAAGACCCTG<br>AGGTCAAGTTCAACTGGTACGTGGACGGCGTGGAGGTGC<br>ATAATGCCAAGACAAAGCCGCGGGAGGAGCAGTACAAC<br>AGCACGTACCGTGTGGTCAGCGTCCTCACCGTCCTGCACC | 9 |

TABLE 1-continued

DNA sequences of polynucleotides encoding exemplary proteins.

| Polynucleotide encoding protein | DNA sequence | SEQ ID NO: |
|---|---|---|
| | AGGACTGGCTGAATGGCAAGGAGTACAAGTGCAAGGTCT CCAACAAAGCCCTCCCAGCCCCCATCGAGAAAACCATCT CCAAAGCCAAAGGGCAGCCCCGAGAACCACAGGTGTACA CCCTGCCCCCATCCCGGGATGAGCTGACCAAGAACCAGG TCAGCCTGACCTGCCTGGTCAAAGGCTTCTATCCCAGCGA CATCGCCGTGGAGTGGGAGAGCAATGGGCAGCCGGAGA ACAACTACAAGACCACGCCTCCCGTGCTGGACTCCGACG GCTCCTTCTTCCTCTACAGCAAGCTCACCGTGGACAAGAG CAGGTGGCAGCAGGGGAACGTCTTCTCATGCTCCGTGAT GCATGAGGCTCTGCACAACCACTACACGCAGAAGAGCCT CTCCCTGTCTCCGGGTAAA | |
| YS scFv linked to N-terminus of heavy chain with Cys mutations | CAGGTGCAGCTGCAGGAGTCTGGAGGAGGACTGGTGCAG CCTGGAGGATCTCTGAGACTGTCTTGTGCTGCTTCTGGAT TCACATTCACAGATTACACAATGGATTGGGTGAGACAGG CTCCTGGAAAGGGACTGGAGTGGGTGGCTGATGTGAATC CTAATTCTGGAGGATCTATCTACAATCAGAGATTCAAGG GAAGATTCACACTGTCTGTGGATAGATCTAAGAATACAC TGTACCTACAGATGAACTCTCTGAGAGCTGAGGATACAG CTGTGTACTACTGTGCTAGAAATCTGGGACCTCACTTCTA CTTCGATTACTGGGGACAGGGAACACTGGTCACGGTCTC CTCGGGAGGTGGCGGATCTGGTGGAGGTGGCAGTGGTGG AGGTGGCTCAGACATCGAGCTCACACAGTCTCCTTCTTCT CTGTCTGCTTCTGTGGGAGATAGAGTGACAATCACATGTA AGGCTTCTCAGGATGTGTCTATCGGAGTGGCTTGGTACCA GCAGAAGCCTGGAAAGGCTCCTAAGCTGCTGATCTACTC TGCTTCTTACAGACACACAGGAGTGCCTTCTAGATTCTCT GGATCTGGATCTGGAACAGATTTCACACTGACAATCTCTT CTCTACAGCCTGAGGATTTCGCTACATACTACTGTCAGCA GTACTACATCTACCCTTACACATTCGGACAGGGAACAAA GCTCGAGATCAAACGGGGTGGCAGCGTTGAGCCCAAATC TTCTGACAAAACTCACACATGCCCACCGTCCCCAGCACCT GAACTCCTGGGGGGACCGTCAGTCTTCCTCTTCCCCCCAA AACCCAAGGACACCCTCATGATCTCCCGGACCCCTGAGG TCACATGCGTGGTGGTGGACGTGAGCCACGAAGACCCTG AGGTCAAGTTCAACTGGTACGTGGACGGCGTGGAGGTGC ATAATGCCAAGACAAAGCCGCGGGAGGAGCAGTACAAC AGCACGTACCGTGTGGTCAGCGTCCTCACCGTCCTGCACC AGGACTGGCTGAATGGCAAGGAGTACAAGTGCAAGGTCT CCAACAAAGCCCTCCCAGCCCCCATCGAGAAAACCATCT CCAAAGCCAAAGGGCAGCCCCGAGAACCACAGGTGTACA CCCTGCCCCCATCCCGGGATGAGCTGACCAAGAACCAGG TCAGCCTGACCTGCCTGGTCAAAGGCTTCTATCCCAGCGA CATCGCCGTGGAGTGGGAGAGCAATGGGCAGCCGGAGA ACAACTACAAGACCACGCCTCCCGTGCTGGACTCCGACG GCTCCTTCTTCCTCTACAGCAAGCTCACCGTGGACAAGAG CAGGTGGCAGCAGGGGAACGTCTTCTCATGCTCCGTGAT GCATGAGGCTCTGCACAACCACTACACGCAGAAGAGCCT CTCCCTGTCTCCGGGTAAA | 11 |
| Heavy chain with Cys mutations and SG scFv linked to C-terminus | GTTGAGCCCAAATCTTCTGACAAAACTCACACATGCCCAC CGTCCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGTGGCA GCCAGGTGCAGCTGCAGGAGTCTGGAGGAGGACTGGTGC AGCCTGGAGGATCTCTGAGACTGTCTTGTGCTGCTTCTGG ATTCACATTCACAGATTACACAATGGATTGGGTGAGACA GGCTCCTGGAAAGGGACTGGAGTGGGTGGCTGATGTGAA TCCTAATCACGGAGAATCTATCTACAATCAGAGATTCAA GGGAAGATTCACACTGTCTGTGGATAGATCTAAGAATAC | 13 |

TABLE 1-continued

DNA sequences of polynucleotides encoding exemplary proteins.

| Polynucleotide encoding protein | DNA sequence | SEQ ID NO: |
|---|---|---|
| | ACTGTACCTACAGATGAACTCTCTGAGAGCTGAGGATAC AGCTGTGTACTACTGTGCTAGAAATCTGGGACCTTCTTTC TACTTCGATTACTGGGGACAGGGAACACTGGTCACGGTC TCCTCGGGAGGTGGCGGATCTGGTGGAGGTGGCAGTGGT GGAGGTGGCTCAGACATCGAGCTCACACAGTCTCCTTCTT CTCTGTCTGCTTCTGTGGGAGATAGAGTGACAATCACATG TAAGGCTTCTCAGGATGTGTCTATCGGAGTGGCTTGGTAC CAGCAGAAGCCTGGAAAGGCTCCTAAGCTGCTGATCTAC TCTGCTTCTTACAGATACACAGGAGTGCCTTCTAGATTCT CTGGATCTGGATCTGGAACAGATTTCACACTGACAATCTC TTCTCTACAGCCTGAGGATTTCGCTACATACTACTGTCAG CAGTACTACATCTACCCTTACACATTCGGACAGGGAACA AAGCTCGAGATCAAACGG | |
| Heavy chain with Cys mutations and YS scFv linked to C-terminus | GTTGAGCCCAAATCTTCTGACAAAACTCACACATGCCCAC CGTCCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGTGGCA GCCAGGTGCAGCTGCAGGAGTCTGGAGGAGGACTGGTGC AGCCTGGAGGATCTCTGAGACTGTCTTGTGCTGCTTCTGG ATTCACATTCACAGATTACACAATGGATTGGGTGAGACA GGCTCCTGGAAAGGGACTGGAGTGGGTGGCTGATGTGAA TCCTAATTCTGGAGGATCTATCTACAATCAGAGATTCAAG GGAAGATTCACACTGTCTGTGGATAGATCTAAGAATACA CTGTACCTACAGATGAACTCTCTGAGAGCTGAGGATACA GCTGTGTACTACTGTGCTAGAAATCTGGGACCTCACTTCT ACTTCGATTACTGGGGACAGGGAACACTGGTCACGGTCT CCTCGGGAGGTGGCGGATCTGGTGGAGGTGGCAGTGGTG GAGGTGGCTCAGACATCGAGCTCACACAGTCTCCTTCTTC TCTGTCTGCTTCTGTGGGAGATAGAGTGACAATCACATGT AAGGCTTCTCAGGATGTGTCTATCGGAGTGGCTTGGTACC AGCAGAAGCCTGGAAAGGCTCCTAAGCTGCTGATCTACT CTGCTTCTTACAGACACACAGGAGTGCCTTCTAGATTCTC TGGATCTGGATCTGGAACAGATTTCACACTGACAATCTCT TCTCTACAGCCTGAGGATTTCGCTACATACTACTGTCAGC AGTACTACATCTACCCTTACACATTCGGACAGGGAACAA AGCTCGAGATCAAACGG | 15 |
| Trastuzumab VH-CH1-hinge-CalD2 | CAGGTCCAACTGCAGGAGTCTGGCGGTGGCCTGGTGCAG CCAGGGGGCTCACTCCGTTTGTCCTGTGCAGCTTCTGGCT TCAACATTAAAGACACCTATATACACTGGGTGCGTCAGG CCCCGGGTAAGGGCCTGGAATGGGTTGCAAGGATTTATC CTACGAATGGTTATACTAGATATGCCGATAGCGTCAAGG GCCGTTTCACTATAAGCGCAGACACATCCAAAAACACAG CCTACCTACAGATGAACAGCCTGCGTGCTGAGGACACTG CCGTCTATTATTGTTCTAGATGGGGAGGGGACGGCTTCTA TGCTATGGACTACTGGGGTCAAGGAACCCTGGTCACCGT CTCCTCAGCCTCCACCAAGGGCCCATCGGTCTTCCCCCTG GCACCCTCCTCCAAGAGCACCTCTGGGGGCACAGCGGCC CTGGGCTGCCTGGTCAAGGACTACTTCCCCGAACCGGTG ACGGTGTCGTGGAACTCAGGCGCCCTGACCAGCGGCGTG CACACCTTCCCGGCTGTCCTACAGTCCTCAGGACTCTACT CCCTCAGCAGCGTGGTGACTGTGCCCTCCAGCAGCTTGGG CACCCAGACCTACATCTGCAACGTGAATCACAACCCCAG CAACACCAAGGTCGACAAGAAAGTTGAGCCCAAATCTTC AACTAAGACGCACACATCAGGAGGTAACACCCTAGATGA TCTCTTTCAAGAACTGGACAAGAATGGAGATGGAGAAGT TAGTTTTGAAGAATTCCAAGTATTAGTAAAAAAGATATCC CAG | 17 |

TABLE 1-continued

DNA sequences of polynucleotides encoding exemplary proteins.

| Polynucleotide encoding protein | DNA sequence | SEQ ID NO: |
|---|---|---|
| Trastuzumab light chain | GACATCGAGCTCACCCAGTCCCCAAGCTCCCTGTCCGCCT<br>CTGTGGGCGATAGAGTCACCATCACCTGCCGTGCCAGTC<br>AGGATGTGAATACTGCTGTAGCCTGGTATCAACAGAAAC<br>CAGGAAAAGCTCCGAAACTACTGATTTACTCGGCATCCTT<br>CCTCTACTCTGGAGTCCCTTCTCGCTTCTCTGGATCCAGAT<br>CTGGGACGGATTTCACTCTAACCATCAGCAGTCTACAGCC<br>GGAAGACTTCGCAACTTATTACTGTCAGCAACATTATACT<br>ACTCCTCCCACGTTCGGACAGGGTACCAAGCTCGAGATC<br>AAACGAACTGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGT<br>ACAGTGGAAGGTGGATAACGCCCTCCAATCGGGTAACTC<br>CCAGGAGAGTGTCACAGAGCAGGACAGCAAGGACAGCA<br>CCTACAGCCTCAGCAGCACCCTGACGCTGAGCAAAGCAG<br>ACTACGAGAAACACAAAGTCTACGCCTGCGAAGTCACCC<br>ATCAGGGCCTGAGTTCGCCCGTCACAAAGAGCTTCAACC<br>GCGGAGAGTCACACCATCACCATCACCAT | 19 |
| CalD1-hinge-Fc | AAGTCTCCTGAGGAACTGAAGAGGATTTTTGAAAAATAT<br>GCAGCCAAAGAAGGTGATCCAGACCAGTTGTCAAAGGAT<br>GAACTGAAGCTATTGATTCAGGCTGAATTCCCCAGTTTAC<br>TCAAAGGTCCAGGCTCGAGCGTTGAGCCCAAATCTTCTG<br>ACAAAACTCACACATGCCCACCGTGCCCAGCACCTGAAC<br>TCCTGGGGGGACCGTCAGTCTTCCTCTTCCCCCCAAAACC<br>CAAGGACACCCTCATGATCTCCCGGACCCCTGAGGTCAC<br>ATGCGTGGTGGTGGACGTGAGCCACGAAGACCCTGAGGT<br>CAAGTTCAACTGGTACGTGGACGGCGTGGAGGTGCATAA<br>TGCCAAGACAAAGCCGCGGGAGGAGCAGTACAACAGCA<br>CGTACCGTGTGGTCAGCGTCCTCACCGTCCTGCACCAGGA<br>CTGGCTGAATGGCAAGGAGTACAAGTGCAAGGTCTCCAA<br>CAAAGCCCTCCCAGCCCCCATCGAGAAAACCATCTCCAA<br>AGCCAAAGGGCAGCCCCGAGAACCACAGGTGTACACCCT<br>GCCCCCATCCCGGGATGAGCTGACCAAGAACCAGGTCAG<br>CCTGACCTGCCTGGTCAAAGGCTTCTATCCCAGCGACATC<br>GCCGTGGAGTGGGAGAGCAATGGGCAGCCGGAGAACAA<br>CTACAAGACCACGCCTCCCGTGCTGGACTCCGACGGCTC<br>CTTCTTCCTCTACAGCAAGCTCACCGTGGACAAGAGCAG<br>GTGGCAGCAGGGGAACGTCTTCTCATGCTCTGTGATGCAT<br>GAGGCTCTGCATAACCACTACACGCAGAAGAGCCTCTCC<br>CTGTCTCCGGGTAAA | 21 |
| 026-VH-CH1-hinge-CalD2 | CAGGTCCAACTGCAGGAGTCTGGGGGAGGCGTGGTCCAG<br>CCTGGGAGGTCCCTGAGACTCTCCTGTGCAGCGTCTGGAT<br>TCACCTTCAGTAACTATGTCATGCACTGGGTCCGCCAGGC<br>TCCAGGCAAGGGGCTGGAGTGGGTGGCAATTATATGGTA<br>TGATGGAAGTAATAAATACTATGCAGACTCCGTGAAGGG<br>CCGATTCACCATCTCCAGAGACAATTCCAAGAACACGCT<br>GTATCTGCAAATGAACAGCCTGAGAGCCGAGGACACGGC<br>TGTGTATTACTGTGCGGGTGGATATAACTGGAACTACGA<br>GTACCACTACTACGGTATGGACGTCTGGGGCCAAGGGAC<br>CACGGTCACCGTCTCCTCAGCCTCCACCAAGGGCCCATCG<br>GTCTTCCCCCTGGCACCCTCCTCCAAGAGCACCTCTGGGG<br>GCACAGCGGCCCTGGGCTGCCTGGTCAAGGACTACTTCC<br>CCGAACCGGTGACGGTGTCGTGGAACTCAGGCGCCCTGA<br>CCAGCGGCGTGCACACCTTCCCGGCTGTCCTACAGTCCTC<br>AGGACTCTACTCCCTCAGCAGCGTGGTGACTGTGCCCTCC<br>AGCAGCTTGGGCACCCAGACCTACATCTGCAACGTGAAT<br>CACAACCCCAGCAACACCAAGGTCGACAAGAAAGTTGAG<br>CCCAAATCTTCAACTAAGACGCACACATCAGGAGGTAAC<br>ACCCTAGATGATCTCTTTCAAGAACTGGACAAGAATGGA<br>GATGGAGAAGTTAGTTTTGAAGAATTCCAAGTATTAGTA<br>AAAAAGATATCCCAG | 23 |
| 026 light chain | GACATCGAGCTCACCCAGTCTCCATCCTCACTGTCTGCAT<br>CTGTAGGAGACAGAGTCACCATCACTTGTCGGGCGAGTC<br>AGGGCATTACCAATTATTTAGCCTGGTTTCAGCAGAAACC<br>AGGGAAAGCCCCTAAGTCCCTTATCTATGCTGCATCCAGT<br>TTGCAAAGTGGGGTCCCATCAAAGTTCAGCGGCAGTGGA<br>TCTGGGACAGATTTCAGTCTCACCATCAGCAGCCTCCAGC<br>CTGAAGATTTTGCAACTTATTACTGCCAACAGTATAATAG<br>TTACCCGATCACCTTCGGCCAAGGGACACGACTCGAGAT<br>CAAACGAACTGTGGCTGCACCATCTGTCTTCATCTTCCCG<br>CCATCTGATGAGCAGTTGAAATCTGGAACTGCCTCTGTTG<br>TGTGCCTGCTGAATAACTTCTATCCCAGAGAGGCCAAAGT | 25 |

TABLE 1-continued

DNA sequences of polynucleotides encoding exemplary proteins.

| Polynucleotide encoding protein | DNA sequence | SEQ ID NO: |
|---|---|---|
| | ACAGTGGAAGGTGGATAACGCCCTCCAATCGGGTAACTC<br>CCAGGAGAGTGTCACAGAGCAGGACAGCAAGGACAGCA<br>CCTACAGCCTCAGCAGCACCCTGACGCTGAGCAAAGCAG<br>ACTACGAGAAACACAAAGTCTACGCCTGCGAAGTCACCC<br>ATCAGGGCCTGAGTTCGCCCGTCACAAAGAGCTTCAACC<br>GCGGAGAGTCACACCATCACCATCACCAT | |
| Fc-Syt1 | GTTGAGCCCAAATCTTCTGACAAAACTCACACATGCCCAC<br>CGTGCCCAGCACCTGAACTCCTGGGGGGACCGTCAGTCTT<br>CCTCTTCCCCCCAAAACCCAAGGACACCCTCATGATCTCC<br>CGGACCCCTGAGGTCACATGCGTGGTGGTGGACGTGAGC<br>CACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCCT<br>CACCGTCCTGCACCAGGACTGGCTGAATGGCAAGGAGTA<br>CAAGTGCAAGGTCTCCAACAAAGCCCTCCCAGCCCCCAT<br>CGAGAAAACCATCTCCAAAGCCAAAGGGCAGCCCCGAGA<br>ACCACAGGTGTACACCCTGCCCCCATCCCGGGATGAGCT<br>GACCAAGAACCAGGTCAGCCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCTTCCTCTACAGCAAGCTC<br>ACCGTGGACAAGAGCAGGTGGCAGCAGGGGAACGTCTTC<br>TCATGCTCCGTGATGCATGAGGCTCTGCACAACCACTACA<br>CGCAGAAGAGCCTCTCCCTGTCTCCGGGTAAAGGAGGCG<br>GTGGATCAGAGAAACTGGGAAAACTTCAGTATTCACTGG<br>ATTATGATTTCCAAAATAACCAGCTGCTGGTAGGGATCAT<br>TCAGGCTGCCGAACTGCCCGCCTTGGACATGGGGGGCAC<br>ATCTGATCCTTACGTGAAAGTGTTTCTGCTACCTGATAAG<br>AAGAAGAAATTTGAGACAAAAGTCCACCGAAAAACCCTT<br>AATCCTGTCTTCAATGAGCAATTTACTTTCAAGGTACCAT<br>ACTCGGAATTGGGTGGCAAAACCCTAGTGATGGCTGTAT<br>ATGATTTTGATCGTTTCTCTAAGCATGACATCATTGGAGA<br>ATTTAAAGTCCCTATGAACACAGTGGATTTTGGCCATGTA<br>ACTGAGGAATGGCGTGACCTGCAAAGTGCT | 27 |
| Syt1-Fc-Syt1 | GAGAAACTGGGAAAACTTCAGTATTCACTGGATTATGAT<br>TTCCAAAATAACCAGCTGCTGGTAGGGATCATTCAGGCT<br>GCCGAACTGCCCGCCTTGGACATGGGGGGCACATCTGAT<br>CCTTACGTGAAAGTGTTTCTGCTACCTGATAAGAAGAAG<br>AAATTTGAGACAAAAGTCCACCGAAAAACCCTTAATCCT<br>GTCTTCAATGAGCAATTTACTTTCAAGGTACCATACTCGG<br>AATTGGGTGGCAAAACCCTAGTGATGGCTGTATATGATTT<br>TGATCGTTTCTCTAAGCATGACATCATTGGAGAATTTAAA<br>GTCCCTATGAACACAGTGGATTTTGGCCATGTAACTGAGG<br>AATGGCGTGACCTGCAAAGTGCTGGAGGCGGTGGATCAG<br>TTGAGCCCAAATCTTCTGACAAAACTCACACATGCCCACC<br>GTGCCCAGCACCTGAACTCCTGGGGGGACCGTCAGTCTTC<br>CTCTTCCCCCCAAAACCCAAGGACACCCTCATGATCTCCC<br>GGACCCCTGAGGTCACATGCGTGGTGGTGGACGTGAGCC<br>ACGAAGACCCTGAGGTCAAGTTCAACTGGTACGTGGACG<br>GCGTGGAGGTGCATAATGCCAAGACAAAGCCGCGGGAG<br>GAGCAGTACAACAGCACGTACCGTGTGGTCAGCGTCCTC<br>ACCGTCCTGCACCAGGACTGGCTGAATGGCAAGGAGTAC<br>AAGTGCAAGGTCTCCAACAAAGCCCTCCCAGCCCCCATC<br>GAGAAAACCATCTCCAAAGCCAAAGGGCAGCCCCGAGA<br>ACCACAGGTGTACACCCTGCCCCCATCCCGGGATGAGCT<br>GACCAAGAACCAGGTCAGCCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCTTCCTCTACAGCAAGCTC<br>ACCGTGGACAAGAGCAGGTGGCAGCAGGGGAACGTCTTC<br>TCATGCTCCGTGATGCATGAGGCTCTGCACAACCACTACA<br>CGCAGAAGAGCCTCTCCCTGTCTCCGGGTAAAGGCGGAG<br>GTGGCAGCGAGAAACTGGGAAAACTTCAGTATTCACTGG<br>ATTATGATTTCCAAAATAACCAGCTGCTGGTAGGGATCAT<br>TCAGGCTGCCGAACTGCCCGCCTTGGACATGGGGGGCAC<br>ATCTGATCCTTACGTGAAAGTGTTTCTGCTACCTGATAAG<br>AAGAAGAAATTTGAGACAAAAGTCCACCGAAAAACCCTT<br>AATCCTGTCTTCAATGAGCAATTTACTTTCAAGGTACCAT<br>ACTCGGAATTGGGTGGCAAAACCCTAGTGATGGCTGTAT<br>ATGATTTTGATCGTTTCTCTAAGCATGACATCATTGGAGA<br>ATTTAAAGTCCCTATGAACACAGTGGATTTTGGCCATGTA<br>ACTGAGGAATGGCGTGACCTGCAAAGTGCT | 29 |

TABLE 1-continued

DNA sequences of polynucleotides encoding exemplary proteins.

| Polynucleotide encoding protein | DNA sequence | SEQ ID NO: |
|---|---|---|
| Fc-PKCα | GTTGAGCCCAAATCTTCTGACAAAACTCACACATGCCCAC CGTGCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGAGGCG GTGGATCAGAGAAGAGGGGGCGGATTTACCTAAAGGCTG AGGTTGCTGATGAAAAGCTCCATGTCACAGTACGAGATG CAAAAAATCTAATCCCTATGGATCCAAACGGGCTTTCAG ATCCTTATGTGAAGCTGAAACTTATTCCTGATCCCAAGAA TGAAAGCAAGCAAAAAACCAAAACCATCCGCTCCACACT AAATCCGCAGTGGAATGAGTCCTTTACATTCAAATTGAA ACCTTCAGACAAAGACCGACGACTGTCTGTAGAAATCTG GGACTGGGATCGAACAACAAGGAATGACTTCATGGGATC CCTTTCCTTTGGAGTTTCGGAGCTGATGAAGATGCCGGCC AGTGGATGGTACAAGTTGCTTAACCAAGAAGAAGGTGAG TACTACAACGTA | 31 |
| Fc-AnxA1 | GTTGAGCCCAAATCTTCTGACAAAACTCACACATGCCCAC CGTGCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGAGGCG GTGGATCAACCTTCAATCCATCCTCGGATGTCGCTGCCTT GCATAAGGCCATAATGGTTAAAGGTGTGGATGAAGCAAC CATCATTGACATTCTAACTAAGCGAAACAATGCACAGCG TCAACAGATCAAAGCAGCATATCTCCAGGAAACAGGAAA GCCCCTGGATGAAACACTGAAGAAAGCCCTTACAGGTCA CCTTGAGGAGGTTGTTTTAGCTCTGCTAAAAACTCCAGCG CAATTTGATGCTGATGAACTTCGTGCTGCCATGAAGGGCC TTGGAACTGATGAAGATACTCTAATTGAGATTTTGGCATC AAGAACTAACAAAGAAATCAGAGACATTAACAGGGTCTA CAGAGAGGAACTGAAGAGAGATCTGGCCAAAGACATAA CCTCAGACACATCTGGAGATTTTCGGAACGCTTTGCTTTC TCTTGCTAAGGGTGACCGATCTGAGGACTTTGGTGTGAAT GAAGACTTGGCTGATTCAGATGCCAGGGCCTTGTATGAA GCAGGAGAAAGGAGAAAGGGGACAGACGTAAACGTGTT CAATACCATCCTTACCACCAGAAGCTATCCACAACTTCGC AGAGTGTTTCAGAAATACACCAAGTACAGTAAGCATGAC ATGAACAAAGTTCTAGACCTGGAGTTGAAAGGTGACATT GAGAAATGCCTCACAGCTATCGTGAAGTGCGCCACAAGC AAACCAGCTTTCTTTGCAGAGAAGCTTCATCAAGCCATGA AAGGTGTTGGAACTCGCCATAAGGCATTGATCAGGATTA TGGTTTCCCGTTCTGAAATTGACATGAATGATATCAAAGC ATTCTATCAGAAGATGTATGGTATCTCCCTTTGCCAAGCC ATCCTGGATGAAACCAAAGGAGATTATGAGAAAATCCTG GTGGCTCTTTGTGGAGGAAAC | 33 |

TABLE 1-continued

DNA sequences of polynucleotides encoding exemplary proteins.

| Polynucleotide encoding protein | DNA sequence | SEQ ID NO: |
|---|---|---|
| Syt1-Fc | GAGAAACTGGGAAAACTTCAGTATTCACTGGATTATGAT TTCCAAAATAACCAGCTGCTGGTAGGGATCATTCAGGCT GCCGAACTGCCCGCCTTGGACATGGGGGGCACATCTGAT CCTTACGTGAAAGTGTTTCTGCTACCTGATAAGAAGAAG AAATTTGAGACAAAAGTCCACCGAAAAACCCTTAATCCT GTCTTCAATGAGCAATTTACTTTCAAGGTACCATACTCGG AATTGGGTGGCAAAACCCTAGTGATGGCTGTATATGATTT TGATCGTTTCTCTAAGCATGACATCATTGGAGAATTTAAA GTCCCTATGAACACAGTGGATTTTGGCCATGTAACTGAGG AATGGCGTGACCTGCAAAGTGCTGGAGGCGGTGGATCAG TTGAGCCCAAATCTTCTGACAAAACTCACACATGCCCACC GTGCCCAGCACCTGAACTCCTGGGGGGACCGTCAGTCTTC CTCTTCCCCCCAAAACCCAAGGACACCCTCATGATCTCCC GGACCCCTGAGGTCACATGCGTGGTGGTGGACGTGAGCC ACGAAGACCCTGAGGTCAAGTTCAACTGGTACGTGGACG GCGTGGAGGTGCATAATGCCAAGACAAAGCCGCGGGAG GAGCAGTACAACAGCACGTACCGTGTGGTCAGCGTCCTC ACCGTCCTGCACCAGGACTGGCTGAATGGCAAGGAGTAC AAGTGCAAGGTCTCCAACAAAGCCCTCCCAGCCCCCATC GAGAAAACCATCTCCAAAGCCAAAGGGCAGCCCCGAGA ACCACAGGTGTACACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAA | 35 |
| PKCα-Fc | GAGAAGAGGGGGCGGATTTACCTAAAGGCTGAGGTTGCT GATGAAAAGCTCCATGTCACAGTACGAGATGCAAAAAAT CTAATCCCTATGGATCCAAACGGGCTTTCAGATCCTTATG TGAAGCTGAAACTTATTCCTGATCCCAAGAATGAAAGCA AGCAAAAAACCAAAACCATCCGCTCCACACTAAATCCGC AGTGGAATGAGTCCTTTACATTCAAATTGAAACCTTCAGA CAAAGACCGACGACTGTCTGTAGAAATCTGGGACTGGGA TCGAACAACAAGGAATGACTTCATGGGATCCCTTTCCTTT GGAGTTTCGGAGCTGATGAAGATGCCGGCCAGTGGATGG TACAAGTTGCTTAACCAAGAAGAAGGTGAGTACTACAAC GTAGGAGGCGGTGGATCAGTTGAGCCCAAATCTTCTGAC AAAACTCACACATGCCCACCGTGCCCAGCACCTGAACTC CTGGGGGGACCGTCAGTCTTCCTCTTCCCCCCAAAACCCA AGGACACCCTCATGATCTCCCGGACCCCTGAGGTCACAT GCGTGGTGGTGGACGTGAGCCACGAAGACCCTGAGGTCA AGTTCAACTGGTACGTGGACGGCGTGGAGGTGCATAATG CCAAGACAAAGCCGCGGGAGGAGCAGTACAACAGCACG TACCGTGTGGTCAGCGTCCTCACCGTCCTGCACCAGGACT GGCTGAATGGCAAGGAGTACAAGTGCAAGGTCTCCAACA AAGCCCTCCCAGCCCCCATCGAGAAAACCATCTCCAAAG CCAAAGGGCAGCCCCGAGAACCACAGGTGTACACCCTGC CCCCATCCCGGGATGAGCTGACCAAGAACCAGGTCAGCC TGACCTGCCTGGTCAAAGGCTTCTATCCCAGCGACATCGC CGTGGAGTGGGAGAGCAATGGGCAGCCGGAGAACAACT ACAAGACCACGCCTCCCGTGCTGGACTCCGACGGCTCCTT CTTCCTCTACAGCAAGCTCACCGTGGACAAGAGCAGGTG GCAGCAGGGGAACGTCTTCTCATGCTCCGTGATGCATGA GGCTCTGCACAACCACTACACGCAGAAGAGCCTCTCCCT GTCTCCGGGTAAA | 37 |
| AnxA1-Fc | ACCTTCAATCCATCCTCGGATGTCGCTGCCTTGCATAAGG CCATAATGGTTAAAGGTGTGGATGAAGCAACCATCATTG ACATTCTAACTAAGCGAAACAATGCACAGCGTCAACAGA TCAAAGCAGCATATCTCCAGGAAACAGGAAAGCCCCTGG ATGAAACACTGAAGAAAGCCCTTACAGGTCACCTTGAGG AGGTTGTTTTAGCTCTGCTAAAAACTCCAGCGCAATTTGA TGCTGATGAACTTCGTGCTGCCATGAAGGGCCTTGGAACT GATGAAGATACTCTAATTGAGATTTTGGCATCAAGAACT AACAAAGAAATCAGAGACATTAACAGGGTCTACAGAGA GGAACTGAAGAGAGATCTGGCCAAAGACATAACCTCAGA CACATCTGGAGATTTTCGGAACGCTTTGCTTTCTCTTGCT AAGGGTGACCGATCTGAGGACTTTGGTGTGAATGAAGAC TTGGCTGATTCAGATGCCAGGGCCTTGTATGAAGCAGGA GAAAGGAGAAAGGGGACAGACGTAAACGTGTTCAATAC CATCCTTACCACCAGAAGCTATCCACAACTTCGCAGAGTG | 39 |

TABLE 1-continued

DNA sequences of polynucleotides encoding exemplary proteins.

| Polynucleotide encoding protein | DNA sequence | SEQ ID NO: |
| --- | --- | --- |
| | TTTCAGAAATACACCAAGTACAGTAAGCATGACATGAAC AAAGTTCTAGACCTGGAGTTGAAAGGTGACATTGAGAAA TGCCTCACAGCTATCGTGAAGTGCGCCACAAGCAAACCA GCTTTCTTTGCAGAGAAGCTTCATCAAGCCATGAAAGGTG TTGGAACTCGCCATAAGGCATTGATCAGGATTATGGTTTC CCGTTCTGAAATTGACATGAATGATATCAAAGCATTCTAT CAGAAGATGTATGGTATCTCCCTTTGCCAAGCCATCCTGG ATGAAACCAAAGGAGATTATGAGAAAATCCTGGTGGCTC TTTGTGGAGGAAACGGAGGCGGTGGATCAGTTGAGCCCA AATCTTCTGACAAAACTCACACATGCCCACCGTGCCCAGC ACCTGAACTCCTGGGGGGACCGTCAGTCTTCCTCTTCCCC CCAAAACCCAAGGACACCCTCATGATCTCCCGGACCCCT GAGGTCACATGCGTGGTGGTGGACGTGAGCCACGAAGAC CCTGAGGTCAAGTTCAACTGGTACGTGGACGGCGTGGAG GTGCATAATGCCAAGACAAAGCCGCGGGAGGAGCAGTAC AACAGCACGTACCGTGTGGTCAGCGTCCTCACCGTCCTGC ACCAGGACTGGCTGAATGGCAAGGAGTACAAGTGCAAGG TCTCCAACAAAGCCCTCCCAGCCCCCATCGAGAAAACCA TCTCCAAAGCCAAAGGGCAGCCCCGAGAACCACAGGTGT ACACCCTGCCCCCATCCCGGGATGAGCTGACCAAGAACC AGGTCAGCCTGACCTGCCTGGTCAAAGGCTTCTATCCCAG CGACATCGCCGTGGAGTGGGAGAGCAATGGGCAGCCGGA GAACAACTACAAGACCACGCCTCCCGTGCTGGACTCCGA CGGCTCCTTCTTCCTCTACAGCAAGCTCACCGTGGACAAG AGCAGGTGGCAGCAGGGGAACGTCTTCTCATGCTCCGTG ATGCATGAGGCTCTGCACAACCACTACACGCAGAAGAGC CTCTCCCTGTCTCCGGGTAAA | |
| Syt1-Fc-Syt1 with knobs into holes mutations (TF) | GAGAAACTGGGAAAACTTCAGTATTCACTGGATTATGAT TTCCAAAATAACCAGCTGCTGGTAGGGATCATTCAGGCT GCCGAACTGCCCGCCTTGGACATGGGGGGCACATCTGAT CCTTACGTGAAAGTGTTTCTGCTACCTGATAAGAAGAAG AAATTTGAGACAAAAGTCCACCGAAAAACCCTTAATCCT GTCTTCAATGAGCAATTTACTTTCAAGGTACCATACTCGG AATTGGGTGGCAAAACCCTAGTGATGGCTGTATATGATTT TGATCGTTTCTCTAAGCATGACATCATTGGAGAATTTAAA GTCCCTATGAACACAGTGGATTTTGGCCATGTAACTGAGG AATGGCGTGACCTGCAAAGTGCTGGAGGCGGTGGATCAG TTGAGCCCAAATCTTCTGACAAAACTCACACATGCCCACC GTGCCCAGCACCTGAACTCCTGGGGGGACCGTCAGTCTTC CTCTTCCCCCCAAAACCCAAGGACACCCTCATGATCTCCC GGACCCCTGAGGTCACATGCGTGGTGGTGGACGTGAGCC ACGAAGACCCTGAGGTCAAGTTCAACTGGTACGTGGACG GCGTGGAGGTGCATAATGCCAAGACAAAGCCGCGGGAG GAGCAGTACAACAGCACGTACCGTGTGGTCAGCGTCCTC ACCGTCCTGCACCAGGACTGGCTGAATGGCAAGGAGTAC AAGTGCAAGGTCTCCAACAAAGCCCTCCCAGCCCCCATC GAGAAAACCATCTCCAAAGCCAAAGGGCAGCCCCGAGA ACCACAGGTGACCACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCTTCCCTCCCGT GCTGGACTCCGACGGCTCCTTCTTCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGCGGAG GTGGCAGCGAGAAACTGGGAAAACTTCAGTATTCACTGG ATTATGATTTCCAAAATAACCAGCTGCTGGTAGGGATCAT TCAGGCTGCCGAACTGCCCGCCTTGGACATGGGGGGCAC ATCTGATCCTTACGTGAAAGTGTTTCTGCTACCTGATAAG AAGAAGAAATTTGAGACAAAAGTCCACCGAAAAACCCTT AATCCTGTCTTCAATGAGCAATTTACTTTCAAGGTACCAT ACTCGGAATTGGGTGGCAAAACCCTAGTGATGGCTGTAT ATGATTTTGATCGTTTCTCTAAGCATGACATCATTGGAGA ATTTAAAGTCCCTATGAACACAGTGGATTTTGGCCATGTA ACTGAGGAATGGCGTGACCTGCAAAGTGCT | 41 |
| Fc with knobs into holes mutations(HA) | GTTGAGCCCAAATCTTCTGACAAAACTCACACATGCCCAC CGTGCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT | 43 |

TABLE 1-continued

DNA sequences of polynucleotides encoding exemplary proteins.

| Polynucleotide encoding protein | DNA sequence | SEQ ID NO: |
|---|---|---|
| | CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAA | |
| Syt1-Fc-Syt1 with knobs into holes mutations (TF) and electrostatic steering mutations | GAGAAACTGGGAAAACTTCAGTATTCACTGGATTATGAT TTCCAAAATAACCAGCTGCTGGTAGGGATCATTCAGGCT GCCGAACTGCCCGCCTTGGACATGGGGGGCACATCTGAT CCTTACGTGAAAGTGTTTCTGCTACCTGATAAGAAGAAG AAATTTGAGACAAAAGTCCACCGAAAAACCCTTAATCCT GTCTTCAATGAGCAATTTACTTTCAAGGTACCATACTCGG AATTGGGTGGCAAAACCCTAGTGATGGCTGTATATGATTT TGATCGTTTCTCTAAGCATGACATCATTGGAGAATTTAAA GTCCCTATGAACACAGTGGATTTTGGCCATGTAACTGAGG AATGGCGTGACCTGCAAAGTGCTGGAGGCGGTGGATCAG TTGAGCCCAAATCTTCTGACAAAACTCACACATGCCCACC GTGCCCAGCACCTGAACTCCTGGGGGGACCGTCAGTCTTC CTCTTCCCCCCAAAACCCAAGGACACCCTCATGATCTCCC GGACCCCTGAGGTCACATGCGTGGTGGTGGACGTGAGCC ACGAAGACCCTGAGGTCAAGTTCAACTGGTACGTGGACG GCGTGGAGGTGCATAATGCCAAGACAAAGCCGCGGGAG GAGCAGTACAACAGCACGTACCGTGTGGTCAGCGTCCTC ACCGTCCTGCACCAGGACTGGCTGAATGGCAAGGAGTAC AAGTGCAAGGTCTCCAACAAAGCCCTCCCAGCCCCCATC GAGAAAACCATCTCCAAAGCCAAAGGGCAGCCCCGAGA ACCACAGGTGACCACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACGACACCTTCCCTCCCGT GCTGGACTCCGACGGCTCCTTCTTCCTCTACAGCGACCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGCGGAG GTGGCAGCGAGAAACTGGGAAAACTTCAGTATTCACTGG ATTATGATTTCCAAAATAACCAGCTGCTGGTAGGGATCAT TCAGGCTGCCGAACTGCCCGCCTTGGACATGGGGGGCAC ATCTGATCCTTACGTGAAAGTGTTTCTGCTACCTGATAAG AAGAAGAAATTTGAGACAAAAGTCCACCGAAAAACCCTT AATCCTGTCTTCAATGAGCAATTTACTTTCAAGGTACCAT ACTCGGAATTGGGTGGCAAAACCCTAGTGATGGCTGTAT ATGATTTTGATCGTTTCTCTAAGCATGACATCATTGGAGA ATTTAAAGTCCCTATGAACACAGTGGATTTTGGCCATGTA ACTGAGGAATGGCGTGACCTGCAAAGTGCT | 45 |
| Fc with knobs into holes mutations (HA) and electrostatic steering mutations | GTTGAGCCCAAATCTTCTGACAAAACTCACACATGCCCAC CGTGCCCAGCACCTGAACTCCTGGGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATAAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGAAGTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAA | 47 |

TABLE 2

Amino acid sequences of exemplary proteins.

| Protein | Amino acid sequence | SEQ ID NO: |
|---|---|---|
| Pertuzumab light chain with Cys mutation | DIELTQSPSSLSASVGDRVTITCKASQDVSIGVAWYQQKPGKA PKLLIYSASYRYTGVPSRFSGSGSGTDFTLTISSLQPEDFATYY CQQYYIYPYTFGQGTKLEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGES | 2 |
| SG heavy chain with Cys mutations | QVQLQESGGGLVQPGGSLRLSCAASGFTFTDYTMDWVRQAP GKGLEWVADVNPNHGESIYNQRFKGRFTLSVDRSKNTLYLQ MNSLRAEDTAVYYCARNLGPSFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSSDKTHTCPPSPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLTCLVKGFYPS DIAVEWESNGQPENNYKTTPPVLDSDGSFFLYSKLTVDKSRW QQGNVFSCSVMHEALHNHYTQKSLSLSPGK | 4 |
| YS light chain with Cys mutation | DIELTQSPSSLSASVGDRVTITCKASQDVSIGVAWYQQKPGKA PKLLIYSASYRHTGVPSRFSGSGSGTDFTLTISSLQPEDFATYY CQQYYIYPYTFGQGTKLEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGES | 6 |
| YS heavy chain with Cys mutations | QVQLQESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPHFYFDYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSSDKTHTCPPSPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPI EKTISKAKGQPREPQVYTLPPSRDELTKNQVSLTCLVKGFYPS DIAVEWESNGQPENNYKTTPPVLDSDGSFFLYSKLTVDKSRW QQGNVFSCSVMHEALHNHYTQKSLSLSPGK | 8 |
| SG scFv linked to N-terminus of heavy chain with Cys mutations | QVQLQESGGGLVQPGGSLRLSCAASGFTFTDYTMDWVRQAP GKGLEWVADVNPNHGESIYNQRFKGRFTLSVDRSKNTLYLQ MNSLRAEDTAVYYCARNLGPSFYFDYWGQGTLVTVSSGGGG SGGGGSGGGGSDIELTQSPSSLSASVGDRVTITCKASQDVSIG VAWYQQKPGKAPKLLIYSASYRYTGVPSRFSGSGSGTDFTLTI SSLQPEDFATYYCQQYYIYPYTFGQGTKLEIKRGGSVEPKSSD KTHTCPPSPAPELLGGPSVFLFPPKPKDTLMISRTPEVTCVVVD VSHEDPEVKFNWYVDGVEVHNAKTKPREEQYNSTYRVVSVL TVLHQDWLNGKEYKCKVSNKALPAPIEKTISKAKGQPREPQV YTLPPSRDELTKNQVSLTCLVKGFYPSDIAVEWESNGQPENN YKTTPPVLDSDGSFFLYSKLTVDKSRWQQGNVFSCSVMHEAL HNHYTQKSLSLSPGK | 10 |
| YS scFv linked to N-terminus of heavy chain with Cys mutations | QVQLQESGGGLVQPGGSLRLSCAASGFTFTDYTMDWVRQAP GKGLEWVADVNPNSGGSIYNQRFKGRFTLSVDRSKNTLYLQ MNSLRAEDTAVYYCARNLGPHFYFDYWGQGTLVTVSSGGG GSGGGGSGGGGSDIELTQSPSSLSASVGDRVTITCKASQDVSI GVAWYQQKPGKAPKLLIYSASYRHTGVPSRFSGSGSGTDFTL TISSLQPEDFATYYCQQYYIYPYTFGQGTKLEIKRGGSVEPKSS DKTHTCPPSPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQ VYTLPPSRDELTKNQVSLTCLVKGFYPSDIAVEWESNGQPEN NYKTTPPVLDSDGSFFLYSKLTVDKSRWQQGNVFSCSVMHE ALHNHYTQKSLSLSPGK | 12 |
| Heavy chain with Cys mutations and SG scFv linked to C-terminus | VEPKSSDKTHTCPPSPAPELLGGPSVFLFPPKPKDTLMISRTPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGKGGSQVQLQESGGGLVQPGG SLRLSCAASGFTFTDYTMDWVRQAPGKGLEWVADVNPNHG ESIYNQRFKGRFTLSVDRSKNTLYLQMNSLRAEDTAVYYCAR NLGPSFYFDYWGQGTLVTVSSGGGGSGGGGSGGGGSDIELTQ SPSSLSASVGDRVTITCKASQDVSIGVAWYQQKPGKAPKLLIY SASYRYTGVPSRFSGSGSGTDFTLTISSLQPEDFATYYCQQYYI YPYTFGQGTKLEIKR | 14 |

TABLE 2-continued

Amino acid sequences of exemplary proteins.

| Protein | Amino acid sequence | SEQ ID NO: |
|---|---|---|
| Heavy chain with Cys mutations and YS scFv linked to C-terminus | VEPKSSDKTHTCPPSPAPELLGGPSVFLFPPKPKDTLMISRTPE<br>VTCVVVDVSHEDPEVKFNWYVDGVEVHNAKTKPREEQYNS<br>TYRVVSVLTVLHQDWLNGKEYKCKVSNKALPAPIEKTISKAK<br>GQPREPQVYTLPPSRDELTKNQVSLTCLVKGFYPSDIAVEWES<br>NGQPENNYKTTPPVLDSDGSFFLYSKLTVDKSRWQQGNVFSC<br>SVMHEALHNHYTQKSLSLSPGKGGSQVQLQESGGGLVQPGG<br>SLRLSCAASGFTFTDYTMDWVRQAPGKGLEWVADVNPNSGG<br>SIYNQRFKGRFTLSVDRSKNTLYLQMNSLRAEDTAVYYCARN<br>LGPHFYFDYWGQGTLVTVSSGGGGSGGGGSGGGGSDIELTQS<br>PSSLSASVGDRVTITCKASQDVSIGVAWYQQKPGKAPKLLIYS<br>ASYRHTGVPSRFSGSGSGTDFTLTISSLQPEDFATYYCQQYYIY<br>PYTFGQGTKLEIKR | 16 |
| Trastuzumab VH-CH1-hinge-CalD2 | QVQLQESGGGLVQPGGSLRLSCAASGFNIKDTYIHWVRQAPG<br>KGLEWVARIYPTNGYTRYADSVKGRFTISADTSKNTAYLQM<br>NSLRAEDTAVYYCSRWGGDGFYAMDYWGQGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNHN<br>PSNTKVDKKVEPKSSTKTHTSGGNTLDDLFQELDKNGDGEVS<br>FEEFQVLVKKISQ | 18 |
| Trastuzumab light chain | DIELTQSPSSLSASVGDRVTITCRASQDVNTAVAWYQQKPGK<br>APKLLIYSASFLYSGVPSRFSGSRSGTDFTLTISSLQPEDFATYY<br>CQQHYTTPPTFGQGTKLEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGES<br>HHHHHH | 20 |
| CalD1-hinge-Fc | KSPEELKRIFEKYAAKEGDPDQLSKDELKLLIQAEFPSLLKGP<br>GSSVEPKSSDKTHTCPPCPAPELLGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALPAPIEKTISK<br>AKGQPREPQVYTLPPSRDELTKNQVSLTCLVKGFYPSDIAVE<br>WESNGQPENNYKTTPPVLDSDGSFFLYSKLTVDKSRWQQGN<br>VFSCSVMHEALHNHYTQKSLSLSPGK | 22 |
| 026-VH-CH1-hinge-CalD2 | QVQLQESGGGVVQPGRSLRLSCAASGFTFSNYVMHWVRQAP<br>GKGLEWVAIIWYDGSNKYYADSVKGRFTISRDNSKNTLYLQ<br>MNSLRAEDTAVYYCAGGYNWNYEYHYYGMDVWGQGTTVT<br>VSSASTKGPSVFPLAPSSKSTSGGTAALGCLVKDYFPEPVTVS<br>WNSGALTSGVHTFPAVLQSSGLYSLSSVVTVPSSSLGTQTYIC<br>NVNHNPSNTKVDKKVEPKSSTKTHTSGGNTLDDLFQELDKN<br>GDGEVSFEEFQVLVKKISQ | 24 |
| 026 light chain | DIELTQSPSSLSASVGDRVTITCRASQGITNYLAWFQQKPGKA<br>PKSLIYAASSLQSGVPSKFSGSGSGTDFSLTISSLQPEDFATYYC<br>QQYNSYPITFGQGTRLEIKRTVAAPSVFIFPPSDEQLKSGTASV<br>VCLLNNFYPREAKVQWKVDNALQSGNSQESVTEQDSKDSTY<br>SLSSTLTLSKADYEKHKVYACEVTHQGLSSPVTKSFNRGESH<br>HHHHH | 26 |
| Fc-Syt1 | VEPKSSDKTHTCPPCPAPELLGGPSVFLFPPKPKDTLMISRTPE<br>VTCVVVDVSHEDPEVKFNWYVDGVEVHNAKTKPREEQYNS<br>TYRVVSVLTVLHQDWLNGKEYKCKVSNKALPAPIEKTISKAK<br>GQPREPQVYTLPPSRDELTKNQVSLTCLVKGFYPSDIAVEWES<br>NGQPENNYKTTPPVLDSDGSFFLYSKLTVDKSRWQQGNVFSC<br>SVMHEALHNHYTQKSLSLSPGKGGGGSEKLGKLQYSLDYDF<br>QNNQLLVGIIQAAELPALDMGGTSDPYVKVFLLPDKKKKFET<br>KVHRKTLNPVFNEQFTFKVPYSELGGKTLVMAVYDFDRFSK<br>HDIIGEFKVPMNTVDFGHVTEEWRDLQSA | 28 |
| Syt1-Fc-Syt1 | EKLGKLQYSLDYDFQNNQLLVGIIQAAELPALDMGGTSDPYV<br>KVFLLPDKKKKFETKVHRKTLNPVFNEQFTFKVPYSELGGKT<br>LVMAVYDFDRFSKHDIIGEFKVPMNTVDFGHVTEEWRDLQS<br>AGGGGSVEPKSSDKTHTCPPCPAPELLGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKALPAPIE<br>KTISKAKGQPREPQVYTLPPSRDELTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGKGGGGSEKLGKLQ<br>YSLDYDFQNNQLLVGIIQAAELPALDMGGTSDPYVKVFLLPD<br>KKKKFETKVHRKTLNPVFNEQFTFKVPYSELGGKTLVMAVY<br>DFDRFSKHDIIGEFKVPMNTVDFGHVTEEWRDLQSA | 30 |

TABLE 2-continued

Amino acid sequences of exemplary proteins.

| Protein | Amino acid sequence | SEQ ID NO: |
|---|---|---|
| Fc-PKCa | VEPKSSDKTHTCPPCPAPELLGGPSVFLFPPKPKDTLMISRTPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGKGGGGSEKRGRIYLKAEVAD EKLHVTVRDAKNLIPMDPNGLSDPYVKLKLIPDPKNESKQKT KTIRSTLNPQWNESFTFKLKPSDKDRRLSVEIWDWDRTTRND FMGSLSFGVSELMKMPASGWYKLLNQEEGEYYNV | 32 |
| Fc-AnxA1 | VEPKSSDKTHTCPPCPAPELLGGPSVFLFPPKPKDTLMISRTPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGKGGGGSTFNPSSDVAALHKAI MVKGVDEATIIDILTKRNNAQRQQIKAAYLQETGKPLDETLK KALTGHLEEVVLALLKTPAQFDADELRAAMKGLGTDEDTHE ILASRTNKEIRDINRVYREELKRDLAKDITSDTSGDFRNALLSL AKGDRSEDFGVNEDLADSDARALYEAGERRKGTDVNVFNTI LTTRSYPQLRRVFQKYTKYSKHDMNKVLDLELKGDIEKCLTA IVKCATSKPAFFAEKLHQAMKGVGTRHKALIREVIVSRSEIDM NDIKAFYQKMYGISLCQAILDETKGDYEKILVALCGGN | 34 |
| Syt1-Fc | EKLGKLQYSLDYDFQNNQLLVGIIQAAELPALDMGGTSDPYV KVFLLPDKKKKFETKVHRKTLNPVFNEQFTFKVPYSELGGKT LVMAVYDFDRFSKHDIIGEFKVPMNTVDFGHVTEEWRDLQS AGGGGSVEPKSSDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVYTLPPSRDELTKNQVSLTCLVKGFYPSD IAVEWESNGQPENNYKTTPPVLDSDGSFFLYSKLTVDKSRWQ QGNVFSCSVMHEALHNHYTQKSLSLSPGK | 36 |
| PKCα-Fc | EKRGRIYLKAEVADEKLHVTVRDAKNLIPMDPNGLSDPYVKL KLIPDPKNESKQKTKTIRSTLNPQWNESFTFKLKPSDKDRRLS VEIWDWDRTTRNDFMGSLSFGVSELMKMPASGWYKLLNQE EGEYYNVGGGGSVEPKSSDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNK ALPAPIEKTISKAKGQPREPQVYTLPPSRDELTKNQVSLTCLV KGFYPSDIAVEWESNGQPENNYKTTPPVLDSDGSFFLYSKLTV DKSRWQQGNVFSCSVMHEALHNHYTQKSLSLSPGK | 38 |
| AnxA1-Fc | TFNPSSDVAALHKAIMVKGVDEATIIDILTKRNNAQRQQIKAA YLQETGKPLDETLKKALTGHLEEVVLALLKTPAQFDADELRA AMKGLGTDEDTLIEILASRTNKEIRDINRVYREELKRDLAKDI TSDTSGDFRNALLSLAKGDRSEDFGVNEDLADSDARALYEAG ERRKGTDVNVFNTILTTRSYPQLRRVFQKYTKYSKHDMNKV LDLELKGDIEKCLTAIVKCATSKPAFFAEKLHQAMKGVGTRH KALIRIMVSRSEIDMNDIKAFYQKMYGISLCQAILDETKGDYE KILVALCGGNGGGGSVEPKSSDKTHTCPPCPAPELLGGPSVFL FPPKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSRDELTKNQVSLTC LVKGFYPSDIAVEWESNGQPENNYKTTPPVLDSDGSFFLYSKL TVDKSRWQQGNVFSCSVMHEALHNHYTQKSLSLSPGK | 40 |
| Syt1-Fc-Syt1 with knobs into holes mutations (TF) | EKLGKLQYSLDYDFQNNQLLVGIIQAAELPALDMGGTSDPYV KVFLLPDKKKKFETKVHRKTLNPVFNEQFTFKVPYSELGGKT LVMAVYDFDRFSKHDIIGEFKVPMNTVDFGHVTEEWRDLQS AGGGGSVEPKSSDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVTTLPPSRDELTKNQVSLTCLVKGFYPSDI AVEWESNGQPENNYKTFPPVLDSDGSFFLYSKLTVDKSRWQ QGNVFSCSVMHEALHNHYTQKSLSLSPGKGGGGSEKLGKLQ YSLDYDFQNNQLLVGIIQAAELPALDMGGTSDPYVKVFLLPD KKKKFETKVHRKTLNPVFNEQFTFKVPYSELGGKTLVMAVY DFDRFSKHDIIGEFKVPMNTVDFGHVTEEWRDLQSA | 42 |

TABLE 2-continued

Amino acid sequences of exemplary proteins.

| Protein | Amino acid sequence | SEQ ID NO: |
|---|---|---|
| Fc with knobs into holes mutations(HA) | VEPKSSDKTHTCPPCPAPELLGGPSVFLFPPKPKDTLMISRTPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALHNHYTQKSLSLSPGK | 44 |
| Syt1-Fc-Syt1 with knobs into holes mutations (TF) and electrostatic steering mutations | EKLGKLQYSLDYDFQNNQLLVGIIQAAELPALDMGGTSDPYV KVFLLPDKKKKFETKVHRKTLNPVFNEQFTFKVPYSELGGKT LVMAVYDFDRFSKHDIIGEFKVPMNTVDFGHVTEEWRDLQS AGGGGSVEPKSSDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVTTLPPSRDELTKNQVSLTCLVKGFYPSDI AVEWESNGQPENNYDTFPPVLDSDGSFFLYSDLTVDKSRWQ QGNVFSCSVMHEALHNHYTQKSLSLSPGKGGGGSEKLGKLQ YSLDYDFQNNQLLVGIIQAAELPALDMGGTSDPYVKVFLLPD KKKKFETKVHRKTLNPVFNEQFTFKVPYSELGGKTLVMAVY DFDRFSKHDIIGEFKVPMNTVDFGHVTEEWRDLQSA | 46 |
| Fc with knobs into holes mutations (HA) and electrostatic steering mutations | VEPKSSDKTHTCPPCPAPELLGGPSVFLFPPKPKDTLMISRTPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDKLTKNQVHLTCLVKGFYPSDIAVEWE SNGQPENNYKTTPPVLKSDGSFALYSKLTVDKSRWQQGNVFS CSVMHEALHNHYTQKSLSLSPGK | 48 |

The DNA sequence of SEQ ID NO:1 is of a polynucleotide encoding an exemplary light chain of a HER2-specific antibody, pertuzumab, (SEQ ID NO:2) with mutation of Cys214 to serine, and is configured, for example, for heterodimer formation with the SG heavy chain variant of pertuzuamb (SEQ ID NO: 4).

In particular, the amino acid sequence of the exemplary light chain of the HER2-specific antibody, pertuzumab, (SEQ ID NO: 2) has, in order from N- to C-terminus a HER2-specific VL domain at residues 1-108, and an immunoglobulin CL domain (human $C_{\kappa}$) at residues 109-214. The cysteine residue (214) that usually pairs with an immunoglobulin heavy chain is mutated to serine. The amino acid residue numbers referred to in SEQ ID NO:2 are those of the protein sequence, and do not refer to the EU numbering convention.

The DNA sequence of SEQ ID NO: 3 is of a polynucleotide encoding an exemplary heavy chain of the HER2-specific antibody, pertuzumab, (SEQ ID NO: 4) with mutation of Cys222 and Cys231 to serines, and the SG mutations. The encoded heavy chain (SEQ ID NO: 4) is configured, for example, to form heterodimers with the light chain variant of pertuzumab (SEQ ID NO: 2) to generate the SG variant of pertuzumab.

In particular, the amino acid sequence of the exemplary antibody heavy chain of SEQ ID NO: 4 has, in order from N- to C-terminus, a HER2-specific VH domain at residues 1-119, an immunoglobulin CH1 domain (human IgG1-derived) at residues 120-216, an immunoglobulin hinge (human IgG1-derived) at residues 217-232, an immunoglobulin CH2 domain (human IgG1-derived) at residues 233-342, an immunoglobulin CH3 domain (human IgG1-derived) at residues 343-449. The exemplary HER2-specific antibody heavy chain of SEQ ID NO: 4 has mutations of Ser55 and Gly57 to histidine and glutamic acid (SG mutations), respectively. The cysteine residues (222 and 231) that usually pair with an immunoglobulin light chain and form a hinge sulfhydryl bridge have been mutated to serine. The amino acid residue numbers referred to in SEQ ID NO: 4 are those of the protein sequence, and do not refer to the EU numbering convention.

The DNA sequence of SEQ ID NO: 5 is of a polynucleotide encoding an exemplary light chain of a HER2-specific antibody, pertuzumab, (SEQ ID NO: 6) with mutation of Cys214 to serine and mutation of Tyr55 to histidine. The encoded light chain (SEQ ID NO: 6) is configured, for example, for heterodimer formation with the YS heavy chain variant of pertuzumab (SEQ ID NO: 8).

In particular, the amino acid sequence of the exemplary light chain of the HER2-specific antibody, pertuzumab, (SEQ ID NO: 6) has, in order from N- to C-terminus a HER2-specific VL domain at residues 1-108, and an immunoglobulin CL domain (human $C_{\kappa}$) at residues 109-214. The exemplary HER2-specific antibody light chain of SEQ ID NO: 6 has mutation of residue 55 to histidine. The cysteine residue (214) that usually pairs with an immunoglobulin heavy chain is mutated to serine. The amino acid residue numbers referred to in SEQ ID NO: 6 are those of the protein sequence, and do not refer to the EU numbering convention.

The DNA sequence of SEQ ID NO: 7 is of a polynucleotide encoding an exemplary heavy chain of the HER2-specific antibody, pertuzumab, (SEQ ID NO: 8) with mutation of Cys222 and Cys231 to serines, and mutation of Ser103 to histidine. The encoded heavy chain (SEQ ID NO: 8) is configured, for example, for heterodimer formation with the light chain variant of pertuzumab (SEQ ID NO: 6) to generate the YS variant of pertuzumab.

In particular, the amino acid sequence of the exemplary antibody heavy chain of SEQ ID NO: 8 has, in order from N- to C-terminus, a HER2-specific VH domain at residues 1-119, an immunoglobulin CH1 domain (human IgG1-derived) at residues 120-216, an immunoglobulin hinge (human IgG1-derived) at residues 217-232, an immunoglobulin CH2 domain (human IgG1-derived) at residues 233-342, an immunoglobulin CH3 domain (human IgG1-derived) at residues 343-449. The exemplary HER2-specific antibody heavy chain of SEQ ID NO: 8 has mutation of residue 103 to histidine. The cysteine residues (222 and 231) that usually pair with an immunoglobulin light chain and form a hinge sulfhydryl bridge have been mutated to serine. The amino acid residue numbers referred to in SEQ ID NO: 8 are those of the protein sequence, and do not refer to the EU numbering convention.

The DNA sequence of SEQ ID NO: 9 is of a polynucleotide encoding an exemplary single chain Fv of the HER2-specific antibody, pertuzumab, fused to the N-terminus of an immunoglobulin Fc fragment (SEQ ID NO: 10) with mutation of Cys251 and Cys260 to serines, and the SG mutations. The encoded fusion protein (SEQ ID NO: 10) is configured to form homodimers.

In particular, the amino acid sequence of the exemplary antibody heavy chain of SEQ ID NO: 10 has, in order from N- to C-terminus, a HER2-specific VH domain at residues 1-119, a $(G_4S)_3$ linker peptide at residues 120-134, a HER2-specific VL domain at residues 135-242, a GGS linker peptide at residues 243-245, an immunoglobulin hinge (human IgG1-derived) at residues 246-261, an immunoglobulin CH2 domain (human IgG1-derived) at residues 262-371, an immunoglobulin CH3 domain (human IgG1-derived) at residues 372-478. The exemplary HER2-specific antibody scFv-heavy chain fusion of SEQ ID NO: 10 has mutations of Ser55 and Gly57 to histidine and glutamic acid (SG mutations), respectively. The cysteine residues (251 and 260) that usually pair with an immunoglobulin light chain and form a hinge sulfhydryl bridge have been mutated to serine. The amino acid residue numbers referred to in SEQ ID NO: 10 are those of the protein sequence, and do not refer to the EU numbering convention.

The DNA sequence of SEQ ID NO: 11 is of a polynucleotide encoding an exemplary single chain Fv of the HER2-specific antibody, pertuzumab, fused to the N-terminus of an immunoglobulin Fc fragment (SEQ ID NO: 12) with mutation of Cys251 and Cys260 to serines and the YS mutations. The encoded fusion protein (SEQ ID NO: 12) is configured to form homodimers.

In particular, the amino acid sequence of the exemplary antibody heavy chain of SEQ ID NO: 12 has, in order from N- to C-terminus, a HER2-specific VH domain at residues 1-119, a $(G_4S)_3$ linker peptide at residues 120-134, a HER2-specific VL domain at residues 135-242, a GGS linker peptide at residues 243-245, an immunoglobulin hinge (human IgG1-derived) at residues 246-261, an immunoglobulin CH2 domain (human IgG1-derived) at residues 262-371, an immunoglobulin CH3 domain (human IgG1-derived) at residues 372-478. The exemplary HER2-specific antibody scFv-heavy chain fusion of SEQ ID NO: 12 has mutations of Ser103 and Tyr189 to histidines (YS mutations). The cysteine residues (251 and 260) that usually pair with an immunoglobulin light chain and form a hinge sulfhydryl bridge have been mutated to serine. The amino acid residue numbers referred to in SEQ ID NO: 12 are those of the protein sequence, and do not refer to the EU numbering convention.

The DNA sequence of SEQ ID NO: 13 is of a polynucleotide encoding an exemplary single chain Fv of the HER2-specific antibody, pertuzumab, fused to the C-terminus of an immunoglobulin Fc fragment (SEQ ID NO: 14) with mutation of Cys6 and Cys15 to serines, and the SG mutations. The encoded fusion protein (SEQ ID NO: 14) is configured to form homodimers.

In particular, the amino acid sequence of the exemplary antibody heavy chain of SEQ ID NO: 14 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233, a GGS linker peptide at residues 234-236, a HER2-specific VH domain at residues 237-355, a $(G_4S)_3$ linker peptide at residues 356-370, a HER2-specific VL domain at residues 371-478. The exemplary HER2-specific antibody scFv-heavy chain fusion of SEQ ID NO: 14 has mutations of Ser291 and Gly293 to histidine and glutamic acid (SG mutations), respectively. The cysteine residues (6 and 15) that usually pair with an immunoglobulin light chain and form a hinge sulfhydryl bridge have been mutated to serine. The amino acid residue numbers referred to in SEQ ID NO: 14 are those of the protein sequence, and do not refer to the EU numbering convention.

The DNA sequence of SEQ ID NO: 15 is of a polynucleotide encoding an exemplary single chain Fv of the HER2-specific antibody, pertuzumab, fused to the C-terminus to an immunoglobulin Fc fragment (SEQ ID NO: 16) with mutation of Cys6 and Cys15 to serines, and the YS mutations. The encoded fusion protein (SEQ ID NO: 16) is configured to form homodimers.

In particular, the amino acid sequence of the exemplary antibody heavy chain of SEQ ID NO: 16 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233, a GGS linker peptide at residues 234-236, a HER2-specific VH domain at residues 237-355, a $(G_4S)_3$ linker peptide at residues 356-370, a HER2-specific VL domain at residues 371-478. The exemplary HER2-specific antibody scFv-heavy chain fusion of SEQ ID NO: 16 has mutations of Ser339 and Tyr425 to histidines (YS mutations). The cysteine residues (6 and 15) that usually pair with an immunoglobulin light chain and form a hinge sulfhydryl bridge have been mutated to serine. The amino acid residue numbers referred to in SEQ ID NO: 16 are those of the protein sequence, and do not refer to the EU numbering convention.

The DNA sequence of SEQ ID NO: 17 is of a polynucleotide encoding an exemplary CalD2 fusion protein comprising the VH domain and CH1 domain of the HER2-specific antibody, trastuzumab, fused to the N-terminus of calbindin domain 2 (CalD2) (SEQ ID NO: 18) via a linker peptide comprising part of the immunoglobulin hinge (with mutation of Cys223 to serine) and SGG. The encoded fusion protein (SEQ ID NO: 18) is configured, for example, to form heterodimers with the light chain of trastuzumab (SEQ ID NO: 20) and associate in a $Ca^{2+}$-dependent way with SEQ ID NO: 22.

In particular, the amino acid sequence of the exemplary CalD2 fusion protein of SEQ ID NO: 18 has, in order from N- to C-terminus, a HER2-specific VH domain at residues 1-120, an immunoglobulin CH1 domain (human IgG1-derived) at residues 121-217, a linker sequence comprising part of the heavy chain hinge region at residues 218-228 followed by a SGG sequence at residues 229-231 and a CalD2 domain at residues 232-263. The cysteine residue (223) that usually pairs with an immunoglobulin light chain is mutated to serine. The amino acid residue numbers referred to in SEQ ID NO: 18 are those of the protein sequence, and do not refer to the EU numbering convention.

The DNA sequence of SEQ ID NO: 19 is of a polynucleotide encoding an exemplary light chain of a HER2-specific antibody, trastuzumab, (SEQ ID NO: 20) with mutation of Cys214 to serine. The encoded light chain (SEQ ID NO: 20) is configured, for example, for heterodimer formation with the trastuzumab VH-CH1: CalD2 fusion protein (SEQ ID NO: 18).

In particular, the amino acid sequence of the exemplary light chain of the HER2-specific antibody, trastuzumab, (SEQ ID NO: 20) has, in order from N- to C-terminus a HER2-specific VL domain at residues 1-108, and an immunoglobulin CL domain (human $C_\kappa$) at residues 109-214 followed by a hexahistidine peptide tag at residues 215-220. The cysteine residue (214) that usually pairs with an immunoglobulin heavy chain is mutated to serine. The amino acid residue numbers referred to in SEQ ID NO: 20 are those of the protein sequence, and do not refer to the EU numbering convention.

The DNA sequence of SEQ ID NO: 21 is of a polynucleotide encoding an exemplary CalD1 fusion protein comprising the calbindin domain 1 (CalD1) fused to the N-terminus of an immunoglobulin Fc fragment (SEQ ID NO: 22) with mutation of Cys52 to serine. The encoded fusion protein (SEQ ID NO: 22) is configured, for example, to associate with the trastuzumab VH-CH1: CalD2 fusion protein (SEQ ID NO: 18) or 026 VH-CH1: CalD2 fusion protein (SEQ ID NO: 24) in a $Ca^{2+}$-dependent way.

In particular, the amino acid sequence of the exemplary CalD1 fusion protein of SEQ ID NO: 22 has, in order from N- to C-terminus, a CalD1 domain at residues 1-43, a GSS linker peptide at residues 44-46, an immunoglobulin hinge (human IgG1-derived) at residues 47-62, an immunoglobulin CH2 domain (human IgG1-derived) at residues 63-172, an immunoglobulin CH3 domain (human IgG1-derived) at residues 173-279. The cysteine residue (52) that usually pairs with an immunoglobulin light chain is mutated to serine. The amino acid residue numbers referred to in SEQ ID NO: 22 are those of the protein sequence, and do not refer to the EU numbering convention.

The DNA sequence of SEQ ID NO: 23 is of a polynucleotide encoding an exemplary CalD2 fusion protein comprising the VH domain and CH1 domain of the PSMA-specific antibody, 026, fused to the N-terminus of calbindin domain 2 (CalD2) (SEQ ID NO: 24) via a linker peptide comprising part of the immunoglobulin hinge (with mutation of Cys227 to serine) and SGG. The encoded fusion protein (SEQ ID NO: 24) is configured, for example, to form heterodimers with the light chain of 026 (SEQ ID NO: 26) and associate in a $Ca^{2+}$-dependent way with SEQ ID NO: 22.

In particular, the amino acid sequence of the exemplary CalD2 fusion protein of SEQ ID NO: 24 has, in order from N- to C-terminus, a PSMA-specific VH domain at residues 1-124, an immunoglobulin CH1 domain (human IgG1-derived) at residues 125-221, a linker sequence comprising part of the heavy chain hinge region at residues 222-232 followed by a SGG sequence at residues 233-235 and a CalD2 domain at residues 236-267. The cysteine residue (227) that usually pairs with an immunoglobulin light chain is mutated to serine. The amino acid residue numbers referred to in SEQ ID NO: 24 are those of the protein sequence, and do not refer to the EU numbering convention.

The DNA sequence of SEQ ID NO: 25 is of a polynucleotide encoding an exemplary light chain of a PSMA-specific antibody, 026, (SEQ ID NO: 26) with mutation of Cys214 to serine. The encoded light chain (SEQ ID NO: 26) is configured, for example, for heterodimer formation with the 026 VH-CH1: CalD2 fusion protein (SEQ ID NO: 24).

In particular, the amino acid sequence of the exemplary light chain of the PSMA-specific antibody, 026, (SEQ ID NO: 26) has, in order from N- to C-terminus a HER2-specific VL domain at residues 1-108, and an immunoglobulin CL domain (human $C_\kappa$) at residues 109-214 followed by a hexahistidine peptide tag at residues 215-220. The cysteine residue (214) that usually pairs with an immunoglobulin heavy chain is mutated to serine. The amino acid residue numbers referred to in SEQ ID NO: 26 are those of the protein sequence, and do not refer to the EU numbering convention.

The DNA sequence of SEQ ID NO: 27 is of a polynucleotide encoding an exemplary Fc fusion protein comprising the Syt1 C2A domain of synaptotagmin fused to the C-terminus of an immunoglobulin Fc fragment (SEQ ID NO: 28) with mutation of Cys6 to serine. The encoded fusion protein (SEQ ID NO: 28) is configured to form homodimers.

In particular, the amino acid sequence of the exemplary Fc-Syt1 of SEQ ID NO: 28 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. Residues 141-266 of the C2A PS-binding domain of synaptotagmin (Syt1) are fused as residues 239-364 to the C-terminus of the CH3 domain via a GGGGS linker peptide (residues 234-238). The cysteine residue (6) that pairs with an immunoglobulin light chain is mutated to serine. The amino acid residue numbers referred to in SEQ ID NO: 28 are those of the protein sequence, and do not refer to the EU numbering convention.

The DNA sequence of SEQ ID NO: 29 is of a polynucleotide encoding an exemplary Fc fusion protein comprising the Syt1 C2A domain of synaptotagmin fused to both the N- and C-termini of an immunoglobulin Fc fragment (SEQ ID NO: 30) with mutation of Cys137 to serine. The encoded fusion protein (SEQ ID NO: 30) is configured to form homodimers.

In particular, the amino acid sequence of the exemplary Syt1-Fc-Syt1 of SEQ ID NO: 30 has, in order from N- to C-terminus, an immunoglobulin hinge (human IgG1-derived) at residues 132-147, an immunoglobulin CH2 domain (human IgG1-derived) at residues 148-257, an immunoglobulin CH3 domain (human IgG1-derived) at residues 258-364. Residues 141-266 of the C2A PS-binding domain of synaptotagmin (Syt1) are fused as residues 1-126 and 370-495, respectively, to the N- and C-termini of the hinge and CH3 domain via GGGGS linker peptides (residues 127-131 and 365-369). The cysteine residue (137) that pairs with an immunoglobulin light chain is mutated to serine. The amino acid residue numbers referred to in SEQ ID NO: 30 are those of the protein sequence, and do not refer to the EU numbering convention.

The DNA sequence of SEQ ID NO: 31 is of a polynucleotide encoding an exemplary Fc fusion protein comprising the C2 domain of PKCα fused to the C-terminus of an immunoglobulin Fc fragment (SEQ ID NO: 32) with mutation of Cys6 to serine. The encoded fusion protein (SEQ ID NO: 32) is configured to form homodimers.

In particular, the amino acid sequence of the exemplary Fc-PKCα of SEQ ID NO: 32 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233.

Residues 157-288 of the C2 domain of PKCα are fused to the C-terminus of the CH3 domain as residues 239-370 via a GGGGS linker peptide (residues 234-238). The cysteine residue (6) that pairs with an immunoglobulin light chain is mutated to serine. The amino acid residue numbers referred to in SEQ ID NO: 32 are those of the protein sequence, and do not refer to the EU numbering convention.

The DNA sequence of SEQ ID NO: 33 is of a polynucleotide encoding an exemplary Fc fusion protein comprising the AnxA1 PS-binding core domain fused to the C-terminus of an immunoglobulin Fc fragment (SEQ ID NO: 34) with mutation of Cys6 to serine. The encoded fusion protein (SEQ ID NO: 34) is configured to form homodimers.

In particular, the amino acid sequence of the exemplary Fc-AnxA1 of SEQ ID NO: 34 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. Residues 41-346 of the AnxA1 core domain are fused to the C-terminus of the CH3 domain as residues 239-544 via a GGGGS linker peptide (residues 234-238). The cysteine residue (6) that pairs with an immunoglobulin light chain is mutated to serine. The amino acid residue numbers referred to in SEQ ID NO: 34 are those of the protein sequence, and do not refer to the EU numbering convention.

The DNA sequence of SEQ ID NO: 35 is of a polynucleotide encoding an exemplary Fc fusion protein comprising the Syt1 C2A domain of synaptotagmin fused to the N-terminus of an immunoglobulin Fc fragment (SEQ ID NO: 36) with mutation of Cys137 to serine. The encoded fusion protein (SEQ ID NO: 36) is configured to form homodimers.

In particular, the amino acid sequence of the exemplary Syt1-Fc of SEQ ID NO: 36 has, in order from N- to C-terminus, residues 141-266 of the C2A PS-binding domain of synaptotagmin (Syt1) as residues 1-126, a GGGGS linker peptide at residues 127-131, an immunoglobulin hinge (human IgG1-derived) at residues 132-147, an immunoglobulin CH2 domain (human IgG1-derived) at residues 148-257, an immunoglobulin CH3 domain (human IgG1-derived) at residues 258-364. The cysteine residue (137) that pairs with an immunoglobulin light chain is mutated to serine. The amino acid residue numbers referred to in SEQ ID NO: 36 are those of the protein sequence, and do not refer to the EU numbering convention.

The DNA sequence of SEQ ID NO: 37 is of a polynucleotide encoding an exemplary Fc fusion protein comprising the C2 domain of PKCα fused to the N-terminus of an immunoglobulin Fc fragment (SEQ ID NO: 38) with mutation of Cys143 to serine. The encoded fusion protein (SEQ ID NO: 38) is configured to form homodimers.

In particular, the amino acid sequence of the exemplary PKCα-Fc of SEQ ID NO: 38 has, in order from N- to C-terminus, residues 157-288 of the C2 domain of PKCα as residues 1-132, a GGGGS linker peptide at residues 133-137, an immunoglobulin hinge (human IgG1-derived) at residues 138-153, an immunoglobulin CH2 domain (human IgG1-derived) at residues 154-263, an immunoglobulin CH3 domain (human IgG1-derived) at residues 264-370. The cysteine residue (143) that pairs with an immunoglobulin light chain is mutated to serine. The amino acid residue numbers referred to in SEQ ID NO: 38 are those of the protein sequence, and do not refer to the EU numbering convention.

The DNA sequence of SEQ ID NO: 39 is of a polynucleotide encoding an exemplary Fc fusion protein comprising the AnxA1 PS-binding core domain fused to the N-terminus of an immunoglobulin Fc fragment (SEQ ID NO: 40) with mutation of Cys317 to serine. The encoded fusion protein (SEQ ID NO: 40) is configured to form homodimers.

In particular, the amino acid sequence of the exemplary AnxA1-Fc of SEQ ID NO: 40 has, in order from N- to C-terminus, residues 41-346 of the AnxA1 core domain as residues 1-306, a GGGGS linker peptide at residues 307-311, an immunoglobulin hinge (human IgG1-derived) at residues 312-327, an immunoglobulin CH2 domain (human IgG1-derived) at residues 328-437, an immunoglobulin CH3 domain (human IgG1-derived) at residues 438-544. The cysteine residue (317) that pairs with an immunoglobulin light chain is mutated to serine. The amino acid residue numbers referred to in SEQ ID NO: 40 are those of the protein sequence, and do not refer to the EU numbering convention.

The DNA sequence of SEQ ID NO: 41 is of a polynucleotide encoding an exemplary Fc fusion protein comprising the Syt1 C2A domain of synaptotagmin fused to the N- and C-termini of an immunoglobulin Fc fragment (SEQ ID NO: 42) with knobs-into-holes mutations and mutation of Cys137 to serine. The encoded fusion protein (SEQ ID NO: 42) is configured, for example, to form heterodimers with an exemplary Fc fragment (SEQ ID NO: 44).

In particular, the amino acid sequence of the exemplary Syt1-Fc-Syt1 of SEQ ID NO: 42 has, in order from N- to C-terminus, an immunoglobulin hinge (human IgG1-derived) at residues 132-147, an immunoglobulin CH2 domain (human IgG1-derived) at residues 148-257, an immunoglobulin CH3 domain (human IgG1-derived) at residues 258-364. Residues 141-266 of the C2A PS-binding domain of synaptotagmin (Syt1) are fused as residues 1-126 and 370-495, respectively, to the N- and C-termini of the hinge and CH3 domain via GGGGS linker peptides (residues 127-131 and 365-369). The exemplary Syt1-Fc-Syt1 of SEQ ID NO: 42 has 'knobs-into-holes' mutations at residues 266 and 311. The cysteine residue (137) that pairs with an immunoglobulin light chain is mutated to serine. The amino acid residue numbers referred to in SEQ ID NO: 42 are those of the protein sequence, and do not refer to the EU numbering convention.

The DNA sequence of SEQ ID NO: 43 is of a polynucleotide encoding an exemplary Fc fragment (SEQ ID NO: 44) having knobs-into-holes mutations and mutation of Cys6 to serine. The Fc fragment of SEQ ID NO: 44 is configured, for example, to form heterodimers with an exemplary Syt1-Fc-Syt1 fusion (SEQ ID NO: 42).

In particular, the amino acid sequence of the exemplary Fc fragment of SEQ ID NO: 44 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The exemplary Fc fragment of SEQ ID NO: 44 has knobs-into-holes mutations at residues 150 and 191. The cysteine residue (6) that usually pairs with an immunoglobulin light chain is mutated to serine. The amino acid residue numbers referred to in SEQ ID NO: 44 are those of the protein sequence, and do not refer to the EU numbering convention.

The DNA sequence of SEQ ID NO: 45 is of a polynucleotide encoding an exemplary Fc fusion protein comprising the Syt1 C2A domain of synaptotagmin fused to both the N- and C-termini of an immunoglobulin Fc fragment (SEQ ID NO: 46) with knobs-into-holes mutations, electrostatic steering mutations and mutation of Cys137 to serine. The encoded fusion protein (SEQ ID NO: 46) is configured, for example, to form heterodimers with an exemplary Fc fragment (SEQ ID NO: 48).

In particular, the amino acid sequence of the exemplary Syt1-Fc-Syt1 of SEQ ID NO: 46 has, in order from N- to C-terminus, an immunoglobulin hinge (human IgG1-derived) at residues 132-147, an immunoglobulin CH2 domain (human IgG1-derived) at residues 148-257, an immunoglobulin CH3 domain (human IgG1-derived) at residues 258-364. Residues 141-266 of the C2A PS-binding domain of synaptotagmin (Syt1) are fused as residues 1-126 and 370-495, respectively, to the N- and C-termini of the hinge and CH3 domain via GGGGS linker peptides (residues 127-131 and 365-369). The exemplary Syt1-Fc-Syt1 of SEQ ID NO: 46 has 'knobs-into-holes' mutations at residues 266 and 311 and electrostatic steering mutations at residues 309 and 326. The cysteine residue (137) that pairs with an immunoglobulin light chain is mutated to serine. The amino acid residue numbers referred to in SEQ ID NO: 46 are those of the protein sequence, and do not refer to the EU numbering convention.

The DNA sequence of SEQ ID NO: 47 is of a polynucleotide encoding an exemplary Fc fragment (SEQ ID NO: 48) having knobs-into-holes mutations, electrostatic steering mutations and mutation of Cys6 to serine. The Fc fragment of SEQ ID NO: 48 is configured, for example, to form heterodimers with an exemplary Syt1-Fc-Syt1 fusion (SEQ ID NO: 46).

In particular, the amino acid sequence of the exemplary Fc fragment of SEQ ID NO: 48 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The exemplary Fc fragment of SEQ ID NO: 48 has knobs-into-holes mutations at residues 150 and 191 and electrostatic steering mutations at residues 143 and 185. The cysteine residue (6) that usually pairs with an immunoglobulin light chain is mutated to serine. The amino acid residue numbers referred to in SEQ ID NO: 48 are those of the protein sequence, and do not refer to the EU numbering convention.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An endolysosomal targeting conjugate, comprising:

a targeting component comprising an antibody or antibody fragment fused directly or indirectly to a cargo component; wherein said antibody or antibody fragment binds to HER2, and wherein said antibody or antibody fragment comprises a heavy chain comprising the CDRs of the heavy chain of pertuzumab and a light chain comprising the CDRs of the light chain chain of pertuzumab, wherein either (a) CDR2 of the heavy chain is modified by replacement of (i) serine at position 55 with histidine and (ii) glycine at position 57 with glutamic acid or (b) CDR3 of the heavy chain is modified by replacement of serine at position 103 with histidine and CDR2 of the light chain is modified by replacement of tyrosine at position 55 with histidine, wherein said positions are defined with respect to the positions in pertuzumab.

2. The conjugate of claim 1, wherein the CDR2 of the heavy chain is modified by replacement of (i) serine at position 55 with histidine and (ii) glycine at position 57 with glutamic acid.

3. The conjugate of claim 1, wherein the CDR3 of the heavy chain is modified by replacement of serine at position 103 with histidine and CDR2 of the light chain is modified by replacement of tyrosine at position 55 with histidine.

4. The conjugate of claim 1, wherein said targeting component comprises a heavy chain having at least 95% sequence identity to the sequence of SEQ ID NO:4 or SEQ ID NO:8.

5. The conjugate of claim 1, wherein said targeting component comprises a light chain having at least 95% sequence identity to the sequence of SEQ ID NO:6.

6. The endolysosomal targeting conjugate of claim 1 wherein the cargo component comprises an antibody, an antibody fragment or an antibody domain comprising an antibody Fc region or a domain of the antibody Fc fragment.

7. The endolysosomal targeting conjugate of claim 6 wherein the antibody Fc region or the domain of the antibody Fc fragment is derived from human IgG1.

8. The endolysosomal targeting conjugate of claim 1 wherein the cargo component comprises an albumin molecule or a domain of albumin.

9. The endolysosomal targeting conjugate of claim 1, wherein the cargo molecule is a cytotoxic drug.

10. The endolysosomal targeting conjugate of claim 1 wherein the cargo molecule is an imaging label.

11. The endolysosomal targeting conjugate of claim 1 comprising a polypeptide having an amino acid sequence selected from the group consisting of SEQ ID NO: 4, SEQ ID NO: 6, SEQ ID NO: 8, SEQ ID NO: 10, SEQ ID NO: 12, SEQ ID NO: 14, and SEQ ID NO: 16.

12. The endolysosomal targeting conjugate of claim 9 wherein the cytotoxic drug is MMAE.

* * * * *

SEQUENCE LISTING

```
<160> NUMBER OF SEQ ID NOS: 60

<210> SEQ ID NO 1
<211> LENGTH: 642
<212> TYPE: DNA
<213> ORGANISM: Artificial Sequence
<220> FEATURE:
<223> OTHER INFORMATION: Synthetic: Pertuzumab light chain with Cys
      mutation

<400> SEQUENCE: 1

gacatcgagc tcacacagtc tccttcttct ctgtctgctt ctgtgggaga tagagtgaca      60

atcacatgta aggcttctca ggatgtgtct atcggagtgg cttggtacca gcagaagcct     120

ggaaaggctc ctaagctgct gatctactct gcttcttaca gatacacagg agtgccttct     180

agattctctg gatctggatc tggaacagat ttcacactga caatctcttc tctacagcct     240

gaggatttcg ctacatacta ctgtcagcag tactacatct acccttacac attcggacag     300

ggaacaaagc tcgagatcaa acgaactgtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagttcgc ccgtcacaaa gagcttcaac aggggagagt ct                        642


<210> SEQ ID NO 2
<211> LENGTH: 214
<212> TYPE: PRT
<213> ORGANISM: Artificial Sequence
<220> FEATURE:
<223> OTHER INFORMATION: Synthetic: Pertuzumab light chain with Cys
      mutation

<400> SEQUENCE: 2

Asp Ile Glu Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210
```

```
<210> SEQ ID NO 3
<211> LENGTH: 1347
<212> TYPE: DNA
<213> ORGANISM: Artificial Sequence
<220> FEATURE:
<223> OTHER INFORMATION: Synthetic: SG heavy chain with Cys mutations

<400> SEQUENCE: 3

caggtccaac tgcaggagtc tggaggagga ctggtgcagc ctggaggatc tctgagactg     60

tcttgtgctg cttctggatt cacattcaca gattacacaa tggattgggt gagacaggct    120

cctggaaagg gactggagtg ggtggctgat gtgaatccta atcacggaga atctatctac    180

aatcagagat tcaagggaag attcacactg tctgtggata gatctaagaa tacactgtac    240

ctacagatga actctctgag agctgaggat acagctgtgt actactgtgc tagaaatctg    300

ggaccttctt tctacttcga ttactgggga cagggaacac tggtcaccgt ctcctcagcc    360

tccaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgactgtg ccctccagca gcttgggcac ccagacctac    600

atctgcaacg tgaatcacaa gcccagcaac accaaggtgg acaagaaagt tgagcccaaa    660

tcttctgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320
```

aagagcctct ccctgtctcc gggtaaa 1347

<210> SEQ ID NO 4
<211> LENGTH: 449
<212> TYPE: PRT
<213> ORGANISM: Artificial Sequence
<220> FEATURE:
<223> OTHER INFORMATION: Synthetic: SG heavy chain with Cys mutations

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn His Gly Glu Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 5
<211> LENGTH: 642
<212> TYPE: DNA
<213> ORGANISM: Artificial Sequence
<220> FEATURE:
<223> OTHER INFORMATION: Synthetic: YS light chain with Cys mutation

<400> SEQUENCE: 5

gacatcgagc tcacacagtc tccttcttct ctgtctgctt ctgtgggaga tagagtgaca      60

atcacatgta aggcttctca ggatgtgtct atcggagtgg cttggtacca gcagaagcct     120

ggaaaggctc ctaagctgct gatctactct gcttcttaca gacacacagg agtgccttct     180

agattctctg gatctggatc tggaacagat ttcacactga caatctcttc tctacagcct     240

gaggatttcg ctacatacta ctgtcagcag tactacatct acccttacac attcggacag     300

ggaacaaagc tcgagatcaa acgaactgtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagttcgc ccgtcacaaa gagcttcaac aggggagagt ct                        642


<210> SEQ ID NO 6
<211> LENGTH: 214
<212> TYPE: PRT
<213> ORGANISM: Artificial Sequence
<220> FEATURE:
<223> OTHER INFORMATION: Synthetic: YS light chain with Cys mutation

<400> SEQUENCE: 6

Asp Ile Glu Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser
    210
```

<210> SEQ ID NO 7
<211> LENGTH: 1347
<212> TYPE: DNA
<213> ORGANISM: Artificial Sequence
<220> FEATURE:
<223> OTHER INFORMATION: Synthetic: YS heavy chain with Cys mutations

<400> SEQUENCE: 7

```
caggtccaac tgcaggagtc tggaggagga ctggtgcagc ctggaggatc tctgagactg     60

tcttgtgctg cttctggatt cacattcaca gattacacaa tggattgggt gagacaggct    120

cctggaaagg gactggagtg ggtggctgat gtgaatccta attctggagg atctatctac    180

aatcagagat tcaagggaag attcacactg tctgtggata gatctaagaa tacactgtac    240

ctacagatga actctctgag agctgaggat acagctgtgt actactgtgc tagaaatctg    300

ggacctcact tctacttcga ttactgggga cagggaacac tggtcaccgt ctcctcagcc    360

tccaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgactgtg ccctccagca gcttgggcac ccagacctac    600

atctgcaacg tgaatcacaa gcccagcaac accaaggtgg acaagaaagt tgagcccaaa    660

tcttctgaca aaactcacac atgcccaccg tccccagcac ctgaactcct gggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 8
<211> LENGTH: 449
<212> TYPE: PRT
<213> ORGANISM: Artificial Sequence
<220> FEATURE:
<223> OTHER INFORMATION: Synthetic: YS heavy chain with Cys mutations

<400> SEQUENCE: 8

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro His Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Ser Asp Lys
    210                 215                 220

Thr His Thr Cys Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 9
<211> LENGTH: 1434
<212> TYPE: DNA
<213> ORGANISM: Artificial Sequence
<220> FEATURE:
<223> OTHER INFORMATION: Synthetic: SG scFv linked to N-terminus of
      heavy chain with Cys mutations

<400> SEQUENCE: 9

caggtgcagc tgcaggagtc tggaggagga ctggtgcagc ctggaggatc tctgagactg     60

tcttgtgctg cttctggatt cacattcaca gattacacaa tggattgggt gagacaggct    120

cctggaaagg gactggagtg ggtggctgat gtgaatccta atcacggaga atctatctac    180

aatcagagat tcaagggaag attcacactg tctgtggata gatctaagaa tacactgtac    240

ctacagatga actctctgag agctgaggat acagctgtgt actactgtgc tagaaatctg    300

ggaccttctt tctacttcga ttactgggga cagggaacac tggtcacggt ctcctcggga    360

ggtggcggat ctggtggagg tggcagtggt ggaggtggct cagacatcga gctcacacag    420

tctccttctt ctctgtctgc ttctgtggga gatagagtga caatcacatg taaggcttct    480

caggatgtgt ctatcggagt ggcttggtac cagcagaagc ctggaaaggc tcctaagctg    540

ctgatctact ctgcttctta cagatacaca ggagtgcctt ctagattctc tggatctgga    600

tctggaacag atttcacact gacaatctct tctctacagc ctgaggattt cgctacatac    660

tactgtcagc agtactacat ctacccttac acattcggac agggaacaaa gctcgagatc    720

aaacggggtg gcagcgttga gcccaaatct tctgacaaaa ctcacacatg cccaccgtcc    780

ccagcacctg aactcctggg gggaccgtca gtcttcctct tccccccaaa acccaaggac    840

accctcatga tctcccggac ccctgaggtc acatgcgtgg tggtggacgt gagccacgaa    900

gaccctgagg tcaagttcaa ctggtacgtg gacggcgtgg aggtgcataa tgccaagaca    960

aagccgcggg aggagcagta caacagcacg taccgtgtgg tcagcgtcct caccgtcctg   1020

caccaggact ggctgaatgg caaggagtac aagtgcaagg tctccaacaa agccctccca   1080

gcccccatcg agaaaaccat ctccaaagcc aaagggcagc cccgagaacc acaggtgtac   1140

accctgcccc catcccggga tgagctgacc aagaaccagg tcagcctgac ctgcctggtc   1200

aaaggcttct atcccagcga catcgccgtg gagtgggaga gcaatgggca gccggagaac   1260

aactacaaga ccacgcctcc cgtgctggac tccgacggct ccttcttcct ctacagcaag   1320

ctcaccgtgg acaagagcag gtggcagcag gggaacgtct tctcatgctc cgtgatgcat   1380

gaggctctgc acaaccacta cacgcagaag agcctctccc tgtctccggg taaa         1434


<210> SEQ ID NO 10
```

<211> LENGTH: 478
<212> TYPE: PRT
<213> ORGANISM: Artificial Sequence
<220> FEATURE:
<223> OTHER INFORMATION: Synthetic: SG scFv linked to N-terminus of heavy chain with Cys mutations

<400> SEQUENCE: 10

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn His Gly Glu Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Asp Ile Glu Leu Thr Gln Ser Pro Ser Ser
130 135 140

Leu Ser Ala Ser Val Gly Asp Arg Val Thr Ile Thr Cys Lys Ala Ser
145 150 155 160

Gln Asp Val Ser Ile Gly Val Ala Trp Tyr Gln Gln Lys Pro Gly Lys
165 170 175

Ala Pro Lys Leu Leu Ile Tyr Ser Ala Ser Tyr Arg Tyr Thr Gly Val
180 185 190

Pro Ser Arg Phe Ser Gly Ser Gly Ser Gly Thr Asp Phe Thr Leu Thr
195 200 205

Ile Ser Ser Leu Gln Pro Glu Asp Phe Ala Thr Tyr Tyr Cys Gln Gln
210 215 220

Tyr Tyr Ile Tyr Pro Tyr Thr Phe Gly Gln Gly Thr Lys Leu Glu Ile
225 230 235 240

Lys Arg Gly Gly Ser Val Glu Pro Lys Ser Ser Asp Lys Thr His Thr
245 250 255

Cys Pro Pro Ser Pro Ala Pro Glu Leu Leu Gly Gly Pro Ser Val Phe
260 265 270

Leu Phe Pro Pro Lys Pro Lys Asp Thr Leu Met Ile Ser Arg Thr Pro
275 280 285

Glu Val Thr Cys Val Val Val Asp Val Ser His Glu Asp Pro Glu Val
290 295 300

Lys Phe Asn Trp Tyr Val Asp Gly Val Glu Val His Asn Ala Lys Thr
305 310 315 320

Lys Pro Arg Glu Glu Gln Tyr Asn Ser Thr Tyr Arg Val Val Ser Val
325 330 335

Leu Thr Val Leu His Gln Asp Trp Leu Asn Gly Lys Glu Tyr Lys Cys
340 345 350

Lys Val Ser Asn Lys Ala Leu Pro Ala Pro Ile Glu Lys Thr Ile Ser
355 360 365

Lys Ala Lys Gly Gln Pro Arg Glu Pro Gln Val Tyr Thr Leu Pro Pro

-continued

```
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 11
<211> LENGTH: 1434
<212> TYPE: DNA
<213> ORGANISM: Artificial Sequence
<220> FEATURE:
<223> OTHER INFORMATION: Synthetic: YS scFv linked to N-terminus of
      heavy chain with Cys mutations

<400> SEQUENCE: 11

caggtgcagc tgcaggagtc tggaggagga ctggtgcagc ctggaggatc tctgagactg     60

tcttgtgctg cttctggatt cacattcaca gattacacaa tggattgggt gagacaggct    120

cctggaaagg gactggagtg ggtggctgat gtgaatccta attctggagg atctatctac    180

aatcagagat tcaagggaag attcacactg tctgtggata gatctaagaa tacactgtac    240

ctacagatga actctctgag agctgaggat acagctgtgt actactgtgc tagaaatctg    300

ggacctcact tctacttcga ttactgggga cagggaacac tggtcacggt ctcctcggga    360

ggtggcggat ctggtggagg tggcagtggt ggaggtggct cagacatcga gctcacacag    420

tctccttctt ctctgtctgc ttctgtggga gatagagtga caatcacatg taaggcttct    480

caggatgtgt ctatcggagt ggcttggtac cagcagaagc ctggaaaggc tcctaagctg    540

ctgatctact ctgcttctta cagacacaca ggagtgcctt ctagattctc tggatctgga    600

tctggaacag atttcacact gacaatctct tctctacagc ctgaggattt cgctacatac    660

tactgtcagc agtactacat ctacccttac acattcggac agggaacaaa gctcgagatc    720

aaacggggtg gcagcgttga gcccaaatct tctgacaaaa ctcacacatg cccaccgtcc    780

ccagcacctg aactcctggg gggaccgtca gtcttcctct tccccccaaa acccaaggac    840

accctcatga tctcccggac ccctgaggtc acatgcgtgg tggtggacgt gagccacgaa    900

gaccctgagg tcaagttcaa ctggtacgtg gacggcgtgg aggtgcataa tgccaagaca    960

aagccgcggg aggagcagta caacagcacg taccgtgtgg tcagcgtcct caccgtcctg   1020

caccaggact ggctgaatgg caaggagtac aagtgcaagg tctccaacaa agccctccca   1080

gcccccatcg agaaaaccat ctccaaagcc aaagggcagc cccgagaacc acaggtgtac   1140

accctgcccc catcccggga tgagctgacc aagaaccagg tcagcctgac ctgcctggtc   1200

aaaggcttct atcccagcga catcgccgtg gagtgggaga gcaatgggca gccggagaac   1260

aactacaaga ccacgcctcc cgtgctggac tccgacggct ccttcttcct ctacagcaag   1320

ctcaccgtgg acaagagcag gtggcagcag gggaacgtct tctcatgctc cgtgatgcat   1380

gaggctctgc acaaccacta cacgcagaag agcctctccc tgtctccggg taaa          1434
```

<210> SEQ ID NO 12
<211> LENGTH: 478
<212> TYPE: PRT
<213> ORGANISM: Artificial Sequence
<220> FEATURE:
<223> OTHER INFORMATION: Synthetic: YS scFv linked to N-terminus of heavy chain with Cys mutations

<400> SEQUENCE: 12

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro His Phe Tyr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Glu Leu Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Ile Gly Val Ala Trp Tyr Gln Gln Lys Pro Gly Lys
                165                 170                 175

Ala Pro Lys Leu Leu Ile Tyr Ser Ala Ser Tyr Arg His Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Tyr Ile Tyr Pro Tyr Thr Phe Gly Gln Gly Thr Lys Leu Glu Ile
225                 230                 235                 240

Lys Arg Gly Gly Ser Val Glu Pro Lys Ser Ser Asp Lys Thr His Thr
                245                 250                 255

Cys Pro Pro Ser Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365
```

```
Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475


<210> SEQ ID NO 13
<211> LENGTH: 1434
<212> TYPE: DNA
<213> ORGANISM: Artificial Sequence
<220> FEATURE:
<223> OTHER INFORMATION: Synthetic: Heavy chain with Cys mutations and
      SG scFv linked to C-terminus

<400> SEQUENCE: 13

gttgagccca aatcttctga caaaactcac acatgcccac cgtccccagc acctgaactc      60

ctgggggggac cgtcagtctt cctcttcccc ccaaaaccca aggacaccct catgatctcc    120

cggacccctg aggtcacatg cgtggtggtg gacgtgagcc acgaagaccc tgaggtcaag    180

ttcaactggt acgtggacgg cgtggaggtg cataatgcca agacaaagcc gcgggaggag    240

cagtacaaca gcacgtaccg tgtggtcagc gtcctcaccg tcctgcacca ggactggctg    300

aatggcaagg agtacaagtg caaggtctcc aacaaagccc tcccagcccc catcgagaaa    360

accatctcca aagccaaagg gcagccccga gaaccacagg tgtacaccct gcccccatcc    420

cgggatgagc tgaccaagaa ccaggtcagc ctgacctgcc tggtcaaagg cttctatccc    480

agcgacatcg ccgtggagtg ggagagcaat gggcagccgg agaacaacta caagaccacg    540

cctcccgtgc tggactccga cggctccttc ttcctctaca gcaagctcac cgtggacaag    600

agcaggtggc agcaggggaa cgtcttctca tgctccgtga tgcatgaggc tctgcacaac    660

cactacacgc agaagagcct ctccctgtct ccgggtaaag gtggcagcca ggtgcagctg    720

caggagtctg gaggaggact ggtgcagcct ggaggatctc tgagactgtc ttgtgctgct    780

tctggattca cattcacaga ttacacaatg gattgggtga gacaggctcc tggaaaggga    840

ctggagtggg tggctgatgt gaatcctaat cacggagaat ctatctacaa tcagagattc    900

aagggaagat tcacactgtc tgtggataga tctaagaata cactgtacct acagatgaac    960

tctctgagag ctgaggatac agctgtgtac tactgtgcta gaaatctggg accttctttc   1020

tacttcgatt actggggaca gggaacactg gtcacggtct cctcgggagg tggcggatct   1080

ggtggaggtg gcagtggtgg aggtggctca gacatcgagc tcacacagtc tccttcttct   1140

ctgtctgctt ctgtgggaga tagagtgaca atcacatgta aggcttctca ggatgtgtct   1200

atcggagtgg cttggtacca gcagaagcct ggaaaggctc ctaagctgct gatctactct   1260

gcttcttaca gatacacagg agtgccttct agattctctg gatctggatc tggaacagat   1320

ttcacactga caatctcttc tctacagcct gaggatttcg ctacatacta ctgtcagcag   1380
```

```
tactacatct acccttacac attcggacag ggaacaaagc tcgagatcaa acgg        1434


<210> SEQ ID NO 14
<211> LENGTH: 478
<212> TYPE: PRT
<213> ORGANISM: Artificial Sequence
<220> FEATURE:
<223> OTHER INFORMATION: Synthetic: Heavy chain with Cys mutations and
      SG scFv linked to C-terminus

<400> SEQUENCE: 14

Val Glu Pro Lys Ser Ser Asp Lys Thr His Thr Cys Pro Pro Ser Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Ser Gln Val Gln Leu
225                 230                 235                 240

Gln Glu Ser Gly Gly Gly Leu Val Gln Pro Gly Gly Ser Leu Arg Leu
                245                 250                 255

Ser Cys Ala Ala Ser Gly Phe Thr Phe Thr Asp Tyr Thr Met Asp Trp
            260                 265                 270

Val Arg Gln Ala Pro Gly Lys Gly Leu Glu Trp Val Ala Asp Val Asn
        275                 280                 285

Pro Asn His Gly Glu Ser Ile Tyr Asn Gln Arg Phe Lys Gly Arg Phe
    290                 295                 300

Thr Leu Ser Val Asp Arg Ser Lys Asn Thr Leu Tyr Leu Gln Met Asn
305                 310                 315                 320

Ser Leu Arg Ala Glu Asp Thr Ala Val Tyr Tyr Cys Ala Arg Asn Leu
                325                 330                 335

Gly Pro Ser Phe Tyr Phe Asp Tyr Trp Gly Gln Gly Thr Leu Val Thr
            340                 345                 350
```

-continued

```
Val Ser Ser Gly Gly Gly Gly Ser Gly Gly Gly Gly Ser Gly Gly Gly
        355                 360                 365

Gly Ser Asp Ile Glu Leu Thr Gln Ser Pro Ser Ser Leu Ser Ala Ser
    370                 375                 380

Val Gly Asp Arg Val Thr Ile Thr Cys Lys Ala Ser Gln Asp Val Ser
385                 390                 395                 400

Ile Gly Val Ala Trp Tyr Gln Gln Lys Pro Gly Lys Ala Pro Lys Leu
                405                 410                 415

Leu Ile Tyr Ser Ala Ser Tyr Arg Tyr Thr Gly Val Pro Ser Arg Phe
            420                 425                 430

Ser Gly Ser Gly Ser Gly Thr Asp Phe Thr Leu Thr Ile Ser Ser Leu
        435                 440                 445

Gln Pro Glu Asp Phe Ala Thr Tyr Tyr Cys Gln Gln Tyr Tyr Ile Tyr
    450                 455                 460

Pro Tyr Thr Phe Gly Gln Gly Thr Lys Leu Glu Ile Lys Arg
465                 470                 475
```

```
<210> SEQ ID NO 15
<211> LENGTH: 1434
<212> TYPE: DNA
<213> ORGANISM: Artificial Sequence
<220> FEATURE:
<223> OTHER INFORMATION: Synthetic: Heavy chain with Cys mutations and
      YS scFv linked to C-terminus

<400> SEQUENCE: 15

gttgagccca aatcttctga caaaactcac acatgcccac cgtccccagc acctgaactc      60

ctggggggac cgtcagtctt cctcttcccc ccaaaaccca aggacaccct catgatctcc     120

cggacccctg aggtcacatg cgtggtggtg gacgtgagcc acgaagaccc tgaggtcaag     180

ttcaactggt acgtggacgg cgtggaggtg cataatgcca agacaaagcc gcgggaggag     240

cagtacaaca gcacgtaccg tgtggtcagc gtcctcaccg tcctgcacca ggactggctg     300

aatggcaagg agtacaagtg caaggtctcc aacaaagccc tcccagcccc catcgagaaa     360

accatctcca aagccaaagg gcagccccga gaaccacagg tgtacaccct gcccccatcc     420

cgggatgagc tgaccaagaa ccaggtcagc ctgacctgcc tggtcaaagg cttctatccc     480

agcgacatcg ccgtggagtg ggagagcaat gggcagccgg agaacaacta caagaccacg     540

cctcccgtgc tggactccga cggctccttc ttcctctaca gcaagctcac cgtggacaag     600

agcaggtggc agcaggggaa cgtcttctca tgctccgtga tgcatgaggc tctgcacaac     660

cactacacgc agaagagcct ctccctgtct ccgggtaaag gtggcagcca ggtgcagctg     720

caggagtctg gaggaggact ggtgcagcct ggaggatctc tgagactgtc ttgtgctgct     780

tctggattca cattcacaga ttacacaatg gattgggtga gacaggctcc tggaaaggga     840

ctggagtggg tggctgatgt gaatcctaat tctggaggat ctatctacaa tcagagattc     900

aagggaagat tcacactgtc tgtggataga tctaagaata cactgtacct acagatgaac     960

tctctgagag ctgaggatac agctgtgtac tactgtgcta gaaatctggg acctcacttc    1020

tacttcgatt actggggaca gggaacactg gtcacggtct cctcgggagg tggcggatct    1080

ggtggaggtg gcagtggtgg aggtggctca gacatcgagc tcacacagtc tccttcttct    1140

ctgtctgctt ctgtgggaga tagagtgaca atcacatgta aggcttctca ggatgtgtct    1200

atcggagtgg cttggtacca gcagaagcct ggaaaggctc ctaagctgct gatctactct    1260

gcttcttaca gacacacagg agtgccttct agattctctg gatctggatc tggaacagat    1320
```

-continued

```
ttcacactga caatctcttc tctacagcct gaggatttcg ctacatacta ctgtcagcag   1380

tactacatct acccttacac attcggacag ggaacaaagc tcgagatcaa acgg         1434


<210> SEQ ID NO 16
<211> LENGTH: 478
<212> TYPE: PRT
<213> ORGANISM: Artificial Sequence
<220> FEATURE:
<223> OTHER INFORMATION: Synthetic: Heavy chain with Cys mutations and
      YS scFv linked to C-terminus

<400> SEQUENCE: 16

Val Glu Pro Lys Ser Ser Asp Lys Thr His Thr Cys Pro Pro Ser Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Ser Gln Val Gln Leu
225                 230                 235                 240

Gln Glu Ser Gly Gly Gly Leu Val Gln Pro Gly Gly Ser Leu Arg Leu
                245                 250                 255

Ser Cys Ala Ala Ser Gly Phe Thr Phe Thr Asp Tyr Thr Met Asp Trp
            260                 265                 270

Val Arg Gln Ala Pro Gly Lys Gly Leu Glu Trp Val Ala Asp Val Asn
        275                 280                 285

Pro Asn Ser Gly Gly Ser Ile Tyr Asn Gln Arg Phe Lys Gly Arg Phe
    290                 295                 300

Thr Leu Ser Val Asp Arg Ser Lys Asn Thr Leu Tyr Leu Gln Met Asn
305                 310                 315                 320

Ser Leu Arg Ala Glu Asp Thr Ala Val Tyr Tyr Cys Ala Arg Asn Leu
                325                 330                 335

Gly Pro His Phe Tyr Phe Asp Tyr Trp Gly Gln Gly Thr Leu Val Thr
```

```
            340                 345                 350

Val Ser Ser Gly Gly Gly Gly Ser Gly Gly Gly Gly Ser Gly Gly Gly
        355                 360                 365

Gly Ser Asp Ile Glu Leu Thr Gln Ser Pro Ser Ser Leu Ser Ala Ser
    370                 375                 380

Val Gly Asp Arg Val Thr Ile Thr Cys Lys Ala Ser Gln Asp Val Ser
385                 390                 395                 400

Ile Gly Val Ala Trp Tyr Gln Gln Lys Pro Gly Lys Ala Pro Lys Leu
                405                 410                 415

Leu Ile Tyr Ser Ala Ser Tyr Arg His Thr Gly Val Pro Ser Arg Phe
            420                 425                 430

Ser Gly Ser Gly Ser Gly Thr Asp Phe Thr Leu Thr Ile Ser Ser Leu
        435                 440                 445

Gln Pro Glu Asp Phe Ala Thr Tyr Tyr Cys Gln Gln Tyr Tyr Ile Tyr
    450                 455                 460

Pro Tyr Thr Phe Gly Gln Gly Thr Lys Leu Glu Ile Lys Arg
465                 470                 475
```

<210> SEQ ID NO 17
<211> LENGTH: 789
<212> TYPE: DNA
<213> ORGANISM: Artificial Sequence
<220> FEATURE:
<223> OTHER INFORMATION: Synthetic: Trastuzumab VH-CH1-hinge-CalD2

<400> SEQUENCE: 17

```
caggtccaac tgcaggagtc tggcggtggc ctggtgcagc caggggggctc actccgtttg      60

tcctgtgcag cttctggctt caacattaaa gacacctata tacactgggt gcgtcaggcc     120

ccgggtaagg gcctggaatg ggttgcaagg atttatccta cgaatggtta tactagatat     180

gccgatagcg tcaagggccg tttcactata agcgcagaca catccaaaaa cacagcctac     240

ctacagatga acagcctgcg tgctgaggac actgccgtct attattgttc tagatgggga     300

ggggacggct tctatgctat ggactactgg ggtcaaggaa ccctggtcac cgtctcctca     360

gcctccacca agggcccatc ggtcttcccc ctggcaccct cctccaagag cacctctggg     420

ggcacagcgg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgact gtgccctcca gcagcttggg cacccagacc     600

tacatctgca acgtgaatca caaccccagc aacaccaagg tcgacaagaa agttgagccc     660

aaatcttcaa ctaagacgca cacatcagga ggtaacaccc tagatgatct ctttcaagaa     720

ctggacaaga atggagatgg agaagttagt tttgaagaat tccaagtatt agtaaaaaag     780

atatcccag                                                             789
```

<210> SEQ ID NO 18
<211> LENGTH: 263
<212> TYPE: PRT
<213> ORGANISM: Artificial Sequence
<220> FEATURE:
<223> OTHER INFORMATION: Synthetic: Trastuzumab VH-CH1-hinge-CalD2

<400> SEQUENCE: 18

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Asn
        195                 200                 205

Pro Ser Asn Thr Lys Val Asp Lys Lys Val Glu Pro Lys Ser Ser Thr
    210                 215                 220

Lys Thr His Thr Ser Gly Gly Asn Thr Leu Asp Asp Leu Phe Gln Glu
225                 230                 235                 240

Leu Asp Lys Asn Gly Asp Gly Glu Val Ser Phe Glu Glu Phe Gln Val
                245                 250                 255

Leu Val Lys Lys Ile Ser Gln
            260

<210> SEQ ID NO 19
<211> LENGTH: 660
<212> TYPE: DNA
<213> ORGANISM: Artificial Sequence
<220> FEATURE:
<223> OTHER INFORMATION: Synthetic: Trastuzumab light chain

<400> SEQUENCE: 19
gacatcgagc tcacccagtc cccaagctcc ctgtccgcct ctgtgggcga tagagtcacc 60
atcacctgcc gtgccagtca ggatgtgaat actgctgtag cctggtatca acagaaacca 120
ggaaaagctc cgaaactact gatttactcg gcatccttcc tctactctgg agtcccttct 180
cgcttctctg gatccagatc tgggacggat ttcactctaa ccatcagcag tctacagccg 240
gaagacttcg caacttatta ctgtcagcaa cattatacta ctcctcccac gttcggacag 300
ggtaccaagc tcgagatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagttcgc ccgtcacaaa gagcttcaac cgcggagagt cacaccatca ccatcaccat 660

<210> SEQ ID NO 20
<211> LENGTH: 220
<212> TYPE: PRT
<213> ORGANISM: Artificial Sequence
<220> FEATURE:
<223> OTHER INFORMATION: Synthetic: Trastuzumab light chain

<400> SEQUENCE: 20

```
Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser His His His His His His
    210                 215                 220
```

<210> SEQ ID NO 21
<211> LENGTH: 837
<212> TYPE: DNA
<213> ORGANISM: Artificial Sequence
<220> FEATURE:
<223> OTHER INFORMATION: Synthetic: CalD1-hinge-Fc

<400> SEQUENCE: 21

```
aagtctcctg aggaactgaa gaggattttt gaaaaatatg cagccaaaga aggtgatcca      60

gaccagttgt caaaggatga actgaagcta ttgattcagg ctgaattccc cagtttactc     120

aaaggtccag gctcgagcgt tgagcccaaa tcttctgaca aaactcacac atgcccaccg     180

tgcccagcac ctgaactcct ggggggaccg tcagtcttcc tcttcccccc aaaacccaag     240

gacaccctca tgatctcccg gacccctgag gtcacatgcg tggtggtgga cgtgagccac     300

gaagaccctg aggtcaagtt caactggtac gtggacggcg tggaggtgca taatgccaag     360

acaaagccgc gggaggagca gtacaacagc acgtaccgtg tggtcagcgt cctcaccgtc     420

ctgcaccagg actggctgaa tggcaaggag tacaagtgca aggtctccaa caaagccctc     480

ccagccccca tcgagaaaac catctccaaa gccaaagggc agccccgaga accacaggtg     540
```

-continued

```
tacaccctgc ccccatcccg ggatgagctg accaagaacc aggtcagcct gacctgcctg    600

gtcaaaggct tctatcccag cgacatcgcc gtggagtggg agagcaatgg gcagccggag    660

aacaactaca agaccacgcc tcccgtgctg gactccgacg gctccttctt cctctacagc    720

aagctcaccg tggacaagag caggtggcag caggggaacg tcttctcatg ctctgtgatg    780

catgaggctc tgcataacca ctacacgcag aagagcctct ccctgtctcc gggtaaa       837


<210> SEQ ID NO 22
<211> LENGTH: 279
<212> TYPE: PRT
<213> ORGANISM: Artificial Sequence
<220> FEATURE:
<223> OTHER INFORMATION: Synthetic: CalD1-hinge-Fc

<400> SEQUENCE: 22

Lys Ser Pro Glu Glu Leu Lys Arg Ile Phe Glu Lys Tyr Ala Ala Lys
1               5                   10                  15

Glu Gly Asp Pro Asp Gln Leu Ser Lys Asp Glu Leu Lys Leu Leu Ile
            20                  25                  30

Gln Ala Glu Phe Pro Ser Leu Leu Lys Gly Pro Gly Ser Ser Val Glu
        35                  40                  45

Pro Lys Ser Ser Asp Lys Thr His Thr Cys Pro Pro Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Lys Phe Asn Trp Tyr Val Asp
            100                 105                 110

Gly Val Glu Val His Asn Ala Lys Thr Lys Pro Arg Glu Glu Gln Tyr
        115                 120                 125

Asn Ser Thr Tyr Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Ala Lys Gly Gln Pro Arg
                165                 170                 175

Glu Pro Gln Val Tyr Thr Leu Pro Pro Ser Arg Asp Glu Leu Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Asn Gly Gln Pro Glu Asn Asn Tyr Lys
    210                 215                 220

Thr Thr Pro Pro Val Leu Asp Ser Asp Gly Ser Phe Phe Leu Tyr Ser
225                 230                 235                 240

Lys Leu Thr Val Asp Lys Ser Arg Trp Gln Gln Gly Asn Val Phe Ser
                245                 250                 255

Cys Ser Val Met His Glu Ala Leu His Asn His Tyr Thr Gln Lys Ser
            260                 265                 270

Leu Ser Leu Ser Pro Gly Lys
        275


<210> SEQ ID NO 23
<211> LENGTH: 801
<212> TYPE: DNA
<213> ORGANISM: Artificial Sequence
```

<220> FEATURE:
<223> OTHER INFORMATION: Synthetic: 026-VH-CH1-hinge-CalD2

<400> SEQUENCE: 23
caggtccaac tgcaggagtc tgggggaggc gtggtccagc ctgggaggtc cctgagactc 60
tcctgtgcag cgtctggatt caccttcagt aactatgtca tgcactgggt ccgccaggct 120
ccaggcaagg ggctggagtg ggtggcaatt atatggtatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gggtggatat 300
aactggaact acgagtacca ctactacggt atggacgtct ggggccaagg gaccacggtc 360
accgtctcct cagcctccac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ctgtgccctc cagcagcttg 600
ggcacccaga cctacatctg caacgtgaat cacaagccca gcaacaccaa ggtcgacaag 660
aaagttgagc ccaaatcttc aactaagacg cacacatcag gaggtaacac cctagatgat 720
ctctttcaag aactggacaa gaatggagat ggagaagtta gttttgaaga attccaagta 780
ttagtaaaaa agatatccca g 801

<210> SEQ ID NO 24
<211> LENGTH: 267
<212> TYPE: PRT
<213> ORGANISM: Artificial Sequence
<220> FEATURE:
<223> OTHER INFORMATION: Synthetic: 026-VH-CH1-hinge-CalD2

<400> SEQUENCE: 24

Gln Val Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Val Met His Trp Val Arg Gln Ala Pro Gly Lys Gly Leu Glu Trp Val
35 40 45

Ala Ile Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gly Gly Tyr Asn Trp Asn Tyr Glu Tyr His Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

```
Val Thr Val Pro Ser Ser Ser Leu Gly Thr Gln Thr Tyr Ile Cys Asn
        195                 200                 205

Val Asn His Asn Pro Ser Asn Thr Lys Val Asp Lys Lys Val Glu Pro
    210                 215                 220

Lys Ser Ser Thr Lys Thr His Thr Ser Gly Gly Asn Thr Leu Asp Asp
225                 230                 235                 240

Leu Phe Gln Glu Leu Asp Lys Asn Gly Asp Gly Glu Val Ser Phe Glu
                245                 250                 255

Glu Phe Gln Val Leu Val Lys Lys Ile Ser Gln
            260                 265


<210> SEQ ID NO 25
<211> LENGTH: 660
<212> TYPE: DNA
<213> ORGANISM: Artificial Sequence
<220> FEATURE:
<223> OTHER INFORMATION: Synthetic: 026 light chain

<400> SEQUENCE: 25

gacatcgagc tcacccagtc tccatcctca ctgtctgcat ctgtaggaga cagagtcacc     60

atcacttgtc gggcgagtca gggcattacc aattatttag cctggtttca gcagaaacca    120

gggaaagccc ctaagtccct tatctatgct gcatccagtt tgcaaagtgg ggtcccatca    180

aagttcagcg gcagtggatc tgggacagat ttcagtctca ccatcagcag cctccagcct    240

gaagattttg caacttatta ctgccaacag tataatagtt acccgatcac cttcggccaa    300

gggacacgac tcgagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagttcgc ccgtcacaaa gagcttcaac cgcggagagt cacaccatca ccatcaccat    660


<210> SEQ ID NO 26
<211> LENGTH: 220
<212> TYPE: PRT
<213> ORGANISM: Artificial Sequence
<220> FEATURE:
<223> OTHER INFORMATION: Synthetic: 026 light chain

<400> SEQUENCE: 26

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Gly Ile Thr Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser His His His His His His
    210                 215                 220


<210> SEQ ID NO 27
<211> LENGTH: 1092
<212> TYPE: DNA
<213> ORGANISM: Artificial Sequence
<220> FEATURE:
<223> OTHER INFORMATION: Synthetic: Fc-Syt1

<400> SEQUENCE: 27

gttgagccca aatcttctga caaaactcac acatgcccac cgtgcccagc acctgaactc     60

ctgggggac cgtcagtctt cctcttcccc ccaaaaccca aggacaccct catgatctcc    120

cggacccctg aggtcacatg cgtggtggtg gacgtgagcc acgaagaccc tgaggtcaag    180

ttcaactggt acgtggacgg cgtggaggtg cataatgcca agacaaagcc gcgggaggag    240

cagtacaaca gcacgtaccg tgtggtcagc gtcctcaccg tcctgcacca ggactggctg    300

aatggcaagg agtacaagtg caaggtctcc aacaaagccc tcccagcccc catcgagaaa    360

accatctcca aagccaaagg gcagccccga gaaccacagg tgtacaccct gcccccatcc    420

cgggatgagc tgaccaagaa ccaggtcagc ctgacctgcc tggtcaaagg cttctatccc    480

agcgacatcg ccgtggagtg ggagagcaat gggcagccgg agaacaacta caagaccacg    540

cctcccgtgc tggactccga cggctccttc ttcctctaca gcaagctcac cgtggacaag    600

agcaggtggc agcaggggaa cgtcttctca tgctccgtga tgcatgaggc tctgcacaac    660

cactacacgc agaagagcct ctccctgtct ccgggtaaag gaggcggtgg atcagagaaa    720

ctgggaaaac ttcagtattc actggattat gatttccaaa ataaccagct gctggtaggg    780

atcattcagg ctgccgaact gcccgccttg gacatggggg gcacatctga tccttacgtg    840

aaagtgtttc tgctacctga taagaagaag aaatttgaga caaaagtcca ccgaaaaacc    900

cttaatcctg tcttcaatga gcaatttact ttcaaggtac catactcgga attgggtggc    960

aaaaccctag tgatggctgt atatgatttt gatcgtttct ctaagcatga catcattgga   1020

gaatttaaag tccctatgaa cacagtggat tttggccatg taactgagga atggcgtgac   1080

ctgcaaagtg ct                                                       1092


<210> SEQ ID NO 28
<211> LENGTH: 364
<212> TYPE: PRT
<213> ORGANISM: Artificial Sequence
<220> FEATURE:
<223> OTHER INFORMATION: Synthetic: Fc-Syt1

<400> SEQUENCE: 28

Val Glu Pro Lys Ser Ser Asp Lys Thr His Thr Cys Pro Pro Cys Pro
```

-continued

```
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Gly Gly Ser Glu Lys
225                 230                 235                 240

Leu Gly Lys Leu Gln Tyr Ser Leu Asp Tyr Asp Phe Gln Asn Asn Gln
                245                 250                 255

Leu Leu Val Gly Ile Ile Gln Ala Ala Glu Leu Pro Ala Leu Asp Met
            260                 265                 270

Gly Gly Thr Ser Asp Pro Tyr Val Lys Val Phe Leu Leu Pro Asp Lys
        275                 280                 285

Lys Lys Lys Phe Glu Thr Lys Val His Arg Lys Thr Leu Asn Pro Val
    290                 295                 300

Phe Asn Glu Gln Phe Thr Phe Lys Val Pro Tyr Ser Glu Leu Gly Gly
305                 310                 315                 320

Lys Thr Leu Val Met Ala Val Tyr Asp Phe Asp Arg Phe Ser Lys His
                325                 330                 335

Asp Ile Ile Gly Glu Phe Lys Val Pro Met Asn Thr Val Asp Phe Gly
            340                 345                 350

His Val Thr Glu Glu Trp Arg Asp Leu Gln Ser Ala
        355                 360
```

<210> SEQ ID NO 29
<211> LENGTH: 1485
<212> TYPE: DNA
<213> ORGANISM: Artificial Sequence
<220> FEATURE:
<223> OTHER INFORMATION: Synthetic: Syt1-Fc-Syt1

<400> SEQUENCE: 29
gagaaactgg gaaaacttca gtattcactg gattatgatt tccaaaataa ccagctgctg     60

```
gtagggatca ttcaggctgc cgaactgccc gccttggaca tggggggcac atctgatcct    120
tacgtgaaag tgtttctgct acctgataag aagaagaaat ttgagacaaa agtccaccga    180
aaaaccctta atcctgtctt caatgagcaa tttactttca aggtaccata ctcggaattg    240
ggtggcaaaa ccctagtgat ggctgtatat gattttgatc gtttctctaa gcatgacatc    300
attggagaat ttaaagtccc tatgaacaca gtggattttg gccatgtaac tgaggaatgg    360
cgtgacctgc aaagtgctgg aggcggtgga tcagttgagc ccaaatcttc tgacaaaact    420
cacacatgcc caccgtgccc agcacctgaa ctcctggggg gaccgtcagt cttcctcttc    480
cccccaaaac ccaaggacac cctcatgatc tcccggaccc ctgaggtcac atgcgtggtg    540
gtggacgtga gccacgaaga ccctgaggtc aagttcaact ggtacgtgga cggcgtggag    600
gtgcataatg ccaagacaaa gccgcgggag gagcagtaca acagcacgta ccgtgtggtc    660
agcgtcctca ccgtcctgca ccaggactgg ctgaatggca aggagtacaa gtgcaaggtc    720
tccaacaaag ccctcccagc ccccatcgag aaaaccatct ccaaagccaa agggcagccc    780
cgagaaccac aggtgtacac cctgccccca tcccgggatg agctgaccaa gaaccaggtc    840
agcctgacct gcctggtcaa aggcttctat cccagcgaca tcgccgtgga gtgggagagc    900
aatgggcagc cggagaacaa ctacaagacc acgcctcccg tgctggactc cgacggctcc    960
ttcttcctct acagcaagct caccgtggac aagagcaggt ggcagcaggg gaacgtcttc   1020
tcatgctccg tgatgcatga ggctctgcac aaccactaca cgcagaagag cctctccctg   1080
tctccgggta aaggcggagg tggcagcgag aaactgggaa aacttcagta ttcactggat   1140
tatgatttcc aaaataacca gctgctggta gggatcattc aggctgccga actgcccgcc   1200
ttggacatgg ggggcacatc tgatccttac gtgaaagtgt ttctgctacc tgataagaag   1260
aagaaatttg agacaaaagt ccaccgaaaa acccttaatc ctgtcttcaa tgagcaattt   1320
actttcaagg taccatactc ggaattgggt ggcaaaaccc tagtgatggc tgtatatgat   1380
tttgatcgtt tctctaagca tgacatcatt ggagaattta aagtccctat gaacacagtg   1440
gattttggcc atgtaactga ggaatggcgt gacctgcaaa gtgct                  1485
```

<210> SEQ ID NO 30
<211> LENGTH: 495
<212> TYPE: PRT
<213> ORGANISM: Artificial Sequence
<220> FEATURE:
<223> OTHER INFORMATION: Synthetic: Syt1-Fc-Syt1

<400> SEQUENCE: 30

```
Glu Lys Leu Gly Lys Leu Gln Tyr Ser Leu Asp Tyr Asp Phe Gln Asn
1               5                   10                  15

Asn Gln Leu Leu Val Gly Ile Ile Gln Ala Ala Glu Leu Pro Ala Leu
            20                  25                  30

Asp Met Gly Gly Thr Ser Asp Pro Tyr Val Lys Val Phe Leu Leu Pro
        35                  40                  45

Asp Lys Lys Lys Lys Phe Glu Thr Lys Val His Arg Lys Thr Leu Asn
    50                  55                  60

Pro Val Phe Asn Glu Gln Phe Thr Phe Lys Val Pro Tyr Ser Glu Leu
65                  70                  75                  80

Gly Gly Lys Thr Leu Val Met Ala Val Tyr Asp Phe Asp Arg Phe Ser
                85                  90                  95

Lys His Asp Ile Ile Gly Glu Phe Lys Val Pro Met Asn Thr Val Asp
            100                 105                 110
```

```
Phe Gly His Val Thr Glu Glu Trp Arg Asp Leu Gln Ser Ala Gly Gly
        115                 120                 125

Gly Gly Ser Val Glu Pro Lys Ser Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys Gly Gly Gly Gly
        355                 360                 365

Ser Glu Lys Leu Gly Lys Leu Gln Tyr Ser Leu Asp Tyr Asp Phe Gln
    370                 375                 380

Asn Asn Gln Leu Leu Val Gly Ile Ile Gln Ala Ala Glu Leu Pro Ala
385                 390                 395                 400

Leu Asp Met Gly Gly Thr Ser Asp Pro Tyr Val Lys Val Phe Leu Leu
                405                 410                 415

Pro Asp Lys Lys Lys Lys Phe Glu Thr Lys Val His Arg Lys Thr Leu
            420                 425                 430

Asn Pro Val Phe Asn Glu Gln Phe Thr Phe Lys Val Pro Tyr Ser Glu
        435                 440                 445

Leu Gly Gly Lys Thr Leu Val Met Ala Val Tyr Asp Phe Asp Arg Phe
    450                 455                 460

Ser Lys His Asp Ile Ile Gly Glu Phe Lys Val Pro Met Asn Thr Val
465                 470                 475                 480

Asp Phe Gly His Val Thr Glu Glu Trp Arg Asp Leu Gln Ser Ala
                485                 490                 495
```

<210> SEQ ID NO 31
<211> LENGTH: 1110
<212> TYPE: DNA
<213> ORGANISM: Artificial Sequence
<220> FEATURE:

<223> OTHER INFORMATION: Synthetic: Fc-PKCa

<400> SEQUENCE: 31
gttgagccca aatcttctga caaaactcac acatgcccac cgtgcccagc acctgaactc 60
ctggggggac cgtcagtctt cctcttcccc ccaaaaccca aggacaccct catgatctcc 120
cggacccctg aggtcacatg cgtggtggtg gacgtgagcc acgaagaccc tgaggtcaag 180
ttcaactggt acgtggacgg cgtggaggtg cataatgcca agacaaagcc gcgggaggag 240
cagtacaaca gcacgtaccg tgtggtcagc gtcctcaccg tcctgcacca ggactggctg 300
aatggcaagg agtacaagtg caaggtctcc aacaaagccc tcccagcccc catcgagaaa 360
accatctcca aagccaaagg gcagccccga gaaccacagg tgtacaccct gcccccatcc 420
cgggatgagc tgaccaagaa ccaggtcagc ctgacctgcc tggtcaaagg cttctatccc 480
agcgacatcg ccgtggagtg ggagagcaat gggcagccgg agaacaacta caagaccacg 540
cctcccgtgc tggactccga cggctccttc ttcctctaca gcaagctcac cgtggacaag 600
agcaggtggc agcaggggaa cgtcttctca tgctccgtga tgcatgaggc tctgcacaac 660
cactacacgc agaagagcct ctccctgtct ccgggtaaag gaggcggtgg atcagagaag 720
agggggcgga tttacctaaa ggctgaggtt gctgatgaaa agctccatgt cacagtacga 780
gatgcaaaaa atctaatccc tatggatcca aacgggcttt cagatcctta tgtgaagctg 840
aaacttattc ctgatcccaa gaatgaaagc aagcaaaaaa ccaaaaccat ccgctccaca 900
ctaaatccgc agtggaatga gtcctttaca ttcaaattga aaccttcaga caaagaccga 960
cgactgtctg tagaaatctg ggactgggat cgaacaacaa ggaatgactt catgggatcc 1020
ctttcctttg gagtttcgga gctgatgaag atgccggcca gtggatggta caagttgctt 1080
aaccaagaag aaggtgagta ctacaacgta 1110

<210> SEQ ID NO 32
<211> LENGTH: 370
<212> TYPE: PRT
<213> ORGANISM: Artificial Sequence
<220> FEATURE:
<223> OTHER INFORMATION: Synthetic: Fc-PKCa

<400> SEQUENCE: 32

Val Glu Pro Lys Ser Ser Asp Lys Thr His Thr Cys Pro Pro Cys Pro
1 5 10 15

Ala Pro Glu Leu Leu Gly Gly Pro Ser Val Phe Leu Phe Pro Pro Lys
20 25 30

Pro Lys Asp Thr Leu Met Ile Ser Arg Thr Pro Glu Val Thr Cys Val
35 40 45

Val Val Asp Val Ser His Glu Asp Pro Glu Val Lys Phe Asn Trp Tyr
50 55 60

Val Asp Gly Val Glu Val His Asn Ala Lys Thr Lys Pro Arg Glu Glu
65 70 75 80

Gln Tyr Asn Ser Thr Tyr Arg Val Val Ser Val Leu Thr Val Leu His
85 90 95

Gln Asp Trp Leu Asn Gly Lys Glu Tyr Lys Cys Lys Val Ser Asn Lys
100 105 110

Ala Leu Pro Ala Pro Ile Glu Lys Thr Ile Ser Lys Ala Lys Gly Gln
115 120 125

Pro Arg Glu Pro Gln Val Tyr Thr Leu Pro Pro Ser Arg Asp Glu Leu
130 135 140

```
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Gly Gly Ser Glu Lys
225                 230                 235                 240

Arg Gly Arg Ile Tyr Leu Lys Ala Glu Val Ala Asp Glu Lys Leu His
                245                 250                 255

Val Thr Val Arg Asp Ala Lys Asn Leu Ile Pro Met Asp Pro Asn Gly
            260                 265                 270

Leu Ser Asp Pro Tyr Val Lys Leu Lys Leu Ile Pro Asp Pro Lys Asn
        275                 280                 285

Glu Ser Lys Gln Lys Thr Lys Thr Ile Arg Ser Thr Leu Asn Pro Gln
    290                 295                 300

Trp Asn Glu Ser Phe Thr Phe Lys Leu Lys Pro Ser Asp Lys Asp Arg
305                 310                 315                 320

Arg Leu Ser Val Glu Ile Trp Asp Trp Asp Arg Thr Thr Arg Asn Asp
                325                 330                 335

Phe Met Gly Ser Leu Ser Phe Gly Val Ser Glu Leu Met Lys Met Pro
            340                 345                 350

Ala Ser Gly Trp Tyr Lys Leu Leu Asn Gln Glu Glu Gly Glu Tyr Tyr
        355                 360                 365

Asn Val
    370
```

<210> SEQ ID NO 33
<211> LENGTH: 1632
<212> TYPE: DNA
<213> ORGANISM: Artificial Sequence
<220> FEATURE:
<223> OTHER INFORMATION: Synthetic: Fc-AnxA1

<400> SEQUENCE: 33

```
gttgagccca aatcttctga caaaactcac acatgcccac cgtgcccagc acctgaactc      60

ctggggggac cgtcagtctt cctcttcccc ccaaaaccca aggacaccct catgatctcc     120

cggacccctg aggtcacatg cgtggtggtg gacgtgagcc acgaagaccc tgaggtcaag     180

ttcaactggt acgtggacgg cgtggaggtg cataatgcca agacaaagcc gcgggaggag     240

cagtacaaca gcacgtaccg tgtggtcagc gtcctcaccg tcctgcacca ggactggctg     300

aatggcaagg agtacaagtg caaggtctcc aacaaagccc tcccagcccc catcgagaaa     360

accatctcca aagccaaagg gcagccccga gaaccacagg tgtacaccct gcccccatcc     420

cgggatgagc tgaccaagaa ccaggtcagc ctgacctgcc tggtcaaagg cttctatccc     480

agcgacatcg ccgtggagtg ggagagcaat gggcagccgg agaacaacta caagaccacg     540

cctcccgtgc tggactccga cggctccttc ttcctctaca gcaagctcac cgtggacaag     600

agcaggtggc agcaggggaa cgtcttctca tgctccgtga tgcatgaggc tctgcacaac     660

cactacacgc agaagagcct ctccctgtct ccgggtaaag gaggcggtgg atcaaccttc     720
```

-continued

```
aatccatcct cggatgtcgc tgccttgcat aaggccataa tggttaaagg tgtggatgaa    780

gcaaccatca ttgacattct aactaagcga aacaatgcac agcgtcaaca gatcaaagca    840

gcatatctcc aggaaacagg aaagcccctg gatgaaacac tgaagaaagc ccttacaggt    900

caccttgagg aggttgtttt agctctgcta aaaactccag cgcaatttga tgctgatgaa    960

cttcgtgctg ccatgaaggg ccttggaact gatgaagata ctctaattga gattttggca   1020

tcaagaacta acaaagaaat cagagacatt aacagggtct acagagagga actgaagaga   1080

gatctggcca aagacataac ctcagacaca tctggagatt ttcggaacgc tttgctttct   1140

cttgctaagg gtgaccgatc tgaggacttt ggtgtgaatg aagacttggc tgattcagat   1200

gccagggcct tgtatgaagc aggagaaagg agaaagggga cagacgtaaa cgtgttcaat   1260

accatcctta ccaccagaag ctatccacaa cttcgcagag tgtttcagaa atacaccaag   1320

tacagtaagc atgacatgaa caaagttcta gacctggagt tgaaaggtga cattgagaaa   1380

tgcctcacag ctatcgtgaa gtgcgccaca agcaaaccag ctttctttgc agagaagctt   1440

catcaagcca tgaaaggtgt tggaactcgc cataaggcat tgatcaggat tatggtttcc   1500

cgttctgaaa ttgacatgaa tgatatcaaa gcattctatc agaagatgta tggtatctcc   1560

ctttgccaag ccatcctgga tgaaaccaaa ggagattatg agaaaatcct ggtggctctt   1620

tgtggaggaa ac                                                        1632
```

<210> SEQ ID NO 34
<211> LENGTH: 544
<212> TYPE: PRT
<213> ORGANISM: Artificial Sequence
<220> FEATURE:
<223> OTHER INFORMATION: Synthetic: Fc-AnxA1

<400> SEQUENCE: 34

```
Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
```

-continued

```
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Gly Gly Ser Thr Phe
225                 230                 235                 240

Asn Pro Ser Ser Asp Val Ala Ala Leu His Lys Ala Ile Met Val Lys
                245                 250                 255

Gly Val Asp Glu Ala Thr Ile Ile Asp Ile Leu Thr Lys Arg Asn Asn
            260                 265                 270

Ala Gln Arg Gln Gln Ile Lys Ala Ala Tyr Leu Gln Glu Thr Gly Lys
        275                 280                 285

Pro Leu Asp Glu Thr Leu Lys Lys Ala Leu Thr Gly His Leu Glu Glu
    290                 295                 300

Val Val Leu Ala Leu Leu Lys Thr Pro Ala Gln Phe Asp Ala Asp Glu
305                 310                 315                 320

Leu Arg Ala Ala Met Lys Gly Leu Gly Thr Asp Glu Asp Thr Leu Ile
                325                 330                 335

Glu Ile Leu Ala Ser Arg Thr Asn Lys Glu Ile Arg Asp Ile Asn Arg
            340                 345                 350

Val Tyr Arg Glu Glu Leu Lys Arg Asp Leu Ala Lys Asp Ile Thr Ser
        355                 360                 365

Asp Thr Ser Gly Asp Phe Arg Asn Ala Leu Leu Ser Leu Ala Lys Gly
    370                 375                 380

Asp Arg Ser Glu Asp Phe Gly Val Asn Glu Asp Leu Ala Asp Ser Asp
385                 390                 395                 400

Ala Arg Ala Leu Tyr Glu Ala Gly Glu Arg Arg Lys Gly Thr Asp Val
                405                 410                 415

Asn Val Phe Asn Thr Ile Leu Thr Thr Arg Ser Tyr Pro Gln Leu Arg
            420                 425                 430

Arg Val Phe Gln Lys Tyr Thr Lys Tyr Ser Lys His Asp Met Asn Lys
        435                 440                 445

Val Leu Asp Leu Glu Leu Lys Gly Asp Ile Glu Lys Cys Leu Thr Ala
    450                 455                 460

Ile Val Lys Cys Ala Thr Ser Lys Pro Ala Phe Phe Ala Glu Lys Leu
465                 470                 475                 480

His Gln Ala Met Lys Gly Val Gly Thr Arg His Lys Ala Leu Ile Arg
                485                 490                 495

Ile Met Val Ser Arg Ser Glu Ile Asp Met Asn Asp Ile Lys Ala Phe
            500                 505                 510

Tyr Gln Lys Met Tyr Gly Ile Ser Leu Cys Gln Ala Ile Leu Asp Glu
        515                 520                 525

Thr Lys Gly Asp Tyr Glu Lys Ile Leu Val Ala Leu Cys Gly Gly Asn
    530                 535                 540
```

<210> SEQ ID NO 35
<211> LENGTH: 1092
<212> TYPE: DNA
<213> ORGANISM: Artificial Sequence
<220> FEATURE:
<223> OTHER INFORMATION: Synthetic: Syt1-Fc

<400> SEQUENCE: 35

```
gagaaactgg gaaaacttca gtattcactg gattatgatt tccaaaataa ccagctgctg      60

gtagggatca ttcaggctgc cgaactgccc gccttggaca tgggggcac atctgatcct     120
```

-continued

```
tacgtgaaag tgtttctgct acctgataag aagaagaaat ttgagacaaa agtccaccga    180

aaaaccctta atcctgtctt caatgagcaa tttactttca aggtaccata ctcggaattg    240

ggtggcaaaa ccctagtgat ggctgtatat gattttgatc gtttctctaa gcatgacatc    300

attggagaat ttaaagtccc tatgaacaca gtggattttg gccatgtaac tgaggaatgg    360

cgtgacctgc aaagtgctgg aggcggtgga tcagttgagc ccaaatcttc tgacaaaact    420

cacacatgcc caccgtgccc agcacctgaa ctcctggggg gaccgtcagt cttcctcttc    480

cccccaaaac ccaaggacac cctcatgatc tcccggaccc ctgaggtcac atgcgtggtg    540

gtggacgtga gccacgaaga ccctgaggtc aagttcaact ggtacgtgga cggcgtggag    600

gtgcataatg ccaagacaaa gccgcgggag gagcagtaca acagcacgta ccgtgtggtc    660

agcgtcctca ccgtcctgca ccaggactgg ctgaatggca aggagtacaa gtgcaaggtc    720

tccaacaaag ccctcccagc ccccatcgag aaaaccatct ccaaagccaa agggcagccc    780

cgagaaccac aggtgtacac cctgccccca tcccgggatg agctgaccaa gaaccaggtc    840

agcctgacct gcctggtcaa aggcttctat cccagcgaca tcgccgtgga gtgggagagc    900

aatgggcagc cggagaacaa ctacaagacc acgcctcccg tgctggactc cgacggctcc    960

ttcttcctct acagcaagct caccgtggac aagagcaggt ggcagcaggg gaacgtcttc   1020

tcatgctccg tgatgcatga ggctctgcac aaccactaca cgcagaagag cctctccctg   1080

tctccgggta aa                                                       1092
```

```
<210> SEQ ID NO 36
<211> LENGTH: 364
<212> TYPE: PRT
<213> ORGANISM: Artificial Sequence
<220> FEATURE:
<223> OTHER INFORMATION: Synthetic: Syt1-Fc

<400> SEQUENCE: 36

Glu Lys Leu Gly Lys Leu Gln Tyr Ser Leu Asp Tyr Asp Phe Gln Asn
1               5                   10                  15

Asn Gln Leu Leu Val Gly Ile Ile Gln Ala Ala Glu Leu Pro Ala Leu
            20                  25                  30

Asp Met Gly Gly Thr Ser Asp Pro Tyr Val Lys Val Phe Leu Leu Pro
        35                  40                  45

Asp Lys Lys Lys Lys Phe Glu Thr Lys Val His Arg Lys Thr Leu Asn
    50                  55                  60

Pro Val Phe Asn Glu Gln Phe Thr Phe Lys Val Pro Tyr Ser Glu Leu
65                  70                  75                  80

Gly Gly Lys Thr Leu Val Met Ala Val Tyr Asp Phe Asp Arg Phe Ser
                85                  90                  95

Lys His Asp Ile Ile Gly Glu Phe Lys Val Pro Met Asn Thr Val Asp
            100                 105                 110

Phe Gly His Val Thr Glu Glu Trp Arg Asp Leu Gln Ser Ala Gly Gly
        115                 120                 125

Gly Gly Ser Val Glu Pro Lys Ser Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190
```

```
Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360


<210> SEQ ID NO 37
<211> LENGTH: 1110
<212> TYPE: DNA
<213> ORGANISM: Artificial Sequence
<220> FEATURE:
<223> OTHER INFORMATION: Synthetic: PKCa-Fc

<400> SEQUENCE: 37

gagaagaggg ggcggattta cctaaaggct gaggttgctg atgaaaagct ccatgtcaca     60

gtacgagatg caaaaaatct aatccctatg gatccaaacg ggctttcaga tccttatgtg    120

aagctgaaac ttattcctga tcccaagaat gaaagcaagc aaaaaaccaa aaccatccgc    180

tccacactaa atccgcagtg gaatgagtcc tttacattca aattgaaacc ttcagacaaa    240

gaccgacgac tgtctgtaga aatctgggac tgggatcgaa caacaaggaa tgacttcatg    300

ggatcccttt cctttggagt ttcggagctg atgaagatgc cggccagtgg atggtacaag    360

ttgcttaacc aagaagaagg tgagtactac aacgtaggag gcggtggatc agttgagccc    420

aaatcttctg acaaaactca cacatgccca ccgtgcccag cacctgaact cctgggggga    480

ccgtcagtct tcctcttccc cccaaaaccc aaggacaccc tcatgatctc ccggacccct    540

gaggtcacat gcgtggtggt ggacgtgagc cacgaagacc ctgaggtcaa gttcaactgg    600

tacgtggacg gcgtggaggt gcataatgcc aagacaaagc cgcgggagga gcagtacaac    660

agcacgtacc gtgtggtcag cgtcctcacc gtcctgcacc aggactggct gaatggcaag    720

gagtacaagt gcaaggtctc caacaaagcc ctcccagccc ccatcgagaa aaccatctcc    780

aaagccaaag ggcagccccg agaaccacag gtgtacaccc tgcccccatc ccgggatgag    840

ctgaccaaga accaggtcag cctgacctgc ctggtcaaag gcttctatcc cagcgacatc    900

gccgtggagt gggagagcaa tgggcagccg gagaacaact acaagaccac gcctcccgtg    960

ctggactccg acggctcctt cttcctctac agcaagctca ccgtggacaa gagcaggtgg   1020

cagcagggga acgtcttctc atgctccgtg atgcatgagg ctctgcacaa ccactacacg   1080
```

```
cagaagagcc tctccctgtc tccgggtaaa                                  1110


<210> SEQ ID NO 38
<211> LENGTH: 370
<212> TYPE: PRT
<213> ORGANISM: Artificial Sequence
<220> FEATURE:
<223> OTHER INFORMATION: Synthetic: PKCa-Fc

<400> SEQUENCE: 38

Glu Lys Arg Gly Arg Ile Tyr Leu Lys Ala Glu Val Ala Asp Glu Lys
1               5                   10                  15

Leu His Val Thr Val Arg Asp Ala Lys Asn Leu Ile Pro Met Asp Pro
            20                  25                  30

Asn Gly Leu Ser Asp Pro Tyr Val Lys Leu Lys Leu Ile Pro Asp Pro
        35                  40                  45

Lys Asn Glu Ser Lys Gln Lys Thr Lys Thr Ile Arg Ser Thr Leu Asn
    50                  55                  60

Pro Gln Trp Asn Glu Ser Phe Thr Phe Lys Leu Lys Pro Ser Asp Lys
65                  70                  75                  80

Asp Arg Arg Leu Ser Val Glu Ile Trp Asp Trp Asp Arg Thr Thr Arg
                85                  90                  95

Asn Asp Phe Met Gly Ser Leu Ser Phe Gly Val Ser Glu Leu Met Lys
            100                 105                 110

Met Pro Ala Ser Gly Trp Tyr Lys Leu Leu Asn Gln Glu Glu Gly Glu
        115                 120                 125

Tyr Tyr Asn Val Gly Gly Gly Gly Ser Val Glu Pro Lys Ser Ser Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350
```

```
Glu Ala Leu His Asn His Tyr Thr Gln Lys Ser Leu Ser Leu Ser Pro
        355                 360                 365

Gly Lys
    370


<210> SEQ ID NO 39
<211> LENGTH: 1632
<212> TYPE: DNA
<213> ORGANISM: Artificial Sequence
<220> FEATURE:
<223> OTHER INFORMATION: Synthetic: AnxA1-Fc

<400> SEQUENCE: 39

accttcaatc catcctcgga tgtcgctgcc ttgcataagg ccataatggt taaaggtgtg     60

gatgaagcaa ccatcattga cattctaact aagcgaaaca atgcacagcg tcaacagatc    120

aaagcagcat atctccagga aacaggaaag cccctggatg aaacactgaa gaaagccctt    180

acaggtcacc ttgaggaggt tgttttagct ctgctaaaaa ctccagcgca atttgatgct    240

gatgaacttc gtgctgccat gaagggcctt ggaactgatg aagatactct aattgagatt    300

ttggcatcaa gaactaacaa agaaatcaga gacattaaca gggtctacag agaggaactg    360

aagagagatc tggccaaaga cataacctca gacacatctg gagattttcg gaacgctttg    420

ctttctcttg ctaagggtga ccgatctgag gactttggtg tgaatgaaga cttggctgat    480

tcagatgcca gggccttgta tgaagcagga gaaaggagaa aggggacaga cgtaaacgtg    540

ttcaatacca tccttaccac cagaagctat ccacaacttc gcagagtgtt tcagaaatac    600

accaagtaca gtaagcatga catgaacaaa gttctagacc tggagttgaa aggtgacatt    660

gagaaatgcc tcacagctat cgtgaagtgc gccacaagca aaccagcttt ctttgcagag    720

aagcttcatc aagccatgaa aggtgttgga actcgccata aggcattgat caggattatg    780

gtttcccgtt ctgaaattga catgaatgat atcaaagcat tctatcagaa gatgtatggt    840

atctcccttt gccaagccat cctggatgaa accaaaggag attatgagaa aatcctggtg    900

gctctttgtg gaggaaacgg aggcggtgga tcagttgagc ccaaatcttc tgacaaaact    960

cacacatgcc caccgtgccc agcacctgaa ctcctggggg gaccgtcagt cttcctcttc   1020

cccccaaaac ccaaggacac cctcatgatc tcccggaccc ctgaggtcac atgcgtggtg   1080

gtggacgtga gccacgaaga ccctgaggtc aagttcaact ggtacgtgga cggcgtggag   1140

gtgcataatg ccaagacaaa gccgcgggag gagcagtaca acagcacgta ccgtgtggtc   1200

agcgtcctca ccgtcctgca ccaggactgg ctgaatggca aggagtacaa gtgcaaggtc   1260

tccaacaaag ccctcccagc ccccatcgag aaaaccatct ccaaagccaa agggcagccc   1320

cgagaaccac aggtgtacac cctgccccca tcccgggatg agctgaccaa gaaccaggtc   1380

agcctgacct gcctggtcaa aggcttctat cccagcgaca tcgccgtgga gtgggagagc   1440

aatgggcagc cggagaacaa ctacaagacc acgcctcccg tgctggactc cgacggctcc   1500

ttcttcctct acagcaagct caccgtggac aagagcaggt ggcagcaggg gaacgtcttc   1560

tcatgctccg tgatgcatga ggctctgcac aaccactaca cgcagaagag cctctccctg   1620

tctccgggta aa                                                        1632


<210> SEQ ID NO 40
<211> LENGTH: 544
<212> TYPE: PRT
<213> ORGANISM: Artificial Sequence
<220> FEATURE:
<223> OTHER INFORMATION: Synthetic: AnxA1-Fc
```

-continued

<400> SEQUENCE: 40

Thr Phe Asn Pro Ser Ser Asp Val Ala Ala Leu His Lys Ala Ile Met
1 5 10 15

Val Lys Gly Val Asp Glu Ala Thr Ile Ile Asp Ile Leu Thr Lys Arg
20 25 30

Asn Asn Ala Gln Arg Gln Gln Ile Lys Ala Ala Tyr Leu Gln Glu Thr
35 40 45

Gly Lys Pro Leu Asp Glu Thr Leu Lys Lys Ala Leu Thr Gly His Leu
50 55 60

Glu Glu Val Val Leu Ala Leu Leu Lys Thr Pro Ala Gln Phe Asp Ala
65 70 75 80

Asp Glu Leu Arg Ala Ala Met Lys Gly Leu Gly Thr Asp Glu Asp Thr
85 90 95

Leu Ile Glu Ile Leu Ala Ser Arg Thr Asn Lys Glu Ile Arg Asp Ile
100 105 110

Asn Arg Val Tyr Arg Glu Glu Leu Lys Arg Asp Leu Ala Lys Asp Ile
115 120 125

Thr Ser Asp Thr Ser Gly Asp Phe Arg Asn Ala Leu Leu Ser Leu Ala
130 135 140

Lys Gly Asp Arg Ser Glu Asp Phe Gly Val Asn Glu Asp Leu Ala Asp
145 150 155 160

Ser Asp Ala Arg Ala Leu Tyr Glu Ala Gly Glu Arg Arg Lys Gly Thr
165 170 175

Asp Val Asn Val Phe Asn Thr Ile Leu Thr Thr Arg Ser Tyr Pro Gln
180 185 190

Leu Arg Arg Val Phe Gln Lys Tyr Thr Lys Tyr Ser Lys His Asp Met
195 200 205

Asn Lys Val Leu Asp Leu Glu Leu Lys Gly Asp Ile Glu Lys Cys Leu
210 215 220

Thr Ala Ile Val Lys Cys Ala Thr Ser Lys Pro Ala Phe Phe Ala Glu
225 230 235 240

Lys Leu His Gln Ala Met Lys Gly Val Gly Thr Arg His Lys Ala Leu
245 250 255

Ile Arg Ile Met Val Ser Arg Ser Glu Ile Asp Met Asn Asp Ile Lys
260 265 270

Ala Phe Tyr Gln Lys Met Tyr Gly Ile Ser Leu Cys Gln Ala Ile Leu
275 280 285

Asp Glu Thr Lys Gly Asp Tyr Glu Lys Ile Leu Val Ala Leu Cys Gly
290 295 300

Gly Asn Gly Gly Gly Gly Ser Val Glu Pro Lys Ser Ser Asp Lys Thr
305 310 315 320

His Thr Cys Pro Pro Cys Pro Ala Pro Glu Leu Leu Gly Gly Pro Ser
325 330 335

Val Phe Leu Phe Pro Pro Lys Pro Lys Asp Thr Leu Met Ile Ser Arg
340 345 350

Thr Pro Glu Val Thr Cys Val Val Val Asp Val Ser His Glu Asp Pro
355 360 365

Glu Val Lys Phe Asn Trp Tyr Val Asp Gly Val Glu Val His Asn Ala
370 375 380

Lys Thr Lys Pro Arg Glu Glu Gln Tyr Asn Ser Thr Tyr Arg Val Val
385 390 395 400

Ser Val Leu Thr Val Leu His Gln Asp Trp Leu Asn Gly Lys Glu Tyr

-continued

```
                405                 410                 415

Lys Cys Lys Val Ser Asn Lys Ala Leu Pro Ala Pro Ile Glu Lys Thr
            420                 425                 430

Ile Ser Lys Ala Lys Gly Gln Pro Arg Glu Pro Gln Val Tyr Thr Leu
        435                 440                 445

Pro Pro Ser Arg Asp Glu Leu Thr Lys Asn Gln Val Ser Leu Thr Cys
    450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
        515                 520                 525

Leu His Asn His Tyr Thr Gln Lys Ser Leu Ser Leu Ser Pro Gly Lys
    530                 535                 540

<210> SEQ ID NO 41
<211> LENGTH: 1485
<212> TYPE: DNA
<213> ORGANISM: Artificial Sequence
<220> FEATURE:
<223> OTHER INFORMATION: Synthetic: Syt1-Fc-Syt1 with knobs into holes
      mutations (TF)

<400> SEQUENCE: 41
gagaaactgg gaaaacttca gtattcactg gattatgatt tccaaaataa ccagctgctg     60
gtagggatca ttcaggctgc cgaactgccc gccttggaca tggggggcac atctgatcct    120
tacgtgaaag tgtttctgct acctgataag aagaagaaat ttgagacaaa agtccaccga    180
aaaaccctta atcctgtctt caatgagcaa tttactttca aggtaccata ctcggaattg    240
ggtggcaaaa ccctagtgat ggctgtatat gattttgatc gtttctctaa gcatgacatc    300
attggagaat ttaaagtccc tatgaacaca gtggattttg gccatgtaac tgaggaatgg    360
cgtgacctgc aaagtgctgg aggcggtgga tcagttgagc ccaaatcttc tgacaaaact    420
cacacatgcc caccgtgccc agcacctgaa ctcctggggg gaccgtcagt cttcctcttc    480
cccccaaaac ccaaggacac cctcatgatc tcccggaccc ctgaggtcac atgcgtggtg    540
gtggacgtga gccacgaaga ccctgaggtc aagttcaact ggtacgtgga cggcgtggag    600
gtgcataatg ccaagacaaa gccgcgggag gagcagtaca acagcacgta ccgtgtggtc    660
agcgtcctca ccgtcctgca ccaggactgg ctgaatggca aggagtacaa gtgcaaggtc    720
tccaacaaag ccctcccagc ccccatcgag aaaaccatct ccaaagccaa agggcagccc    780
cgagaaccac aggtgaccac cctgccccca tcccgggatg agctgaccaa gaaccaggtc    840
agcctgacct gcctggtcaa aggcttctat cccagcgaca tcgccgtgga gtgggagagc    900
aatgggcagc cggagaacaa ctacaagacc ttccctcccg tgctggactc cgacggctcc    960
ttcttcctct acagcaagct caccgtggac aagagcaggt ggcagcaggg gaacgtcttc   1020
tcatgctccg tgatgcatga ggctctgcac aaccactaca cgcagaagag cctctccctg   1080
tctccgggta aaggcggagg tggcagcgag aaactgggaa aacttcagta ttcactggat   1140
tatgatttcc aaaataacca gctgctggta gggatcattc aggctgccga actgcccgcc   1200
ttggacatgg ggggcacatc tgatccttac gtgaaagtgt ttctgctacc tgataagaag   1260
```

-continued

```
aagaaatttg agacaaaagt ccaccgaaaa acccttaatc ctgtcttcaa tgagcaattt   1320

actttcaagg taccatactc ggaattgggt ggcaaaaccc tagtgatggc tgtatatgat   1380

tttgatcgtt tctctaagca tgacatcatt ggagaattta aagtccctat gaacacagtg   1440

gattttggcc atgtaactga ggaatggcgt gacctgcaaa gtgct                   1485


<210> SEQ ID NO 42
<211> LENGTH: 495
<212> TYPE: PRT
<213> ORGANISM: Artificial Sequence
<220> FEATURE:
<223> OTHER INFORMATION: Synthetic: Syt1-Fc-Syt1 with knobs into holes
      mutations (TF)

<400> SEQUENCE: 42

Glu Lys Leu Gly Lys Leu Gln Tyr Ser Leu Asp Tyr Asp Phe Gln Asn
1               5                   10                  15

Asn Gln Leu Leu Val Gly Ile Ile Gln Ala Ala Glu Leu Pro Ala Leu
            20                  25                  30

Asp Met Gly Gly Thr Ser Asp Pro Tyr Val Lys Val Phe Leu Leu Pro
        35                  40                  45

Asp Lys Lys Lys Lys Phe Glu Thr Lys Val His Arg Lys Thr Leu Asn
    50                  55                  60

Pro Val Phe Asn Glu Gln Phe Thr Phe Lys Val Pro Tyr Ser Glu Leu
65                  70                  75                  80

Gly Gly Lys Thr Leu Val Met Ala Val Tyr Asp Phe Asp Arg Phe Ser
                85                  90                  95

Lys His Asp Ile Ile Gly Glu Phe Lys Val Pro Met Asn Thr Val Asp
            100                 105                 110

Phe Gly His Val Thr Glu Glu Trp Arg Asp Leu Gln Ser Ala Gly Gly
        115                 120                 125

Gly Gly Ser Val Glu Pro Lys Ser Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Thr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Phe Pro Pro Val Leu Asp Ser Asp Gly Ser
305                 310                 315                 320
```

-continued

```
Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys Gly Gly Gly Gly
        355                 360                 365

Ser Glu Lys Leu Gly Lys Leu Gln Tyr Ser Leu Asp Tyr Asp Phe Gln
    370                 375                 380

Asn Asn Gln Leu Leu Val Gly Ile Ile Gln Ala Ala Glu Leu Pro Ala
385                 390                 395                 400

Leu Asp Met Gly Gly Thr Ser Asp Pro Tyr Val Lys Val Phe Leu Leu
                405                 410                 415

Pro Asp Lys Lys Lys Lys Phe Glu Thr Lys Val His Arg Lys Thr Leu
            420                 425                 430

Asn Pro Val Phe Asn Glu Gln Phe Thr Phe Lys Val Pro Tyr Ser Glu
        435                 440                 445

Leu Gly Gly Lys Thr Leu Val Met Ala Val Tyr Asp Phe Asp Arg Phe
    450                 455                 460

Ser Lys His Asp Ile Ile Gly Glu Phe Lys Val Pro Met Asn Thr Val
465                 470                 475                 480

Asp Phe Gly His Val Thr Glu Glu Trp Arg Asp Leu Gln Ser Ala
                485                 490                 495
```

<210> SEQ ID NO 43
<211> LENGTH: 699
<212> TYPE: DNA
<213> ORGANISM: Artificial Sequence
<220> FEATURE:
<223> OTHER INFORMATION: Synthetic: Fc with knobs into holes mutations(HA)

<400> SEQUENCE: 43

```
gttgagccca aatcttctga caaaactcac acatgcccac cgtgcccagc acctgaactc     60

ctggggggac cgtcagtctt cctcttcccc ccaaaaccca aggacaccct catgatctcc    120

cggacccctg aggtcacatg cgtggtggtg gacgtgagcc acgaagaccc tgaggtcaag    180

ttcaactggt acgtggacgg cgtggaggtg cataatgcca agacaaagcc gcgggaggag    240

cagtacaaca gcacgtaccg tgtggtcagc gtcctcaccg tcctgcacca ggactggctg    300

aatggcaagg agtacaagtg caaggtctcc aacaaagccc tcccagcccc catcgagaaa    360

accatctcca aagccaaagg gcagccccga gaaccacagg tgtacaccct gcccccatcc    420

cgggatgagc tgaccaagaa ccaggtccac ctgacctgcc tggtcaaagg cttctatccc    480

agcgacatcg ccgtggagtg ggagagcaat gggcagccgg agaacaacta caagaccacg    540

cctcccgtgc tggactccga cggctccttc gccctctaca gcaagctcac cgtggacaag    600

agcaggtggc agcaggggaa cgtcttctca tgctccgtga tgcatgaggc tctgcacaac    660

cactacacgc agaagagcct ctccctgtct ccgggtaaa                           699
```

<210> SEQ ID NO 44
<211> LENGTH: 233
<212> TYPE: PRT
<213> ORGANISM: Artificial Sequence
<220> FEATURE:
<223> OTHER INFORMATION: Synthetic: Fc with knobs into holes mutations(HA)

<400> SEQUENCE: 44

-continued

```
Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

```
<210> SEQ ID NO 45
<211> LENGTH: 1485
<212> TYPE: DNA
<213> ORGANISM: Artificial Sequence
<220> FEATURE:
<223> OTHER INFORMATION: Synthetic: Syt1-Fc-Syt1 with knobs into holes
      mutations (TF) and electrostatic steering mutations

<400> SEQUENCE: 45

gagaaactgg gaaaacttca gtattcactg gattatgatt tccaaaataa ccagctgctg     60

gtagggatca ttcaggctgc cgaactgccc gccttggaca tggggggcac atctgatcct    120

tacgtgaaag tgtttctgct acctgataag aagaagaaat ttgagacaaa agtccaccga    180

aaaaccctta atcctgtctt caatgagcaa tttactttca aggtaccata ctcggaattg    240

ggtggcaaaa ccctagtgat ggctgtatat gattttgatc gtttctctaa gcatgacatc    300

attggagaat ttaaagtccc tatgaacaca gtggattttg gccatgtaac tgaggaatgg    360

cgtgacctgc aaagtgctgg aggcggtgga tcagttgagc ccaaatcttc tgacaaaact    420

cacacatgcc caccgtgccc agcacctgaa ctcctggggg gaccgtcagt cttcctcttc    480

cccccaaaac ccaaggacac cctcatgatc tcccggaccc ctgaggtcac atgcgtggtg    540

gtggacgtga gccacgaaga ccctgaggtc aagttcaact ggtacgtgga cggcgtggag    600

gtgcataatg ccaagacaaa gccgcgggag gagcagtaca acagcacgta ccgtgtggtc    660

agcgtcctca ccgtcctgca ccaggactgg ctgaatggca aggagtacaa gtgcaaggtc    720
```

```
tccaacaaag ccctcccagc ccccatcgag aaaaccatct ccaaagccaa agggcagccc    780

cgagaaccac aggtgaccac cctgccccca tcccgggatg agctgaccaa gaaccaggtc    840

agcctgacct gcctggtcaa aggcttctat cccagcgaca tcgccgtgga gtgggagagc    900

aatgggcagc cggagaacaa ctacgacacc ttccctcccg tgctggactc cgacggctcc    960

ttcttcctct acagcgacct caccgtggac aagagcaggt ggcagcaggg gaacgtcttc   1020

tcatgctccg tgatgcatga ggctctgcac aaccactaca cgcagaagag cctctccctg   1080

tctccgggta aaggcggagg tggcagcgag aaactgggaa aacttcagta ttcactggat   1140

tatgatttcc aaaataacca gctgctggta gggatcattc aggctgccga actgcccgcc   1200

ttggacatgg ggggcacatc tgatccttac gtgaaagtgt ttctgctacc tgataagaag   1260

aagaaatttg agacaaaagt ccaccgaaaa acccttaatc ctgtcttcaa tgagcaattt   1320

actttcaagg taccatactc ggaattgggt ggcaaaaccc tagtgatggc tgtatatgat   1380

tttgatcgtt tctctaagca tgacatcatt ggagaattta aagtccctat gaacacagtg   1440

gattttggcc atgtaactga ggaatggcgt gacctgcaaa gtgct                  1485
```

```
<210> SEQ ID NO 46
<211> LENGTH: 495
<212> TYPE: PRT
<213> ORGANISM: Artificial Sequence
<220> FEATURE:
<223> OTHER INFORMATION: Synthetic: Syt1-Fc-Syt1 with knobs into holes
      mutations (TF) and electrostatic steering mutations

<400> SEQUENCE: 46

Glu Lys Leu Gly Lys Leu Gln Tyr Ser Leu Asp Tyr Asp Phe Gln Asn
1               5                   10                  15

Asn Gln Leu Leu Val Gly Ile Ile Gln Ala Ala Glu Leu Pro Ala Leu
            20                  25                  30

Asp Met Gly Gly Thr Ser Asp Pro Tyr Val Lys Val Phe Leu Leu Pro
        35                  40                  45

Asp Lys Lys Lys Lys Phe Glu Thr Lys Val His Arg Lys Thr Leu Asn
    50                  55                  60

Pro Val Phe Asn Glu Gln Phe Thr Phe Lys Val Pro Tyr Ser Glu Leu
65                  70                  75                  80

Gly Gly Lys Thr Leu Val Met Ala Val Tyr Asp Phe Asp Arg Phe Ser
                85                  90                  95

Lys His Asp Ile Ile Gly Glu Phe Lys Val Pro Met Asn Thr Val Asp
            100                 105                 110

Phe Gly His Val Thr Glu Glu Trp Arg Asp Leu Gln Ser Ala Gly Gly
        115                 120                 125

Gly Gly Ser Val Glu Pro Lys Ser Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220
```

Val Leu His Gln Asp Trp Leu Asn Gly Lys Glu Tyr Lys Cys Lys Val
225 230 235 240

Ser Asn Lys Ala Leu Pro Ala Pro Ile Glu Lys Thr Ile Ser Lys Ala
245 250 255

Lys Gly Gln Pro Arg Glu Pro Gln Val Thr Thr Leu Pro Pro Ser Arg
260 265 270

Asp Glu Leu Thr Lys Asn Gln Val Ser Leu Thr Cys Leu Val Lys Gly
275 280 285

Phe Tyr Pro Ser Asp Ile Ala Val Glu Trp Glu Ser Asn Gly Gln Pro
290 295 300

Glu Asn Asn Tyr Asp Thr Phe Pro Pro Val Leu Asp Ser Asp Gly Ser
305 310 315 320

Phe Phe Leu Tyr Ser Asp Leu Thr Val Asp Lys Ser Arg Trp Gln Gln
325 330 335

Gly Asn Val Phe Ser Cys Ser Val Met His Glu Ala Leu His Asn His
340 345 350

Tyr Thr Gln Lys Ser Leu Ser Leu Ser Pro Gly Lys Gly Gly Gly Gly
355 360 365

Ser Glu Lys Leu Gly Lys Leu Gln Tyr Ser Leu Asp Tyr Asp Phe Gln
370 375 380

Asn Asn Gln Leu Leu Val Gly Ile Ile Gln Ala Ala Glu Leu Pro Ala
385 390 395 400

Leu Asp Met Gly Gly Thr Ser Asp Pro Tyr Val Lys Val Phe Leu Leu
405 410 415

Pro Asp Lys Lys Lys Lys Phe Glu Thr Lys Val His Arg Lys Thr Leu
420 425 430

Asn Pro Val Phe Asn Glu Gln Phe Thr Phe Lys Val Pro Tyr Ser Glu
435 440 445

Leu Gly Gly Lys Thr Leu Val Met Ala Val Tyr Asp Phe Asp Arg Phe
450 455 460

Ser Lys His Asp Ile Ile Gly Glu Phe Lys Val Pro Met Asn Thr Val
465 470 475 480

Asp Phe Gly His Val Thr Glu Glu Trp Arg Asp Leu Gln Ser Ala
485 490 495

<210> SEQ ID NO 47
<211> LENGTH: 699
<212> TYPE: DNA
<213> ORGANISM: Artificial Sequence
<220> FEATURE:
<223> OTHER INFORMATION: Synthetic: Fc with knobs into holes mutations (HA) and electrostatic steering mutations

<400> SEQUENCE: 47
gttgagccca aatcttctga caaaactcac acatgcccac cgtgcccagc acctgaactc 60
ctggggggac cgtcagtctt cctcttcccc ccaaaaccca aggacaccct catgatctcc 120
cggacccctg aggtcacatg cgtggtggtg gacgtgagcc acgaagaccc tgaggtcaag 180
ttcaactggt acgtggacgg cgtggaggtg cataatgcca agacaaagcc gcgggaggag 240
cagtacaaca gcacgtaccg tgtggtcagc gtcctcaccg tcctgcacca ggactggctg 300
aatggcaagg agtacaagtg caaggtctcc aacaaagccc tcccagcccc catcgagaaa 360
accatctcca aagccaaagg gcagccccga gaaccacagg tgtacaccct gcccccatcc 420
cgggataagc tgaccaagaa ccaggtccac ctgacctgcc tggtcaaagg cttctatccc 480

```
agcgacatcg ccgtggagtg ggagagcaat gggcagccgg agaacaacta caagaccacg    540

cctcccgtgc tgaagtccga cggctccttc gccctctaca gcaagctcac cgtggacaag    600

agcaggtggc agcaggggaa cgtcttctca tgctccgtga tgcatgaggc tctgcacaac    660

cactacacgc agaagagcct ctccctgtct ccgggtaaa                          699


<210> SEQ ID NO 48
<211> LENGTH: 233
<212> TYPE: PRT
<213> ORGANISM: Artificial Sequence
<220> FEATURE:
<223> OTHER INFORMATION: Synthetic: Fc with knobs into holes mutations
      (HA) and electrostatic steering mutations

<400> SEQUENCE: 48

Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Lys Leu
    130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Lys Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 49
<211> LENGTH: 51
<212> TYPE: DNA
<213> ORGANISM: Artificial Sequence
<220> FEATURE:
<223> OTHER INFORMATION: Synthetic: CDRH1Back
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
```

<220> FEATURE:
<221> NAME/KEY: misc_feature
<222> LOCATION: (28)..(29)
<223> OTHER INFORMATION: n is a, c, g, or t

<400> SEQUENCE: 49
gcttctggat tcacattcac annbnnbnnb atggattggg tgagacaggc t 51

<210> SEQ ID NO 50
<211> LENGTH: 21
<212> TYPE: DNA
<213> ORGANISM: Artificial Sequence
<220> FEATURE:
<223> OTHER INFORMATION: Synthetic: CDRH1For

<400> SEQUENCE: 50
tgtgaatgtg aatccagaag c 21

<210> SEQ ID NO 51
<211> LENGTH: 54
<212> TYPE: DNA
<213> ORGANISM: Artificial Sequence
<220> FEATURE:
<223> OTHER INFORMATION: Synthetic: CDRH2Back
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 51
tgggtggctg atgtgaatcc tnnbnnbnnb nnbtctatct acaatcagag attc 54

<210> SEQ ID NO 52
<211> LENGTH: 21
<212> TYPE: DNA
<213> ORGANISM: Artificial Sequence
<220> FEATURE:
<223> OTHER INFORMATION: Synthetic: CDRH2For

<400> SEQUENCE: 52
aggattcaca tcagccaccc a 21

<210> SEQ ID NO 53
<211> LENGTH: 63
<212> TYPE: DNA
<213> ORGANISM: Artificial Sequence
<220> FEATURE:
<223> OTHER INFORMATION: Synthetic: CDRH3Back
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)

<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 53
tactactgtg ctagaaatct gnnbcctnnb ttcnnbttcg atnnbtgggg acagggaaca 60
ctg 63

<210> SEQ ID NO 54
<211> LENGTH: 21
<212> TYPE: DNA
<213> ORGANISM: Artificial Sequence
<220> FEATURE:
<223> OTHER INFORMATION: Synthetic: CDRH3For

<400> SEQUENCE: 54
cagatttcta gcacagtagt a 21

<210> SEQ ID NO 55
<211> LENGTH: 54
<212> TYPE: DNA
<213> ORGANISM: Artificial Sequence
<220> FEATURE:
<223> OTHER INFORMATION: Synthetic: CDRL2-1Back
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 55
cctaagctgc tgatctactc tnnbtctnnb agannbacag gagtgccttc taga 54

<210> SEQ ID NO 56
<211> LENGTH: 21
<212> TYPE: DNA
<213> ORGANISM: Artificial Sequence
<220> FEATURE:
<223> OTHER INFORMATION: Synthetic: CDRL2-1For

<400> SEQUENCE: 56
agagtagatc agcagcttag g 21

<210> SEQ ID NO 57
<211> LENGTH: 51
<212> TYPE: DNA
<213> ORGANISM: Artificial Sequence
<220> FEATURE:
<223> OTHER INFORMATION: Synthetic: CDRL2-2Back
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t -continued

```
<400> SEQUENCE: 57

ggaaaggctc ctaagctgct gnnbnnbnnb gcttcttaca gatacacagg a            51


<210> SEQ ID NO 58
<211> LENGTH: 21
<212> TYPE: DNA
<213> ORGANISM: Artificial Sequence
<220> FEATURE:
<223> OTHER INFORMATION: Synthetic: CDRL2-2For5

<400> SEQUENCE: 58

cagcagctta ggagcctttc c                                             21


<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Gly Gly Gly Gly Ser Gly Gly Gly Gly Ser Gly Gly Gly Gly Ser
1               5                   10                  15


<210> SEQ ID NO 60
<211> LENGTH: 5
<212> TYPE: PRT
<213> ORGANISM: Artificial Sequence
<220> FEATURE:
<223> OTHER INFORMATION: Synthetic

<400> SEQUENCE: 60

Gly Gly Gly Gly Ser
1               5
```